US012715903B2

(12) United States Patent
Peng et al.

(10) Patent No.: US 12,715,903 B2
(45) Date of Patent: Aug. 25, 2026

(54) MULTIMERIC PROTEINS FOR DETECTING A CARBOHYDRATE AND/OR TREATING A SIGLEC-MEDIATED DISORDER

(71) Applicant: Palleon Pharmaceuticals Inc., Waltham, MA (US)

(72) Inventors: Li Peng, Lexington, MA (US); Adam Petrone, Woburn, MA (US); Lihui Xu, Chestnut Hill, MA (US); Adam Shoemaker, Somerville, MA (US)

(73) Assignee: Palleon Pharmaceuticals Inc., Waltham, MA (US)

( * ) Notice: Subject to any disclaimer, the term of this patent is extended or adjusted under 35 U.S.C. 154(b) by 1169 days.

(21) Appl. No.: 17/058,223

(22) PCT Filed: Jun. 7, 2019

(86) PCT No.: PCT/US2019/036161
§ 371 (c)(1),
(2) Date: Nov. 24, 2020

(87) PCT Pub. No.: WO2019/237070
PCT Pub. Date: Dec. 12, 2019

(65) Prior Publication Data

US 2021/0395333 A1 Dec. 23, 2021

Related U.S. Application Data

(60) Provisional application No. 62/755,285, filed on Nov. 2, 2018, provisional application No. 62/681,849, filed on Jun. 7, 2018.

(51) Int. Cl.

| | |
|---|---|
| ***C07K 14/705*** | (2006.01) |
| ***A61K 38/00*** | (2006.01) |
| ***A61P 35/00*** | (2006.01) |
| ***A61P 35/02*** | (2006.01) |
| ***C07K 14/005*** | (2006.01) |
| ***C12N 7/00*** | (2006.01) |
| ***G01N 33/566*** | (2006.01) |
| ***G01N 33/66*** | (2006.01) |

(52) U.S. Cl.
CPC .......... *C07K 14/7056* (2013.01); *A61P 35/00* (2018.01); *A61P 35/02* (2018.01); *C07K 14/005* (2013.01); *C07K 14/70503* (2013.01); *C12N 7/00* (2013.01); *G01N 33/566* (2013.01); *G01N 33/66* (2013.01); *A61K 38/00* (2013.01); *C07K 2319/30* (2013.01); *C12N 2795/10122* (2013.01); *G01N 2333/4724* (2013.01); *G01N 2400/00* (2013.01); *G01N 2800/52* (2013.01)

(58) Field of Classification Search
CPC .............. C07K 14/7056; C07K 14/005; C07K 14/70503; C07K 2319/30; A61P 35/02; A61P 35/00; C12N 7/00; C12N 2795/10122; G01N 33/566; G01N 33/66; G01N 2333/4724; G01N 2400/00; A61K 38/00
See application file for complete search history.

(56) References Cited

U.S. PATENT DOCUMENTS

| | | | | |
|---|---|---|---|---|
| 2016/0312207 | A1* | 10/2016 | Kuo | C12N 9/93 |
| 2017/0072045 | A1 | 3/2017 | Marshall et al. | |
| 2019/0085077 | A1 | 3/2019 | Cornen et al. | |
| 2021/0024631 | A1 | 1/2021 | Kley et al. | |
| 2024/0156979 | A1 | 5/2024 | Peng et al. | |

FOREIGN PATENT DOCUMENTS

| | | | | |
|---|---|---|---|---|
| WO | WO-2006/113311 | A2 | 10/2006 | |
| WO | WO-2010/049688 | A1 | 5/2010 | |
| WO | WO-2010/096126 | A1 | 8/2010 | |
| WO | WO-2014/098249 | A1 | 6/2014 | |
| WO | WO-2015/003149 | A2 | 1/2015 | |
| WO | WO-2016/038064 | A1 | 3/2016 | |
| WO | WO-2017024114 | A1 * | 2/2017 | C07K 14/00 |
| WO | WO-2017/040301 | A1 | 3/2017 | |
| WO | WO-2017/075432 | A2 | 5/2017 | |
| WO | WO-2017/153433 | A1 | 9/2017 | |
| WO | WO-2018/006034 | A1 | 1/2018 | |
| WO | WO-2022/221707 | A2 | 10/2022 | |
| WO | WO-2023/201051 | A2 | 10/2023 | |

OTHER PUBLICATIONS

Sriwilaijaroen et al, Molecular basis of the structure and function of H1 hemagglutinin of influenza virus, Proc. Jpn. Acad., 2012, 88, pp. 226-249.*
Saito et al, A soluble form of Siglec-9 provides a resistance against Group B *Streptococcus* (GBS) infection in transgenic mice, Microbial Pathogenesis, 2016, 99, pp. 106-110.*
Sialic acid-binding immunoglobulin-like lectin-9 [*Homo sapiens*], from https://www.ncbi.nlm.nih.gov/protein/AAD26428.2?report=genbank&log$=protalign&blast_rank=1&RID=EHAPXOGN016, 2000, pp. 1-3.*
Protein Refolding, from https://web.archive.org/web/20170514105126/https://www.biologicscorp.com/protein-refolding/, 2017, pp. 1-5.*
Angata, et al. (2000) "Cloning, Characterization, and Phylogenetic Analysis of Siglec-9, a New 'Member of the CD33-related Group of Siglecs," Journal of Biological Chemistry, 275(29): 22127-22135.
Angata, et al. (2015) "Therapeutic Targeting of Siglecs using Antibody- and Glycan-Based Approaches," Trends in Pharmacological Sciences, 36(10): 645-660.
Du, et al. (2011) "A Recombinant Vaccine of H5N1 HA1 Fused with Foldon and Human IgG Fc Induced Complete Cross-Clade Protection against Divergent H5N1 Viruses," PLoS One, 6(1): e16555.

(Continued)

*Primary Examiner* — Li N Komatsu
(74) *Attorney, Agent, or Firm* — Goodwin Procter LLP

(57) ABSTRACT

The invention relates generally to polypeptides comprising a lectin domain, multimeric proteins comprising the polypeptides, and use of the polypeptides or multimeric proteins in the detection of a carbohydrate (e.g., a sialic acid containing carbohydrate or Siglec ligand) or the treatment of a Siglec-mediated disorder.

4 Claims, 43 Drawing Sheets

Specification includes a Sequence Listing.

(56) References Cited

OTHER PUBLICATIONS

Fuster, et al. (2005) "The sweet and sour of cancer: glycans as novel therapeutic targets," Nat. Rev. Cancer, 5(7): 526-542.
International Search Report for International Application No. PCT/US2019/036161, mailed Sep. 14, 2019 (5 pages).
International Search Report for International Application No. PCT/US2022/025087, mailed Sep. 28, 2022 (5 pages).
International Search Report for International Application No. PCT/US2023/018674, mailed Jan. 23, 2024 (5 pages).
Jandus, et al. (2014) "Interactions between Siglec-7/9 receptors and ligands influence NK cell-dependent tumor immunosurveillance," J. Clin. Invest., 124: 1810-1820.
Lee, et al. (2000) "Affinity enhancement by multivalent lectin-carbohydrate interaction" Glycoconjugate Journal, 17: 543-551.
Pegon, et al. (2010) "Siglecs as Novel Cellular Partners for Von Willebrand Factor," Blood, 116(21): 4306.
Toscano, et al. (2007) "Dissecting the pathophysiologic role of endogenous lectins: Glycan-binding proteins with cytokine-like activity?" Cytokine & Growth Factor Reviews, 18: 57-71.
White, et al. (2010) "Enhancement of Antiviral Activity of Collectin Trimers through Cross-Linking and Mutagenesis of the Carbohydrate Recognition Domain" J. Innate Immunol., 2: 267-279.
Written Opinion for International Application No. PCT/US2019/036161, mailed Sep. 14, 2019 (5 pages).
Written Opinion for International Application No. PCT/US2022/025087, mailed Sep. 28, 2022 (11 pages).
Written Opinion for International Application No. PCT/US2023/018674, mailed Jan. 23, 2024 (7 pages).
Zou, et al. (2011) "Siglecs Facilitate HIV-1 Infection of Macrophages through Adhesion with Viral Sialic Acids" PLoS One, 6(9): e24559.
Ono, et al. (2018) "Implication of Soluble Forms of Cell Adhesion Molecules in Infectious Disease and Tumor: Insights from Transgenic Animal Models," Int. J. Mol. Sci., 19(1):239.

* cited by examiner

| KD (M) | n/a |
|---|---|
| kon (1/Ms) | n/a |
| kdis (1/s) | n/a |

| KD (M) | 4.8E-10 |
|---|---|
| kon (1/Ms) | 8.4E+05 |
| kdis (1/s) | 1.9E-04 |

| KD (M) | n/a |
|---|---|
| kon (1/Ms) | n/a |
| kdis (1/s) | n/a |

| KD (M) | 1.4E-09 |
|---|---|
| kon (1/Ms) | 7.0E+05 |
| kdis (1/s) | 5.1E-04 |

Complex and Hybrid N-Glycans

N000 N001 N002 N003 N004 N005
N010 N011 N012 N013 N014 N015
N020 N021 N022 N023 N024 N025
N030 N031 N032 N033 N034 N035
N040 N041 N042 N043 N044 N045
N050 N051 N052 N053 N054 N055

Complex and Hybrid N-Glycans, continued

Complex and Hybrid N-Glycans, continued

High-Mannose N-Glycans

NeuGGc N-Glycans

Neu5Gc N-Glycans

Neu5Gc N-Glycans

Neu5Ac N-Glycans

Neu5Ac N-Glycans

Version 1.0

Version 2.0

FIGURE 24

| | Hydra 9 WT Mock Tx | Hydra 9 WT VC | Hydra 9 WT LOB Mock Tx | Hydra 9 WT LOB VC Treat |
|---|---|---|---|---|
| Pre-Dialysis | 7.3mg | 7.1mg | 9.3mg | 9.8mg |
| Post-Dialysis | 1.7mg | 4mg | 5mg | 5.5mg |
| Recovery | 24% | 55% | 53% | 56% |

| | Hydra 9 DM Mock Tx | Hydra 9 DM VC |
|---|---|---|
| Pre-Dialysis | 6.9mg | 6.9mg |
| Post-Dialysis | 1.9mg | 4.5mg |
| Recovery | 27% | 65% |

SEQUENCE LISTING

<160> NUMBER OF SEQ ID NOS: 73

<210> SEQ ID NO 1
<211> LENGTH: 119
<212> TYPE: PRT
<213> ORGANISM: Homo sapiens

<400> SEQUENCE: 1

```
Tyr Ser Leu Thr Met Gln Ser Ser Val Thr Val Gln Glu Gly Met Cys
1               5                   10                  15

Val His Val Arg Cys Ser Phe Ser Tyr Pro Val Asp Ser Gln Thr Asp
            20                  25                  30

Ser Asp Pro Val His Gly Tyr Trp Phe Arg Ala Gly Asn Asp Ile Ser
        35                  40                  45

Trp Lys Ala Pro Val Ala Thr Asn Asn Pro Ala Trp Ala Val Gln Glu
    50                  55                  60

Glu Thr Arg Asp Arg Phe His Leu Leu Gly Asp Pro Gln Thr Lys Asn
65                  70                  75                  80

Cys Thr Leu Ser Ile Arg Asp Ala Arg Met Ser Asp Ala Gly Arg Tyr
                85                  90                  95

Phe Phe Arg Met Glu Lys Gly Asn Ile Lys Trp Asn Tyr Lys Tyr Asp
            100                 105                 110

Gln Leu Ser Val Asn Val Thr
```

```
        115


<210> SEQ ID NO 2
<211> LENGTH: 122
<212> TYPE: PRT
<213> ORGANISM: Homo sapiens

<400> SEQUENCE: 2

Leu Thr Met Gln Ser Ser Val Thr Val Gln Glu Gly Leu Cys Val His
1               5                   10                  15

Val Pro Cys Ser Phe Ser Tyr Pro Ser His Gly Trp Ile Tyr Pro Gly
            20                  25                  30

Pro Val Val His Gly Tyr Trp Phe Arg Glu Gly Ala Asn Thr Asp Gln
        35                  40                  45

Asp Ala Pro Val Ala Thr Asn Asn Pro Ala Arg Ala Val Trp Glu Glu
    50                  55                  60

Thr Arg Asp Arg Phe His Leu Leu Gly Asp Pro His Thr Lys Asn Cys
65                  70                  75                  80

Thr Leu Ser Ile Arg Asp Ala Arg Arg Ser Asp Ala Gly Arg Tyr Phe
                85                  90                  95

Phe Arg Met Glu Lys Gly Ser Ile Lys Trp Asn Tyr Lys His His Arg
            100                 105                 110

Leu Ser Val Asn Val Thr Ala Leu Thr His
        115                 120


<210> SEQ ID NO 3
<211> LENGTH: 221
<212> TYPE: PRT
<213> ORGANISM: Homo sapiens

<400> SEQUENCE: 3

Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
            20                  25                  30

Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Ala Leu
        115                 120                 125

Thr His Arg Pro Asn Ile Leu Ile Pro Gly Thr Leu Glu Ser Gly Cys
    130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
```

```
        195                 200                 205

Thr Thr Asn Arg Thr Ile Gln Leu Asn Val Ser Tyr Pro
    210                 215                 220


<210> SEQ ID NO 4
<211> LENGTH: 218
<212> TYPE: PRT
<213> ORGANISM: Homo sapiens

<400> SEQUENCE: 4

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30

Trp Ile Tyr Pro Gly Pro Val Val His Gly Tyr Trp Phe Arg Glu Gly
        35                  40                  45

Ala Asn Thr Asp Gln Asp Ala Pro Val Ala Thr Asn Asn Pro Ala Arg
    50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
    130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro
    210                 215


<210> SEQ ID NO 5
<211> LENGTH: 27
<212> TYPE: PRT
<213> ORGANISM: Escherichia virus T4

<400> SEQUENCE: 5

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25


<210> SEQ ID NO 6
<211> LENGTH: 233
<212> TYPE: PRT
<213> ORGANISM: Mus musculus

<400> SEQUENCE: 6

Glu Pro Arg Gly Pro Thr Ile Lys Pro Cys Pro Pro Cys Lys Cys Pro
1               5                   10                  15
```

```
Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230


<210> SEQ ID NO 7
<211> LENGTH: 599
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
            20                  25                  30

Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Ala Leu
        115                 120                 125

Thr His Arg Pro Asn Ile Leu Ile Pro Gly Thr Leu Glu Ser Gly Cys
```

-continued

```
    130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
        195                 200                 205

Thr Thr Asn Arg Thr Ile Gln Leu Asn Val Ser Tyr Pro Pro Gln Asn
    210                 215                 220

Leu Thr Val Thr Val Phe Gln Gly Glu Gly Thr Ala Ser Thr Ala Leu
225                 230                 235                 240

Gly Asn Ser Ser Ser Leu Ser Val Leu Glu Gly Gln Ser Leu Arg Leu
                245                 250                 255

Val Cys Ala Val Asp Ser Asn Pro Pro Ala Arg Leu Ser Trp Thr Trp
            260                 265                 270

Arg Ser Leu Thr Leu Tyr Pro Ser Gln Pro Ser Asn Pro Leu Val Leu
        275                 280                 285

Glu Leu Gln Val His Leu Gly Asp Glu Gly Glu Phe Thr Cys Arg Ala
    290                 295                 300

Gln Asn Ser Leu Gly Ser Gln His Val Ser Leu Asn Leu Ser Leu Gln
305                 310                 315                 320

Gln Glu Tyr Thr Gly Lys Met Arg Pro Val Ser Gly Val Leu Leu Gly
                325                 330                 335

Ala Val Gly Gly Tyr Ile Pro Glu Ala Pro Arg Asp Gly Gln Ala Tyr
            340                 345                 350

Val Arg Lys Asp Gly Glu Trp Val Leu Leu Ser Thr Phe Leu Glu Pro
        355                 360                 365

Arg Gly Pro Thr Ile Lys Pro Cys Pro Pro Cys Lys Cys Pro Ala Pro
    370                 375                 380

Asn Leu Leu Gly Gly Pro Ser Val Phe Ile Phe Pro Pro Lys Ile Lys
385                 390                 395                 400

Asp Val Leu Met Ile Ser Leu Ser Pro Ile Val Thr Cys Val Val Val
                405                 410                 415

Asp Val Ser Glu Asp Asp Pro Asp Val Gln Ile Ser Trp Phe Val Asn
            420                 425                 430

Asn Val Glu Val His Thr Ala Gln Thr Gln Thr His Arg Glu Asp Tyr
        435                 440                 445

Asn Ser Thr Leu Arg Val Val Ser Ala Leu Pro Ile Gln His Gln Asp
    450                 455                 460

Trp Met Ser Gly Lys Glu Phe Lys Cys Lys Val Asn Asn Lys Asp Leu
465                 470                 475                 480

Pro Ala Pro Ile Glu Arg Thr Ile Ser Lys Pro Lys Gly Ser Val Arg
                485                 490                 495

Ala Pro Gln Val Tyr Val Leu Pro Pro Pro Glu Glu Glu Met Thr Lys
            500                 505                 510

Lys Gln Val Thr Leu Thr Cys Met Val Thr Asp Phe Met Pro Glu Asp
        515                 520                 525

Ile Tyr Val Glu Trp Thr Asn Asn Gly Lys Thr Glu Leu Asn Tyr Lys
    530                 535                 540

Asn Thr Glu Pro Val Leu Asp Ser Asp Gly Ser Tyr Phe Met Tyr Ser
545                 550                 555                 560
```

```
Lys Leu Arg Val Glu Lys Lys Asn Trp Val Glu Arg Asn Ser Tyr Ser
                565                 570                 575

Cys Ser Val Val His Glu Gly Leu His Asn His His Thr Thr Lys Ser
            580                 585                 590

Phe Ser Arg Thr Pro Gly Lys
        595


<210> SEQ ID NO 8
<211> LENGTH: 591
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30

Trp Ile Tyr Pro Gly Pro Val Val His Gly Tyr Trp Phe Arg Glu Gly
        35                  40                  45

Ala Asn Thr Asp Gln Asp Ala Pro Val Ala Thr Asn Asn Pro Ala Arg
    50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
    130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro Pro Gln Asn Leu Thr Met
    210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
                245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
        275                 280                 285

Glu Leu Pro Trp Val His Leu Arg Asp Ala Ala Glu Phe Thr Cys Arg
    290                 295                 300

Ala Gln Asn Pro Leu Gly Ser Gln Gln Val Tyr Leu Asn Val Ser Leu
```

-continued

```
305                 310                 315                 320

Gln Ser Lys Ala Thr Ser Gly Val Thr Gln Gly Gly Tyr Ile Pro Glu
                325                 330                 335

Ala Pro Arg Asp Gly Gln Ala Tyr Val Arg Lys Asp Gly Glu Trp Val
            340                 345                 350

Leu Leu Ser Thr Phe Leu Glu Pro Arg Gly Pro Thr Ile Lys Pro Cys
        355                 360                 365

Pro Pro Cys Lys Cys Pro Ala Pro Asn Leu Leu Gly Gly Pro Ser Val
    370                 375                 380

Phe Ile Phe Pro Pro Lys Ile Lys Asp Val Leu Met Ile Ser Leu Ser
385                 390                 395                 400

Pro Ile Val Thr Cys Val Val Val Asp Val Ser Glu Asp Asp Pro Asp
                405                 410                 415

Val Gln Ile Ser Trp Phe Val Asn Asn Val Glu Val His Thr Ala Gln
            420                 425                 430

Thr Gln Thr His Arg Glu Asp Tyr Asn Ser Thr Leu Arg Val Val Ser
        435                 440                 445

Ala Leu Pro Ile Gln His Gln Asp Trp Met Ser Gly Lys Glu Phe Lys
    450                 455                 460

Cys Lys Val Asn Asn Lys Asp Leu Pro Ala Pro Ile Glu Arg Thr Ile
465                 470                 475                 480

Ser Lys Pro Lys Gly Ser Val Arg Ala Pro Gln Val Tyr Val Leu Pro
                485                 490                 495

Pro Pro Glu Glu Glu Met Thr Lys Lys Gln Val Thr Leu Thr Cys Met
            500                 505                 510

Val Thr Asp Phe Met Pro Glu Asp Ile Tyr Val Glu Trp Thr Asn Asn
        515                 520                 525

Gly Lys Thr Glu Leu Asn Tyr Lys Asn Thr Glu Pro Val Leu Asp Ser
    530                 535                 540

Asp Gly Ser Tyr Phe Met Tyr Ser Lys Leu Arg Val Glu Lys Lys Asn
545                 550                 555                 560

Trp Val Glu Arg Asn Ser Tyr Ser Cys Ser Val Val His Glu Gly Leu
                565                 570                 575

His Asn His His Thr Thr Lys Ser Phe Ser Arg Thr Pro Gly Lys
            580                 585                 590


<210> SEQ ID NO 9
<211> LENGTH: 690
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
            20                  25                  30

Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80
```

-continued

```
Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Ala Leu
        115                 120                 125

Thr His Arg Pro Asn Ile Leu Ile Pro Gly Thr Leu Glu Ser Gly Cys
    130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
        195                 200                 205

Thr Thr Asn Arg Thr Ile Gln Leu Asn Val Ser Tyr Pro Gly Gly Gly
    210                 215                 220

Gly Ser Gly Gly Gly Gly Ser Gly Gly Gly Gly Ser Gln Lys Ser Asn
225                 230                 235                 240

Arg Lys Asp Tyr Ser Leu Thr Met Gln Ser Ser Val Thr Val Gln Glu
                245                 250                 255

Gly Met Cys Val His Val Arg Cys Ser Phe Ser Tyr Pro Val Asp Ser
            260                 265                 270

Gln Thr Asp Ser Asp Pro Val His Gly Tyr Trp Phe Arg Ala Gly Asn
        275                 280                 285

Asp Ile Ser Trp Lys Ala Pro Val Ala Thr Asn Asn Pro Ala Trp Ala
    290                 295                 300

Val Gln Glu Glu Thr Arg Asp Arg Phe His Leu Leu Gly Asp Pro Gln
305                 310                 315                 320

Thr Lys Asn Cys Thr Leu Ser Ile Arg Asp Ala Arg Met Ser Asp Ala
                325                 330                 335

Gly Arg Tyr Phe Phe Arg Met Glu Lys Gly Asn Ile Lys Trp Asn Tyr
            340                 345                 350

Lys Tyr Asp Gln Leu Ser Val Asn Val Thr Ala Leu Thr His Arg Pro
        355                 360                 365

Asn Ile Leu Ile Pro Gly Thr Leu Glu Ser Gly Cys Phe Gln Asn Leu
    370                 375                 380

Thr Cys Ser Val Pro Trp Ala Cys Glu Gln Gly Thr Pro Pro Met Ile
385                 390                 395                 400

Ser Trp Met Gly Thr Ser Val Ser Pro Leu His Pro Ser Thr Thr Arg
                405                 410                 415

Ser Ser Val Leu Thr Leu Ile Pro Gln Pro Gln His His Gly Thr Ser
            420                 425                 430

Leu Thr Cys Gln Val Thr Leu Pro Gly Ala Gly Val Thr Thr Asn Arg
        435                 440                 445

Thr Ile Gln Leu Asn Val Ser Tyr Pro Glu Pro Arg Gly Pro Thr Ile
    450                 455                 460

Lys Pro Cys Pro Pro Cys Lys Cys Pro Ala Pro Asn Leu Leu Gly Gly
465                 470                 475                 480

Pro Ser Val Phe Ile Phe Pro Pro Lys Ile Lys Asp Val Leu Met Ile
                485                 490                 495

Ser Leu Ser Pro Ile Val Thr Cys Val Val Val Asp Val Ser Glu Asp
```

-continued

```
            500                 505                 510

Asp Pro Asp Val Gln Ile Ser Trp Phe Val Asn Asn Val Glu Val His
        515                 520                 525

Thr Ala Gln Thr Gln Thr His Arg Glu Asp Tyr Asn Ser Thr Leu Arg
    530                 535                 540

Val Val Ser Ala Leu Pro Ile Gln His Gln Asp Trp Met Ser Gly Lys
545                 550                 555                 560

Glu Phe Lys Cys Lys Val Asn Asn Lys Asp Leu Pro Ala Pro Ile Glu
                565                 570                 575

Arg Thr Ile Ser Lys Pro Lys Gly Ser Val Arg Ala Pro Gln Val Tyr
            580                 585                 590

Val Leu Pro Pro Pro Glu Glu Glu Met Thr Lys Lys Gln Val Thr Leu
        595                 600                 605

Thr Cys Met Val Thr Asp Phe Met Pro Glu Asp Ile Tyr Val Glu Trp
    610                 615                 620

Thr Asn Asn Gly Lys Thr Glu Leu Asn Tyr Lys Asn Thr Glu Pro Val
625                 630                 635                 640

Leu Asp Ser Asp Gly Ser Tyr Phe Met Tyr Ser Lys Leu Arg Val Glu
                645                 650                 655

Lys Lys Asn Trp Val Glu Arg Asn Ser Tyr Ser Cys Ser Val Val His
            660                 665                 670

Glu Gly Leu His Asn His His Thr Thr Lys Ser Phe Ser Arg Thr Pro
        675                 680                 685

Gly Lys
    690


<210> SEQ ID NO 10
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30

Trp Ile Tyr Pro Gly Pro Val Val His Gly Tyr Trp Phe Arg Glu Gly
        35                  40                  45

Ala Asn Thr Asp Gln Asp Ala Pro Val Ala Thr Asn Asn Pro Ala Arg
    50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
    130                 135                 140

Leu Thr Cys Ser Val Pro Trp Ala Cys Glu Gln Gly Thr Pro Pro Met
145                 150                 155                 160
```

-continued

```
Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro Gly Gly Gly Gly Ser Gly
    210                 215                 220

Gly Gly Gly Ser Gly Gly Gly Gly Ser Gln Thr Ser Lys Leu Leu Thr
225                 230                 235                 240

Met Gln Ser Ser Val Thr Val Gln Glu Gly Leu Cys Val His Val Pro
                245                 250                 255

Cys Ser Phe Ser Tyr Pro Ser His Gly Trp Ile Tyr Pro Gly Pro Val
            260                 265                 270

Val His Gly Tyr Trp Phe Arg Glu Gly Ala Asn Thr Asp Gln Asp Ala
        275                 280                 285

Pro Val Ala Thr Asn Asn Pro Ala Arg Ala Val Trp Glu Glu Thr Arg
    290                 295                 300

Asp Arg Phe His Leu Leu Gly Asp Pro His Thr Lys Asn Cys Thr Leu
305                 310                 315                 320

Ser Ile Arg Asp Ala Arg Arg Ser Asp Ala Gly Arg Tyr Phe Phe Arg
                325                 330                 335

Met Glu Lys Gly Ser Ile Lys Trp Asn Tyr Lys His His Arg Leu Ser
            340                 345                 350

Val Asn Val Thr Ala Leu Thr His Arg Pro Asn Ile Leu Ile Pro Gly
        355                 360                 365

Thr Leu Glu Ser Gly Cys Pro Gln Asn Leu Thr Cys Ser Val Pro Trp
    370                 375                 380

Ala Cys Glu Gln Gly Thr Pro Pro Met Ile Ser Trp Ile Gly Thr Ser
385                 390                 395                 400

Val Ser Pro Leu Asp Pro Ser Thr Thr Arg Ser Ser Val Leu Thr Leu
                405                 410                 415

Ile Pro Gln Pro Gln Asp His Gly Thr Ser Leu Thr Cys Gln Val Thr
            420                 425                 430

Phe Pro Gly Ala Ser Val Thr Thr Asn Lys Thr Val His Leu Asn Val
        435                 440                 445

Ser Tyr Pro Glu Pro Arg Gly Pro Thr Ile Lys Pro Cys Pro Pro Cys
    450                 455                 460

Lys Cys Pro Ala Pro Asn Leu Leu Gly Gly Pro Ser Val Phe Ile Phe
465                 470                 475                 480

Pro Pro Lys Ile Lys Asp Val Leu Met Ile Ser Leu Ser Pro Ile Val
                485                 490                 495

Thr Cys Val Val Val Asp Val Ser Glu Asp Asp Pro Asp Val Gln Ile
            500                 505                 510

Ser Trp Phe Val Asn Asn Val Glu Val His Thr Ala Gln Thr Gln Thr
        515                 520                 525

His Arg Glu Asp Tyr Asn Ser Thr Leu Arg Val Val Ser Ala Leu Pro
    530                 535                 540

Ile Gln His Gln Asp Trp Met Ser Gly Lys Glu Phe Lys Cys Lys Val
545                 550                 555                 560

Asn Asn Lys Asp Leu Pro Ala Pro Ile Glu Arg Thr Ile Ser Lys Pro
                565                 570                 575

Lys Gly Ser Val Arg Ala Pro Gln Val Tyr Val Leu Pro Pro Pro Glu
```

580 585 590

Glu Glu Met Thr Lys Lys Gln Val Thr Leu Thr Cys Met Val Thr Asp
595 600 605

Phe Met Pro Glu Asp Ile Tyr Val Glu Trp Thr Asn Asn Gly Lys Thr
610 615 620

Glu Leu Asn Tyr Lys Asn Thr Glu Pro Val Leu Asp Ser Asp Gly Ser
625 630 635 640

Tyr Phe Met Tyr Ser Lys Leu Arg Val Glu Lys Lys Asn Trp Val Glu
645 650 655

Arg Asn Ser Tyr Ser Cys Ser Val Val His Glu Gly Leu His Asn His
660 665 670

His Thr Thr Lys Ser Phe Ser Arg Thr Pro Gly Lys
675 680

<210> SEQ ID NO 11
<211> LENGTH: 926
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Gln Lys Ser Asn Arg Lys Asp Tyr Ser Leu Thr Met Gln Ser Ser Val
1 5 10 15

Thr Val Gln Glu Gly Met Cys Val His Val Arg Cys Ser Phe Ser Tyr
20 25 30

Pro Val Asp Ser Gln Thr Asp Ser Asp Pro Val His Gly Tyr Trp Phe
35 40 45

Arg Ala Gly Asn Asp Ile Ser Trp Lys Ala Pro Val Ala Thr Asn Asn
50 55 60

Pro Ala Trp Ala Val Gln Glu Glu Thr Arg Asp Arg Phe His Leu Leu
65 70 75 80

Gly Asp Pro Gln Thr Lys Asn Cys Thr Leu Ser Ile Arg Asp Ala Arg
85 90 95

Met Ser Asp Ala Gly Arg Tyr Phe Phe Arg Met Glu Lys Gly Asn Ile
100 105 110

Lys Trp Asn Tyr Lys Tyr Asp Gln Leu Ser Val Asn Val Thr Ala Leu
115 120 125

Thr His Arg Pro Asn Ile Leu Ile Pro Gly Thr Leu Glu Ser Gly Cys
130 135 140

Phe Gln Asn Leu Thr Cys Ser Val Pro Trp Ala Cys Glu Gln Gly Thr
145 150 155 160

Pro Pro Met Ile Ser Trp Met Gly Thr Ser Val Ser Pro Leu His Pro
165 170 175

Ser Thr Thr Arg Ser Ser Val Leu Thr Leu Ile Pro Gln Pro Gln His
180 185 190

His Gly Thr Ser Leu Thr Cys Gln Val Thr Leu Pro Gly Ala Gly Val
195 200 205

Thr Thr Asn Arg Thr Ile Gln Leu Asn Val Ser Tyr Pro Pro Gln Asn
210 215 220

Leu Thr Val Thr Val Phe Gln Gly Glu Gly Thr Ala Ser Thr Ala Leu
225 230 235 240

Gly Asn Ser Ser Ser Leu Ser Val Leu Glu Gly Gln Ser Leu Arg Leu
245 250 255

-continued

```
Val Cys Ala Val Asp Ser Asn Pro Pro Ala Arg Leu Ser Trp Thr Trp
            260                 265                 270

Arg Ser Leu Thr Leu Tyr Pro Ser Gln Pro Ser Asn Pro Leu Val Leu
        275                 280                 285

Glu Leu Gln Val His Leu Gly Asp Glu Gly Glu Phe Thr Cys Arg Ala
    290                 295                 300

Gln Asn Ser Leu Gly Ser Gln His Val Ser Leu Asn Leu Ser Leu Gln
305                 310                 315                 320

Gln Glu Tyr Thr Gly Lys Met Arg Pro Val Ser Gly Val Leu Leu Gly
                325                 330                 335

Ala Val Gly Glu Pro Arg Gly Pro Thr Ile Lys Pro Cys Pro Pro Cys
            340                 345                 350

Lys Cys Pro Ala Pro Asn Leu Leu Gly Gly Pro Ser Val Phe Ile Phe
        355                 360                 365

Pro Pro Lys Ile Lys Asp Val Leu Met Ile Ser Leu Ser Pro Ile Val
    370                 375                 380

Thr Cys Val Val Val Asp Val Ser Glu Asp Asp Pro Asp Val Gln Ile
385                 390                 395                 400

Ser Trp Phe Val Asn Asn Val Glu Val His Thr Ala Gln Thr Gln Thr
                405                 410                 415

His Arg Glu Asp Tyr Asn Ser Thr Leu Arg Val Val Ser Ala Leu Pro
            420                 425                 430

Ile Gln His Gln Asp Trp Met Ser Gly Lys Glu Phe Lys Cys Lys Val
        435                 440                 445

Asn Asn Lys Asp Leu Pro Ala Pro Ile Glu Arg Thr Ile Ser Lys Pro
    450                 455                 460

Lys Gly Ser Val Arg Ala Pro Gln Val Tyr Val Leu Pro Pro Pro Glu
465                 470                 475                 480

Glu Glu Met Thr Lys Lys Gln Val Thr Leu Thr Cys Met Val Thr Asp
                485                 490                 495

Phe Met Pro Glu Asp Ile Tyr Val Glu Trp Thr Asn Asn Gly Lys Thr
            500                 505                 510

Glu Leu Asn Tyr Lys Asn Thr Glu Pro Val Leu Asp Ser Asp Gly Ser
        515                 520                 525

Tyr Phe Met Tyr Ser Lys Leu Arg Val Glu Lys Lys Asn Trp Val Glu
    530                 535                 540

Arg Asn Ser Tyr Ser Cys Ser Val Val His Glu Gly Leu His Asn His
545                 550                 555                 560

His Thr Thr Lys Ser Phe Ser Arg Thr Pro Gly Lys Gly Gly Gly Gly
                565                 570                 575

Ser Gly Gly Gly Gly Ser Gly Gly Gly Gly Ser Gln Lys Ser Asn Arg
            580                 585                 590

Lys Asp Tyr Ser Leu Thr Met Gln Ser Ser Val Thr Val Gln Glu Gly
        595                 600                 605

Met Cys Val His Val Arg Cys Ser Phe Ser Tyr Pro Val Asp Ser Gln
    610                 615                 620

Thr Asp Ser Asp Pro Val His Gly Tyr Trp Phe Arg Ala Gly Asn Asp
625                 630                 635                 640

Ile Ser Trp Lys Ala Pro Val Ala Thr Asn Asn Pro Ala Trp Ala Val
                645                 650                 655

Gln Glu Glu Thr Arg Asp Arg Phe His Leu Leu Gly Asp Pro Gln Thr
            660                 665                 670

Lys Asn Cys Thr Leu Ser Ile Arg Asp Ala Arg Met Ser Asp Ala Gly
```

675                 680                 685

Arg Tyr Phe Phe Arg Met Glu Lys Gly Asn Ile Lys Trp Asn Tyr Lys
    690                 695                 700

Tyr Asp Gln Leu Ser Val Asn Val Thr Ala Leu Thr His Arg Pro Asn
705                 710                 715                 720

Ile Leu Ile Pro Gly Thr Leu Glu Ser Gly Cys Phe Gln Asn Leu Thr
                725                 730                 735

Cys Ser Val Pro Trp Ala Cys Glu Gln Gly Thr Pro Pro Met Ile Ser
            740                 745                 750

Trp Met Gly Thr Ser Val Ser Pro Leu His Pro Ser Thr Thr Arg Ser
        755                 760                 765

Ser Val Leu Thr Leu Ile Pro Gln Pro Gln His His Gly Thr Ser Leu
    770                 775                 780

Thr Cys Gln Val Thr Leu Pro Gly Ala Gly Val Thr Thr Asn Arg Thr
785                 790                 795                 800

Ile Gln Leu Asn Val Ser Tyr Pro Pro Gln Asn Leu Thr Val Thr Val
                805                 810                 815

Phe Gln Gly Glu Gly Thr Ala Ser Thr Ala Leu Gly Asn Ser Ser Ser
            820                 825                 830

Leu Ser Val Leu Glu Gly Gln Ser Leu Arg Leu Val Cys Ala Val Asp
        835                 840                 845

Ser Asn Pro Pro Ala Arg Leu Ser Trp Thr Trp Arg Ser Leu Thr Leu
    850                 855                 860

Tyr Pro Ser Gln Pro Ser Asn Pro Leu Val Leu Glu Leu Gln Val His
865                 870                 875                 880

Leu Gly Asp Glu Gly Glu Phe Thr Cys Arg Ala Gln Asn Ser Leu Gly
                885                 890                 895

Ser Gln His Val Ser Leu Asn Leu Ser Leu Gln Gln Glu Tyr Thr Gly
            900                 905                 910

Lys Met Arg Pro Val Ser Gly Val Leu Leu Gly Ala Val Gly
        915                 920                 925

<210> SEQ ID NO 12
<211> LENGTH: 910
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30

Trp Ile Tyr Pro Gly Pro Val Val His Gly Tyr Trp Phe Arg Glu Gly
        35                  40                  45

Ala Asn Thr Asp Gln Asp Ala Pro Val Ala Thr Asn Asn Pro Ala Arg
    50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

-continued

```
Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
    130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro Pro Gln Asn Leu Thr Met
    210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
                245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
        275                 280                 285

Glu Leu Pro Trp Val His Leu Arg Asp Ala Ala Glu Phe Thr Cys Arg
    290                 295                 300

Ala Gln Asn Pro Leu Gly Ser Gln Gln Val Tyr Leu Asn Val Ser Leu
305                 310                 315                 320

Gln Ser Lys Ala Thr Ser Gly Val Thr Gln Gly Glu Pro Arg Gly Pro
                325                 330                 335

Thr Ile Lys Pro Cys Pro Pro Cys Lys Cys Pro Ala Pro Asn Leu Leu
            340                 345                 350

Gly Gly Pro Ser Val Phe Ile Phe Pro Pro Lys Ile Lys Asp Val Leu
        355                 360                 365

Met Ile Ser Leu Ser Pro Ile Val Thr Cys Val Val Val Asp Val Ser
    370                 375                 380

Glu Asp Asp Pro Asp Val Gln Ile Ser Trp Phe Val Asn Asn Val Glu
385                 390                 395                 400

Val His Thr Ala Gln Thr Gln Thr His Arg Glu Asp Tyr Asn Ser Thr
                405                 410                 415

Leu Arg Val Val Ser Ala Leu Pro Ile Gln His Gln Asp Trp Met Ser
            420                 425                 430

Gly Lys Glu Phe Lys Cys Lys Val Asn Asn Lys Asp Leu Pro Ala Pro
        435                 440                 445

Ile Glu Arg Thr Ile Ser Lys Pro Lys Gly Ser Val Arg Ala Pro Gln
    450                 455                 460

Val Tyr Val Leu Pro Pro Pro Glu Glu Glu Met Thr Lys Lys Gln Val
465                 470                 475                 480

Thr Leu Thr Cys Met Val Thr Asp Phe Met Pro Glu Asp Ile Tyr Val
                485                 490                 495

Glu Trp Thr Asn Asn Gly Lys Thr Glu Leu Asn Tyr Lys Asn Thr Glu
            500                 505                 510

Pro Val Leu Asp Ser Asp Gly Ser Tyr Phe Met Tyr Ser Lys Leu Arg
        515                 520                 525

Val Glu Lys Lys Asn Trp Val Glu Arg Asn Ser Tyr Ser Cys Ser Val
```

-continued

```
    530                 535                 540

Val His Glu Gly Leu His Asn His His Thr Thr Lys Ser Phe Ser Arg
545                 550                 555                 560

Thr Pro Gly Lys Gly Gly Gly Gly Ser Gly Gly Gly Gly Ser Gly Gly
                565                 570                 575

Gly Gly Ser Gln Thr Ser Lys Leu Leu Thr Met Gln Ser Ser Val Thr
            580                 585                 590

Val Gln Glu Gly Leu Cys Val His Val Pro Cys Ser Phe Ser Tyr Pro
        595                 600                 605

Ser His Gly Trp Ile Tyr Pro Gly Pro Val Val His Gly Tyr Trp Phe
    610                 615                 620

Arg Glu Gly Ala Asn Thr Asp Gln Asp Ala Pro Val Ala Thr Asn Asn
625                 630                 635                 640

Pro Ala Arg Ala Val Trp Glu Glu Thr Arg Asp Arg Phe His Leu Leu
                645                 650                 655

Gly Asp Pro His Thr Lys Asn Cys Thr Leu Ser Ile Arg Asp Ala Arg
            660                 665                 670

Arg Ser Asp Ala Gly Arg Tyr Phe Phe Arg Met Glu Lys Gly Ser Ile
        675                 680                 685

Lys Trp Asn Tyr Lys His His Arg Leu Ser Val Asn Val Thr Ala Leu
    690                 695                 700

Thr His Arg Pro Asn Ile Leu Ile Pro Gly Thr Leu Glu Ser Gly Cys
705                 710                 715                 720

Pro Gln Asn Leu Thr Cys Ser Val Pro Trp Ala Cys Glu Gln Gly Thr
                725                 730                 735

Pro Pro Met Ile Ser Trp Ile Gly Thr Ser Val Ser Pro Leu Asp Pro
            740                 745                 750

Ser Thr Thr Arg Ser Ser Val Leu Thr Leu Ile Pro Gln Pro Gln Asp
        755                 760                 765

His Gly Thr Ser Leu Thr Cys Gln Val Thr Phe Pro Gly Ala Ser Val
    770                 775                 780

Thr Thr Asn Lys Thr Val His Leu Asn Val Ser Tyr Pro Pro Gln Asn
785                 790                 795                 800

Leu Thr Met Thr Val Phe Gln Gly Asp Gly Thr Val Ser Thr Val Leu
                805                 810                 815

Gly Asn Gly Ser Ser Leu Ser Leu Pro Glu Gly Gln Ser Leu Arg Leu
            820                 825                 830

Val Cys Ala Val Asp Ala Val Asp Ser Asn Pro Pro Ala Arg Leu Ser
        835                 840                 845

Leu Ser Trp Arg Gly Leu Thr Leu Cys Pro Ser Gln Pro Ser Asn Pro
    850                 855                 860

Gly Val Leu Glu Leu Pro Trp Val His Leu Arg Asp Ala Ala Glu Phe
865                 870                 875                 880

Thr Cys Arg Ala Gln Asn Pro Leu Gly Ser Gln Gln Val Tyr Leu Asn
                885                 890                 895

Val Ser Leu Gln Ser Lys Ala Thr Ser Gly Val Thr Gln Gly
            900                 905                 910
```

<210> SEQ ID NO 13
<211> LENGTH: 339
<212> TYPE: PRT
<213> ORGANISM: Homo sapiens

<400> SEQUENCE: 13

-continued

```
Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
            20                  25                  30

Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Ala Leu
        115                 120                 125

Thr His Arg Pro Asn Ile Leu Ile Pro Gly Thr Leu Glu Ser Gly Cys
    130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
        195                 200                 205

Thr Thr Asn Arg Thr Ile Gln Leu Asn Val Ser Tyr Pro Pro Gln Asn
    210                 215                 220

Leu Thr Val Thr Val Phe Gln Gly Glu Gly Thr Ala Ser Thr Ala Leu
225                 230                 235                 240

Gly Asn Ser Ser Ser Leu Ser Val Leu Glu Gly Gln Ser Leu Arg Leu
                245                 250                 255

Val Cys Ala Val Asp Ser Asn Pro Pro Ala Arg Leu Ser Trp Thr Trp
            260                 265                 270

Arg Ser Leu Thr Leu Tyr Pro Ser Gln Pro Ser Asn Pro Leu Val Leu
        275                 280                 285

Glu Leu Gln Val His Leu Gly Asp Glu Gly Glu Phe Thr Cys Arg Ala
    290                 295                 300

Gln Asn Ser Leu Gly Ser Gln His Val Ser Leu Asn Leu Ser Leu Gln
305                 310                 315                 320

Gln Glu Tyr Thr Gly Lys Met Arg Pro Val Ser Gly Val Leu Leu Gly
                325                 330                 335

Ala Val Gly


<210> SEQ ID NO 14
<211> LENGTH: 331
<212> TYPE: PRT
<213> ORGANISM: Homo sapiens

<400> SEQUENCE: 14

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30
```

```
Trp Ile Tyr Pro Gly Pro Val Val His Gly Tyr Trp Phe Arg Glu Gly
        35                  40                  45

Ala Asn Thr Asp Gln Asp Ala Pro Val Ala Thr Asn Asn Pro Ala Arg
    50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
    130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro Pro Gln Asn Leu Thr Met
    210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
                245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
        275                 280                 285

Glu Leu Pro Trp Val His Leu Arg Asp Ala Ala Glu Phe Thr Cys Arg
    290                 295                 300

Ala Gln Asn Pro Leu Gly Ser Gln Gln Val Tyr Leu Asn Val Ser Leu
305                 310                 315                 320

Gln Ser Lys Ala Thr Ser Gly Val Thr Gln Gly
                325                 330
```

<210> SEQ ID NO 15
<211> LENGTH: 1709
<212> TYPE: PRT
<213> ORGANISM: Homo sapiens

<400> SEQUENCE: 15

```
Met Gly Phe Leu Pro Lys Leu Leu Leu Leu Ala Ser Phe Phe Pro Ala
1               5                   10                  15

Gly Gln Ala Ser Trp Gly Val Ser Ser Pro Gln Asp Val Gln Gly Val
            20                  25                  30

Lys Gly Ser Cys Leu Leu Ile Pro Cys Ile Phe Ser Phe Pro Ala Asp
        35                  40                  45

Val Glu Val Pro Asp Gly Ile Thr Ala Ile Trp Tyr Tyr Asp Tyr Ser
    50                  55                  60

Gly Gln Arg Gln Val Val Ser His Ser Ala Asp Pro Lys Leu Val Glu
65                  70                  75                  80
```

```
Ala Arg Phe Arg Gly Arg Thr Glu Phe Met Gly Asn Pro Glu His Arg
                85                  90                  95

Val Cys Asn Leu Leu Leu Lys Asp Leu Gln Pro Glu Asp Ser Gly Ser
            100                 105                 110

Tyr Asn Phe Arg Phe Glu Ile Ser Glu Val Asn Arg Trp Ser Asp Val
        115                 120                 125

Lys Gly Thr Leu Val Thr Val Thr Glu Glu Pro Arg Val Pro Thr Ile
    130                 135                 140

Ala Ser Pro Val Glu Leu Leu Glu Gly Thr Glu Val Asp Phe Asn Cys
145                 150                 155                 160

Ser Thr Pro Tyr Val Cys Leu Gln Glu Gln Val Arg Leu Gln Trp Gln
                165                 170                 175

Gly Gln Asp Pro Ala Arg Ser Val Thr Phe Asn Ser Gln Lys Phe Glu
            180                 185                 190

Pro Thr Gly Val Gly His Leu Glu Thr Leu His Met Ala Met Ser Trp
        195                 200                 205

Gln Asp His Gly Arg Ile Leu Arg Cys Gln Leu Ser Val Ala Asn His
    210                 215                 220

Arg Ala Gln Ser Glu Ile His Leu Gln Val Lys Tyr Ala Pro Lys Gly
225                 230                 235                 240

Val Lys Ile Leu Leu Ser Pro Ser Gly Arg Asn Ile Leu Pro Gly Glu
                245                 250                 255

Leu Val Thr Leu Thr Cys Gln Val Asn Ser Ser Tyr Pro Ala Val Ser
            260                 265                 270

Ser Ile Lys Trp Leu Lys Asp Gly Val Arg Leu Gln Thr Lys Thr Gly
        275                 280                 285

Val Leu His Leu Pro Gln Ala Ala Trp Ser Asp Ala Gly Val Tyr Thr
    290                 295                 300

Cys Gln Ala Glu Asn Gly Val Gly Ser Leu Val Ser Pro Pro Ile Ser
305                 310                 315                 320

Leu His Ile Phe Met Ala Glu Val Gln Val Ser Pro Ala Gly Pro Ile
                325                 330                 335

Leu Glu Asn Gln Thr Val Thr Leu Val Cys Asn Thr Pro Asn Glu Ala
            340                 345                 350

Pro Ser Asp Leu Arg Tyr Ser Trp Tyr Lys Asn His Val Leu Leu Glu
        355                 360                 365

Asp Ala His Ser His Thr Leu Arg Leu His Leu Ala Thr Arg Ala Asp
    370                 375                 380

Thr Gly Phe Tyr Phe Cys Glu Val Gln Asn Val His Gly Ser Glu Arg
385                 390                 395                 400

Ser Gly Pro Val Ser Val Val Val Asn His Pro Pro Leu Thr Pro Val
                405                 410                 415

Leu Thr Ala Phe Leu Glu Thr Gln Ala Gly Leu Val Gly Ile Leu His
            420                 425                 430

Cys Ser Val Val Ser Glu Pro Leu Ala Thr Leu Val Leu Ser His Gly
        435                 440                 445

Gly His Ile Leu Ala Ser Thr Ser Gly Asp Ser Asp His Ser Pro Arg
    450                 455                 460

Phe Ser Gly Thr Ser Gly Pro Asn Ser Leu Arg Leu Glu Ile Arg Asp
465                 470                 475                 480

Leu Glu Glu Thr Asp Ser Gly Glu Tyr Lys Cys Ser Ala Thr Asn Ser
                485                 490                 495
```

-continued

```
Leu Gly Asn Ala Thr Ser Thr Leu Asp Phe His Ala Asn Ala Ala Arg
            500                 505                 510

Leu Leu Ile Ser Pro Ala Ala Glu Val Val Glu Gly Gln Ala Val Thr
        515                 520                 525

Leu Ser Cys Arg Ser Gly Leu Ser Pro Thr Pro Asp Ala Arg Phe Ser
    530                 535                 540

Trp Tyr Leu Asn Gly Ala Leu Leu His Glu Gly Pro Gly Ser Ser Leu
545                 550                 555                 560

Leu Leu Pro Ala Ala Ser Ser Thr Asp Ala Gly Ser Tyr His Cys Arg
                565                 570                 575

Ala Arg Asp Gly His Ser Ala Ser Gly Pro Ser Ser Pro Ala Val Leu
            580                 585                 590

Thr Val Leu Tyr Pro Pro Arg Gln Pro Thr Phe Thr Thr Arg Leu Asp
        595                 600                 605

Leu Asp Ala Ala Gly Ala Gly Ala Gly Arg Arg Gly Leu Leu Leu Cys
    610                 615                 620

Arg Val Asp Ser Asp Pro Pro Ala Arg Leu Gln Leu Leu His Lys Asp
625                 630                 635                 640

Arg Val Val Ala Thr Ser Leu Pro Ser Gly Gly Gly Cys Ser Thr Cys
                645                 650                 655

Gly Gly Cys Ser Pro Arg Met Lys Val Thr Lys Ala Pro Asn Leu Leu
            660                 665                 670

Arg Val Glu Ile His Asn Pro Leu Leu Glu Glu Glu Gly Leu Tyr Leu
        675                 680                 685

Cys Glu Ala Ser Asn Ala Leu Gly Asn Ala Ser Thr Ser Ala Thr Phe
    690                 695                 700

Asn Gly Gln Ala Thr Val Leu Ala Ile Ala Pro Ser His Thr Leu Gln
705                 710                 715                 720

Glu Gly Thr Glu Ala Asn Leu Thr Cys Asn Val Ser Arg Glu Ala Ala
                725                 730                 735

Gly Ser Pro Ala Asn Phe Ser Trp Phe Arg Asn Gly Val Leu Trp Ala
            740                 745                 750

Gln Gly Pro Leu Glu Thr Val Thr Leu Leu Pro Val Ala Arg Thr Asp
        755                 760                 765

Ala Ala Leu Tyr Ala Cys Arg Ile Leu Thr Glu Ala Gly Ala Gln Leu
    770                 775                 780

Ser Thr Pro Val Leu Leu Ser Val Leu Tyr Pro Pro Asp Arg Pro Lys
785                 790                 795                 800

Leu Ser Ala Leu Leu Asp Met Gly Gln Gly His Met Ala Leu Phe Ile
                805                 810                 815

Cys Thr Val Asp Ser Arg Pro Leu Ala Leu Leu Ala Leu Phe His Gly
            820                 825                 830

Glu His Leu Leu Ala Thr Ser Leu Gly Pro Gln Val Pro Ser His Gly
        835                 840                 845

Arg Phe Gln Ala Lys Ala Glu Ala Asn Ser Leu Lys Leu Glu Val Arg
    850                 855                 860

Glu Leu Gly Leu Gly Asp Ser Gly Ser Tyr Arg Cys Glu Ala Thr Asn
865                 870                 875                 880

Val Leu Gly Ser Ser Asn Thr Ser Leu Phe Phe Gln Val Arg Gly Ala
                885                 890                 895

Trp Val Gln Val Ser Pro Ser Pro Glu Leu Gln Glu Gly Gln Ala Val
            900                 905                 910

Val Leu Ser Cys Gln Val His Thr Gly Val Pro Glu Gly Thr Ser Tyr
```

```
        915                 920                 925

Arg Trp Tyr Arg Asp Gly Gln Pro Leu Gln Glu Ser Thr Ser Ala Thr
    930                 935                 940

Leu Arg Phe Ala Ala Ile Thr Leu Thr Gln Ala Gly Ala Tyr His Cys
945                 950                 955                 960

Gln Ala Gln Ala Pro Gly Ser Ala Thr Thr Ser Leu Ala Ala Pro Ile
                965                 970                 975

Ser Leu His Val Ser Tyr Ala Pro Arg His Val Thr Leu Thr Thr Leu
            980                 985                 990

Met Asp Thr Gly Pro Gly Arg Leu  Gly Leu Leu Leu Cys  Arg Val Asp
        995                 1000                1005

Ser Asp  Pro Pro Ala Gln Leu  Arg Leu Leu His Gly  Asp Arg Leu
    1010                1015                1020

Val Ala  Ser Thr Leu Gln Gly  Val Gly Gly Pro Glu  Gly Ser Ser
    1025                1030                1035

Pro Arg  Leu His Val Ala Val  Ala Pro Asn Thr Leu  Arg Leu Glu
    1040                1045                1050

Ile His  Gly Ala Met Leu Glu  Asp Glu Gly Val Tyr  Ile Cys Glu
    1055                1060                1065

Ala Ser  Asn Thr Leu Gly Gln  Ala Ser Ala Ser Ala  Asp Phe Asp
    1070                1075                1080

Ala Gln  Ala Val Asn Val Gln  Val Trp Pro Gly Ala  Thr Val Arg
    1085                1090                1095

Glu Gly  Gln Leu Val Asn Leu  Thr Cys Leu Val Trp  Thr Thr His
    1100                1105                1110

Pro Ala  Gln Leu Thr Tyr Thr  Trp Tyr Gln Asp Gly  Gln Gln Arg
    1115                1120                1125

Leu Asp  Ala His Ser Ile Pro  Leu Pro Asn Val Thr  Val Arg Asp
    1130                1135                1140

Ala Thr  Ser Tyr Arg Cys Gly  Val Gly Pro Pro Gly  Arg Ala Pro
    1145                1150                1155

Arg Leu  Ser Arg Pro Ile Thr  Leu Asp Val Leu Tyr  Ala Pro Arg
    1160                1165                1170

Asn Leu  Arg Leu Thr Tyr Leu  Leu Glu Ser His Gly  Gly Gln Leu
    1175                1180                1185

Ala Leu  Val Leu Cys Thr Val  Asp Ser Arg Pro Pro  Ala Gln Leu
    1190                1195                1200

Ala Leu  Ser His Ala Gly Arg  Leu Leu Ala Ser Ser  Thr Ala Ala
    1205                1210                1215

Ser Val  Pro Asn Thr Leu Arg  Leu Glu Leu Arg Gly  Pro Gln Pro
    1220                1225                1230

Arg Asp  Glu Gly Phe Tyr Ser  Cys Ser Ala Arg Ser  Pro Leu Gly
    1235                1240                1245

Gln Ala  Asn Thr Ser Leu Glu  Leu Arg Leu Glu Gly  Val Arg Val
    1250                1255                1260

Ile Leu  Ala Pro Glu Ala Ala  Val Pro Glu Gly Ala  Pro Ile Thr
    1265                1270                1275

Val Thr  Cys Ala Asp Pro Ala  Ala His Ala Pro Thr  Leu Tyr Thr
    1280                1285                1290

Trp Tyr  His Asn Gly Arg Trp  Leu Gln Glu Gly Pro  Ala Ala Ser
    1295                1300                1305

Leu Ser  Phe Leu Val Ala Thr  Arg Ala His Ala Gly  Ala Tyr Ser
    1310                1315                1320
```

-continued

```
Cys Gln Ala Gln Asp Ala Gln Gly Thr Arg Ser Ser Arg Pro Ala
    1325                1330                1335

Ala Leu Gln Val Leu Tyr Ala Pro Gln Asp Ala Val Leu Ser Ser
    1340                1345                1350

Phe Arg Asp Ser Arg Ala Arg Ser Met Ala Val Ile Gln Cys Thr
    1355                1360                1365

Val Asp Ser Glu Pro Pro Ala Glu Leu Ala Leu Ser His Asp Gly
    1370                1375                1380

Lys Val Leu Ala Thr Ser Ser Gly Val His Ser Leu Ala Ser Gly
    1385                1390                1395

Thr Gly His Val Gln Val Ala Arg Asn Ala Leu Arg Leu Gln Val
    1400                1405                1410

Gln Asp Val Pro Ala Gly Asp Asp Thr Tyr Val Cys Thr Ala Gln
    1415                1420                1425

Asn Leu Leu Gly Ser Ile Ser Thr Ile Gly Arg Leu Gln Val Glu
    1430                1435                1440

Gly Ala Arg Val Val Ala Glu Pro Gly Leu Asp Val Pro Glu Gly
    1445                1450                1455

Ala Ala Leu Asn Leu Ser Cys Arg Leu Leu Gly Gly Pro Gly Pro
    1460                1465                1470

Val Gly Asn Ser Thr Phe Ala Trp Phe Trp Asn Asp Arg Arg Leu
    1475                1480                1485

His Ala Glu Pro Val Pro Thr Leu Ala Phe Thr His Val Ala Arg
    1490                1495                1500

Ala Gln Ala Gly Met Tyr His Cys Leu Ala Glu Leu Pro Thr Gly
    1505                1510                1515

Ala Ala Ala Ser Ala Pro Val Met Leu Arg Val Leu Tyr Pro Pro
    1520                1525                1530

Lys Thr Pro Thr Met Met Val Phe Val Glu Pro Glu Gly Gly Leu
    1535                1540                1545

Arg Gly Ile Leu Asp Cys Arg Val Asp Ser Glu Pro Leu Ala Ser
    1550                1555                1560

Leu Thr Leu His Leu Gly Ser Arg Leu Val Ala Ser Ser Gln Pro
    1565                1570                1575

Gln Gly Ala Pro Ala Glu Pro His Ile His Val Leu Ala Ser Pro
    1580                1585                1590

Asn Ala Leu Arg Val Asp Ile Glu Ala Leu Arg Pro Ser Asp Gln
    1595                1600                1605

Gly Glu Tyr Ile Cys Ser Ala Ser Asn Val Leu Gly Ser Ala Ser
    1610                1615                1620

Thr Ser Thr Tyr Phe Gly Val Arg Ala Leu His Arg Leu His Gln
    1625                1630                1635

Phe Gln Gln Leu Leu Trp Val Leu Gly Leu Leu Val Gly Leu Leu
    1640                1645                1650

Leu Leu Leu Leu Gly Leu Gly Ala Cys Tyr Thr Trp Arg Arg Arg
    1655                1660                1665

Arg Val Cys Lys Gln Ser Met Gly Glu Asn Ser Val Glu Met Ala
    1670                1675                1680

Phe Gln Lys Glu Thr Thr Gln Leu Ile Asp Pro Asp Ala Ala Thr
    1685                1690                1695

Cys Glu Thr Ser Thr Cys Ala Pro Pro Leu Gly
    1700                1705
```

<210> SEQ ID NO 16
<211> LENGTH: 6736
<212> TYPE: DNA
<213> ORGANISM: Homo sapiens

<400> SEQUENCE: 16
atgggcttct tgcccaagct tctcctcctg gcctcattct tcccagcagg ccaggcctca 60
tggggcgtct ccagtcccca ggacgtgcag ggtgtgaagg ggtcttgcct gcttatcccc 120
tgcatcttca gcttccctgc cgacgtggag gtgcccgacg gcatcacggc catctggtac 180
tacgactact cgggccagcg gcaggtggtg agccactcgg cggaccccaa gctggtggag 240
gcccgcttcc gcggccgcac cgagttcatg gggaaccccg agcacagggt gtgcaacctg 300
ctgctgaagg acctgcagcc cgaggactct ggttcctaca acttccgctt cgagatcagt 360
gaggtcaacc gctggtcaga tgtgaaaggc accttggtca cagtaacaga ggagcccagg 420
gtgcccacca ttgcctcccc ggtggagctt ctcgagggca cagaggtgga cttcaactgc 480
tccactccct acgtatgcct gcaggagcag gtcagactgc agtggcaagg ccaggaccct 540
gctcgctctg tcaccttcaa cagccagaag tttgagccca ccggcgtcgg ccacctggag 600
accctccaca tggccatgtc ctggcaggac cacggccgga tcctgcgctg ccagctctcc 660
gtggccaatc acagggctca gagcgagatt cacctccaag tgaagtatgc ccccaagggt 720
gtgaagatcc tcctcagccc ctcggggagg aacatccttc caggtgagct ggtcacactc 780
acctgccagg tgaacagcag ctaccctgca gtcagttcca ttaagtggct caaggatggg 840
gtacgcctcc aaaccaagac tggtgtgctg cacctgcccc aggcagcctg gagcgatgct 900
ggcgtctaca cctgccaagc tgagaacggc gtgggctctt tggtctcacc ccccatcagc 960
ctccacatct tcatggctga ggtccaggtg agcccagcag gtcccatcct ggagaaccag 1020
acagtgacac tagtctgcaa cacacccaat gaggcaccca gtgatctccg ctacagctgg 1080
tacaagaacc atgtcctgct ggaggatgcc cactcccata ccctccggct gcacttggcc 1140
actagggctg atactggctt ctacttctgt gaggtgcaga acgtccatgg cagcgagcgc 1200
tcgggccctg tcagcgtggt agtcaaccac ccgcctctca ctccagtcct gacagccttc 1260
ctggagaccc aggcgggact tgtgggcatc cttcactgct ctgtggtcag tgagcccctg 1320
gccacactgg tgctgtcaca tgggggtcat atcctggcct ccacctccgg ggacagtgat 1380
cacagcccac gcttcagtgg tacctctggt cccaactccc tgcgcctgga gatccgagac 1440
ctggaggaaa ctgacagtgg ggagtacaag tgctcagcca ccaactccct tggaaatgca 1500
acctccaccc tggacttcca tgccaatgcc gcccgtctcc tcatcagccc ggcagccgag 1560
gtggtggaag gacaggcagt gacactgagc tgcagaagcg gcctaagccc cacacctgat 1620
gcccgcttct cctggtacct gaatggagcc ctgcttcacg agggtcccgg cagcagcctc 1680
ctgctccccg cggcctccag cactgacgcc ggctcatacc actgccgggc ccgggacggc 1740
cacagtgcca gtggcccctc ttcgccagct gttctcactg tgctctaccc ccctcgacaa 1800
ccaacattca ccaccaggct ggaccttgat gccgctgggg ccggggctgg acggcgaggc 1860
ctccttttgt gccgtgtgga cagcgacccc cccgccaggc tgcagctgct ccacaaggac 1920
cgtgttgtgg ccacttccct gccatcaggg ggtggctgca gcacctgtgg gggctgttcc 1980
ccacgcatga aggtcaccaa agcccccaac ttgctgcgtg tggagattca caaccctttg 2040
ctggaagagg agggcttgta cctctgtgag gccagcaatg ccctgggcaa cgcctccacc 2100
tcagccacct tcaatggcca ggccactgtc ctggccattg caccatcaca cacacttcag 2160

-continued

```
gagggcacag aagccaactt gacttgcaac gtgagccggg aagctgctgg cagccctgct   2220
aacttctcct ggttccgaaa tggggtgctg tgggcccagg gtcccctgga gaccgtgaca   2280
ctgctgcccg tggccagaac tgatgctgcc ctttacgcct gccgcatcct gactgaggct   2340
ggtgcccagc tctccactcc cgtgctcctg agtgtactct atcccccgga ccgtccaaag   2400
ctgtcagccc tcctagacat gggccagggc cacatggctc tgttcatctg cactgtggac   2460
agccgccccc tggccttgct ggccttgttc catggggagc acctcctggc caccagcctg   2520
ggtccccagg tcccatccca tggtcggttc caggctaaag ctgaggccaa ctccctgaag   2580
ttagaggtcc gagaactggg ccttggggac tctggcagct accgctgtga ggccacaaat   2640
gttcttggat catccaacac ctcactcttc ttccaggtcc gaggagcctg ggtccaggtg   2700
tcaccatcac ctgagctcca agagggccag gctgtggtcc tgagctgcca ggtacacaca   2760
ggagtcccag aggggacctc atatcgttgg tatcgggatg gccagcccct ccaggagtcg   2820
acctcggcca cgctccgctt tgcagccata actttgacac aagctggggc ctatcattgc   2880
caagcccagg ccccaggctc agccaccacg agcctagctg cacccatcag cctccacgtg   2940
tcctatgccc cacgccacgt cacactcact accctgatgg acacaggccc tggacgactg   3000
ggcctcctcc tgtgccgtgt ggacagtgac cctccggccc agctgcggct gctccacggg   3060
gatcgccttg tggcctccac cctacaaggt gtggggggac ccgaaggcag ctctcccagg   3120
ctgcatgtgg ctgtggcccc caacacactg cgtctggaga tccacggggc tatgctggag   3180
gatgagggtg tctatatctg tgaggcctcc aacaccctgg gccaggcctc ggcctcagct   3240
gacttcgacg ctcaagctgt gaatgtgcag gtgtggcccg gggctaccgt gcgggagggg   3300
cagctggtga acctgacctg ccttgtgtgg accactcacc cggcccagct cacctacaca   3360
tggtaccagg atgggcagca gcgcctggat gcccactcca tcccccctgcc caacgtcaca   3420
gtcagggatg ccacctccta ccgctgcggt gtgggccccc ctggtcgggc accccgcctc   3480
tccagaccta tcaccttgga cgtcctctac gcgccccgca acctgcgcct gacctacctc   3540
ctggagagcc atggcgggca gctggccctg gtactgtgca ctgtggacag ccgcccgccc   3600
gcccagctgg ccctcagcca cgccggtcgc ctcttggcct cctcgacagc agcctctgtc   3660
cccaacaccc tgcgcctgga gctgcgaggg ccacagccca gggatgaggg tttctacagc   3720
tgctctgccc gcagccctct gggccaggcc aacacgtccc tggagctgcg gctggagggt   3780
gtgcgggtga tcctggctcc ggaggctgcc gtgcctgaag gtgcccccat cacagtgacc   3840
tgtgcggacc ctgctgccca cgcacccaca ctctatactt ggtaccacaa cggtcgttgg   3900
ctgcaggagg gtccagctgc ctcactctca ttcctggtgg ccacgcgggc tcatgcaggc   3960
gcctactctt gccaggccca ggatgcccag ggcacccgca gctcccgtcc tgctgccctg   4020
caagtcctct atgcccctca ggacgctgtc ctgtcctcct tccgggactc cagggccaga   4080
tccatggctg tgatacagtg cactgtggac agtgagccac ctgctgagct ggccctatct   4140
catgatggca aggtgctggc cacgagcagc ggggtccaca gcttggcatc agggacaggc   4200
catgtccagg tggcccgaaa cgccctacgg ctgcaggtgc aagatgtgcc tgcaggtgat   4260
gacacctatg tttgcacagc ccaaaacttg ctgggctcaa tcagcaccat cgggcggttg   4320
caggtagaag gtgcacgcgt ggtggcagag cctggcctgg acgtgcctga gggcgctgcc   4380
ctgaacctca gctgccgcct cctgggtggc cctgggcctg tgggcaactc cacctttgca   4440
tggttctgga atgaccggcg gctgcacgcg gagcctgtgc ccactctcgc cttcacccac   4500
```

-continued

```
gtggctcgtg ctcaagctgg gatgtaccac tgcctggctg agctccccac tggggctgct   4560
gcctctgctc cagtcatgct ccgtgtgctc taccctccca agacgcccac catgatggtc   4620
ttcgtggagc ctgagggtgg cctccggggc atcctggatt gccgagtgga cagcgagccg   4680
ctcgccagcc tgactctcca ccttggcagt cgactggtgg cctccagtca gccccagggt   4740
gctcctgcag agccacacat ccatgtcctg gcttccccca atgccctgag ggtggacatc   4800
gaggcgctga ggcccagcga ccaaggggaa tacatctgtt ctgcctcaaa tgtcctgggc   4860
tctgcctcta cctccaccta ctttggggtc agagccctgc accgcctgca tcagttccag   4920
cagctgctct gggtcctggg actgctggtg ggcctcctgc tcctgctgtt gggcctgggg   4980
gcctgctaca cctggagaag gaggcgtgtt tgtaagcaga gcatgggcga gaattcggtg   5040
gagatggctt ttcagaaaga gaccacgcag ctcattgatc ctgatgcagc cacatgtgag   5100
acctcaacct gtgccccacc cctgggctga ccagtggtgt tgcctgccct ccggaggaga   5160
aagtggccag aatctgtgat gactccagcc tatgaatgtg aatgaggcag tgttgagtcc   5220
tgcccgcctc tacgaaaaca gctctgtgac atctgacttt ttatgacctg gccccaagcc   5280
tcttgccccc ccaaaaatgg gtggtgagag gtctgcccag gagggtgttg accctggagg   5340
acactgaaga gcactgagct gatctcgctc tctcttctct ggatctcctc ccttctctcc   5400
atttctccct caaaggaagc cctgcccttt cacatccttc tcctcgaaag tcaccctgga   5460
ctttggttgg attgcagcat cctgcatcct cagaggctca ccaaggcatt ctgtattcaa   5520
cagagtatca gtcagcctgc tctaacaaga gaccaaatac agtgacttca acatgataga   5580
attttatttt tctctcccac gctagtctgg ctgttacgat ggtttatgat gttggggctc   5640
aggatccttc tatcttcctt ttctctatcc ctaaaatgat gcctttgatt gtgaggctca   5700
ccatggcccc gctttgtcca catgccctcc agccagaaga aggaagagtg gaggtagaag   5760
cacacccatg cccatggtgg acgcaactca gaagctgcac aggacttttc cactcacttc   5820
ccattggctg gagtattgtc acatggctac tgcaagctac aagggagact gggaaatgta   5880
gtttttattt tgagtccaga ggacatttgg aattggactt ccaaaggact cccaactgtg   5940
agctcatccc tgagactttt gacattgttg ggaatgccac cagcaggcca tgtttttgtct   6000
cagtgcccat ctactgaggg ccagggtgtg cccctggcca ttctggttgt gggcttcctg   6060
gaagaggtga tcactctcac actaagactg aggaaataaa aaaggtttgg tgttttccta   6120
gggagagagc atgccaggca gtggagttgc ctaagcagac atccttgtgc cagatttggc   6180
ccctgaaaga agagatgccc tcattcccac caccaccccc cctaccccca gggactgggt   6240
actaccttac tggcccttac aagagtggag ggcagacaca gatgttgtca gcatccttat   6300
tcctgctcca gatgcatctc tgttcatgac tgtgtgagct cctgtccttt tcctggagac   6360
cctgtgtcgg gctgttaaag agaatgagtt accaagaagg aatgacgtgc ccctgcgaat   6420
cagggaccaa caggagagag ctcttgagtg ggctagtgac tccccctgca gcctggtgga   6480
gatggtgtga ggagcgaaga gccctctgct ctaggatttg ggttgaaaaa cagagagaga   6540
agtggggagt tgccacagga gctaacacgc tgggaggcag ttgggggcgg gtgaactttg   6600
tgtagccgag gccgcaccct ccctcattcc aggctcattc attttcatgc tccattgcca   6660
gactcttgct gggagcccgt ccagaatgtc ctcccaataa aactccatcc tatgacgcaa   6720
aaaaaaaaaa aaaaaa                                                   6736
```

<210> SEQ ID NO 17
<211> LENGTH: 847

```
<212> TYPE: PRT
<213> ORGANISM: Homo sapiens

<400> SEQUENCE: 17

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
    370                 375                 380

Lys Ile Leu Pro Trp His Ala Gly Thr Tyr Ser Cys Val Ala Glu Asn
385                 390                 395                 400
```

-continued

```
Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
    530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
        595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815
```

```
Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845


<210> SEQ ID NO 18
<211> LENGTH: 2544
<212> TYPE: DNA
<213> ORGANISM: Homo sapiens

<400> SEQUENCE: 18

atgcatctcc tcggcccctg gctcctgctc ctggttctag aatacttggc tttctctgac     60

tcaagtaaat gggtttttga gcaccctgaa accctctacg cctgggaggg ggcctgcgtc    120

tggatcccct gcacctacag agccctagat ggtgacctgg aaagcttcat cctgttccac    180

aatcctgagt ataacaagaa cacctcgaag tttgatggga caagactcta tgaaagcaca    240

aaggatggga aggttccttc tgagcagaaa agggtgcaat tcctgggaga caagaataag    300

aactgcacac tgagtatcca cccggtgcac ctcaatgaca gtggtcagct ggggctgagg    360

atggagtcca agactgagaa atggatggaa cgaatacacc tcaatgtctc tgaaaggcct    420

tttccacctc atatccagct ccctccagaa attcaagagt cccaggaagt cactctgacc    480

tgcttgctga atttctcctg ctatgggtat ccgatccaat tgcagtggct cctagagggg    540

gttccaatga ggcaggctgc tgtcacctcg acctccttga ccatcaagtc tgtcttcacc    600

cggagcgagc tcaagttctc cccacagtgg agtcaccatg ggaagattgt gacctgccag    660

cttcaggatg cagatgggaa gttcctctcc aatgacacgg tgcagctgaa cgtgaagcac    720

accccgaagt tggagatcaa ggtcactccc agtgatgcca tagtgaggga gggggactct    780

gtgaccatga cctgcgaggt cagcagcagc aacccggagt acacgacggt atcctggctc    840

aaggatggga cctcgctgaa gaagcagaat acattcacgc taaacctgcg cgaagtgacc    900

aaggaccaga gtgggaagta ctgctgtcag gtctccaatg acgtgggccc gggaaggtcg    960

gaagaagtgt tcctgcaagt gcagtatgcc ccggaacctt ccacggttca gatcctccac   1020

tcaccggctg tggagggaag tcaagtcgag tttctttgca tgtcactggc caatcctctt   1080

ccaacaaatt acacgtggta ccacaatggg aaagaaatgc agggaaggac agaggagaaa   1140

gtccacatcc caaagatcct cccctggcac gctgggactt attcctgtgt ggcagaaaac   1200

attcttggta ctggacagag gggcccggga gctgagctgg atgtccagta tcctcccaag   1260

aaggtgacca cagtgattca aaaccccatg ccgattcgag aaggagacac agtgaccctt   1320

tcctgtaact acaattccag taaccccagt gttacccggt atgaatggaa accccatggc   1380

gcctgggagg agccatcgct tggggtgctg aagatccaaa acgttggctg ggacaacaca   1440

accatcgcct gcgcagcttg taatagttgg tgctcgtggg cctcccctgt cgccctgaat   1500

gtccagtatg ccccccgaga cgtgagggtc cggaaaatca agcccctttc cgagattcac   1560

tctggaaact cggtcagcct ccaatgtgac ttctcaagca gccaccccaa agaagtccag   1620

ttcttctggg agaaaaatgg caggcttctg gggaaagaaa gccagctgaa ttttgactcc   1680

atctccccag aagatgctgg gagttacagc tgctgggtga acaactccat aggacagaca   1740

gcgtccaagg cctggacact tgaagtgctg tatgcaccca ggaggctgcg tgtgtccatg   1800

agcccggggg accaagtgat ggaggggaag agtgcaaccc tgacctgtga gagcgacgcc   1860

aaccctcccg tctcccacta cacctggttt gactggaata accaaagcct cccctaccac   1920

agccagaagc tgagattgga gccggtgaag gtccagcact cgggtgccta ctggtgccag   1980
```

```
gggaccaaca gtgtgggcaa gggccgttcg cctctcagca ccctcaccgt ctactatagc   2040

ccggagacca tcggcaggcg agtggctgtg ggactcgggt cctgcctcgc catcctcatc   2100

ctggcaatct gtgggctcaa gctccagcga cgttggaaga ggacacagag ccagcagggg   2160

cttcaggaga attccagcgg ccagagcttc tttgtgagga ataaaaaggt tagaagggcc   2220

cccctctctg aaggccccca ctccctggga tgctacaatc caatgatgga agatggcatt   2280

agctacacca ccctgcgctt tcccgagatg aacataccac gaactggaga tgcagagtcc   2340

tcagagatgc agagacctcc cccggactgc gatgacacgg tcacttattc agcattgcac   2400

aagcgccaag tgggcgacta tgagaacgtc attccagatt ttccagaaga tgaggggatt   2460

cattactcag agctgatcca gtttggggtc ggggagcggc ctcaggcaca agaaaatgtg   2520

gactatgtga tcctcaaaca ttga                                          2544


<210> SEQ ID NO 19
<211> LENGTH: 364
<212> TYPE: PRT
<213> ORGANISM: Homo sapiens

<400> SEQUENCE: 19

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270
```

-continued

```
Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360
```

<210> SEQ ID NO 20
<211> LENGTH: 1466
<212> TYPE: DNA
<213> ORGANISM: Homo sapiens

<400> SEQUENCE: 20

```
tctgctcaca caggaagccc tggaagctgc ttcctcagac atgccgctgc tgctactgct     60

gcccctgctg tgggcagggg ccctggctat ggatccaaat ttctggctgc aagtgcagga    120

gtcagtgacg gtacaggagg gtttgtgcgt cctcgtgccc tgcactttct tccatcccat    180

accctactac gacaagaact ccccagttca tggttactgg ttccgggaag gagccattat    240

atccagggac tctccagtgg ccacaaacaa gctagatcaa gaagtacagg aggagactca    300

gggcagattc cgcctccttg gggatcccag taggaacaac tgctccctga gcatcgtaga    360

cgccaggagg agggataatg gttcatactt ctttcggatg gagagaggaa gtaccaaata    420

cagttacaaa tctccccagc tctctgtgca tgtgacagac ttgacccaca ggcccaaaat    480

cctcatccct ggcactctag aacccggcca ctccaaaaac ctgacctgct ctgtgtcctg    540

ggcctgtgag cagggaacac ccccgatctt ctcctggttg tcagctgccc ccacctccct    600

gggccccagg actactcact cctcggtgct cataatcacc ccacggcccc aggaccacgg    660

caccaacctg acctgtcagg tgaagttcgc tggagctggt gtgactacgg agagaaccat    720

ccagctcaac gtcacctatg ttccacagaa cccaacaact ggtatctttc caggagatgg    780

ctcagggaaa caagagacca gagcaggagt ggttcatggg gccattggag gagctggtgt    840

tacagccctg ctcgctcttt gtctctgcct catcttcttc atagtgaaga cccacaggag    900

gaaagcagcc aggacagcag tgggcaggaa tgacacccac cctaccacag ggtcagcctc    960

cccgaaacac cagaagaagt ccaagttaca tggccccact gaaacctcaa gctgttcagg   1020

tgccgcccct actgtggaga tggatgagga gctgcattat gcttccctca actttcatgg   1080

gatgaatcct tccaaggaca cctccaccga atactcagag gtcaggaccc agtgaggaac   1140

ccacaagagc atcaggctca gctagaagat ccacatcctc tacaggtcgg ggaccaaagg   1200

ctgattcttg gagatttaac accccacagg caatgggttt atagacatta tgtgagtttc   1260

ctgctatatt aacatcatct tagactttgc aagcagagag tcgtggaatc aaatctgtgc   1320

tctttcattt gctaagtgta tgatgtcaca caagctcctt aaccttccat gtctccattt   1380

tcttctctgt gaagtaggta taagaagtcc tatctcatag ggatgctgtg agcattaaat   1440

aaaggtacac atggaaaaca ccagtc                                        1466
```

<210> SEQ ID NO 21

<211> LENGTH: 626
<212> TYPE: PRT
<213> ORGANISM: Homo sapiens

<400> SEQUENCE: 21

```
Met Ile Phe Leu Thr Ala Leu Pro Leu Phe Trp Ile Met Ile Ser Ala
1               5                   10                  15

Ser Arg Gly Gly His Trp Gly Ala Trp Met Pro Ser Ser Ile Ser Ala
            20                  25                  30

Phe Glu Gly Thr Cys Val Ser Ile Pro Cys Arg Phe Asp Phe Pro Asp
        35                  40                  45

Glu Leu Arg Pro Ala Val Val His Gly Val Trp Tyr Phe Asn Ser Pro
    50                  55                  60

Tyr Pro Lys Asn Tyr Pro Pro Val Val Phe Lys Ser Arg Thr Gln Val
65                  70                  75                  80

Val His Glu Ser Phe Gln Gly Arg Ser Arg Leu Leu Gly Asp Leu Gly
                85                  90                  95

Leu Arg Asn Cys Thr Leu Leu Leu Ser Asn Val Ser Pro Glu Leu Gly
            100                 105                 110

Gly Lys Tyr Tyr Phe Arg Gly Asp Leu Gly Gly Tyr Asn Gln Tyr Thr
        115                 120                 125

Phe Ser Glu His Ser Val Leu Asp Ile Val Asn Thr Pro Asn Ile Val
    130                 135                 140

Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
                165                 170                 175

His Glu Gly Leu Gly Glu Pro Ala Val Leu Gly Arg Leu Arg Glu Asp
            180                 185                 190

Glu Gly Thr Trp Val Gln Val Ser Leu Leu His Phe Val Pro Thr Arg
        195                 200                 205

Glu Ala Asn Gly His Arg Leu Gly Cys Gln Ala Ser Phe Pro Asn Thr
    210                 215                 220

Thr Leu Gln Phe Glu Gly Tyr Ala Ser Met Asp Val Lys Tyr Pro Pro
225                 230                 235                 240

Val Ile Val Glu Met Asn Ser Ser Val Glu Ala Ile Glu Gly Ser His
                245                 250                 255

Val Ser Leu Leu Cys Gly Ala Asp Ser Asn Pro Pro Pro Leu Leu Thr
            260                 265                 270

Trp Met Arg Asp Gly Thr Val Leu Arg Glu Ala Val Ala Glu Ser Leu
        275                 280                 285

Leu Leu Glu Leu Glu Glu Val Thr Pro Ala Glu Asp Gly Val Tyr Ala
    290                 295                 300

Cys Leu Ala Glu Asn Ala Tyr Gly Gln Asp Asn Arg Thr Val Gly Leu
305                 310                 315                 320

Ser Val Met Tyr Ala Pro Trp Lys Pro Thr Val Asn Gly Thr Met Val
                325                 330                 335

Ala Val Glu Gly Glu Thr Val Ser Ile Leu Cys Ser Thr Gln Ser Asn
            340                 345                 350

Pro Asp Pro Ile Leu Thr Ile Phe Lys Glu Lys Gln Ile Leu Ser Thr
        355                 360                 365

Val Ile Tyr Glu Ser Glu Leu Gln Leu Glu Leu Pro Ala Val Ser Pro
    370                 375                 380

Glu Asp Asp Gly Glu Tyr Trp Cys Val Ala Glu Asn Gln Tyr Gly Gln
```

-continued

```
385                 390                 395                 400

Arg Ala Thr Ala Phe Asn Leu Ser Val Glu Phe Ala Pro Val Leu Leu
                405                 410                 415

Leu Glu Ser His Cys Ala Ala Ala Arg Asp Thr Val Gln Cys Leu Cys
            420                 425                 430

Val Val Lys Ser Asn Pro Glu Pro Ser Val Ala Phe Glu Leu Pro Ser
        435                 440                 445

Arg Asn Val Thr Val Asn Glu Ser Glu Arg Glu Phe Val Tyr Ser Glu
    450                 455                 460

Arg Ser Gly Leu Val Leu Thr Ser Ile Leu Thr Leu Arg Gly Gln Ala
465                 470                 475                 480

Gln Ala Pro Pro Arg Val Ile Cys Thr Ala Arg Asn Leu Tyr Gly Ala
                485                 490                 495

Lys Ser Leu Glu Leu Pro Phe Gln Gly Ala His Arg Leu Met Trp Ala
            500                 505                 510

Lys Ile Gly Pro Val Gly Ala Val Val Ala Phe Ala Ile Leu Ile Ala
        515                 520                 525

Ile Val Cys Tyr Ile Thr Gln Thr Arg Arg Lys Lys Asn Val Thr Glu
    530                 535                 540

Ser Pro Ser Phe Ser Ala Gly Asp Asn Pro Pro Val Leu Phe Ser Ser
545                 550                 555                 560

Asp Phe Arg Ile Ser Gly Ala Pro Glu Lys Tyr Glu Ser Glu Arg Arg
                565                 570                 575

Leu Gly Ser Glu Arg Arg Leu Leu Gly Leu Arg Gly Glu Pro Pro Glu
            580                 585                 590

Leu Asp Leu Ser Tyr Ser His Ser Asp Leu Gly Lys Arg Pro Thr Lys
        595                 600                 605

Asp Ser Tyr Thr Leu Thr Glu Glu Leu Ala Glu Tyr Ala Glu Ile Arg
    610                 615                 620

Val Lys
625


<210> SEQ ID NO 22
<211> LENGTH: 1881
<212> TYPE: DNA
<213> ORGANISM: Homo sapiens

<400> SEQUENCE: 22

atgatattcc tcacggcact gcctctgttc tggattatga tttcagcctc ccgagggggt      60

cactggggtg cctggatgcc ctcgtccatc tcggccttcg aaggcacgtg cgtctccatc     120

ccctgccgct ttgacttccc ggatgagctg cggcccgctg tggtgcatgg tgtctggtac     180

ttcaatagcc cctaccccaa gaactacccc ccggtggtct tcaagtcgcg cacccaagta     240

gtccacgaga gcttccaggg ccgcagccgc ctcctggggg acctgggcct gcgaaactgc     300

accctcctgc tcagcaacgt cagccccgag ctgggcggga agtactactt ccgtggggac     360

ctgggcggct acaaccagta caccttctca gagcacagcg tcctggatat cgtcaacacc     420

cccaacatcg tggtgccccc agaggtggtg gcaggcacgg aggtggaggt cagctgcatg     480

gtgccggaca actgcccaga gctgcgccct gagctgagct ggctgggcca cgaggggctg     540

ggggagcccg ctgtgctggg ccggctgcgg gaggacgagg gcacctgggt gcaggtgtca     600

ctgctgcact tcgtgcccac gagggaggcc aacggccaca ggctgggctg ccaggcctcc     660

ttccccaaca ccaccctgca gttcgagggc tacgccagca tggacgtcaa gtaccccccg     720
```

```
gtgattgtgg agatgaactc ctcggtggag gccatcgagg gctcccacgt gagcctgctc    780

tgtggggctg acagcaaccc cccgccgctg ctgacctgga tgcgggacgg gacagtcctc    840

cgggaggcgg tggccgagag cctgctcctg gagctggagg aggtgacccc cgccgaagac    900

ggcgtctatg cctgcctggc cgagaatgcc tatggccagg acaaccgcac cgtggggctc    960

agtgtcatgt atgcaccctg gaagccaaca gtgaacggga caatggtggc cgtagagggg   1020

gagacggtct ctatcttgtg ctccacacag agcaacccgg accctattct caccatcttc   1080

aaggagaagc agatcctgtc cacggtcatc tacgagagcg agctgcagct ggagctgccg   1140

gccgtgtcac ccgaggatga tggagagtac tggtgtgtgg ctgagaacca gtatggccag   1200

agggccaccg ccttcaacct gtctgtggag ttcgcccctg tgctcctcct ggagtcccac   1260

tgcgcggcag cccgagacac ggtgcagtgc ctgtgcgtgg tgaagtccaa cccggagccg   1320

tccgtggcct ttgagctgcc atcgcgcaat gtgaccgtga acgagagcga gcgggagttc   1380

gtgtactcgg agcgcagcgg cctcgtgctc accagcatcc tcacgctgcg ggggcaggcc   1440

caggccccgc cccgcgtcat ctgcaccgcg aggaacctct atggcgccaa gagcctggag   1500

ctgcccttcc agggagccca tcgactgatg tgggccaaga tcgggcctgt gggcgccgtg   1560

gtcgcctttg ccatcctgat tgccatcgtc tgctacatta cccagacacg caggaaaaag   1620

aacgtgacag agagccccag cttctcggca ggggacaacc ctcccgtcct gttcagcagc   1680

gacttccgca tctctggggc accagagaag tacgagagcg agaggcgcct gggatctgag   1740

aggaggctgc tgggccttcg gggtgagccc ccagagctgg acctgagcta ttctcactcg   1800

gacctgggga aacggcccac caaggacagc tacacgctga cggaggagct agctgagtat   1860

gctgaaatcc gggtcaagtg a                                             1881
```

```
<210> SEQ ID NO 23
<211> LENGTH: 551
<212> TYPE: PRT
<213> ORGANISM: Homo sapiens

<400> SEQUENCE: 23

Met Leu Pro Leu Leu Leu Leu Pro Leu Leu Trp Gly Gly Ser Leu Gln
1               5                   10                  15

Glu Lys Pro Val Tyr Glu Leu Gln Val Gln Lys Ser Val Thr Val Gln
            20                  25                  30

Glu Gly Leu Cys Val Leu Val Pro Cys Ser Phe Ser Tyr Pro Trp Arg
        35                  40                  45

Ser Trp Tyr Ser Ser Pro Pro Leu Tyr Val Tyr Trp Phe Arg Asp Gly
    50                  55                  60

Glu Ile Pro Tyr Tyr Ala Glu Val Val Ala Thr Asn Asn Pro Asp Arg
65                  70                  75                  80

Arg Val Lys Pro Glu Thr Gln Gly Arg Phe Arg Leu Leu Gly Asp Val
                85                  90                  95

Gln Lys Lys Asn Cys Ser Leu Ser Ile Gly Asp Ala Arg Met Glu Asp
            100                 105                 110

Thr Gly Ser Tyr Phe Phe Arg Val Glu Arg Gly Arg Asp Val Lys Tyr
        115                 120                 125

Ser Tyr Gln Gln Asn Lys Leu Asn Leu Glu Val Thr Ala Leu Ile Glu
    130                 135                 140

Lys Pro Asp Ile His Phe Leu Glu Pro Leu Glu Ser Gly Arg Pro Thr
145                 150                 155                 160

Arg Leu Ser Cys Ser Leu Pro Gly Ser Cys Glu Ala Gly Pro Pro Leu
```

```
                165                 170                 175

Thr Phe Ser Trp Thr Gly Asn Ala Leu Ser Pro Leu Asp Pro Glu Thr
            180                 185                 190

Thr Arg Ser Ser Glu Leu Thr Leu Thr Pro Arg Pro Glu Asp His Gly
        195                 200                 205

Thr Asn Leu Thr Cys Gln Met Lys Arg Gln Gly Ala Gln Val Thr Thr
    210                 215                 220

Glu Arg Thr Val Gln Leu Asn Val Ser Tyr Ala Pro Gln Thr Ile Thr
225                 230                 235                 240

Ile Phe Arg Asn Gly Ile Ala Leu Glu Ile Leu Gln Asn Thr Ser Tyr
                245                 250                 255

Leu Pro Val Leu Glu Gly Gln Ala Leu Arg Leu Leu Cys Asp Ala Pro
            260                 265                 270

Ser Asn Pro Pro Ala His Leu Ser Trp Phe Gln Gly Ser Pro Ala Leu
        275                 280                 285

Asn Ala Thr Pro Ile Ser Asn Thr Gly Ile Leu Glu Leu Arg Arg Val
    290                 295                 300

Arg Ser Ala Glu Glu Gly Gly Phe Thr Cys Arg Ala Gln His Pro Leu
305                 310                 315                 320

Gly Phe Leu Gln Ile Phe Leu Asn Leu Ser Val Tyr Ser Leu Pro Gln
                325                 330                 335

Leu Leu Gly Pro Ser Cys Ser Trp Glu Ala Glu Gly Leu His Cys Arg
            340                 345                 350

Cys Ser Phe Arg Ala Arg Pro Ala Pro Ser Leu Cys Trp Arg Leu Glu
        355                 360                 365

Glu Lys Pro Leu Glu Gly Asn Ser Ser Gln Gly Ser Phe Lys Val Asn
    370                 375                 380

Ser Ser Ser Ala Gly Pro Trp Ala Asn Ser Ser Leu Ile Leu His Gly
385                 390                 395                 400

Gly Leu Ser Ser Asp Leu Lys Val Ser Cys Lys Ala Trp Asn Ile Tyr
                405                 410                 415

Gly Ser Gln Ser Gly Ser Val Leu Leu Leu Gln Gly Arg Ser Asn Leu
            420                 425                 430

Gly Thr Gly Val Val Pro Ala Ala Leu Gly Gly Ala Gly Val Met Ala
        435                 440                 445

Leu Leu Cys Ile Cys Leu Cys Leu Ile Phe Phe Leu Ile Val Lys Ala
    450                 455                 460

Arg Arg Lys Gln Ala Ala Gly Arg Pro Glu Lys Met Asp Asp Glu Asp
465                 470                 475                 480

Pro Ile Met Gly Thr Ile Thr Ser Gly Ser Arg Lys Lys Pro Trp Pro
                485                 490                 495

Asp Ser Pro Gly Asp Gln Ala Ser Pro Pro Gly Asp Ala Pro Pro Leu
            500                 505                 510

Glu Glu Gln Lys Glu Leu His Tyr Ala Ser Leu Ser Phe Ser Glu Met
        515                 520                 525

Lys Ser Arg Glu Pro Lys Asp Gln Glu Ala Pro Ser Thr Thr Glu Tyr
    530                 535                 540

Ser Glu Ile Lys Thr Ser Lys
545                 550
```

<210> SEQ ID NO 24
<211> LENGTH: 2523
<212> TYPE: DNA
<213> ORGANISM: Homo sapiens

<400> SEQUENCE: 24

```
gtgcgcgtcc acagctctca ctcaccctcc ggcttcctgt cggggctttc tcagccccac     60
cccacgtttg gacatttgga gcatttcctt ccctgacagc cggacctggg actgggctgg    120
ggccctggcg gatggagaca tgctgcccct gctgctgctg cccctgctgt ggggggggtc    180
cctgcaggag aagccagtgt acgagctgca agtgcagaag tcggtgacgg tgcaggaggg    240
cctgtgcgtc cttgtgccct gctccttctc ttacccctgg agatcctggt attcctctcc    300
cccactctac gtctactggt tccgggacgg ggagatccca tactacgctg aggttgtggc    360
cacaaacaac ccagacagaa gagtgaagcc agagacccag ggccgattcc gcctccttgg    420
ggatgtccag aagaagaact gctccctgag catcggagat gccagaatgg aggacacggg    480
aagctatttc ttccgcgtgg agagaggaag ggatgtaaaa tatagctacc aacagaataa    540
gctgaacttg gaggtgacag ccctgataga gaaacccgac atccactttc tggagcctct    600
ggagtccggc cgccccacaa ggctgagctg cagccttcca ggatcctgtg aagcgggacc    660
acctctcaca ttctcctgga cggggaatgc cctcagcccc ctggaccccg agaccacccg    720
ctcctcggag ctcaccctca cccccaggcc cgaggaccat ggcaccaacc tcacctgtca    780
gatgaaacgc caaggagctc aggtgaccac ggagagaact gtccagctca atgtctccta    840
tgctccacag accatcacca tcttcaggaa cggcatagcc ctagagatcc tgcaaaacac    900
ctcatacctt ccggtcctgg agggccaggc tctgcggctg ctctgtgatg ctcccagcaa    960
ccccccctgca cacctgagct ggttccaggg ctcccctgcc ctgaacgcca cccccatctc   1020
caataccggg atcttggagc ttcgtcgagt aaggtctgca gaagaaggag gcttcacctg   1080
ccgcgctcag cacccgctgg gcttcctgca aatttttctg aatctctcag tttactccct   1140
cccacagttg ctgggcccct cctgctcctg ggaggctgag ggtctgcact gcagatgctc   1200
ctttcgagcc cggccggccc cctccctgtg ctggcggctt gaggagaagc cgctggaggg   1260
gaacagcagc cagggctcat tcaaggtcaa ctccagctca gctgggccct gggccaacag   1320
ctccctgatc ctccacgggg ggctcagctc cgacctcaaa gtcagctgca aggcctggaa   1380
catctatggg tcccagagcg gctctgtcct gctgctgcaa gggagatcga acctcgggac   1440
aggagtggtt cctgcagccc ttggtggtgc tggtgtcatg gccctgctct gtatctgtct   1500
gtgcctcatc ttcttttttaa tagtgaaagc ccgcaggaag caagcagctg ggagaccaga   1560
gaaaatggat gatgaagacc ccattatggg taccatcacc tcgggttcca ggaagaagcc   1620
ctggccagac agccccggag atcaagcatc tcctcctggg gatgcccctc ccttggaaga   1680
acaaaaggag ctccattatg cctcccttag tttttctgag atgaagtcga gggagcctaa   1740
ggaccaggag gccccaagca ccacggagta ctcggagatc aagacaagca agtgaggatt   1800
tgcccagagt tcagtcctgg ctggaggagc cacagcctgt ctgggggaaa ggacaagtca   1860
gggaccactt gctgaagcac gaagagccct tgtggcaatg ttaacattaa ctgatgttta   1920
agtgctccaa gcagatggaa ttagagaggt gggctcaaat ctaggccctg gcactgtcat   1980
caagcaattc actgcatccc tctgtgcctc agtttcccat tctgtaaatc agagatcatg   2040
catgctacct caaaggttgt tgtgaacatt aaagaaatca acacatggaa atcaaccaac   2100
atgggtcctg gaacagggcg ttgtgctcag tgctttctgg tctctcttcc ttgaatagaa   2160
aggtcctgct ggcaagttct ctcaaggctg gggatgacca ggcacaaaaa acagggcagc   2220
aatatgttgg tgtcactccc cttcccaaaa ctcttcgaag actccctagg aaagaccagc   2280
```

-continued ccctcagcct ggcacttggt tcatgatgtg ggatcttata tccttgccag agtcatatct 2340
ttgcccactt ttacctgcaa tccttgcatc atattccttt ggctccagtc cttcatttat 2400
gagacccata ggaatccttc caacagccaa agagttgagt ctaactcttt cctgcccaaa 2460
cccattcacg gccccctggc cttagacaat atatcacaag catctcccct gacacataaa 2520
gtc 2523

<210> SEQ ID NO 25
<211> LENGTH: 453
<212> TYPE: PRT
<213> ORGANISM: Homo sapiens

<400> SEQUENCE: 25

Met Gln Gly Ala Gln Glu Ala Ser Ala Ser Glu Met Leu Pro Leu Leu
1 5 10 15

Leu Pro Leu Leu Trp Ala Gly Ala Leu Ala Gln Glu Arg Arg Phe Gln
20 25 30

Leu Glu Gly Pro Glu Ser Leu Thr Val Gln Glu Gly Leu Cys Val Leu
35 40 45

Val Pro Cys Arg Leu Pro Thr Thr Leu Pro Ala Ser Tyr Tyr Gly Tyr
50 55 60

Gly Tyr Trp Phe Leu Glu Gly Ala Asp Val Pro Val Ala Thr Asn Asp
65 70 75 80

Pro Asp Glu Glu Val Gln Glu Glu Thr Arg Gly Arg Phe His Leu Leu
85 90 95

Trp Asp Pro Arg Arg Lys Asn Cys Ser Leu Ser Ile Arg Asp Ala Arg
100 105 110

Arg Arg Asp Asn Ala Ala Tyr Phe Phe Arg Leu Lys Ser Lys Trp Met
115 120 125

Lys Tyr Gly Tyr Thr Ser Ser Lys Leu Ser Val Arg Val Met Ala Leu
130 135 140

Thr His Arg Pro Asn Ile Ser Ile Pro Gly Thr Leu Glu Ser Gly His
145 150 155 160

Pro Ser Asn Leu Thr Cys Ser Val Pro Trp Val Cys Glu Gln Gly Thr
165 170 175

Pro Pro Ile Phe Ser Trp Met Ser Ala Ala Pro Thr Ser Leu Gly Pro
180 185 190

Arg Thr Thr Gln Ser Ser Val Leu Thr Ile Thr Pro Arg Pro Gln Asp
195 200 205

His Ser Thr Asn Leu Thr Cys Gln Val Thr Phe Pro Gly Ala Gly Val
210 215 220

Thr Met Glu Arg Thr Ile Gln Leu Asn Val Ser Tyr Ala Pro Gln Lys
225 230 235 240

Val Ala Ile Ser Ile Phe Gln Gly Asn Ser Ala Ala Phe Lys Ile Leu
245 250 255

Gln Asn Thr Ser Ser Leu Pro Val Leu Glu Gly Gln Ala Leu Arg Leu
260 265 270

Leu Cys Asp Ala Asp Gly Asn Pro Pro Ala His Leu Ser Trp Phe Gln
275 280 285

Gly Phe Pro Ala Leu Asn Ala Thr Pro Ile Ser Asn Thr Gly Val Leu
290 295 300

Glu Leu Pro Gln Val Gly Ser Ala Glu Glu Gly Asp Phe Thr Cys Arg
305 310 315 320

Ala Gln His Pro Leu Gly Ser Leu Gln Ile Ser Leu Ser Leu Phe Val

-continued

```
                325                 330                 335

His Trp Lys Pro Glu Gly Arg Ala Gly Gly Val Leu Gly Ala Val Trp
            340                 345                 350

Gly Ala Ser Ile Thr Thr Leu Val Phe Leu Cys Val Cys Phe Ile Phe
        355                 360                 365

Arg Val Lys Thr Arg Arg Lys Lys Ala Ala Gln Pro Val Gln Asn Thr
    370                 375                 380

Asp Asp Val Asn Pro Val Met Val Ser Gly Ser Arg Gly His Gln His
385                 390                 395                 400

Gln Phe Gln Thr Gly Ile Val Ser Asp His Pro Ala Glu Ala Gly Pro
                405                 410                 415

Ile Ser Glu Asp Glu Gln Glu Leu His Tyr Ala Val Leu His Phe His
            420                 425                 430

Lys Val Gln Pro Gln Glu Pro Lys Val Thr Asp Thr Glu Tyr Ser Glu
        435                 440                 445

Ile Lys Ile His Lys
    450
```

<210> SEQ ID NO 26
<211> LENGTH: 3815
<212> TYPE: DNA
<213> ORGANISM: Homo sapiens

<400> SEQUENCE: 26

```
gcgggacaca gtctcttctc ctctgctctt ctttgggcag gtctctgggt ctcaaagttt     60

ccgtctgctc tgtgcagagg gagtggagct ccgagggctt gtggcttcgc agttcctctt    120

ctgtgaacag ccgagatcac gcgctcctcc ccagccaccc gttcctcccc gcagtccttc    180

ccctccactc ccttcccctt ctctgctcat gcagggagcc caggaagcct ccgcctcaga    240

gatgctaccg ctgctgctgc ccctgctgtg ggcaggggcc ctggctcagg agcggagatt    300

ccagctggag gggccagagt cactgacggt gcaggagggt ctgtgcgtcc tcgtaccctg    360

cagattgccc actacccttc cagcctcgta ctatggttat ggctactggt tcctggaagg    420

ggctgatgtt ccagtggcca caaacgaccc agacgaagaa gtgcaggagg agacccgggg    480

ccgattccac ctcctctggg atcccagaag gaagaactgc tccctgagca tcagagatgc    540

ccggaggagg gacaatgctg catacttctt tcggttgaag tccaaatgga tgaaatacgg    600

ttatacatct tccaagctct ctgtgcgtgt gatggccctg acccacaggc ccaacatctc    660

catcccaggg accctggagt ctggccatcc cagcaatctg acctgctctg tgccctgggt    720

ctgtgagcag gggacgcccc ccatcttctc ctggatgtca gctgccccca cctccctggg    780

ccccaggacc acccagtcct cggtgctcac aatcacccca cggccccagg accacagcac    840

caacctcacc tgtcaggtga cgttccctgg agccggtgtg accatggaga gaaccatcca    900

gctcaatgtc tcctccttca aatcctgca aaacacctcg tccctccctg tcctggaggg     960

ccaggctctg cggctgctct gtgatgctga cggcaacccc cctgcacacc tgagctggtt   1020

ccagggcttc cccgccctga acgccacccc catctccaat accggggtcc tggagctgcc   1080

tcaagtaggg tctgcagaag aaggagattt cacctgccgt gctcagcatc ctctgggctc   1140

cctgcaaatc tctctgagtc tctttgtgca ttggaaacca gaaggcaggg ctggtggtgt   1200

cctgggagca gtctggggag ctagcatcac aaccctggtt ttcctctgtg tttgcttcat   1260

cttcagagtg aagactagaa ggaagaaagc agcccagcca gtgcaaaaca cggatgatgt   1320

gaaccccgtc atggtctcag gctccagggg tcatcagcac cagttccaga caggcatagt   1380
```

-continued

```
ttcagaccac cctgctgagg ctggccccat ctcagaagat gagcaggagc tccactacgc   1440
tgtcctacac ttccacaagg tgcaacctca ggaaccaaag gtcaccgaca ctgagtactc   1500
agaaatcaag atacacaagt gaggaattgt ccaaagccat aaccttgatt ggagagaaca   1560
tggtacctct cagtgtattg gttactaggg ctgccacagc aatgtaccac aaaccgagtg   1620
acataaacac agaactttat tttcgtatag tttcagatgt tagaggtctg agaacaaggt   1680
gttatcaggg ttggtccctt ctaaggcctc tcttgttggc ttgtagatgg ctgtctcctc   1740
cttgtgtctt cacatggtct ttcctctgag tgtgtttgtg tcctaatctt ctcttcttat   1800
aaagacacta gtcatattgg attagggcct ccccatgacc taatttaaat aaattaacta   1860
tttaaagacc ctccaaatac agtaaccttc tgagatattg agatttagga cttccaacat   1920
atgaatttta gaagggaaca atttagccca taacactgtg tccaattctt ttaaaattaa   1980
tgtttttgtt gtaaatggac tatataaata ccttcgtata tatggcagac cacaggactt   2040
ctgtccaaga gaactgagtt caactccatc tatgccagct attgagcaag tcgctttatg   2100
tccctgctct gtaaggcagg gaaataattt ccatctaacc agattattgt gaaaggtcaa   2160
agaaagcata cagctaacat acagctttgt tagctgtaaa acagctaaca aaggccctga   2220
cacaaaggtt ttcataaagt ctgtatattt ttgtaaatga atgccttgta tctggctttg   2280
gctagctttt tttttttttt tttttttctg agatggagtc ttgctgtatc tcccaggctg   2340
gagtgcagtg gtgcgatctt ggctcagtgc aagcttcgcc ccctgggttc acaccattct   2400
cctgcctcag cctcccaagt agctgggact acaggcaccc accaccacac ccggctaatt   2460
ttttgtattt ttagtagaga cggggtttca ccgtgttagc caggatggtc ttgatctcct   2520
gacctcgtga tctgccctcc tcggcctccc aaagtgctga gattacaggc atgagccacc   2580
gcacccggct ttgattagct gttttaacag acggtttctg ctggcaattt cttctaaggc   2640
tgaaaaggag taggcccaga ggccacagca ccaggtgtct gtgtcacccc ctgttcagaa   2700
ctcttcacga ctccccaaaa taaggtttcc atccatcatc tttctgctca aggctctcta   2760
catgatcttg tccatccaga tttccccaga tcaattcctc accagtcacc aataccccat   2820
gtccatttcc acagcttcct cttacaaatc ccagtctcca ctattccagt gaaattgaag   2880
aaagcattta atgaagacca actattaagg aaaattctta agagtagcca tgaaaaataa   2940
aaagatagat tacacttaaa agaccacagt tagcagtggc tcacgcctgt aatcccagca   3000
ctttgggagg ctgaggtggg tggatcactg gaggtcagga gttcgagact ggtctggcca   3060
acatggtgaa accccatctc tactaaaata caaaaattag ctcggtgtgg tggcacttgc   3120
ctgtaatccc aggtacttct gcaggttgaa gcaggagaat tgcttgaacc tgggaggtgg   3180
aggttgaagt gagctgagat tgcatcactg cactccagcc tgggcaacag agcgagactc   3240
caactcagaa aaagcaaaac aaaacaaaca aacaagcaaa aaaccacaat tagactgaca   3300
gctgactttt ttaggagcaa tattggaagg ctaaatgcaa tagaaagatg tctttgatgg   3360
cttaagagaa ataaatgttg ttttagaaag cctactcaat gaaaacacat tttaagactg   3420
aaagtgaaat atagatattt taaggaaaac caaaatatgt gagtgttaat aaagaaaaga   3480
tttctcaaat aaattctaaa acatataatt caggtattag gaaagtgatc ccagattaga   3540
tttttgagat ccaaaaaaaa tgaaaaccta ggaaagtagc aaatatgtga gcaaaatgaa   3600
acaaatactt gttgtaaaaa tgatggtttg tagaggggtc aaacatcaaa tgtaatattg   3660
aaataccaat attatatagc ccagaaacta taataacata aagttcagaa gagtgtaaat   3720
```

-continued

```
agaatttata ttacataaag tctttatatt tttccagaga aaattaaatg ttatgatgaa   3780

tgttaaaaaa aaaaaaaaaa aaaaaaaaaa aaaaa                              3815


<210> SEQ ID NO 27
<211> LENGTH: 467
<212> TYPE: PRT
<213> ORGANISM: Homo sapiens

<400> SEQUENCE: 27

Met Leu Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
    130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
        195                 200                 205

Gln His His Gly Thr Ser Leu Thr Cys Gln Val Thr Leu Pro Gly Ala
    210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
            260                 265                 270

Arg Leu Val Cys Ala Val Asp Ser Asn Pro Pro Ala Arg Leu Ser Trp
        275                 280                 285

Thr Trp Arg Ser Leu Thr Leu Tyr Pro Ser Gln Pro Ser Asn Pro Leu
    290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
            340                 345                 350

Leu Gly Ala Val Gly Gly Ala Gly Ala Thr Ala Leu Val Phe Leu Ser
```

```
        355                 360                 365

Phe Cys Val Ile Phe Ile Val Val Arg Ser Cys Arg Lys Lys Ser Ala
    370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His His Gly Leu Ala Ala His Ser Ser Gly Glu Glu
            420                 425                 430

Arg Glu Ile Gln Tyr Ala Pro Leu Ser Phe His Lys Gly Glu Pro Gln
        435                 440                 445

Asp Leu Ser Gly Gln Glu Ala Thr Asn Asn Glu Tyr Ser Glu Ile Lys
    450                 455                 460

Ile Pro Lys
465


<210> SEQ ID NO 28
<211> LENGTH: 1769
<212> TYPE: DNA
<213> ORGANISM: Homo sapiens

<400> SEQUENCE: 28

gcagttcctg agagaagaac cctgaggaac agacgttccc tcgcggccct ggcacctcca     60

accccagata tgctgctgct gctgctgctg cccctgctct gggggaggga gagggtggaa    120

ggacagaaga gtaaccggaa ggattactcg ctgacgatgc agagttccgt gaccgtgcaa    180

gagggcatgt gtgtccatgt gcgctgctcc ttctcctacc cagtggacag ccagactgac    240

tctgacccag ttcatggcta ctggttccgg gcagggaatg atataagctg gaaggctcca    300

gtggccacaa acaacccagc ttgggcagtg caggaggaaa ctcgggaccg attccacctc    360

cttggggacc cacagaccaa aaattgcacc ctgagcatca gagatgccag aatgagtgat    420

gcggggagat acttctttcg tatggagaaa ggaaatataa aatggaatta taaatatgac    480

cagctctctg tgaacgtgac agccttgacc cacaggccca acatccttat ccccggtacc    540

ctggagtctg gctgcttcca gaatctgacc tgctctgtgc cctgggcctg tgagcagggg    600

acgcccccta tgatctcctg gatggggacc tctgtgtccc ccctgcaccc ctccaccacc    660

cgctcctcag tgctcaccct catcccacag ccccagcacc acggcaccag cctcacctgt    720

caggtgacct tgcctggggc cggcgtgacc acgaacagga ccatccaact caatgtgtcc    780

taccctcctc agaacttgac tgtgactgtc ttccaaggag aaggcacagc atccacagct    840

ctggggaaca gctcatctct ttcagtccta gagggccagt ctctgcgctt ggtctgtgct    900

gttgacagca atccccctgc caggctgagc tggacctgga ggagtctgac cctgtacccc    960

tcacagccct caaaccctct ggtactggag ctgcaagtgc acctggggga tgaaggggaa   1020

ttcacctgtc gagctcagaa ctctctgggt tcccagcacg tttccctgaa cctctccctg   1080

caacaggagt acacaggcaa aatgaggcct gtatcaggag tgttgctggg ggcggtcggg   1140

ggagctggag ccacagccct ggtcttcctc tccttctgtg tcatcttcat tgtagtgagg   1200

tcctgcagga agaaatcggc aaggccagca gcggacgtgg gagacatagg catgaaggat   1260

gcaaacacca tcaggggctc agcctctcag ggtaacctga ctgagtcctg ggcagatgat   1320

aacccccgac accatggcct ggctgcccac tcctcagggg aggaaagaga gatccagtat   1380

gcacccctca gctttcataa gggggagcct caggacctat caggacaaga agccaccaac   1440
```

-continued

```
aatgagtact cagagatcaa gatccccaag taagaaaatg cagaggctcg ggcttgtttg   1500

agggttcacg acccctccag caaaggagtc tgaggctgat tccagtagaa ttagcagccc   1560

tcaatgctgt gcaacaagac atcagaactt attcctcttg tctaactgaa aatgcatgcc   1620

tgatgaccaa actctccctt tccccatcca atcggtccac actccccgcc ctggcctctg   1680

gtacccacca ttctcctctg tacttctcta aggatgacta ctttagattc cgaatatagt   1740

gagattgtaa cgtgaaaaaa aaaaaaaaa                                     1769
```

<210> SEQ ID NO 29
<211> LENGTH: 499
<212> TYPE: PRT
<213> ORGANISM: Homo sapiens

<400> SEQUENCE: 29

```
Met Leu Leu Leu Leu Leu Leu Leu Pro Leu Leu Trp Gly Thr Lys Gly
1               5                   10                  15

Met Glu Gly Asp Arg Gln Tyr Gly Asp Gly Tyr Leu Leu Gln Val Gln
            20                  25                  30

Glu Leu Val Thr Val Gln Glu Gly Leu Cys Val His Val Pro Cys Ser
        35                  40                  45

Phe Ser Tyr Pro Gln Asp Gly Trp Thr Asp Ser Asp Pro Val His Gly
    50                  55                  60

Tyr Trp Phe Arg Ala Gly Asp Arg Pro Tyr Gln Asp Ala Pro Val Ala
65                  70                  75                  80

Thr Asn Asn Pro Asp Arg Glu Val Gln Ala Glu Thr Gln Gly Arg Phe
                85                  90                  95

Gln Leu Leu Gly Asp Ile Trp Ser Asn Asp Cys Ser Leu Ser Ile Arg
            100                 105                 110

Asp Ala Arg Lys Arg Asp Lys Gly Ser Tyr Phe Phe Arg Leu Glu Arg
        115                 120                 125

Gly Ser Met Lys Trp Ser Tyr Lys Ser Gln Leu Asn Tyr Lys Thr Lys
    130                 135                 140

Gln Leu Ser Val Phe Val Thr Ala Leu Thr His Arg Pro Asp Ile Leu
145                 150                 155                 160

Ile Leu Gly Thr Leu Glu Ser Gly His Ser Arg Asn Leu Thr Cys Ser
                165                 170                 175

Val Pro Trp Ala Cys Lys Gln Gly Thr Pro Pro Met Ile Ser Trp Ile
            180                 185                 190

Gly Ala Ser Val Ser Ser Pro Gly Pro Thr Thr Ala Arg Ser Ser Val
        195                 200                 205

Leu Thr Leu Thr Pro Lys Pro Gln Asp His Gly Thr Ser Leu Thr Cys
    210                 215                 220

Gln Val Thr Leu Pro Gly Thr Gly Val Thr Thr Thr Ser Thr Val Arg
225                 230                 235                 240

Leu Asp Val Ser Tyr Pro Pro Trp Asn Leu Thr Met Thr Val Phe Gln
                245                 250                 255

Gly Asp Ala Thr Ala Ser Thr Ala Leu Gly Asn Gly Ser Ser Leu Ser
            260                 265                 270

Val Leu Glu Gly Gln Ser Leu Arg Leu Val Cys Ala Val Asn Ser Asn
        275                 280                 285

Pro Pro Ala Arg Leu Ser Trp Thr Arg Gly Ser Leu Thr Leu Cys Pro
    290                 295                 300

Ser Arg Ser Ser Asn Pro Gly Leu Leu Glu Leu Pro Arg Val His Val
305                 310                 315                 320
```

```
Arg Asp Glu Gly Glu Phe Thr Cys Arg Ala Gln Asn Ala Gln Gly Ser
                325                 330                 335

Gln His Ile Ser Leu Ser Leu Ser Leu Gln Asn Glu Gly Thr Gly Thr
            340                 345                 350

Ser Arg Pro Val Ser Gln Val Thr Leu Ala Ala Val Gly Gly Ala Gly
        355                 360                 365

Ala Thr Ala Leu Ala Phe Leu Ser Phe Cys Ile Ile Phe Ile Ile Val
    370                 375                 380

Arg Ser Cys Arg Lys Lys Ser Ala Arg Pro Ala Ala Gly Val Gly Asp
385                 390                 395                 400

Thr Gly Met Glu Asp Ala Lys Ala Ile Arg Gly Ser Ala Ser Gln Gly
                405                 410                 415

Pro Leu Thr Glu Ser Trp Lys Asp Gly Asn Pro Leu Lys Lys Pro Pro
            420                 425                 430

Pro Ala Val Ala Pro Ser Ser Gly Glu Glu Gly Glu Leu His Tyr Ala
        435                 440                 445

Thr Leu Ser Phe His Lys Val Lys Pro Gln Asp Pro Gln Gly Gln Glu
    450                 455                 460

Ala Thr Asp Ser Glu Tyr Ser Glu Ile Lys Ile His Lys Arg Glu Thr
465                 470                 475                 480

Ala Glu Thr Gln Ala Cys Leu Arg Asn His Asn Pro Ser Ser Lys Glu
                485                 490                 495

Val Arg Gly


<210> SEQ ID NO 30
<211> LENGTH: 2967
<212> TYPE: DNA
<213> ORGANISM: Homo sapiens

<400> SEQUENCE: 30

agtttctgag agaagaaccc tgaggaacag acgttccctg gcggccctgg cgccttcaaa      60

cccagacatg ctgctgctgc tgctgctgct gcccctgctc tgggggacaa aggggatgga     120

gggagacaga caatatgggg atggttactt gctgcaagtg caggagctgg tgacggtgca     180

ggagggcctg tgtgtccatg tgccctgctc cttctcctac ccccaggatg gctggactga     240

ctctgaccca gttcatggct actggttccg ggcaggagac agaccatacc aagacgctcc     300

agtggccaca aacaacccag acagagaagt gcaggcagag acccagggcc gattccaact     360

ccttggggac atttggagca acgactgctc cctgagcatc agagacgcca ggaagaggga     420

taaggggtca tatttctttc ggctagagag aggaagcatg aaatggagtt acaaatcaca     480

gttgaattac aaaactaagc agctgtctgt gtttgtgaca gccctgaccc ataggcctga     540

catcctcatc ctagggaccc tagagtctgg ccactccagg aacctgacct gctctgtgcc     600

ctgggcctgt aagcagggga caccccccat gatctcctgg attggggcct ccgtgtcctc     660

cccgggcccc actactgccc gctcctcagt gctcaccctt accccaaagc cccaggacca     720

cggcaccagc ctcacctgtc aggtgacctt gcctgggaca ggtgtgacca cgaccagtac     780

cgtccgcctc gatgtgtcct accctccttg gaacttgacc atgactgtct tccaaggaga     840

tgccacagca tccacagccc tgggaaatgg ctcatctctt tcagtccttg agggccagtc     900

tctgcgcctg gtctgtgctg tcaacagcaa tccccctgcc aggctgagct ggacccgggg     960

gagcctgacc ctgtgcccct cacggtcctc aaaccctggg ctgctggagc tgcctcgagt    1020

gcacgtgagg gatgaagggg aattcacctg ccgagctcag aacgctcagg gctcccagca    1080
```

```
catttccctg agcctctccc tgcagaatga gggcacaggc acctcaagac ctgtatcaca   1140

agtgacactg gcagcagtcg ggggagctgg agccacagcc ctggccttcc tgtccttctg   1200

catcatcttc atcatagtga ggtcctgcag gaagaaatcg gcaaggccag cagcgggcgt   1260

gggggataca ggcatggaag atgcaaaggc catcaggggc tcggcctctc agggacccct   1320

gactgaatcc tggaaagatg gcaacccccct gaagaagcct cccccagctg ttgccccctc   1380

gtcaggggag gaaggagagc tccattatgc aaccctcagc ttccataaag tgaagcctca   1440

ggacccgcag ggacaggagg ccactgacag tgaatactcg gagatcaaga tccacaagcg   1500

agaaactgca gagactcagg cctgtttgag gaatcacaac ccctccagca aagaagtcag   1560

aggctgattc tcatagaaca agaaccctct agagccccat gctatgcagt aggtcaccag   1620

ggctccctcc tcctgtctaa ccaaaacttg gaccaatgtc tcccctttcc ccggctacca   1680

gggacccatc cctgcctcta gcttctacta cccaccattc tcctctcgac ctctctgagg   1740

ttgactattt tagattccac atagagatga ggtcatgtgg tacttgcctc tctgtgtgtg   1800

gctcatttta cacaaaaaaa tatcccctag gttcatccat gttctctcaa atgacagaat   1860

caagcactga atattttttt ttctttgaga gatggagttt cgctctgttg cccaggctgg   1920

agtgcagtgg ttcaatctct gctcactgca acctccacct cctgggttca aacgattctc   1980

ctgcctcagc ttcccaagta gctggtacta caggcgtgtg tcaccacgcc cagctaattt   2040

ttgtattttt tagtagagac ggggtttcac tataagtggg ccaggctagt ctcaaactcc   2100

tgacctcaag tgatctgcct gccttggcct cccaaagtgc tgggatttca ggcatgagcc   2160

accgcaccca gcttgcattg aatattttca aggagctaaa agaagatttt aaatggtctc   2220

acaaaaacag ataaatattt gcacagatgg gtgtgctaat cattgtgcct tgatggttcc   2280

acgatgtatc cgggtgtgga aatctcactg ggtctctctc aaggccactc ggctactcag   2340

gacagggctg gaatttaaag cctgtccgat tctgaggtct cttctctcat ctagcactga   2400

gtcaagcaat cagcaggctg ggcacccctt agccataagt tttcaggaaa taaattcctt   2460

gagggcattg acttttacaa aagagggagc agcaatggcc tagagtctca ggaacaagac   2520

aggtgcactg aggagatgaa ggccgggacc ccctgcccaa cctgtatggc gggtctgtac   2580

ttattttgtt tacccccaat ttaaaacgtt tttttttatt gcaggttgtt tgtttgatat   2640

ggtttggctg tgtccccacc caaatcttat ctagaattgt aatcagaatt ataatcccca   2700

tgtgttgggg gagggacctg gtgggaggtg ataggatcat gggggtggtt cccccatgct   2760

gttctgatag tgagtgagtt atcacgagat ctgatggttt tgtaagtggt ggtttcccct   2820

gctcttctct cttgcctgcc accatgtaag atgtgcctgg ttccccttcc gccatgattg   2880

taagtttcct gaggcctccc ccgccatgtg gaactgtgag tcaattacac ctctttcatt   2940

tataaattaa aaaaaaaaaa aaaaaaa                                       2967
```

<210> SEQ ID NO 31
<211> LENGTH: 463
<212> TYPE: PRT
<213> ORGANISM: Homo sapiens

<400> SEQUENCE: 31

```
Met Leu Leu Leu Leu Leu Pro Leu Leu Trp Gly Arg Glu Arg Ala Glu
1               5                   10                  15

Gly Gln Thr Ser Lys Leu Leu Thr Met Gln Ser Ser Val Thr Val Gln
            20                  25                  30
```

-continued

```
Glu Gly Leu Cys Val His Val Pro Cys Ser Phe Ser Tyr Pro Ser His
        35                  40                  45

Gly Trp Ile Tyr Pro Gly Pro Val Val His Gly Tyr Trp Phe Arg Glu
    50                  55                  60

Gly Ala Asn Thr Asp Gln Asp Ala Pro Val Ala Thr Asn Asn Pro Ala
65                  70                  75                  80

Arg Ala Val Trp Glu Glu Thr Arg Asp Arg Phe His Leu Leu Gly Asp
                85                  90                  95

Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
        115                 120                 125

Asn Tyr Lys His His Arg Leu Ser Val Asn Val Thr Ala Leu Thr His
    130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
            180                 185                 190

Thr Arg Ser Ser Val Leu Thr Leu Ile Pro Gln Pro Gln Asp His Gly
        195                 200                 205

Thr Ser Leu Thr Cys Gln Val Thr Phe Pro Gly Ala Ser Val Thr Thr
    210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255

Gly Ser Ser Leu Ser Leu Pro Glu Gly Gln Ser Leu Arg Leu Val Cys
            260                 265                 270

Ala Val Asp Ala Val Asp Ser Asn Pro Pro Ala Arg Leu Ser Leu Ser
        275                 280                 285

Trp Arg Gly Leu Thr Leu Cys Pro Ser Gln Pro Ser Asn Pro Gly Val
    290                 295                 300

Leu Glu Leu Pro Trp Val His Leu Arg Asp Ala Ala Glu Phe Thr Cys
305                 310                 315                 320

Arg Ala Gln Asn Pro Leu Gly Ser Gln Gln Val Tyr Leu Asn Val Ser
                325                 330                 335

Leu Gln Ser Lys Ala Thr Ser Gly Val Thr Gln Gly Val Val Gly Gly
            340                 345                 350

Ala Gly Ala Thr Ala Leu Val Phe Leu Ser Phe Cys Val Ile Phe Val
        355                 360                 365

Val Val Arg Ser Cys Arg Lys Lys Ser Ala Arg Pro Ala Ala Gly Val
    370                 375                 380

Gly Asp Thr Gly Ile Glu Asp Ala Asn Ala Val Arg Gly Ser Ala Ser
385                 390                 395                 400

Gln Gly Pro Leu Thr Glu Pro Trp Ala Glu Asp Ser Pro Pro Asp Gln
                405                 410                 415

Pro Pro Pro Ala Ser Ala Arg Ser Ser Val Gly Glu Gly Glu Leu Gln
            420                 425                 430

Tyr Ala Ser Leu Ser Phe Gln Met Val Lys Pro Trp Asp Ser Arg Gly
        435                 440                 445

Gln Glu Ala Thr Asp Thr Glu Tyr Ser Glu Ile Lys Ile His Arg
```

450 455 460

<210> SEQ ID NO 32
<211> LENGTH: 1737
<212> TYPE: DNA
<213> ORGANISM: Homo sapiens

<400> SEQUENCE: 32

```
tagggcctcc tctaagtctt gagcccgcag ttcctgagag aagaaccctg aggaacagac     60
gttccctcgc ggccctggca cctctaaccc cagacatgct gctgctgctg ctgcccctgc    120
tctgggggag ggagagggcg gaaggacaga caagtaaact gctgacgatg cagagttccg    180
tgacggtgca ggaaggcctg tgtgtccatg tgccctgctc cttctcctac ccctcgcatg    240
gctggattta ccctggccca gtagttcatg gctactggtt ccgggaaggg gccaatacag    300
accaggatgc tccagtggcc acaaacaacc cagctcgggc agtgtgggag gagactcggg    360
accgattcca cctccttggg gacccacata ccaagaattg caccctgagc atcagagatg    420
ccagaagaag tgatgcgggg agatacttct ttcgtatgga gaaaggaagt ataaaatgga    480
attataaaca tcaccggctc tctgtgaatg tgacagcctt gacccacagg cccaacatcc    540
tcatcccagg caccctggag tccggctgcc cccagaatct gacctgctct gtgccctggg    600
cctgtgagca ggggacaccc cctatgatct cctggatagg gacctccgtg tccccccctgg    660
acccctccac cacccgctcc tcggtgctca ccctcatccc acagccccag gaccatggca    720
ccagcctcac ctgtcaggtg accttccctg gggccagcgt gaccacgaac aagaccgtcc    780
atctcaacgt gtcctacccg cctcagaact tgaccatgac tgtcttccaa ggagacggca    840
cagtatccac agtcttggga aatggctcat ctctgtcact cccagagggc cagtctctgc    900
gcctggtctg tgcagttgat gcagttgaca gcaatccccc tgccaggctg agcctgagct    960
ggagaggcct gaccctgtgc cctcacagc cctcaaaccc gggggtgctg gagctgcctt   1020
gggtgcacct gagggatgca gctgaattca cctgcagagc tcagaaccct ctcggctctc   1080
agcaggtcta cctgaacgtc tccctgcaga gcaaagccac atcaggagtg actcaggggg   1140
tggtcggggg agctggagcc acagccctgg tcttcctgtc cttctgcgtc atcttcgttg   1200
tagtgaggtc ctgcaggaag aaatcggcaa ggccagcagc gggcgtggga gatacgggca   1260
tagaggatgc aaacgctgtc aggggttcag cctctcaggg gcccctgact gaaccttggg   1320
cagaagacag tcccccagac cagcctcccc cagcttctgc ccgctcctca gtgggggaag   1380
gagagctcca gtatgcatcc ctcagcttcc agatggtgaa gccttgggac tcgcggggac   1440
aggaggccac tgacaccgag tactcggaga tcaagatcca cagatgagaa actgcagaga   1500
ctcaccctga ttgagggatc acagcccctc caggcaaggg agaagtcaga ggctgattct   1560
tgtagaatta acagccctca acgtgatgag ctatgataac actatgaatt atgtgcagag   1620
tgaaaagcac acaggcttta gagtcaaagt atctcaaacc tgaatccaca ctgtgccctc   1680
ccttttattt ttttaactaa aagacagaca aattcctaaa aaaaaaaaaa aaaaaaa      1737
```

<210> SEQ ID NO 33
<211> LENGTH: 697
<212> TYPE: PRT
<213> ORGANISM: Homo sapiens

<400> SEQUENCE: 33

```
Met Leu Leu Pro Leu Leu Leu Ser Ser Leu Leu Gly Gly Ser Gln Ala
1               5                   10                  15
```

```
Met Asp Gly Arg Phe Trp Ile Arg Val Gln Glu Ser Val Met Val Pro
            20                  25                  30

Glu Gly Leu Cys Ile Ser Val Pro Cys Ser Phe Ser Tyr Pro Arg Gln
        35                  40                  45

Asp Trp Thr Gly Ser Thr Pro Ala Tyr Gly Tyr Trp Phe Lys Ala Val
    50                  55                  60

Thr Glu Thr Thr Lys Gly Ala Pro Val Ala Thr Asn His Gln Ser Arg
65                  70                  75                  80

Glu Val Glu Met Ser Thr Arg Gly Arg Phe Gln Leu Thr Gly Asp Pro
                85                  90                  95

Ala Lys Gly Asn Cys Ser Leu Val Ile Arg Asp Ala Gln Met Gln Asp
            100                 105                 110

Glu Ser Gln Tyr Phe Phe Arg Val Glu Arg Gly Ser Tyr Val Arg Tyr
        115                 120                 125

Asn Phe Met Asn Asp Gly Phe Phe Leu Lys Val Thr Ala Leu Thr Gln
    130                 135                 140

Lys Pro Asp Val Tyr Ile Pro Glu Thr Leu Glu Pro Gly Gln Pro Val
145                 150                 155                 160

Thr Val Ile Cys Val Phe Asn Trp Ala Phe Glu Glu Cys Pro Pro Pro
                165                 170                 175

Ser Phe Ser Trp Thr Gly Ala Ala Leu Ser Ser Gln Gly Thr Lys Pro
            180                 185                 190

Thr Thr Ser His Phe Ser Val Leu Ser Phe Thr Pro Arg Pro Gln Asp
        195                 200                 205

His Asn Thr Asp Leu Thr Cys His Val Asp Phe Ser Arg Lys Gly Val
    210                 215                 220

Ser Ala Gln Arg Thr Val Arg Leu Arg Val Ala Tyr Ala Pro Arg Asp
225                 230                 235                 240

Leu Val Ile Ser Ile Ser Arg Asp Asn Thr Pro Ala Leu Glu Pro Gln
                245                 250                 255

Pro Gln Gly Asn Val Pro Tyr Leu Glu Ala Gln Lys Gly Gln Phe Leu
            260                 265                 270

Arg Leu Leu Cys Ala Ala Asp Ser Gln Pro Pro Ala Thr Leu Ser Trp
        275                 280                 285

Val Leu Gln Asn Arg Val Leu Ser Ser Ser His Pro Trp Gly Pro Arg
    290                 295                 300

Pro Leu Gly Leu Glu Leu Pro Gly Val Lys Ala Gly Asp Ser Gly Arg
305                 310                 315                 320

Tyr Thr Cys Arg Ala Glu Asn Arg Leu Gly Ser Gln Gln Arg Ala Leu
                325                 330                 335

Asp Leu Ser Val Gln Tyr Pro Pro Glu Asn Leu Arg Val Met Val Ser
            340                 345                 350

Gln Ala Asn Arg Thr Val Leu Glu Asn Leu Gly Asn Gly Thr Ser Leu
        355                 360                 365

Pro Val Leu Glu Gly Gln Ser Leu Cys Leu Val Cys Val Thr His Ser
    370                 375                 380

Ser Pro Pro Ala Arg Leu Ser Trp Thr Gln Arg Gly Gln Val Leu Ser
385                 390                 395                 400

Pro Ser Gln Pro Ser Asp Pro Gly Val Leu Glu Leu Pro Arg Val Gln
                405                 410                 415

Val Glu His Glu Gly Glu Phe Thr Cys His Ala Arg His Pro Leu Gly
            420                 425                 430

Ser Gln His Val Ser Leu Ser Leu Ser Val His Tyr Ser Pro Lys Leu
```

-continued

```
        435                 440                 445

Leu Gly Pro Ser Cys Ser Trp Glu Ala Glu Gly Leu His Cys Ser Cys
    450                 455                 460

Ser Ser Gln Ala Ser Pro Ala Pro Ser Leu Arg Trp Trp Leu Gly Glu
465                 470                 475                 480

Glu Leu Leu Glu Gly Asn Ser Ser Gln Asp Ser Phe Glu Val Thr Pro
                485                 490                 495

Ser Ser Ala Gly Pro Trp Ala Asn Ser Ser Leu Ser Leu His Gly Gly
            500                 505                 510

Leu Ser Ser Gly Leu Arg Leu Arg Cys Glu Ala Trp Asn Val His Gly
        515                 520                 525

Ala Gln Ser Gly Ser Ile Leu Gln Leu Pro Asp Lys Lys Gly Leu Ile
    530                 535                 540

Ser Thr Ala Phe Ser Asn Gly Ala Phe Leu Gly Ile Gly Ile Thr Ala
545                 550                 555                 560

Leu Leu Phe Leu Cys Leu Ala Leu Ile Ile Met Lys Ile Leu Pro Lys
                565                 570                 575

Arg Arg Thr Gln Thr Glu Thr Pro Arg Pro Arg Phe Ser Arg His Ser
            580                 585                 590

Thr Ile Leu Asp Tyr Ile Asn Val Val Pro Thr Ala Gly Pro Leu Ala
        595                 600                 605

Gln Lys Arg Asn Gln Lys Ala Thr Pro Asn Ser Pro Arg Thr Pro Leu
    610                 615                 620

Pro Pro Gly Ala Pro Ser Pro Glu Ser Lys Lys Asn Gln Lys Lys Gln
625                 630                 635                 640

Tyr Gln Leu Pro Ser Phe Pro Glu Pro Lys Ser Ser Thr Gln Ala Pro
                645                 650                 655

Glu Ser Gln Glu Ser Gln Glu Glu Leu His Tyr Ala Thr Leu Asn Phe
            660                 665                 670

Pro Gly Val Arg Pro Arg Pro Glu Ala Arg Met Pro Lys Gly Thr Gln
        675                 680                 685

Ala Asp Tyr Ala Glu Val Lys Phe Gln
    690                 695


<210> SEQ ID NO 34
<211> LENGTH: 3400
<212> TYPE: DNA
<213> ORGANISM: Homo sapiens

<400> SEQUENCE: 34

gcccccagga gacccagagg acaactgggc aaggtgggcc ggagagtgtg ggggaaggca      60

aaggagttct gtgagctcag cgtctgaagc tcatttcatg catcaggccc cagggctcag     120

cttccgcctt cggcttcccc ttctgccaag agccctgagc cactcacagc acgaccagag     180

aacaggcctg tctcaggcag gccctgcgcc tcctatgcgg agatgctact gccactgctg     240

ctgtcctcgc tgctgggcgg gtcccaggct atggatggga gattctggat acgagtgcag     300

gagtcagtga tggtgccgga gggcctgtgc atctctgtgc cctgctcttt ctcctacccc     360

cgacaagact ggacagggtc taccccagct tatggctact ggttcaaagc agtgactgag     420

acaaccaagg gtgctcctgt ggccacaaac caccagagtc gagaggtgga aatgagcacc     480

cggggccgat tccagctcac tggggatccc gccaagggga actgctcctt ggtgatcaga     540

gacgcgcaga tgcaggatga gtcacagtac ttctttcggg tggagagagg aagctatgtg     600

agatataatt tcatgaacga tgggttcttt ctaaaagtaa cagccctgac tcagaagcct     660
```

-continued

```
gatgtctaca tccccgagac cctggagccc gggcagccgg tgacggtcat ctgtgtgttt    720
aactgggcct ttgaggaatg tccacccccct tctttctcct ggacgggggc tgccctctcc    780
tcccaaggaa ccaaaccaac gacctcccac ttctcagtgc tcagcttcac gcccagaccc    840
caggaccaca acaccgacct cacctgccat gtggacttct ccagaaaggg tgtgagcgca    900
cagaggaccg tccgactccg tgtggcctat gcccccagag accttgttat cagcatttca    960
cgtgacaaca cgccagccct ggagccccag ccccagggaa atgtcccata cctggaagcc   1020
caaaaaggcc agttcctgcg gctcctctgt gctgctgaca gccagccccc tgccacactg   1080
agctgggtcc tgcagaacag agtcctctcc tcgtcccatc cctggggccc tagacccctg   1140
gggctggagc tgcccggggt gaaggctggg gattcagggc gctacacctg ccgagcggag   1200
aacaggcttg gctcccagca gcgagccctg gacctctctg tgcagtatcc tccagagaac   1260
ctgagagtga tggtttccca agcaaacagg acagtcctgg aaaaccttgg gaacggcacg   1320
tctctcccag tactggaggg ccaaagcctg tgcctggtct gtgtcacaca cagcagcccc   1380
ccagccaggc tgagctggac ccagagggga caggttctga gcccctccca gccctcagac   1440
cccggggtcc tggagctgcc tcgggttcaa gtggagcacg aaggagagtt cacctgccac   1500
gctcggcacc cactgggctc ccagcacgtc tctctcagcc tctccgtgca ctactccccg   1560
aagctgctgg gcccctcctg ctcctgggag gctgagggtc tgcactgcag ctgctcctcc   1620
caggccagcc cggcccccctc tctgcgctgg tggcttgggg aggagctgct ggaggggaac   1680
agcagccagg actccttcga ggtcaccccc agctcagccg ggccctgggc caacagctcc   1740
ctgagcctcc atggagggct cagctccggc ctcaggctcc gctgtgaggc ctggaacgtc   1800
catggggccc agagtggatc catcctgcag ctgccagata agaagggact catctcaacg   1860
gcattctcca acggagcgtt tctgggaatc ggcatcacgg ctcttctttt cctctgcctg   1920
gccctgatca tcatgaagat tctaccgaag agacggactc agacagaaac cccgaggccc   1980
aggttctccc ggcacagcac gatcctggat tacatcaatg tggtcccgac ggctggcccc   2040
ctggctcaga agcggaatca gaaagccaca ccaaacagtc ctcggacccc tcttccacca   2100
ggtgctccct ccccagaatc aaagaagaac cagaaaaagc agtatcagtt gcccagtttc   2160
ccagaaccca aatcatccac tcaagcccca gaatcccagg agagccaaga ggagctccat   2220
tatgccacgc tcaacttccc aggcgtcaga cccaggcctg aggcccggat gcccaagggc   2280
acccaggcgg attatgcaga agtcaagttc caatgagggt ctcttaggct ttaggactgg   2340
gacttcggct agggaggaag gtagagtaag aggttgaaga taacagagtg caaagtttcc   2400
ttctctccct ctctctctct ctttctctct ctctctctct ttctctctct tttaaaaaaa   2460
catctggcca gggcacagtg gctcacgcct gtaatcccag cactttggga ggttgaggtg   2520
ggcagatcgc ctgaggtcgg gagttcgaga ccagcctggc caacttggtg aaaccccgtc   2580
tctactaaaa atacaaaaat tagctgggca tggtggcagg cgcctgtaat cctacctact   2640
tgggaagctg aggcaggaga atcacttgaa cctgggagac ggaggttgca gtgagccaag   2700
atcacaccat tgcacgccag cctgggcaac aaagcgagac tccatctcaa aaaaaaaatc   2760
ctccaaatgg gttgggtgtc tgtaatccca gcactttggg aggctaaggt gggtggattg   2820
cttgagccca ggagttcgag accagcctgg gcaacatggt gaaaccccat ctctacaaaa   2880
aatacaaaac atagctgggc ttggtggtgt gtgcctgtag tcccagctgt cagacattta   2940
aaccagagca actccatctg gaataggagc tgaataaaat gaggctgaga cctactgggc   3000
```

tgcattctca gacagtggag gcattctaag tcacaggatg agacaggagg tccgtacaag 3060
atacaggtca taaagacttt gctgataaaa cagattgcag taaagaagcc aaccaaatcc 3120
caccaaaacc aagttggcca cgagagtgac ctctggtcgt cctcactgct acactcctga 3180
cagcaccatg acagtttaca aatgccatgg caacatcagg aagttacccg atatgtccca 3240
aaagggggag gaatgaataa tccacccctt gtttagcaaa taagcaagaa ataaccataa 3300
aagtgggcaa ccagcagctc taggcgctgc tcttgtctat ggagtagcca ttcttttgtt 3360
cctttacttt cttaataaac ttgctttcac cttaaaaaaa 3400

<210> SEQ ID NO 35
<211> LENGTH: 698
<212> TYPE: PRT
<213> ORGANISM: Homo sapiens

<400> SEQUENCE: 35

Met Val Pro Gly Gln Ala Gln Pro Gln Ser Pro Glu Met Leu Leu Leu
1 5 10 15

Pro Leu Leu Leu Pro Val Leu Gly Ala Gly Ser Leu Asn Lys Asp Pro
20 25 30

Ser Tyr Ser Leu Gln Val Gln Arg Gln Val Pro Val Pro Glu Gly Leu
35 40 45

Cys Val Ile Val Ser Cys Asn Leu Ser Tyr Pro Arg Asp Gly Trp Asp
50 55 60

Glu Ser Thr Ala Ala Tyr Gly Tyr Trp Phe Lys Gly Arg Thr Ser Pro
65 70 75 80

Lys Thr Gly Ala Pro Val Ala Thr Asn Asn Gln Ser Arg Glu Val Glu
85 90 95

Met Ser Thr Arg Asp Arg Phe Gln Leu Thr Gly Asp Pro Gly Lys Gly
100 105 110

Ser Cys Ser Leu Val Ile Arg Asp Ala Gln Arg Glu Asp Glu Ala Trp
115 120 125

Tyr Phe Phe Arg Val Glu Arg Gly Ser Arg Val Arg His Ser Phe Leu
130 135 140

Ser Asn Ala Phe Phe Leu Lys Val Thr Ala Leu Thr Lys Lys Pro Asp
145 150 155 160

Val Tyr Ile Pro Glu Thr Leu Glu Pro Gly Gln Pro Val Thr Val Ile
165 170 175

Cys Val Phe Asn Trp Ala Phe Lys Lys Cys Pro Ala Pro Ser Phe Ser
180 185 190

Trp Thr Gly Ala Ala Leu Ser Pro Arg Arg Thr Arg Pro Ser Thr Ser
195 200 205

His Phe Ser Val Leu Ser Phe Thr Pro Ser Pro Gln Asp His Asp Thr
210 215 220

Asp Leu Thr Cys His Val Asp Phe Ser Arg Lys Gly Val Ser Ala Gln
225 230 235 240

Arg Thr Val Arg Leu Arg Val Ala Tyr Ala Pro Lys Asp Leu Ile Ile
245 250 255

Ser Ile Ser His Asp Asn Thr Ser Ala Leu Glu Leu Gln Gly Asn Val
260 265 270

Ile Tyr Leu Glu Val Gln Lys Gly Gln Phe Leu Arg Leu Leu Cys Ala
275 280 285

Ala Asp Ser Gln Pro Pro Ala Thr Leu Ser Trp Val Leu Gln Asp Arg
290 295 300

-continued

```
Val Leu Ser Ser Ser His Pro Trp Gly Pro Arg Thr Leu Gly Leu Glu
305                 310                 315                 320

Leu Arg Gly Val Arg Ala Gly Asp Ser Gly Arg Tyr Thr Cys Arg Ala
                325                 330                 335

Glu Asn Arg Leu Gly Ser Gln Gln Gln Ala Leu Asp Leu Ser Val Gln
            340                 345                 350

Tyr Pro Pro Glu Asn Leu Arg Val Met Val Ser Gln Ala Asn Arg Thr
        355                 360                 365

Val Leu Glu Asn Leu Gly Asn Gly Thr Ser Leu Pro Val Leu Glu Gly
    370                 375                 380

Gln Ser Leu Arg Leu Val Cys Val Thr His Ser Ser Pro Pro Ala Arg
385                 390                 395                 400

Leu Ser Trp Thr Arg Trp Gly Gln Thr Val Gly Pro Ser Gln Pro Ser
                405                 410                 415

Asp Pro Gly Val Leu Glu Leu Pro Pro Ile Gln Met Glu His Glu Gly
            420                 425                 430

Glu Phe Thr Cys His Ala Gln His Pro Leu Gly Ser Gln His Val Ser
        435                 440                 445

Leu Ser Leu Ser Val His Tyr Pro Pro Gln Leu Leu Gly Pro Ser Cys
    450                 455                 460

Ser Trp Glu Ala Glu Gly Leu His Cys Ser Cys Ser Ser Gln Ala Ser
465                 470                 475                 480

Pro Ala Pro Ser Leu Arg Trp Trp Leu Gly Glu Glu Leu Leu Glu Gly
                485                 490                 495

Asn Ser Ser Gln Gly Ser Phe Glu Val Thr Pro Ser Ser Ala Gly Pro
            500                 505                 510

Trp Ala Asn Ser Ser Leu Ser Leu His Gly Gly Leu Ser Ser Gly Leu
        515                 520                 525

Arg Leu Arg Cys Lys Ala Trp Asn Val His Gly Ala Gln Ser Gly Ser
    530                 535                 540

Val Phe Gln Leu Leu Pro Gly Lys Leu Glu His Gly Gly Gly Leu Gly
545                 550                 555                 560

Leu Gly Ala Ala Leu Gly Ala Gly Val Ala Ala Leu Leu Ala Phe Cys
                565                 570                 575

Ser Cys Leu Val Val Phe Arg Val Lys Ile Cys Arg Lys Glu Ala Arg
            580                 585                 590

Lys Arg Ala Ala Ala Glu Gln Asp Val Pro Ser Thr Leu Gly Pro Ile
        595                 600                 605

Ser Gln Gly His Gln His Glu Cys Ser Ala Gly Ser Ser Gln Asp His
    610                 615                 620

Pro Pro Pro Gly Ala Ala Thr Tyr Thr Pro Gly Lys Gly Glu Glu Gln
625                 630                 635                 640

Glu Leu His Tyr Ala Ser Leu Ser Phe Gln Gly Leu Arg Leu Trp Glu
                645                 650                 655

Pro Ala Asp Gln Glu Ala Pro Ser Thr Thr Glu Tyr Ser Glu Ile Lys
            660                 665                 670

Ile His Thr Gly Gln Pro Leu Arg Gly Pro Gly Phe Gly Leu Gln Leu
        675                 680                 685

Glu Arg Glu Met Ser Gly Met Val Pro Lys
    690                 695
```

<210> SEQ ID NO 36
<211> LENGTH: 3183
<212> TYPE: DNA

<213> ORGANISM: Homo sapiens

<400> SEQUENCE: 36

```
cgaggctcct cctctgtgga tggtcactgc ccctccacca ggcttcctgc tggaggagtt     60
tccttcccag ccaggccggc ccagaagcca gatggtcccg ggacaggccc agccccagag    120
cccagagatg ctgctgctgc ccctgctgct gcccgtgctg ggggcggggt ccctgaacaa    180
ggatcccagt tacagtcttc aagtgcagag gcaggtgccg gtgccggagg gcctgtgtgt    240
catcgtgtct tgcaacctct cctacccccg ggatggctgg gacgagtcta ctgctgctta    300
tggctactgg ttcaaaggac ggaccagccc aaagacgggt gctcctgtgg ccactaacaa    360
ccagagtcga gaggtggaaa tgagcacccg ggaccgattc cagctcactg gggatcccgg    420
caaagggagc tgctccttgg tgatcagaga cgcgcagagg gaggatgagg catggtactt    480
ctttcgggtg gagagaggaa gccgtgtgag acatagtttc ctgagcaatg cgttctttct    540
aaaagtaaca gccctgacta agaagcctga tgtctacatc cccgagaccc tggagcccgg    600
gcagccggtg acggtcatct gtgtgtttaa ctgggctttc aagaaatgtc cagccccttc    660
tttctcctgg acgggggctg ccctctcccc tagaagaacc agaccaagca cctcccactt    720
ctcagtgctc agcttcacgc ccagccccca ggaccacgac accgacctca cctgccatgt    780
ggacttctcc agaaagggtg tgagcgcaca gaggaccgtc cgactccgtg tggcctatgc    840
ccccaaagac cttattatca gcatttcaca tgacaacacg tcagccctgg aactccaggg    900
aaacgtcata tatctggaag ttcagaaagg ccagttcctg cggctcctct gtgctgctga    960
cagccagccc cctgccacgc tgagctgggt cctgcaggac agagtcctct cctcgtccca   1020
cccctggggc cccagaaccc tggggctgga gctgcgtggg gtaagggccg gggattcagg   1080
gcgctacacc tgccgagcgg agaacaggct tggctcccag cagcaagccc tggacctctc   1140
tgtgcagtat cctccagaga acctgagagt gatggtttcc caagcaaaca ggacagtcct   1200
ggaaaacctc gggaacggca catccctccc ggtcctggag ggccaaagcc tgcgcctggt   1260
ctgtgtcacc cacagcagcc ccccagccag gctgagctgg acccggtggg gacagaccgt   1320
gggcccctcc cagccctcag accccggggt cctggagctg ccacccattc aaatggagca   1380
cgaaggagag ttcacctgcc acgctcagca ccctctgggc tcccagcacg tctctctcag   1440
cctctccgtg cactaccctc cacagctgct gggcccctcc tgctcctggg aggctgaggg   1500
tctgcactgc agctgctcct cccaggccag cccggccccc tctctgcgct ggtggcttgg   1560
ggaggagctg ctggagggga acagcagtca gggctccttc gaggtcaccc ccagctcagc   1620
cgggccctgg gccaacagct ccctgagcct ccatggaggg ctcagctccg gcctcaggct   1680
ccgctgtaag gcctggaacg tccacggggc ccagagtggc tctgtcttcc agctgctacc   1740
agggaagctg gagcatgggg gaggacttgg cctgggggct gccctgggag ctggcgtcgc   1800
tgccctgctc gctttctgtt cctgccttgt cgtcttcagg gtgaagatct gcaggaagga   1860
agctcgcaag agggcagcag ctgagcagga cgtgccctcc accctgggac ccatctccca   1920
gggtcaccag catgaatgct cggcaggcag ctcccaagac cacccgcccc caggtgcagc   1980
cacctacacc ccggggaagg gggaagagca ggagctccac tatgcctccc tcagcttcca   2040
gggcctgagg ctctgggagc ctgcggacca ggaggccccc agcaccaccg agtactcgga   2100
gatcaagatc cacacaggac agcccctgag gggcccaggc tttgggcttc aattggagag   2160
ggagatgtca gggatggttc caaagtgaag aggtctccat ggcaacagga caccagcaag   2220
tgtgtgggag tcgcactggt gtgacggcca gaactggact cagatttcag ccccatcccc   2280
```

```
aatgaagagc ttgagtttga agattatact ttttttgaga cagggtctga ctctgtcctc   2340
caggccagag tccagtggtg caatctcagc tcactgtagc ctcaacctgc caggttgaag   2400
tgagcctccc atttcagcct cccaagtagc tgggactaca attgtgagcc accatgccag   2460
gctcattgtt atatttttag tagagacagg gttttgccat gtttccctgg ctggtctcag   2520
actcctgggc tcaagcaatc tgcccgcctc tgcctcccaa agtgctggga ttacagacgt   2580
gagccaccac agctggctga agattatact ttcaattcag agcgagtttg aagatgacac   2640
tttgaggcat cgtgtctatg gttcattact acagaagctt ctctggatgt gtaaagcaca   2700
ggaaaccagg cagaggaggc acagggtgct ctccagaacg agaagccagc tcctggagtt   2760
gtttgctgca actgccattc cccgttgatg accatgctct tccttcagaa gagggagagt   2820
gagaggacca agtccaagtg gttcccattt gaacatttaa aaaaaaaaaa aaggctgggc   2880
atggtggctc acgcctgtaa tctcaacact ttgggaggct gaagtgggtg gatcacaagt   2940
caggagttca agaccagcct gggcaagatg gtgaaacccc atctctacta aaaatacaaa   3000
aattagccgg gcatggtggc gggcgcctaa aatcccagct actcgggaga ctaggcagag   3060
aattggttga acccgggagg tggaggttgc agtgagccga gatcgtccca ctgcactcca   3120
gcctgggcaa cagagtgaga ctctgtttct aaataaataa atgaaaaaaa aaaaaaaaaa   3180
aaa                                                                 3183

<210> SEQ ID NO 37
<211> LENGTH: 595
<212> TYPE: PRT
<213> ORGANISM: Homo sapiens

<400> SEQUENCE: 37

Met Leu Leu Leu Leu Leu Leu Leu Pro Pro Leu Leu Cys Gly Arg Val
1               5                   10                  15

Gly Ala Lys Glu Gln Lys Asp Tyr Leu Leu Thr Met Gln Lys Ser Val
            20                  25                  30

Thr Val Gln Glu Gly Leu Cys Val Ser Val Leu Cys Ser Phe Ser Tyr
        35                  40                  45

Pro Gln Asn Gly Trp Thr Ala Ser Asp Pro Val His Gly Tyr Trp Phe
    50                  55                  60

Arg Ala Gly Asp His Val Ser Arg Asn Ile Pro Val Ala Thr Asn Asn
65                  70                  75                  80

Pro Ala Arg Ala Val Gln Glu Glu Thr Arg Asp Arg Phe His Leu Leu
                85                  90                  95

Gly Asp Pro Gln Asn Lys Asp Cys Thr Leu Ser Ile Arg Asp Thr Arg
            100                 105                 110

Glu Ser Asp Ala Gly Thr Tyr Val Phe Cys Val Glu Arg Gly Asn Met
        115                 120                 125

Lys Trp Asn Tyr Lys Tyr Asp Gln Leu Ser Val Asn Val Thr Ala Ser
    130                 135                 140

Gln Asp Leu Leu Ser Arg Tyr Arg Leu Glu Val Pro Glu Ser Val Thr
145                 150                 155                 160

Val Gln Glu Gly Leu Cys Val Ser Val Pro Cys Ser Val Leu Tyr Pro
                165                 170                 175

His Tyr Asn Trp Thr Ala Ser Ser Pro Val Tyr Gly Ser Trp Phe Lys
            180                 185                 190

Glu Gly Ala Asp Ile Pro Trp Asp Ile Pro Val Ala Thr Asn Thr Pro
        195                 200                 205
```

```
Ser Gly Lys Val Gln Glu Asp Thr His Gly Arg Phe Leu Leu Leu Gly
    210                 215                 220

Asp Pro Gln Thr Asn Asn Cys Ser Leu Ser Ile Arg Asp Ala Arg Lys
225                 230                 235                 240

Gly Asp Ser Gly Lys Tyr Tyr Phe Gln Val Glu Arg Gly Ser Arg Lys
                245                 250                 255

Trp Asn Tyr Ile Tyr Asp Lys Leu Ser Val His Val Thr Ala Leu Thr
            260                 265                 270

His Met Pro Thr Phe Ser Ile Pro Gly Thr Leu Glu Ser Gly His Pro
        275                 280                 285

Arg Asn Leu Thr Cys Ser Val Pro Trp Ala Cys Glu Gln Gly Thr Pro
    290                 295                 300

Pro Thr Ile Thr Trp Met Gly Ala Ser Val Ser Ser Leu Asp Pro Thr
305                 310                 315                 320

Ile Thr Arg Ser Ser Met Leu Ser Leu Ile Pro Gln Pro Gln Asp His
                325                 330                 335

Gly Thr Ser Leu Thr Cys Gln Val Thr Leu Pro Gly Ala Gly Val Thr
            340                 345                 350

Met Thr Arg Ala Val Arg Leu Asn Ile Ser Tyr Pro Pro Gln Asn Leu
        355                 360                 365

Thr Met Thr Val Phe Gln Gly Asp Gly Thr Ala Ser Thr Thr Leu Arg
    370                 375                 380

Asn Gly Ser Ala Leu Ser Val Leu Glu Gly Gln Ser Leu His Leu Val
385                 390                 395                 400

Cys Ala Val Asp Ser Asn Pro Pro Ala Arg Leu Ser Trp Thr Trp Gly
                405                 410                 415

Ser Leu Thr Leu Ser Pro Ser Gln Ser Ser Asn Leu Gly Val Leu Glu
            420                 425                 430

Leu Pro Arg Val His Val Lys Asp Glu Gly Glu Phe Thr Cys Arg Ala
        435                 440                 445

Gln Asn Pro Leu Gly Ser Gln His Ile Ser Leu Ser Leu Ser Leu Gln
    450                 455                 460

Asn Glu Tyr Thr Gly Lys Met Arg Pro Ile Ser Gly Val Thr Leu Gly
465                 470                 475                 480

Ala Phe Gly Gly Ala Gly Ala Thr Ala Leu Val Phe Leu Tyr Phe Cys
                485                 490                 495

Ile Ile Phe Val Val Val Arg Ser Cys Arg Lys Lys Ser Ala Arg Pro
            500                 505                 510

Ala Val Gly Val Gly Asp Thr Gly Met Glu Asp Ala Asn Ala Val Arg
        515                 520                 525

Gly Ser Ala Ser Gln Gly Pro Leu Ile Glu Ser Pro Ala Asp Asp Ser
    530                 535                 540

Pro Pro His His Ala Pro Pro Ala Leu Ala Thr Pro Ser Pro Glu Glu
545                 550                 555                 560

Gly Glu Ile Gln Tyr Ala Ser Leu Ser Phe His Lys Ala Arg Pro Gln
                565                 570                 575

Tyr Pro Gln Glu Gln Glu Ala Ile Gly Tyr Glu Tyr Ser Glu Ile Asn
            580                 585                 590

Ile Pro Lys
        595
```

<210> SEQ ID NO 38
<211> LENGTH: 1788

<212> TYPE: DNA
<213> ORGANISM: Homo sapiens

<400> SEQUENCE: 38
atgctactgc tgctgctact gctgccaccc ctgctctgtg ggagagtggg ggctaaggaa 60
cagaaggatt acctgctgac aatgcagaag tccgtgacgg tgcaggaggg cctgtgtgtc 120
tctgtgcttt gctccttctc ctaccccaa aatggctgga ctgcctccga tccagttcat 180
ggctactggt tccgggcagg ggaccatgta agccggaaca ttccagtggc cacaaacaac 240
ccagctcgag cagtgcagga ggagactcgg gaccgattcc acctccttgg ggacccacag 300
aacaaggatt gtaccctgag catcagagac accagagaga gtgatgcagg gacatacgtc 360
ttttgtgtag agagaggaaa tatgaaatgg aattataaat atgaccagct ctctgtgaat 420
gtgacagcgt cccaggacct actgtcaaga tacaggctgg aggtgccaga gtcggtgact 480
gtgcaggagg gtctgtgtgt ctctgtgccc tgcagtgtcc tttaccccca ttacaactgg 540
actgcctcta gccctgttta tggatcctgg ttcaaggaag ggccgatat accatgggat 600 attccagtgg ccacaaacac cccaagtgga aaagtgcaag aggataccca cggtcgattc 660
ctcctccttg gggacccaca gaccaacaac tgctccctga gcatcagaga tgccaggaag 720
ggggattcag ggaagtacta cttccaggtg gagagaggaa gcaggaaatg gaactacata 780
tatgacaagc tctctgtgca tgtgacagcc ctgactcaca tgcccacctt ctccatcccg 840
gggaccctgg agtctggcca ccccaggaac ctgacctgct ctgtgccctg ggcctgtgaa 900
caggggacgc ccccacgat cacctggatg gggcctccg tgtcctccct ggaccccact 960
atcactcgct cctcgatgct cagcctcatc ccacagcccc aggaccatgg caccagcctc 1020
acctgtcagg tgaccttgcc tggggccggc gtgaccatga ccagggctgt ccgactcaac 1080
atatcctatc ctcctcagaa cttgaccatg actgtcttcc aaggagatgg cacagcatcc 1140
acaaccttga ggaatggctc ggccctttca gtcctggagg gccagtccct gcaccttgtc 1200
tgtgctgtcg acagcaatcc ccctgccagg ctgagctgga cctgggggag cctgaccctg 1260
agcccctcac agtcctcgaa ccttggggtg ctggagctgc ctcgagtgca tgtgaaggat 1320
gaaggggaat tcacctgccg agctcagaac cctctaggct cccagcacat ttccctgagc 1380
ctctccctgc aaaacgagta cacaggcaaa atgaggccta tatcaggagt gacgctaggg 1440
gcattcgggg gagctggagc cacagccctg gtcttcctgt acttctgcat catcttcgtt 1500
gtagtgaggt cctgcaggaa gaaatcggca aggccagcag tgggcgtggg ggatacaggc 1560
atggaggacg caaacgctgt caggggctca gcctctcagg gacccctgat tgaatccccg 1620
gcagatgaca gcccccaca ccatgctccg ccagccctgg ccacccctc cccagaggaa 1680 ggagagatcc agtatgcatc cctcagcttc cacaaagcga ggcctcagta cccacaggaa 1740
caggaggcca tcggctatga gtactccgag atcaacatcc ccaagtga 1788

<210> SEQ ID NO 39
<211> LENGTH: 396
<212> TYPE: PRT
<213> ORGANISM: Homo sapiens

<400> SEQUENCE: 39

Met Leu Pro Leu Leu Leu Leu Pro Leu Leu Trp Gly Gly Ser Leu Gln
1 5 10 15

Glu Lys Pro Val Tyr Glu Leu Gln Val Gln Lys Ser Val Thr Val Gln
20 25 30

```
Glu Gly Leu Cys Val Leu Val Pro Cys Ser Phe Ser Tyr Pro Trp Arg
        35                  40                  45

Ser Trp Tyr Ser Ser Pro Pro Leu Tyr Val Tyr Trp Phe Arg Asp Gly
    50                  55                  60

Glu Ile Pro Tyr Tyr Ala Glu Val Val Ala Thr Asn Asn Pro Asp Arg
65                  70                  75                  80

Arg Val Lys Pro Glu Thr Gln Gly Arg Phe Arg Leu Leu Gly Asp Val
                85                  90                  95

Gln Lys Lys Asn Cys Ser Leu Ser Ile Gly Asp Ala Arg Met Glu Asp
            100                 105                 110

Thr Gly Ser Tyr Phe Phe Arg Val Glu Arg Gly Arg Asp Val Lys Tyr
        115                 120                 125

Ser Tyr Gln Gln Asn Lys Leu Asn Leu Glu Val Thr Ala Leu Ile Glu
    130                 135                 140

Lys Pro Asp Ile His Phe Leu Glu Pro Leu Glu Ser Gly Arg Pro Thr
145                 150                 155                 160

Arg Leu Ser Cys Ser Leu Pro Gly Ser Cys Glu Ala Gly Pro Pro Leu
                165                 170                 175

Thr Phe Ser Trp Thr Gly Asn Ala Leu Ser Pro Leu Asp Pro Glu Thr
            180                 185                 190

Thr Arg Ser Ser Glu Leu Thr Leu Thr Pro Arg Pro Glu Asp His Gly
        195                 200                 205

Thr Asn Leu Thr Cys Gln Val Lys Arg Gln Gly Ala Gln Val Thr Thr
    210                 215                 220

Glu Arg Thr Val Gln Leu Asn Val Ser Tyr Ala Pro Gln Asn Leu Ala
225                 230                 235                 240

Ile Ser Ile Phe Phe Arg Asn Gly Thr Gly Thr Ala Leu Arg Ile Leu
                245                 250                 255

Ser Asn Gly Met Ser Val Pro Ile Gln Glu Gly Gln Ser Leu Phe Leu
            260                 265                 270

Ala Cys Thr Val Asp Ser Asn Pro Pro Ala Ser Leu Ser Trp Phe Arg
        275                 280                 285

Glu Gly Lys Ala Leu Asn Pro Ser Gln Thr Ser Met Ser Gly Thr Leu
    290                 295                 300

Glu Leu Pro Asn Ile Gly Ala Arg Glu Gly Gly Glu Phe Thr Cys Arg
305                 310                 315                 320

Val Gln His Pro Leu Gly Ser Gln His Leu Ser Phe Ile Leu Ser Val
                325                 330                 335

Gln Arg Ser Ser Ser Ser Cys Ile Cys Val Thr Glu Lys Gln Gln Gly
            340                 345                 350

Ser Trp Pro Leu Val Leu Thr Leu Ile Arg Gly Ala Leu Met Gly Ala
        355                 360                 365

Gly Phe Leu Leu Thr Tyr Gly Leu Thr Trp Ile Tyr Tyr Thr Arg Cys
    370                 375                 380

Gly Gly Pro Gln Gln Ser Arg Ala Glu Arg Pro Gly
385                 390                 395
```

```
<210> SEQ ID NO 40
<211> LENGTH: 1191
<212> TYPE: DNA
<213> ORGANISM: Homo sapiens

<400> SEQUENCE: 40

atgctgcccc tgctgctgct gcccctgctg tggggggggt ccctgcagga gaagccagtg      60
```

```
tacgagctgc aagtgcagaa gtcggtgacg gtgcaggagg gcctgtgcgt ccttgtgccc    120

tgctccttct cttaccccctg gagatcctgg tattcctctc cccactcta cgtctactgg    180

ttccgggacg gggagatccc atactacgct gaggttgtgg ccacaaacaa cccagacaga    240

agagtgaagc cagagaccca gggccgattc cgcctccttg gggatgtcca gaagaagaac    300

tgctccctga gcatcggaga tgccagaatg gaggacacgg gaagctattt cttccgcgtg    360

gagagaggaa gggatgtaaa atatagctac caacagaata agctgaactt ggaggtgaca    420

gccctgatag agaaacccga catccacttt ctggagcctc tggagtccgg ccgccccaca    480

aggctgagct gcagccttcc aggatcctgt gaagcgggac cacctctcac attctcctgg    540

acggggaatg ccctcagccc cctggacccc gagaccaccc gctcctcgga gctcaccctc    600

acccccaggc ccgaggacca tggcaccaac ctcacctgtc aggtgaaacg ccaaggagct    660

caggtgacca cggagagaac tgtccagctc aatgtctcct atgctccaca gaacctcgcc    720

atcagcatct tcttcagaaa tggcacaggc acagccctgc ggatcctgag caatggcatg    780

tcggtgccca tccaggaggg ccagtccctg ttcctcgcct gcacagttga cagcaacccc    840

cctgcctcac tgagctggtt ccgggaggga aaagccctca atccttccca gacctcaatg    900

tctgggaccc tggagctgcc taacatagga gctagagagg gaggggaatt cacctgccgg    960

gttcagcatc cgctgggctc ccagcacctg tccttcatcc tttctgtgca gagaagctcc   1020

tcttcctgca tatgtgtaac tgagaaacag cagggctcct ggcccctcgt cctcaccctg   1080

atcagggggg ctctcatggg ggctggcttc ctcctcacct atggcctcac ctggatctac   1140

tataccaggt gtggaggccc ccagcagagc agggctgaga ggcctggctg a            1191
```

```
<210> SEQ ID NO 41
<211> LENGTH: 328
<212> TYPE: PRT
<213> ORGANISM: Homo sapiens

<400> SEQUENCE: 41

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175
```

```
Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Leu Gly Ala Leu Gly
            260                 265                 270

Phe Lys Ala Leu Leu Leu Leu Gly Val Leu Ala Ala Arg Ala Ala Arg
        275                 280                 285

Arg Arg Pro Glu His Leu Asp Thr Pro Asp Thr Pro Pro Arg Ser Gln
    290                 295                 300

Ala Gln Glu Ser Asn Tyr Glu Asn Leu Ser Gln Met Asn Pro Arg Ser
305                 310                 315                 320

Pro Pro Ala Thr Met Cys Ser Pro
                325
```

```
<210> SEQ ID NO 42
<211> LENGTH: 987
<212> TYPE: DNA
<213> ORGANISM: Homo sapiens

<400> SEQUENCE: 42

atggaaaagt ccatctggct gctggcctgc ttggcgtggg ttctcccgac aggctcattt     60

gtgagaacta aaatagatac tacggagaac ttgctcaaca cagaggtgca cagctcgcca    120

gcgcagcgct ggtccatgca ggtgccaccc gaggtgagcg cggaggcagg cgacgcggca    180

gtgctgccct gcaccttcac gcacccgcac cgccactacg acgggccgct gacggccatc    240

tggcgcgcgg gcgagcccta tgcgggcccg caggtgttcc gctgcgctgc ggcgcggggc    300

agcgagctct gccagacggc gctgagcctg cacggccgct tccggctgct gggcaacccg    360

cgccgcaacg acctctcgct gcgcgtcgag cgcctcgccc tggctgacga ccgccgctac    420

ttctgccgcg tcgagttcgc cggcgacgtc catgaccgct acgagagccg ccacggcgtc    480

cggctgcacg tgacagccgc gccgcggatc gtcaacatct cggtgctgcc cagtccggct    540

cacgccttcc gcgcgctctg cactgccgaa ggggagccgc cgcccgccct cgcctggtcc    600

ggcccggccc tgggcaacag cttggcagcc gtgcggagcc cgcgtgaggg tcacggccac    660

ctagtgaccg ccgaactgcc cgcactgacc catgacggcc gctacacgtg tacggccgcc    720

aacagcctgg gccgctccga ggccagcgtc tacctgttcc gcttccatgg cgccagcggg    780

gcctcgacgg tcgccctcct gctcggcgct ctcggcttca aggcgctgct gctgctcggg    840

gtcctggccg cccgcgctgc ccgccgccgc ccagagcatc tggacacccc ggacacccca    900

ccacggtccc aggcccagga gtccaattat gaaaatttga gccagatgaa cccccggagc    960

ccaccagcca ccatgtgctc accgtga                                        987
```

```
<210> SEQ ID NO 43
<211> LENGTH: 92
<212> TYPE: PRT
<213> ORGANISM: Homo sapiens

<400> SEQUENCE: 43
```

Gln Ser Ser Val Thr Val Gln Glu Gly Met Cys Val His Val Arg Cys
1 5 10 15

Ser Phe Ser Tyr Pro Val Asp Ser Gln Thr Asp Ser Asp Pro Val His
20 25 30

Gly Tyr Trp Phe Arg Ala Gly Asn Asp Ile Ser Trp Lys Ala Pro Val
35 40 45

Ala Thr Asn Asn Pro Ala Trp Ala Val Gln Glu Glu Thr Arg Asp Arg
50 55 60

Phe His Leu Leu Gly Asp Pro Gln Thr Lys Asn Cys Thr Leu Ser Ile
65 70 75 80

Arg Asp Ala Arg Met Ser Asp Ala Gly Arg Tyr Phe
85 90

<210> SEQ ID NO 44
<211> LENGTH: 118
<212> TYPE: PRT
<213> ORGANISM: Homo sapiens

<400> SEQUENCE: 44

Leu Thr Met Gln Ser Ser Val Thr Val Gln Glu Gly Leu Cys Val His
1 5 10 15

Val Pro Cys Ser Phe Ser Tyr Pro Ser His Gly Trp Ile Tyr Pro Gly
20 25 30

Pro Val Val His Gly Tyr Trp Phe Arg Glu Gly Ala Asn Thr Asp Gln
35 40 45

Asp Ala Pro Val Ala Thr Asn Asn Pro Ala Arg Ala Val Trp Glu Glu
50 55 60

Thr Arg Asp Arg Phe His Leu Leu Gly Asp Pro His Thr Lys Asn Cys
65 70 75 80

Thr Leu Ser Ile Arg Asp Ala Arg Arg Ser Asp Ala Gly Arg Tyr Phe
85 90 95

Phe Arg Met Glu Lys Gly Ser Ile Lys Trp Asn Tyr Lys His His Arg
100 105 110

Leu Ser Val Asn Val Thr
115

<210> SEQ ID NO 45
<211> LENGTH: 1773
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
cagaccagca agctgctgac catgcagagc agcgtgaccg tgcaggaggg cctgtgcgtg 60
catgtgccct gcagcttcag ctaccccagc cacggctgga tctaccccgg tcccgtagtg 120
cacggctact ggttcaggga gggcgccaac accgaccagg acgctcccgt ggcaaccaac 180
aaccccgcca gggccgtgtg ggaggagacc agggacaggt tccacctgct gggcgacccc 240
cacaccaaga actgcaccct gagcatcagg gacgccagga ggagcgacgc cggcaggtac 300
ttcttcagga tggagaaggg gtctatcaag tggaactaca agcaccaccg gctgagcgtg 360
aatgtgaccg ccctgaccca ccggcccaat atcctcatcc ccggcaccct ggagagcggc 420
tgcccccaga atcttacctg cagcgtaccc tgggcctgcg agcagggcac ccctccaatg 480
atcagctgga tcggcaccag cgtgagcccc ctggacccta gtaccaccag gagcagcgtg 540
ctgaccctga tcccccagcc ccaggaccac ggaaccagcc tgacctgcca ggtgaccttc 600
cccggagcca gcgtaaccac caacaagacc gtgcacctga acgtgagcta cccaccccaa 660
aacctgacca tgaccgtgtt ccagggcgac ggcacggtga gcaccgtact gggcaacggc 720
agctctctga gcctgcccga gggccagagc ttgcggctgg tctgcgccgt ggatgctgtg 780
gacagcaacc ctcccgccag gctgagcctg agctggaggg gcctgaccct gtgccccagc 840
cagcccagca atcccggcgt gctggagctg ccctgggttc acctgaggga cgctgccgag 900
ttcacatgta gggcccagaa ccccctgggc tctcagcagg tgtacctgaa cgtgtctctt 960
cagagtaagg ccaccagcgg cgtgacccaa ggaggctata tccccgaggc tcctagagat 1020
ggccaggcct atgttcggaa ggatggcgaa tgggtgctgc tgagcacctt ccttgaacct 1080
cgagggccta ccatcaagcc ctgtcctcca tgcaagtgcc ccgctcctaa tctgctcgga 1140
ggccccagcg tgttcatctt cccacctaag atcaaggacg tgctgatgat ctctctgagc 1200
cccatcgtga cctgcgtggt ggtggatgtg tccgaggacg atcccgatgt gcagatcagt 1260
tggttcgtga acaacgtgga agtgcacaca gcccagacac agacccacag agaggactac 1320
aacagcaccc tgagagtggt gtctgccctg cctatccagc accaggattg gatgagcggc 1380
aaagaattca agtgcaaagt gaacaacaag gacctgcctg ctcctatcga gcggaccatc 1440
tctaagccta agggctctgt tagagcccct caggtgtacg tgctgcctcc tccagaggaa 1500
gagatgacca agaaacaagt gaccctgacc tgcatggtca ccgacttcat gcccgaggac 1560
atctacgtgg aatggaccaa caacggcaag accgagctga actacaagaa caccgagcct 1620
gtgctggaca gcgacggcag ctacttcatg tactccaagc tgcgcgtgga aaagaagaac 1680
tgggtcgagc ggaacagcta cagctgctct gtggtgcacg agggcctgca caatcaccac 1740
accaccaaga gcttcagccg tacgcctgga aag 1773

<210> SEQ ID NO 46
<211> LENGTH: 1797
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46
cagaagtcca acagaaagga ctacagcctg accatgcaga gcagcgtgac agtgcaagag 60
gggatgtgcg tccacgtccg gtgcagcttt agctaccctg tggacagcca gaccgacagc 120
gatcctgtgc acggctactg gttcagagcc ggcaacgaca tctcttggaa agccccagtg 180
gccaccaaca atcctgcctg ggctgtgcaa gaagagacac gggacagatt ccatctgctg 240
ggcgaccctc agaccaagaa ctgcacactg agcatccggg acgccagaat gtctgacgcc 300
ggcagatact tcttccggat ggaaaagggc aacatcaagt ggaactataa gtacgaccag 360
ctgagcgtga acgtgacagc cctgacacac agacccaaca ttctgatccc cggcacactg 420
gaaagcggct gcttccagaa tctgacctgc tctgtgcctt gggcctgcga gcagggaaca 480
cctcctatga tcagctggat gggaaccagc gtgtcccctc tgcaccctag caccacaaga 540
tccagcgtgc tgacactgat ccctcagcct cagcaccacg gcacaagcct gacctgtcaa 600
gttacacttc ctggcgctgg cgtgaccacc aacagaacaa tccagctcaa cgtgtcctat 660
cctcctcaga acctgaccgt gaccgtgttc caaggcgagg gcacagcttc tacagccctg 720
ggcaatagca gcagcctgtc tgtgctggaa ggccagtctc tgagactcgt gtgcgccgtg 780
gatagcaacc ctcctgctag actgagctgg acttggcgga gcctgacact gtaccctagc 840
cagcctagca atcccctggt gctggaactg caagtgcacc tgggagatga gggcgagttc 900
acctgtagag cccagaatag cctgggcagc cagcacgtgt ccctgaacct gtctctgcag 960
caagagtaca ccggcaagat gaggcctgtg tctggcgttc tgctgggagc cgtgggaggc 1020
tatatccccg aggctcctag agatggccag gcctatgttc ggaaggatgg cgaatgggtg 1080
ctgctgagca ccttccttga acctcgaggg cctaccatca agccctgtcc tccatgcaag 1140
tgccccgctc ctaatctgct cggaggcccc agcgtgttca tcttcccacc taagatcaag 1200
gacgtgctga tgatctctct gagccccatc gtgacctgcg tggtggtgga tgtgtccgag 1260
gacgatcccg atgtgcagat cagttggttc gtgaacaacg tggaagtgca cacagcccag 1320
acacagaccc acagagagga ctacaacagc accctgagag tggtgtctgc cctgcctatc 1380
cagcaccagg attggatgag cggcaaagaa ttcaagtgca aagtgaacaa caaggacctg 1440
cctgctccta tcgagcggac catctctaag cctaagggct ctgttagagc ccctcaggtg 1500
tacgtgctgc ctcctccaga ggaagagatg accaagaaac aagtgaccct gacctgcatg 1560
gtcaccgact tcatgcccga ggacatctac gtggaatgga ccaacaacgg caagaccgag 1620
ctgaactaca agaacaccga gcctgtgctg gacagcgacg gcagctactt catgtactcc 1680
aagctgcgcg tggaaaagaa gaactgggtc gagcggaaca gctacagctg ctctgtggtg 1740
cacgagggcc tgcacaatca ccacaccacc aagagcttca gccgtacgcc tggaaag 1797

<210> SEQ ID NO 47
<211> LENGTH: 2070
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
cagaagtcca acagaaagga ctacagcctg accatgcaga gcagcgtgac agtgcaagag 60
gggatgtgcg tccacgtccg gtgcagcttt agctaccctg tggacagcca gaccgacagc 120
gatcctgtgc acggctactg gttcagagcc ggcaacgaca tctcttggaa agccccagtg 180
gccaccaaca atcctgcctg ggctgtgcaa gaagagacac gggacagatt ccatctgctg 240
ggcgaccctc agaccaagaa ctgcacactg agcatccggg acgccagaat gtctgacgcc 300
ggcagatact tcttccggat ggaaaagggc aacatcaagt ggaactataa gtacgaccag 360
ctgagcgtga acgtgacagc cctgacacac agacccaaca ttctgatccc cggcacactg 420
gaaagcggct gcttccagaa tctgacctgc tctgtgcctt gggcctgcga gcagggaaca 480
cctcctatga tcagctggat gggaaccagc gtgtcccctc tgcaccctag caccacaaga 540
tccagcgtgc tgacactgat ccctcagcct cagcaccacg gcacaagcct gacctgtcaa 600
gttacacttc ctggcgctgg cgtgaccacc aacagaacaa tccagctcaa cgtgtcctat 660
cctggtggcg gaggatctgg cggaggtgga agcggcggag gcggatctca gaagtccaac 720
agaaaggact acagcctgac catgcagagc agcgtgacag tgcaagaggg gatgtgcgtc 780
cacgtccggt gcagctttag ctaccctgtg gacagccaga ccgacagcga tcctgtgcac 840
ggctactggt tcagagccgg caacgacatc tcttggaaag ccccagtggc caccaacaat 900
cctgcctggg ctgtgcaaga agagacacgg gacagattcc atctgctggg cgaccctcag 960
accaagaact gcacactgag catccgggac gccagaatgt ctgacgccgg cagatacttc 1020

```
ttccggatgg aaaagggcaa catcaagtgg aactataagt acgaccagct gagcgtgaac   1080
gtgacagccc tgacacacag acccaacatt ctgatccccg gcacactgga aagcggctgc   1140
ttccagaatc tgacctgctc tgtgccttgg gcctgcgagc agggaacacc tcctatgatc   1200
agctggatgg gaaccagcgt gtcccctctg caccctagca ccacaagatc cagcgtgctg   1260
acactgatcc ctcagcctca gcaccacggc acaagcctga cctgtcaagt tacacttcct   1320
ggcgctggcg tgaccaccaa cagaacaatc cagctcaacg tgtcctatcc tgaacctcga   1380
gggcctacca tcaagccctg tcctccatgc aagtgccccg ctcctaatct gctcggaggc   1440
cccagcgtgt tcatcttccc acctaagatc aaggacgtgc tgatgatctc tctgagcccc   1500
atcgtgacct gcgtggtggt ggatgtgtcc gaggacgatc ccgatgtgca gatcagttgg   1560
ttcgtgaaca acgtggaagt gcacacagcc cagacacaga cccacagaga ggactacaac   1620
agcaccctga gagtggtgtc tgccctgcct atccagcacc aggattggat gagcggcaaa   1680
gaattcaagt gcaaagtgaa caacaaggac ctgcctgctc ctatcgagcg gaccatctct   1740
aagcctaagg gctctgttag agcccctcag gtgtacgtgc tgcctcctcc agaggaagag   1800
atgaccaaga aacaagtgac cctgacctgc atggtcaccg acttcatgcc cgaggacatc   1860
tacgtggaat ggaccaacaa cggcaagacc gagctgaact acaagaacac cgagcctgtg   1920
ctggacagcg acggcagcta cttcatgtac tccaagctgc gcgtggaaaa gaagaactgg   1980
gtcgagcgga acagctacag ctgctctgtg gtgcacgagg gcctgcacaa tcaccacacc   2040
accaagagct tcagccgtac gcctggaaag                                    2070
```

<210> SEQ ID NO 48
<211> LENGTH: 2778
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
cagaagtcca acagaaagga ctacagcctg accatgcaga gcagcgtgac agtgcaagag     60
gggatgtgcg tccacgtccg gtgcagcttt agctaccctg tggacagcca gaccgacagc    120
gatcctgtgc acggctactg gttcagagcc ggcaacgaca tctcttggaa agccccagtg    180
gccaccaaca atcctgcctg ggctgtgcaa gaagagacac gggacagatt ccatctgctg    240
ggcgaccctc agaccaagaa ctgcacactg agcatccggg acgccagaat gtctgacgcc    300
ggcagatact tcttccggat ggaaaagggc aacatcaagt ggaactataa gtacgaccag    360
ctgagcgtga acgtgacagc cctgacacac agacccaaca ttctgatccc cggcacactg    420
gaaagcggct gcttccagaa tctgacctgc tctgtgcctt gggcctgcga gcagggaaca    480
cctcctatga tcagctggat gggaaccagc gtgtcccctc tgcaccctag caccacaaga    540
tccagcgtgc tgacactgat ccctcagcct cagcaccacg gcacaagcct gacctgtcaa    600
gttacacttc ctggcgctgg cgtgaccacc aacagaacaa tccagctcaa cgtgtcctat    660
cctcctcaga acctgaccgt gaccgtgttc caaggcgagg gcacagcttc tacagccctg    720
ggcaatagca gcagcctgtc tgtgctggaa ggccagtctc tgagactcgt gtgcgccgtg    780
gatagcaacc ctcctgctag actgagctgg acttggcgga gcctgacact gtaccctagc    840
cagcctagca atcccctggt gctggaactg caagtgcacc tgggagatga gggcgagttc    900
acctgtagag cccagaatag cctgggcagc cagcacgtgt ccctgaacct gtctctgcag    960
```

```
caagagtaca ccggcaagat gaggcctgtg tctggcgttc tgctgggagc cgtgggagaa   1020
cctcgagggc ctaccatcaa gccctgtcct ccatgcaagt gccccgctcc taatctgctc   1080
ggaggcccca gcgtgttcat cttcccacct aagatcaagg acgtgctgat gatctctctg   1140
agccccatcg tgacctgcgt ggtggtggat gtgtccgagg acgatcccga tgtgcagatc   1200
agttggttcg tgaacaacgt ggaagtgcac acagcccaga cacagaccca cagagaggac   1260
tacaacagca ccctgagagt ggtgtctgcc ctgcctatcc agcaccagga ttggatgagc   1320
ggcaaagaat tcaagtgcaa agtgaacaac aaggacctgc ctgctcctat cgagcggacc   1380
atctctaagc ctaagggctc tgttagagcc cctcaggtgt acgtgctgcc tcctccagag   1440
gaagagatga ccaagaaaca agtgaccctg acctgcatgg tcaccgactt catgcccgag   1500
gacatctacg tggaatggac caacaacggc aagaccgagc tgaactacaa gaacaccgag   1560
cctgtgctgg acagcgacgg cagctacttc atgtactcca agctgcgcgt ggaaaagaag   1620
aactgggtcg agcggaacag ctacagctgc tctgtggtgc acgagggcct gcacaatcac   1680
cacaccacca agagcttcag ccgtacgcct ggaaagggtg gcggaggatc tggcggaggt   1740
ggaagcggcg gaggcggatc tcagaagtcc aacagaaagg actacagcct gaccatgcag   1800
agcagcgtga cagtgcaaga ggggatgtgc gtccacgtcc ggtgcagctt tagctaccct   1860
gtggacagcc agaccgacag cgatcctgtg cacggctact ggttcagagc cggcaacgac   1920
atctcttgga aagccccagt ggccaccaac aatcctgcct gggctgtgca agaagagaca   1980
cgggacagat tccatctgct gggcgaccct cagaccaaga actgcacact gagcatccgg   2040
gacgccagaa tgtctgacgc cggcagatac ttcttccgga tggaaaaggg caacatcaag   2100
tggaactata agtacgacca gctgagcgtg aacgtgacag ccctgacaca cagacccaac   2160
attctgatcc ccggcacact ggaaagcggc tgcttccaga atctgacctg ctctgtgcct   2220
tgggcctgcg agcagggaac acctcctatg atcagctgga tgggaaccag cgtgtcccct   2280
ctgcacccta gcaccacaag atccagcgtg ctgacactga tccctcagcc tcagcaccac   2340
ggcacaagcc tgacctgtca agttacactt cctggcgctg gcgtgaccac caacagaaca   2400
atccagctca acgtgtccta tcctcctcag aacctgaccg tgaccgtgtt ccaaggcgag   2460
ggcacagctt ctacagccct gggcaatagc agcagcctgt ctgtgctgga aggccagtct   2520
ctgagactcg tgtgcgccgt ggatagcaac cctcctgcta gactgagctg gacttggcgg   2580
agcctgacac tgtaccctag ccagcctagc aatcccctgg tgctggaact gcaagtgcac   2640
ctgggagatg agggcgagtt cacctgtaga gcccagaata gcctgggcag ccagcacgtg   2700
tccctgaacc tgtctctgca gcaagagtac accggcaaga tgaggcctgt gtctggcgtt   2760
ctgctgggag ccgtggga                                                 2778
```

<210> SEQ ID NO 49
<211> LENGTH: 572
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
            20                  25                  30
```

```
Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Ala Leu
        115                 120                 125

Thr His Arg Pro Asn Ile Leu Ile Pro Gly Thr Leu Glu Ser Gly Cys
    130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
        195                 200                 205

Thr Thr Asn Arg Thr Ile Gln Leu Asn Val Ser Tyr Pro Pro Gln Asn
    210                 215                 220

Leu Thr Val Thr Val Phe Gln Gly Glu Gly Thr Ala Ser Thr Ala Leu
225                 230                 235                 240

Gly Asn Ser Ser Ser Leu Ser Val Leu Glu Gly Gln Ser Leu Arg Leu
                245                 250                 255

Val Cys Ala Val Asp Ser Asn Pro Pro Ala Arg Leu Ser Trp Thr Trp
            260                 265                 270

Arg Ser Leu Thr Leu Tyr Pro Ser Gln Pro Ser Asn Pro Leu Val Leu
        275                 280                 285

Glu Leu Gln Val His Leu Gly Asp Glu Gly Glu Phe Thr Cys Arg Ala
    290                 295                 300

Gln Asn Ser Leu Gly Ser Gln His Val Ser Leu Asn Leu Ser Leu Gln
305                 310                 315                 320

Gln Glu Tyr Thr Gly Lys Met Arg Pro Val Ser Gly Val Leu Leu Gly
                325                 330                 335

Ala Val Gly Glu Pro Arg Gly Pro Thr Ile Lys Pro Cys Pro Pro Cys
            340                 345                 350

Lys Cys Pro Ala Pro Asn Leu Leu Gly Gly Pro Ser Val Phe Ile Phe
        355                 360                 365

Pro Pro Lys Ile Lys Asp Val Leu Met Ile Ser Leu Ser Pro Ile Val
    370                 375                 380

Thr Cys Val Val Val Asp Val Ser Glu Asp Asp Pro Asp Val Gln Ile
385                 390                 395                 400

Ser Trp Phe Val Asn Asn Val Glu Val His Thr Ala Gln Thr Gln Thr
                405                 410                 415

His Arg Glu Asp Tyr Asn Ser Thr Leu Arg Val Val Ser Ala Leu Pro
            420                 425                 430

Ile Gln His Gln Asp Trp Met Ser Gly Lys Glu Phe Lys Cys Lys Val
        435                 440                 445
```

-continued

```
Asn Asn Lys Asp Leu Pro Ala Pro Ile Glu Arg Thr Ile Ser Lys Pro
    450                 455                 460

Lys Gly Ser Val Arg Ala Pro Gln Val Tyr Val Leu Pro Pro Pro Glu
465                 470                 475                 480

Glu Glu Met Thr Lys Lys Gln Val Thr Leu Thr Cys Met Val Thr Asp
                485                 490                 495

Phe Met Pro Glu Asp Ile Tyr Val Glu Trp Thr Asn Asn Gly Lys Thr
            500                 505                 510

Glu Leu Asn Tyr Lys Asn Thr Glu Pro Val Leu Asp Ser Asp Gly Ser
        515                 520                 525

Tyr Phe Met Tyr Ser Lys Leu Arg Val Glu Lys Lys Asn Trp Val Glu
    530                 535                 540

Arg Asn Ser Tyr Ser Cys Ser Val Val His Glu Gly Leu His Asn His
545                 550                 555                 560

His Thr Thr Lys Ser Phe Ser Arg Thr Pro Gly Lys
                565                 570


<210> SEQ ID NO 50
<211> LENGTH: 1716
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

cagaagtcca acagaaagga ctacagcctg accatgcaga gcagcgtgac agtgcaagag      60

gggatgtgcg tccacgtccg gtgcagcttt agctaccctg tggacagcca gaccgacagc     120

gatcctgtgc acggctactg gttcagagcc ggcaacgaca tctcttggaa agccccagtg     180

gccaccaaca atcctgcctg ggctgtgcaa gaagagacac gggacagatt ccatctgctg     240

ggcgaccctc agaccaagaa ctgcacactg agcatccggg acgccagaat gtctgacgcc     300

ggcagatact tcttccggat ggaaaagggc aacatcaagt ggaactataa gtacgaccag     360

ctgagcgtga acgtgacagc cctgacacac agacccaaca ttctgatccc cggcacactg     420

gaaagcggct gcttccagaa tctgacctgc tctgtgcctt gggcctgcga gcagggaaca     480

cctcctatga tcagctggat gggaaccagc gtgtcccctc tgcaccctag caccacaaga     540

tccagcgtgc tgacactgat ccctcagcct cagcaccacg gcacaagcct gacctgtcaa     600

gttacacttc ctggcgctgg cgtgaccacc aacagaacaa tccagctcaa cgtgtcctat     660

cctcctcaga acctgaccgt gaccgtgttc caaggcgagg gcacagcttc tacagccctg     720

ggcaatagca gcagcctgtc tgtgctggaa ggccagtctc tgagactcgt gtgcgccgtg     780

gatagcaacc ctcctgctag actgagctgg acttggcgga gcctgacact gtaccctagc     840

cagcctagca atcccctggt gctggaactg caagtgcacc tgggagatga gggcgagttc     900

acctgtagag cccagaatag cctgggcagc cagcacgtgt ccctgaacct gtctctgcag     960

caagagtaca ccggcaagat gaggcctgtg tctggcgttc tgctgggagc cgtgggagaa    1020

cctcgagggc ctaccatcaa gccctgtcct ccatgcaagt gccccgctcc taatctgctc    1080

ggaggcccca gcgtgttcat cttcccacct aagatcaagg acgtgctgat gatctctctg    1140

agccccatcg tgacctgcgt ggtggtggat gtgtccgagg acgatcccga tgtgcagatc    1200

agttggttcg tgaacaacgt ggaagtgcac acagcccaga cacagaccca cagagaggac    1260

tacaacagca ccctgagagt ggtgtctgcc ctgcctatcc agcaccagga ttggatgagc    1320
```

ggcaaagaat tcaagtgcaa agtgaacaac aaggacctgc ctgctcctat cgagcggacc 1380
atctctaagc ctaagggctc tgttagagcc cctcaggtgt acgtgctgcc tcctccagag 1440
gaagagatga ccaagaaaca agtgaccctg acctgcatgg tcaccgactt catgcccgag 1500
gacatctacg tggaatggac caacaacggc aagaccgagc tgaactacaa gaacaccgag 1560
cctgtgctgg acagcgacgg cagctacttc atgtactcca agctgcgcgt ggaaaagaag 1620
aactgggtcg agcggaacag ctacagctgc tctgtggtgc acgagggcct gcacaatcac 1680
cacaccacca agagcttcag ccgtacgcct ggaaag 1716

<210> SEQ ID NO 51
<211> LENGTH: 117
<212> TYPE: PRT
<213> ORGANISM: Homo sapiens

<400> SEQUENCE: 51

Leu Gln Val Gln Glu Ser Val Thr Val Gln Glu Gly Leu Cys Val Leu
1 5 10 15

Val Pro Cys Thr Phe Phe His Pro Ile Pro Tyr Tyr Asp Lys Asn Ser
20 25 30

Pro Val His Gly Tyr Trp Phe Arg Glu Gly Ala Ile Ile Ser Arg Asp
35 40 45

Ser Pro Val Ala Thr Asn Lys Leu Asp Gln Glu Val Gln Glu Glu Thr
50 55 60

Gln Gly Arg Phe Arg Leu Leu Gly Asp Pro Ser Arg Asn Asn Cys Ser
65 70 75 80

Leu Ser Ile Val Asp Ala Arg Arg Arg Asp Asn Gly Ser Tyr Phe Phe
85 90 95

Arg Met Glu Arg Gly Ser Thr Lys Tyr Ser Tyr Lys Ser Pro Gln Leu
100 105 110

Ser Val His Val Thr
115

<210> SEQ ID NO 52
<211> LENGTH: 205
<212> TYPE: PRT
<213> ORGANISM: Homo sapiens

<400> SEQUENCE: 52

Leu Gln Val Gln Glu Ser Val Thr Val Gln Glu Gly Leu Cys Val Leu
1 5 10 15

Val Pro Cys Thr Phe Phe His Pro Ile Pro Tyr Tyr Asp Lys Asn Ser
20 25 30

Pro Val His Gly Tyr Trp Phe Arg Glu Gly Ala Ile Ile Ser Arg Asp
35 40 45

Ser Pro Val Ala Thr Asn Lys Leu Asp Gln Glu Val Gln Glu Glu Thr
50 55 60

Gln Gly Arg Phe Arg Leu Leu Gly Asp Pro Ser Arg Asn Asn Cys Ser
65 70 75 80

Leu Ser Ile Val Asp Ala Arg Arg Arg Asp Asn Gly Ser Tyr Phe Phe
85 90 95

Arg Met Glu Arg Gly Ser Thr Lys Tyr Ser Tyr Lys Ser Pro Gln Leu
100 105 110

Ser Val His Val Thr Asp Leu Thr His Arg Pro Lys Ile Leu Ile Pro
115 120 125

Gly Thr Leu Glu Pro Gly His Ser Lys Asn Leu Thr Cys Ser Val Ser

```
    130                 135                 140

Trp Ala Cys Glu Gln Gly Thr Pro Pro Ile Phe Ser Trp Leu Ser Ala
145                 150                 155                 160

Ala Pro Thr Ser Leu Gly Pro Arg Thr Thr His Ser Ser Val Leu Ile
                165                 170                 175

Ile Thr Pro Arg Pro Gln Asp His Gly Thr Asn Leu Thr Cys Gln Val
            180                 185                 190

Lys Phe Ala Gly Ala Gly Val Thr Thr Glu Arg Thr Ile
        195                 200                 205


<210> SEQ ID NO 53
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gly Trp Ser Cys Ile Ile Leu Phe Leu Val Ala Thr Ala Thr Gly
1               5                   10                  15

Val His Ser Asp Pro Asn Phe Trp Leu Gln Val Gln Glu Ser Val Thr
            20                  25                  30

Val Gln Glu Gly Leu Cys Val Leu Val Pro Cys Thr Phe Phe His Pro
        35                  40                  45

Ile Pro Tyr Tyr Asp Lys Asn Ser Pro Val His Gly Tyr Trp Phe Arg
    50                  55                  60

Glu Gly Ala Ile Ile Ser Arg Asp Ser Pro Val Ala Thr Asn Lys Leu
65                  70                  75                  80

Asp Gln Glu Val Gln Glu Glu Thr Gln Gly Arg Phe Arg Leu Leu Gly
                85                  90                  95

Asp Pro Ser Arg Asn Asn Cys Ser Leu Ser Ile Val Asp Ala Arg Arg
            100                 105                 110

Arg Asp Asn Gly Ser Tyr Phe Phe Arg Met Glu Arg Gly Ser Thr Lys
        115                 120                 125

Tyr Ser Tyr Lys Ser Pro Gln Leu Ser Val His Val Thr Asp Leu Thr
    130                 135                 140

His Arg Pro Lys Ile Leu Ile Pro Gly Thr Leu Glu Pro Gly His Ser
145                 150                 155                 160

Lys Asn Leu Thr Cys Ser Val Ser Trp Ala Cys Glu Gln Gly Thr Pro
                165                 170                 175

Pro Ile Phe Ser Trp Leu Ser Ala Ala Pro Thr Ser Leu Gly Pro Arg
            180                 185                 190

Thr Thr His Ser Ser Val Leu Ile Ile Thr Pro Arg Pro Gln Asp His
        195                 200                 205

Gly Thr Asn Leu Thr Cys Gln Val Lys Phe Ala Gly Ala Gly Val Thr
    210                 215                 220

Thr Glu Arg Thr Ile Gln Leu Asn Val Thr Tyr Val Pro Gln Asn Pro
225                 230                 235                 240

Thr Thr Gly Ile Phe Pro Gly Asp Gly Ser Gly Lys Gln Glu Thr Arg
                245                 250                 255

Ala Gly Val Val His Gly Tyr Ile Pro Glu Ala Pro Arg Asp Gly Gln
            260                 265                 270

Ala Tyr Val Arg Lys Asp Gly Glu Trp Val Leu Leu Ser Thr Phe Leu
        275                 280                 285
```

```
Glu Pro Arg Gly Pro Thr Ile Lys Pro Cys Pro Pro Cys Lys Cys Pro
    290                 295                 300

Ala Pro Asn Leu Leu Gly Gly Pro Ser Val Phe Ile Phe Pro Pro Lys
305                 310                 315                 320

Ile Lys Asp Val Leu Met Ile Ser Leu Ser Pro Ile Val Thr Cys Val
                325                 330                 335

Val Val Asp Val Ser Glu Asp Asp Pro Asp Val Gln Ile Ser Trp Phe
            340                 345                 350

Val Asn Asn Val Glu Val His Thr Ala Gln Thr Gln Thr His Arg Glu
        355                 360                 365

Asp Tyr Asn Ser Thr Leu Arg Val Val Ser Ala Leu Pro Ile Gln His
    370                 375                 380

Gln Asp Trp Met Ser Gly Lys Glu Phe Lys Cys Lys Val Asn Asn Lys
385                 390                 395                 400

Asp Leu Pro Ala Pro Ile Glu Arg Thr Ile Ser Lys Pro Lys Gly Ser
                405                 410                 415

Val Arg Ala Pro Gln Val Tyr Val Leu Pro Pro Pro Glu Glu Glu Met
            420                 425                 430

Thr Lys Lys Gln Val Thr Leu Thr Cys Met Val Thr Asp Phe Met Pro
        435                 440                 445

Glu Asp Ile Tyr Val Glu Trp Thr Asn Asn Gly Lys Thr Glu Leu Asn
    450                 455                 460

Tyr Lys Asn Thr Glu Pro Val Leu Asp Ser Asp Gly Ser Tyr Phe Met
465                 470                 475                 480

Tyr Ser Lys Leu Arg Val Glu Lys Lys Asn Trp Val Glu Arg Asn Ser
                485                 490                 495

Tyr Ser Cys Ser Val Val His Glu Gly Leu His Asn His His Thr Thr
            500                 505                 510

Lys Ser Phe Ser Arg Thr Pro Gly Lys
        515                 520
```

<210> SEQ ID NO 54
<211> LENGTH: 1565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atgggctggt cctgcatcat cctgtttctg gtggccacag ccacaggcgt gcacagcgat     60

cccaatttct ggctgcaagt gcaagagtcc gtgaccgtgc aagagggcct gtgtgtgctg    120

gtgccctgca ccttctttca ccccattcct tactacgaca agaacagccc tgtgcacggc    180

tactggttta gagagggcgc catcatcagc agagatagcc ctgtggccac caacaagctg    240

gaccaagagg tgcaagaaga gacacagggc agattcagac tgctgggcga ccccagcaga    300

aacaactgca gcctgtctat cgtggacgcc aggcggagag acaacggcag ctacttcttc    360

cggatggaac ggggcagcac caagtacagc tacaagagcc ctcagctgtc cgtgcacgtg    420

accgacctga cacacagacc caagattctg atccccggca cactggaacc tggccacagc    480

aagaatctga cctgctccgt gtcctgggcc tgcgaacagg gaacccctcc tatctttagc    540

tggctgagcg ccgctcctac atctctgggc cctagaacaa cacacagcag cgtgctgatc    600

atcaccccta gacctcagga ccacggcacc aacctgacct gccaagtgaa atttgctggc    660

gctggcgtga ccaccgagag aaccatccag ctgaacgtga cctacgtgcc acagaaccct    720
```

-continued

```
accaccggca tctttccagg cgacggctct ggcaagcaag aaacaagagc tggcgtggtg    780

cacggctata tccccgaggc tcctagagat ggccaggcct atgttcggaa ggatggcgaa    840

tgggtgctgc tgagcacctt ccttgaacct cgagggccta ccatcaagcc ctgtcctcca    900

tgcaagtgcc ccgctcctaa tctgctcgga ggccccagcg tgttcatctt cccacctaag    960

atcaaggacg tgctgatgat ctctctgagc cccatcgtga cctgcgtggt ggtggatgtg   1020

tccgaggacg atcccgatgt gcagatcagt tggttcgtga acaacgtgga agtgcacaca   1080

gcccagacac agacccacag agaggactac aacagcaccc tgagagtggt gtctgccctg   1140

cctatccagc accaggattg gatgagcggc aaagaattca agtgcaaagt gaacaacaag   1200

gacctgcctg ctcctatcga gcggaccatc tctaagccta agggctctgt tagagcccct   1260

caggtgtacg tgctgcctcc tccagaggaa gagatgacca agaaacaagt gaccctgacc   1320

tgcatggtca ccgacttcat gcccgaggac atctacgtgg aatggaccaa caacggcaag   1380

accgagctga actacaagaa caccgagcct gtgctggaca gcgacggcag ctacttcatg   1440

tactccaagc tgcgcgtgga aaagaagaac tgggtcgagc ggaacagcta cagctgctct   1500

gtggtgcacg agggcctgca caatcaccac accaccaaga gcttcagccg tacgcctgga   1560

aagta                                                               1565
```

```
<210> SEQ ID NO 55
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Trp Ser Cys Ile Ile Leu Phe Leu Val Ala Thr Ala Thr Gly
1               5                   10                  15

Val His Ser Asp Pro Asn Phe Trp Leu Gln Val Gln Glu Ser Val Thr
            20                  25                  30

Val Gln Glu Gly Leu Cys Val Leu Val Pro Cys Thr Phe Phe His Pro
        35                  40                  45

Ile Pro Tyr Tyr Asp Lys Asn Ser Pro Val His Gly Tyr Trp Phe Arg
    50                  55                  60

Glu Gly Ala Ile Ile Ser Arg Asp Ser Pro Val Ala Thr Asn Lys Leu
65                  70                  75                  80

Asp Gln Glu Val Gln Glu Glu Thr Gln Gly Arg Phe Arg Leu Leu Gly
                85                  90                  95

Asp Pro Ser Arg Asn Asn Cys Ser Leu Ser Ile Val Asp Ala Arg Arg
            100                 105                 110

Arg Asp Asn Gly Ser Tyr Phe Phe Arg Met Glu Arg Gly Ser Thr Lys
        115                 120                 125

Tyr Ser Tyr Lys Ser Pro Gln Leu Ser Val His Val Thr Asp Leu Thr
    130                 135                 140

His Arg Pro Lys Ile Leu Ile Pro Gly Thr Leu Glu Pro Gly His Ser
145                 150                 155                 160

Lys Asn Leu Thr Cys Ser Val Ser Trp Ala Cys Glu Gln Gly Thr Pro
                165                 170                 175

Pro Ile Phe Ser Trp Leu Ser Ala Ala Pro Thr Ser Leu Gly Pro Arg
            180                 185                 190

Thr Thr His Ser Ser Val Leu Ile Ile Thr Pro Arg Pro Gln Asp His
```

```
        195                 200                 205

Gly Thr Asn Leu Thr Cys Gln Val Lys Phe Ala Gly Ala Gly Val Thr
    210                 215                 220

Thr Glu Arg Thr Ile Gln Leu Asn Val Thr Tyr Val Pro Gln Asn Pro
225                 230                 235                 240

Thr Thr Gly Ile Phe Pro Gly Asp Gly Ser Gly Lys Gln Glu Thr Arg
                245                 250                 255

Ala Gly Val Val His Gly Gly Gly Gly Ser Gly Gly Gly Gly Ser Gly
            260                 265                 270

Tyr Ile Pro Glu Ala Pro Arg Asp Gly Gln Ala Tyr Val Arg Lys Asp
        275                 280                 285

Gly Glu Trp Val Leu Leu Ser Thr Phe Leu Glu Pro Arg Gly Pro Thr
    290                 295                 300

Ile Lys Pro Cys Pro Pro Cys Lys Cys Pro Ala Pro Asn Leu Leu Gly
305                 310                 315                 320

Gly Pro Ser Val Phe Ile Phe Pro Pro Lys Ile Lys Asp Val Leu Met
                325                 330                 335

Ile Ser Leu Ser Pro Ile Val Thr Cys Val Val Val Asp Val Ser Glu
            340                 345                 350

Asp Asp Pro Asp Val Gln Ile Ser Trp Phe Val Asn Asn Val Glu Val
        355                 360                 365

His Thr Ala Gln Thr Gln Thr His Arg Glu Asp Tyr Asn Ser Thr Leu
    370                 375                 380

Arg Val Val Ser Ala Leu Pro Ile Gln His Gln Asp Trp Met Ser Gly
385                 390                 395                 400

Lys Glu Phe Lys Cys Lys Val Asn Asn Lys Asp Leu Pro Ala Pro Ile
                405                 410                 415

Glu Arg Thr Ile Ser Lys Pro Lys Gly Ser Val Arg Ala Pro Gln Val
            420                 425                 430

Tyr Val Leu Pro Pro Pro Glu Glu Glu Met Thr Lys Lys Gln Val Thr
        435                 440                 445

Leu Thr Cys Met Val Thr Asp Phe Met Pro Glu Asp Ile Tyr Val Glu
    450                 455                 460

Trp Thr Asn Asn Gly Lys Thr Glu Leu Asn Tyr Lys Asn Thr Glu Pro
465                 470                 475                 480

Val Leu Asp Ser Asp Gly Ser Tyr Phe Met Tyr Ser Lys Leu Arg Val
                485                 490                 495

Glu Lys Lys Asn Trp Val Glu Arg Asn Ser Tyr Ser Cys Ser Val Val
            500                 505                 510

His Glu Gly Leu His Asn His His Thr Thr Lys Ser Phe Ser Arg Thr
        515                 520                 525

Pro Gly Lys
    530


<210> SEQ ID NO 56
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

atgggctggt cctgcatcat cctgtttctg gtggccacag ccacaggcgt gcacagcgat      60

cccaatttct ggctgcaagt gcaagagtcc gtgaccgtgc aagagggcct gtgtgtgctg     120
```

```
gtgccctgca ccttctttca ccccattcct tactacgaca agaacagccc tgtgcacggc    180

tactggttta gagagggcgc catcatcagc agagatagcc ctgtggccac caacaagctg    240

gaccaagagg tgcaagaaga gacacagggc agattcagac tgctgggcga ccccagcaga    300

aacaactgca gcctgtctat cgtggacgcc aggcggagag acaacggcag ctacttcttc    360

cggatggaac ggggcagcac caagtacagc tacaagagcc ctcagctgtc cgtgcacgtg    420

accgacctga cacacagacc caagattctg atccccggca cactggaacc tggccacagc    480

aagaatctga cctgctccgt gtcctgggcc tgcgaacagg gaacccctcc tatctttagc    540

tggctgagcg ccgctcctac atctctgggc cctagaacaa cacacagcag cgtgctgatc    600

atcaccccta gacctcagga ccacggcacc aacctgacct gccaagtgaa atttgctggc    660

gctggcgtga ccaccgagag aaccatccag ctgaacgtga cctacgtgcc acagaaccct    720

accaccggca tctttccagg cgacggctct ggcaagcaag aaacaagagc tggcgtggtg    780

cacggaggcg gaggatctgg cggaggtgga agtggctata tccccgaggc tcctagagat    840

ggccaggcct atgttcggaa ggatggcgaa tgggtgctgc tgagcacctt ccttgaacct    900

cgagggccta ccatcaagcc ctgtcctcca tgcaagtgcc ccgctcctaa tctgctcgga    960

ggccccagcg tgttcatctt cccacctaag atcaaggacg tgctgatgat ctctctgagc   1020

cccatcgtga cctgcgtggt ggtggatgtg tccgaggacg atcccgatgt gcagatcagt   1080

tggttcgtga acaacgtgga agtgcacaca gcccagacac agacccacag agaggactac   1140

aacagcaccc tgagagtggt gtctgccctg cctatccagc accaggattg gatgagcggc   1200

aaagaattca agtgcaaagt gaacaacaag gacctgcctg ctcctatcga gcggaccatc   1260

tctaagccta agggctctgt tagagcccct caggtgtacg tgctgcctcc tccagaggaa   1320

gagatgacca agaaacaagt gaccctgacc tgcatggtca ccgacttcat gcccgaggac   1380

atctacgtgg aatggaccaa caacggcaag accgagctga actacaagaa caccgagcct   1440

gtgctggaca gcgacggcag ctacttcatg tactccaagc tgcgcgtgga aaagaagaac   1500

tgggtcgagc ggaacagcta cagctgctct gtggtgcacg agggcctgca caatcaccac   1560

accaccaaga gcttcagccg tacgcctgga aagtag                              1596
```

<210> SEQ ID NO 57
<211> LENGTH: 531
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Met Gly Trp Ser Cys Ile Ile Leu Phe Leu Val Ala Thr Ala Thr Gly
1               5                   10                  15

Val His Ser Asp Pro Asn Phe Trp Leu Gln Val Gln Glu Ser Val Thr
            20                  25                  30

Val Gln Glu Gly Leu Cys Val Leu Val Pro Cys Thr Phe Phe His Pro
        35                  40                  45

Ile Pro Tyr Tyr Asp Lys Asn Ser Pro Val His Gly Tyr Trp Phe Arg
    50                  55                  60

Glu Gly Ala Ile Ile Ser Arg Asp Ser Pro Val Ala Thr Asn Lys Leu
65                  70                  75                  80

Asp Gln Glu Val Gln Glu Glu Thr Gln Gly Arg Phe Arg Leu Leu Gly
                85                  90                  95
```

-continued

```
Asp Pro Ser Arg Asn Asn Cys Ser Leu Ser Ile Val Asp Ala Arg Arg
            100                 105                 110

Arg Asp Asn Gly Ser Tyr Phe Phe Arg Met Glu Arg Gly Ser Thr Lys
        115                 120                 125

Tyr Ser Tyr Lys Ser Pro Gln Leu Ser Val His Val Thr Asp Leu Thr
    130                 135                 140

His Arg Pro Lys Ile Leu Ile Pro Gly Thr Leu Glu Pro Gly His Ser
145                 150                 155                 160

Lys Asn Leu Thr Cys Ser Val Ser Trp Ala Cys Glu Gln Gly Thr Pro
                165                 170                 175

Pro Ile Phe Ser Trp Leu Ser Ala Ala Pro Thr Ser Leu Gly Pro Arg
            180                 185                 190

Thr Thr His Ser Ser Val Leu Ile Ile Thr Pro Arg Pro Gln Asp His
        195                 200                 205

Gly Thr Asn Leu Thr Cys Gln Val Lys Phe Ala Gly Ala Gly Val Thr
    210                 215                 220

Thr Glu Arg Thr Ile Gln Leu Asn Val Thr Tyr Val Pro Gln Asn Pro
225                 230                 235                 240

Thr Thr Gly Ile Phe Pro Gly Asp Gly Ser Gly Lys Gln Glu Thr Arg
                245                 250                 255

Ala Gly Val Val His Glu Pro Arg Gly Pro Thr Ile Lys Pro Cys Pro
            260                 265                 270

Pro Cys Lys Cys Pro Ala Pro Asn Leu Leu Gly Gly Pro Ser Val Phe
        275                 280                 285

Ile Phe Pro Pro Lys Ile Lys Asp Val Leu Met Ile Ser Leu Ser Pro
    290                 295                 300

Ile Val Thr Cys Val Val Val Asp Val Ser Glu Asp Asp Pro Asp Val
305                 310                 315                 320

Gln Ile Ser Trp Phe Val Asn Asn Val Glu Val His Thr Ala Gln Thr
                325                 330                 335

Gln Thr His Arg Glu Asp Tyr Asn Ser Thr Leu Arg Val Val Ser Ala
            340                 345                 350

Leu Pro Ile Gln His Gln Asp Trp Met Ser Gly Lys Glu Phe Lys Cys
        355                 360                 365

Lys Val Asn Asn Lys Asp Leu Pro Ala Pro Ile Glu Arg Thr Ile Ser
    370                 375                 380

Lys Pro Lys Gly Ser Val Arg Ala Pro Gln Val Tyr Val Leu Pro Pro
385                 390                 395                 400

Pro Glu Glu Glu Met Thr Lys Lys Gln Val Thr Leu Thr Cys Met Val
                405                 410                 415

Thr Asp Phe Met Pro Glu Asp Ile Tyr Val Glu Trp Thr Asn Asn Gly
            420                 425                 430

Lys Thr Glu Leu Asn Tyr Lys Asn Thr Glu Pro Val Leu Asp Ser Asp
        435                 440                 445

Gly Ser Tyr Phe Met Tyr Ser Lys Leu Arg Val Glu Lys Lys Asn Trp
    450                 455                 460

Val Glu Arg Asn Ser Tyr Ser Cys Ser Val Val His Glu Gly Leu His
465                 470                 475                 480

Asn His His Thr Thr Lys Ser Phe Ser Arg Thr Pro Gly Lys Gly Gly
                485                 490                 495

Gly Gly Ser Gly Gly Gly Gly Ser Gly Tyr Ile Pro Glu Ala Pro Arg
            500                 505                 510
```

```
Asp Gly Gln Ala Tyr Val Arg Lys Asp Gly Glu Trp Val Leu Leu Ser
        515                 520                 525

Thr Phe Leu
    530


<210> SEQ ID NO 58
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

atgggctggt cctgcatcat cctgtttctg gtggccacag ccacaggcgt gcacagcgat     60

cccaatttct ggctgcaagt gcaagagtcc gtgaccgtgc aagagggcct gtgtgtgctg    120

gtgccctgca ccttctttca ccccattcct tactacgaca agaacagccc tgtgcacggc    180

tactggttta gagagggcgc catcatcagc agagatagcc ctgtggccac caacaagctg    240

gaccaagagg tgcaagaaga gacacagggc agattcagac tgctgggcga ccccagcaga    300

aacaactgca gcctgtctat cgtggacgcc aggcggagag acaacggcag ctacttcttc    360

cggatggaac ggggcagcac caagtacagc tacaagagcc ctcagctgtc cgtgcacgtg    420

accgacctga cacacagacc caagattctg atccccggca cactggaacc tggccacagc    480

aagaatctga cctgctccgt gtcctgggcc tgcgaacagg gaacccctcc tatctttagc    540

tggctgagcg ccgctcctac atctctgggc cctagaacaa cacacagcag cgtgctgatc    600

atcaccccta gacctcagga ccacggcacc aacctgacct gccaagtgaa atttgctggc    660

gctggcgtga ccaccgagag aaccatccag ctgaacgtga cctacgtgcc acagaaccct    720

accaccggca tctttccagg cgacggctct ggcaagcaag aaacaagagc tggcgtggtg    780

cacgaacctc gagggcctac catcaagccc tgtcctccat gcaagtgccc cgctcctaat    840

ctgctcggag gccccagcgt gttcatcttc ccacctaaga tcaaggacgt gctgatgatc    900

tctctgagcc ccatcgtgac ctgcgtggtg gtggatgtgt ccgaggacga tcccgatgtg    960

cagatcagtt ggttcgtgaa caacgtggaa gtgcacacag cccagacaca gacccacaga   1020

gaggactaca acagcaccct gagagtggtg tctgccctgc ctatccagca ccaggattgg   1080

atgagcggca aagaattcaa gtgcaaagtg aacaacaagg acctgcctgc tcctatcgag   1140

cggaccatct ctaagcctaa gggctctgtt agagcccctc aggtgtacgt gctgcctcct   1200

ccagaggaag agatgaccaa gaaacaagtg accctgacct gcatggtcac cgacttcatg   1260

cccgaggaca tctacgtgga atggaccaac aacggcaaga ccgagctgaa ctacaagaac   1320

accgagcctg tgctggacag cgacggcagc tacttcatgt actccaagct gcgcgtggaa   1380

aagaagaact gggtcgagcg gaacagctac agctgctctg tggtgcacga gggcctgcac   1440

aatcaccaca ccaccaagag cttcagccgt acgcctggaa agggaggcgg aggatctggc   1500

ggaggtggaa gtggctatat ccccgaggct cctagagatg gccaggccta tgttcggaag   1560

gatggcgaat gggtgctgct gagcaccttc ctttag                             1596


<210> SEQ ID NO 59
<211> LENGTH: 751
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 59

Met Gly Trp Ser Cys Ile Ile Leu Phe Leu Val Ala Thr Ala Thr Gly
1               5                   10                  15

Val His Ser Asp Pro Asn Phe Trp Leu Gln Val Gln Glu Ser Val Thr
            20                  25                  30

Val Gln Glu Gly Leu Cys Val Leu Val Pro Cys Thr Phe Phe His Pro
        35                  40                  45

Ile Pro Tyr Tyr Asp Lys Asn Ser Pro Val His Gly Tyr Trp Phe Arg
    50                  55                  60

Glu Gly Ala Ile Ile Ser Arg Asp Ser Pro Val Ala Thr Asn Lys Leu
65                  70                  75                  80

Asp Gln Glu Val Gln Glu Glu Thr Gln Gly Arg Phe Arg Leu Leu Gly
                85                  90                  95

Asp Pro Ser Arg Asn Asn Cys Ser Leu Ser Ile Val Asp Ala Arg Arg
            100                 105                 110

Arg Asp Asn Gly Ser Tyr Phe Phe Arg Met Glu Arg Gly Ser Thr Lys
        115                 120                 125

Tyr Ser Tyr Lys Ser Pro Gln Leu Ser Val His Val Thr Asp Leu Thr
    130                 135                 140

His Arg Pro Lys Ile Leu Ile Pro Gly Thr Leu Glu Pro Gly His Ser
145                 150                 155                 160

Lys Asn Leu Thr Cys Ser Val Ser Trp Ala Cys Glu Gln Gly Thr Pro
                165                 170                 175

Pro Ile Phe Ser Trp Leu Ser Ala Ala Pro Thr Ser Leu Gly Pro Arg
            180                 185                 190

Thr Thr His Ser Ser Val Leu Ile Ile Thr Pro Arg Pro Gln Asp His
        195                 200                 205

Gly Thr Asn Leu Thr Cys Gln Val Lys Phe Ala Gly Ala Gly Val Thr
    210                 215                 220

Thr Glu Arg Thr Ile Gln Leu Asn Val Thr Tyr Val Pro Gln Asn Pro
225                 230                 235                 240

Thr Thr Gly Ile Phe Pro Gly Asp Gly Ser Gly Lys Gln Glu Thr Arg
                245                 250                 255

Ala Gly Val Val His Gly Gly Gly Gly Ser Gly Gly Gly Gly Ser Gly
            260                 265                 270

Gly Gly Gly Ser Asp Pro Asn Phe Trp Leu Gln Val Gln Glu Ser Val
        275                 280                 285

Thr Val Gln Glu Gly Leu Cys Val Leu Val Pro Cys Thr Phe Phe His
    290                 295                 300

Pro Ile Pro Tyr Tyr Asp Lys Asn Ser Pro Val His Gly Tyr Trp Phe
305                 310                 315                 320

Arg Glu Gly Ala Ile Ile Ser Arg Asp Ser Pro Val Ala Thr Asn Lys
                325                 330                 335

Leu Asp Gln Glu Val Gln Glu Glu Thr Gln Gly Arg Phe Arg Leu Leu
            340                 345                 350

Gly Asp Pro Ser Arg Asn Asn Cys Ser Leu Ser Ile Val Asp Ala Arg
        355                 360                 365

Arg Arg Asp Asn Gly Ser Tyr Phe Phe Arg Met Glu Arg Gly Ser Thr
    370                 375                 380

Lys Tyr Ser Tyr Lys Ser Pro Gln Leu Ser Val His Val Thr Asp Leu
385                 390                 395                 400

Thr His Arg Pro Lys Ile Leu Ile Pro Gly Thr Leu Glu Pro Gly His

```
                405                 410                 415

Ser Lys Asn Leu Thr Cys Ser Val Ser Trp Ala Cys Glu Gln Gly Thr
            420                 425                 430

Pro Pro Ile Phe Ser Trp Leu Ser Ala Ala Pro Thr Ser Leu Gly Pro
        435                 440                 445

Arg Thr Thr His Ser Ser Val Leu Ile Ile Thr Pro Arg Pro Gln Asp
    450                 455                 460

His Gly Thr Asn Leu Thr Cys Gln Val Lys Phe Ala Gly Ala Gly Val
465                 470                 475                 480

Thr Thr Glu Arg Thr Ile Gln Leu Asn Val Thr Tyr Val Pro Gln Asn
                485                 490                 495

Pro Thr Thr Gly Ile Phe Pro Gly Asp Gly Ser Gly Lys Gln Glu Thr
            500                 505                 510

Arg Ala Gly Val Val His Glu Pro Arg Gly Pro Thr Ile Lys Pro Cys
        515                 520                 525

Pro Pro Cys Lys Cys Pro Ala Pro Asn Leu Leu Gly Gly Pro Ser Val
    530                 535                 540

Phe Ile Phe Pro Pro Lys Ile Lys Asp Val Leu Met Ile Ser Leu Ser
545                 550                 555                 560

Pro Ile Val Thr Cys Val Val Val Asp Val Ser Glu Asp Asp Pro Asp
                565                 570                 575

Val Gln Ile Ser Trp Phe Val Asn Asn Val Glu Val His Thr Ala Gln
            580                 585                 590

Thr Gln Thr His Arg Glu Asp Tyr Asn Ser Thr Leu Arg Val Val Ser
        595                 600                 605

Ala Leu Pro Ile Gln His Gln Asp Trp Met Ser Gly Lys Glu Phe Lys
    610                 615                 620

Cys Lys Val Asn Asn Lys Asp Leu Pro Ala Pro Ile Glu Arg Thr Ile
625                 630                 635                 640

Ser Lys Pro Lys Gly Ser Val Arg Ala Pro Gln Val Tyr Val Leu Pro
                645                 650                 655

Pro Pro Glu Glu Glu Met Thr Lys Lys Gln Val Thr Leu Thr Cys Met
            660                 665                 670

Val Thr Asp Phe Met Pro Glu Asp Ile Tyr Val Glu Trp Thr Asn Asn
        675                 680                 685

Gly Lys Thr Glu Leu Asn Tyr Lys Asn Thr Glu Pro Val Leu Asp Ser
    690                 695                 700

Asp Gly Ser Tyr Phe Met Tyr Ser Lys Leu Arg Val Glu Lys Lys Asn
705                 710                 715                 720

Trp Val Glu Arg Asn Ser Tyr Ser Cys Ser Val Val His Glu Gly Leu
                725                 730                 735

His Asn His His Thr Thr Lys Ser Phe Ser Arg Thr Pro Gly Lys
            740                 745                 750


<210> SEQ ID NO 60
<211> LENGTH: 751
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gly Trp Ser Cys Ile Ile Leu Phe Leu Val Ala Thr Ala Thr Gly
1               5                   10                  15
```

-continued

```
Val His Ser Asp Pro Asn Phe Trp Leu Gln Val Gln Glu Ser Val Thr
            20                  25                  30

Val Gln Glu Gly Leu Cys Val Leu Val Pro Cys Thr Phe Phe His Pro
        35                  40                  45

Ile Pro Tyr Tyr Asp Lys Asn Ser Pro Val His Gly Tyr Trp Phe Arg
    50                  55                  60

Glu Gly Ala Ile Ile Ser Arg Asp Ser Pro Val Ala Thr Asn Lys Leu
65                  70                  75                  80

Asp Gln Glu Val Gln Glu Glu Thr Gln Gly Arg Phe Arg Leu Leu Gly
                85                  90                  95

Asp Pro Ser Arg Asn Asn Cys Ser Leu Ser Ile Val Asp Ala Arg Arg
            100                 105                 110

Arg Asp Asn Gly Ser Tyr Phe Phe Arg Met Glu Arg Gly Ser Thr Lys
        115                 120                 125

Tyr Ser Tyr Lys Ser Pro Gln Leu Ser Val His Val Thr Asp Leu Thr
    130                 135                 140

His Arg Pro Lys Ile Leu Ile Pro Gly Thr Leu Glu Pro Gly His Ser
145                 150                 155                 160

Lys Asn Leu Thr Cys Ser Val Ser Trp Ala Cys Glu Gln Gly Thr Pro
                165                 170                 175

Pro Ile Phe Ser Trp Leu Ser Ala Ala Pro Thr Ser Leu Gly Pro Arg
            180                 185                 190

Thr Thr His Ser Ser Val Leu Ile Ile Thr Pro Arg Pro Gln Asp His
        195                 200                 205

Gly Thr Asn Leu Thr Cys Gln Val Lys Phe Ala Gly Ala Gly Val Thr
    210                 215                 220

Thr Glu Arg Thr Ile Gln Leu Asn Val Thr Tyr Val Pro Gln Asn Pro
225                 230                 235                 240

Thr Thr Gly Ile Phe Pro Gly Asp Gly Ser Gly Lys Gln Glu Thr Arg
                245                 250                 255

Ala Gly Val Val His Glu Pro Arg Gly Pro Thr Ile Lys Pro Cys Pro
            260                 265                 270

Pro Cys Lys Cys Pro Ala Pro Asn Leu Leu Gly Gly Pro Ser Val Phe
        275                 280                 285

Ile Phe Pro Pro Lys Ile Lys Asp Val Leu Met Ile Ser Leu Ser Pro
    290                 295                 300

Ile Val Thr Cys Val Val Val Asp Val Ser Glu Asp Asp Pro Asp Val
305                 310                 315                 320

Gln Ile Ser Trp Phe Val Asn Asn Val Glu Val His Thr Ala Gln Thr
                325                 330                 335

Gln Thr His Arg Glu Asp Tyr Asn Ser Thr Leu Arg Val Val Ser Ala
            340                 345                 350

Leu Pro Ile Gln His Gln Asp Trp Met Ser Gly Lys Glu Phe Lys Cys
        355                 360                 365

Lys Val Asn Asn Lys Asp Leu Pro Ala Pro Ile Glu Arg Thr Ile Ser
    370                 375                 380

Lys Pro Lys Gly Ser Val Arg Ala Pro Gln Val Tyr Val Leu Pro Pro
385                 390                 395                 400

Pro Glu Glu Glu Met Thr Lys Lys Gln Val Thr Leu Thr Cys Met Val
                405                 410                 415

Thr Asp Phe Met Pro Glu Asp Ile Tyr Val Glu Trp Thr Asn Asn Gly
            420                 425                 430

Lys Thr Glu Leu Asn Tyr Lys Asn Thr Glu Pro Val Leu Asp Ser Asp
```

```
        435                 440                 445

Gly Ser Tyr Phe Met Tyr Ser Lys Leu Arg Val Glu Lys Lys Asn Trp
    450                 455                 460

Val Glu Arg Asn Ser Tyr Ser Cys Ser Val Val His Glu Gly Leu His
465                 470                 475                 480

Asn His His Thr Thr Lys Ser Phe Ser Arg Thr Pro Gly Lys Gly Gly
                485                 490                 495

Gly Gly Ser Gly Gly Gly Gly Ser Gly Gly Gly Gly Ser Asp Pro Asn
            500                 505                 510

Phe Trp Leu Gln Val Gln Glu Ser Val Thr Val Gln Glu Gly Leu Cys
        515                 520                 525

Val Leu Val Pro Cys Thr Phe Phe His Pro Ile Pro Tyr Tyr Asp Lys
    530                 535                 540

Asn Ser Pro Val His Gly Tyr Trp Phe Arg Glu Gly Ala Ile Ile Ser
545                 550                 555                 560

Arg Asp Ser Pro Val Ala Thr Asn Lys Leu Asp Gln Glu Val Gln Glu
                565                 570                 575

Glu Thr Gln Gly Arg Phe Arg Leu Leu Gly Asp Pro Ser Arg Asn Asn
            580                 585                 590

Cys Ser Leu Ser Ile Val Asp Ala Arg Arg Arg Asp Asn Gly Ser Tyr
        595                 600                 605

Phe Phe Arg Met Glu Arg Gly Ser Thr Lys Tyr Ser Tyr Lys Ser Pro
    610                 615                 620

Gln Leu Ser Val His Val Thr Asp Leu Thr His Arg Pro Lys Ile Leu
625                 630                 635                 640

Ile Pro Gly Thr Leu Glu Pro Gly His Ser Lys Asn Leu Thr Cys Ser
                645                 650                 655

Val Ser Trp Ala Cys Glu Gln Gly Thr Pro Pro Ile Phe Ser Trp Leu
            660                 665                 670

Ser Ala Ala Pro Thr Ser Leu Gly Pro Arg Thr Thr His Ser Ser Val
        675                 680                 685

Leu Ile Ile Thr Pro Arg Pro Gln Asp His Gly Thr Asn Leu Thr Cys
    690                 695                 700

Gln Val Lys Phe Ala Gly Ala Gly Val Thr Thr Glu Arg Thr Ile Gln
705                 710                 715                 720

Leu Asn Val Thr Tyr Val Pro Gln Asn Pro Thr Thr Gly Ile Phe Pro
                725                 730                 735

Gly Asp Gly Ser Gly Lys Gln Glu Thr Arg Ala Gly Val Val His
            740                 745                 750


<210> SEQ ID NO 61
<211> LENGTH: 628
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gly Trp Ser Cys Ile Ile Leu Phe Leu Val Ala Thr Ala Thr Gly
1               5                   10                  15

Val His Ser Gln Lys Ser Asn Arg Lys Asp Tyr Ser Leu Thr Met Gln
            20                  25                  30

Ser Ser Val Thr Val Gln Glu Gly Met Cys Val His Val Arg Cys Ser
        35                  40                  45
```

-continued

```
Phe Ser Tyr Pro Val Asp Ser Gln Thr Asp Ser Asp Pro Val His Gly
    50                  55                  60

Tyr Trp Phe Arg Ala Gly Asn Asp Ile Ser Trp Lys Ala Pro Val Ala
65                  70                  75                  80

Thr Asn Asn Pro Ala Trp Ala Val Gln Glu Glu Thr Arg Asp Arg Phe
                85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
        115                 120                 125

Gly Asn Ile Lys Trp Asn Tyr Lys Tyr Asp Gln Leu Ser Val Asn Val
    130                 135                 140

Thr Ala Leu Thr His Arg Pro Asn Ile Leu Ile Pro Gly Thr Leu Glu
145                 150                 155                 160

Ser Gly Cys Phe Gln Asn Leu Thr Cys Ser Val Pro Trp Ala Cys Glu
                165                 170                 175

Gln Gly Thr Pro Pro Met Ile Ser Trp Met Gly Thr Ser Val Ser Pro
            180                 185                 190

Leu His Pro Ser Thr Thr Arg Ser Ser Val Leu Thr Leu Ile Pro Gln
        195                 200                 205

Pro Gln His His Gly Thr Ser Leu Thr Cys Gln Val Thr Leu Pro Gly
    210                 215                 220

Ala Gly Val Thr Thr Asn Arg Thr Ile Gln Leu Asn Val Ser Tyr Pro
225                 230                 235                 240

Pro Gln Asn Leu Thr Val Thr Val Phe Gln Gly Glu Gly Thr Ala Ser
                245                 250                 255

Thr Ala Leu Gly Asn Ser Ser Ser Leu Ser Val Leu Glu Gly Gln Ser
            260                 265                 270

Leu Arg Leu Val Cys Ala Val Asp Ser Asn Pro Pro Ala Arg Leu Ser
        275                 280                 285

Trp Thr Trp Arg Ser Leu Thr Leu Tyr Pro Ser Gln Pro Ser Asn Pro
    290                 295                 300

Leu Val Leu Glu Leu Gln Val His Leu Gly Asp Glu Gly Glu Phe Thr
305                 310                 315                 320

Cys Arg Ala Gln Asn Ser Leu Gly Ser Gln His Val Ser Leu Asn Leu
                325                 330                 335

Ser Leu Gln Gln Glu Tyr Thr Gly Lys Met Arg Pro Val Ser Gly Val
            340                 345                 350

Leu Leu Gly Ala Val Gly Gly Gly Gly Gly Ser Gly Gly Gly Gly Ser
        355                 360                 365

Gly Tyr Ile Pro Glu Ala Pro Arg Asp Gly Gln Ala Tyr Val Arg Lys
    370                 375                 380

Asp Gly Glu Trp Val Leu Leu Ser Thr Phe Leu Glu Pro Arg Gly Pro
385                 390                 395                 400

Thr Ile Lys Pro Cys Pro Pro Cys Lys Cys Pro Ala Pro Asn Leu Leu
                405                 410                 415

Gly Gly Pro Ser Val Phe Ile Phe Pro Pro Lys Ile Lys Asp Val Leu
            420                 425                 430

Met Ile Ser Leu Ser Pro Ile Val Thr Cys Val Val Val Asp Val Ser
        435                 440                 445

Glu Asp Asp Pro Asp Val Gln Ile Ser Trp Phe Val Asn Asn Val Glu
    450                 455                 460

Val His Thr Ala Gln Thr Gln Thr His Arg Glu Asp Tyr Asn Ser Thr
```

465 470 475 480

Leu Arg Val Val Ser Ala Leu Pro Ile Gln His Gln Asp Trp Met Ser
485 490 495

Gly Lys Glu Phe Lys Cys Lys Val Asn Asn Lys Asp Leu Pro Ala Pro
500 505 510

Ile Glu Arg Thr Ile Ser Lys Pro Lys Gly Ser Val Arg Ala Pro Gln
515 520 525

Val Tyr Val Leu Pro Pro Pro Glu Glu Glu Met Thr Lys Lys Gln Val
530 535 540

Thr Leu Thr Cys Met Val Thr Asp Phe Met Pro Glu Asp Ile Tyr Val
545 550 555 560

Glu Trp Thr Asn Asn Gly Lys Thr Glu Leu Asn Tyr Lys Asn Thr Glu
565 570 575

Pro Val Leu Asp Ser Asp Gly Ser Tyr Phe Met Tyr Ser Lys Leu Arg
580 585 590

Val Glu Lys Lys Asn Trp Val Glu Arg Asn Ser Tyr Ser Cys Ser Val
595 600 605

Val His Glu Gly Leu His Asn His His Thr Thr Lys Ser Phe Ser Arg
610 615 620

Thr Pro Gly Lys
625

<210> SEQ ID NO 62
<211> LENGTH: 628
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Met Gly Trp Ser Cys Ile Ile Leu Phe Leu Val Ala Thr Ala Thr Gly
1 5 10 15

Val His Ser Gln Lys Ser Asn Arg Lys Asp Tyr Ser Leu Thr Met Gln
20 25 30

Ser Ser Val Thr Val Gln Glu Gly Met Cys Val His Val Arg Cys Ser
35 40 45

Phe Ser Tyr Pro Val Asp Ser Gln Thr Asp Ser Asp Pro Val His Gly
50 55 60

Tyr Trp Phe Arg Ala Gly Asn Asp Ile Ser Trp Lys Ala Pro Val Ala
65 70 75 80

Thr Asn Asn Pro Ala Trp Ala Val Gln Glu Glu Thr Arg Asp Arg Phe
85 90 95

His Leu Leu Gly Asp Pro Gln Thr Lys Asn Cys Thr Leu Ser Ile Arg
100 105 110

Asp Ala Arg Met Ser Asp Ala Gly Arg Tyr Phe Phe Arg Met Glu Lys
115 120 125

Gly Asn Ile Lys Trp Asn Tyr Lys Tyr Asp Gln Leu Ser Val Asn Val
130 135 140

Thr Ala Leu Thr His Arg Pro Asn Ile Leu Ile Pro Gly Thr Leu Glu
145 150 155 160

Ser Gly Cys Phe Gln Asn Leu Thr Cys Ser Val Pro Trp Ala Cys Glu
165 170 175

Gln Gly Thr Pro Pro Met Ile Ser Trp Met Gly Thr Ser Val Ser Pro
180 185 190

-continued

```
Leu His Pro Ser Thr Thr Arg Ser Ser Val Leu Thr Leu Ile Pro Gln
        195                 200                 205

Pro Gln His His Gly Thr Ser Leu Thr Cys Gln Val Thr Leu Pro Gly
    210                 215                 220

Ala Gly Val Thr Thr Asn Arg Thr Ile Gln Leu Asn Val Ser Tyr Pro
225                 230                 235                 240

Pro Gln Asn Leu Thr Val Thr Val Phe Gln Gly Glu Gly Thr Ala Ser
                245                 250                 255

Thr Ala Leu Gly Asn Ser Ser Ser Leu Ser Val Leu Glu Gly Gln Ser
            260                 265                 270

Leu Arg Leu Val Cys Ala Val Asp Ser Asn Pro Pro Ala Arg Leu Ser
        275                 280                 285

Trp Thr Trp Arg Ser Leu Thr Leu Tyr Pro Ser Gln Pro Ser Asn Pro
    290                 295                 300

Leu Val Leu Glu Leu Gln Val His Leu Gly Asp Glu Gly Glu Phe Thr
305                 310                 315                 320

Cys Arg Ala Gln Asn Ser Leu Gly Ser Gln His Val Ser Leu Asn Leu
                325                 330                 335

Ser Leu Gln Gln Glu Tyr Thr Gly Lys Met Arg Pro Val Ser Gly Val
            340                 345                 350

Leu Leu Gly Ala Val Gly Glu Pro Arg Gly Pro Thr Ile Lys Pro Cys
        355                 360                 365

Pro Pro Cys Lys Cys Pro Ala Pro Asn Leu Leu Gly Gly Pro Ser Val
    370                 375                 380

Phe Ile Phe Pro Pro Lys Ile Lys Asp Val Leu Met Ile Ser Leu Ser
385                 390                 395                 400

Pro Ile Val Thr Cys Val Val Val Asp Val Ser Glu Asp Asp Pro Asp
                405                 410                 415

Val Gln Ile Ser Trp Phe Val Asn Asn Val Glu Val His Thr Ala Gln
            420                 425                 430

Thr Gln Thr His Arg Glu Asp Tyr Asn Ser Thr Leu Arg Val Val Ser
        435                 440                 445

Ala Leu Pro Ile Gln His Gln Asp Trp Met Ser Gly Lys Glu Phe Lys
    450                 455                 460

Cys Lys Val Asn Asn Lys Asp Leu Pro Ala Pro Ile Glu Arg Thr Ile
465                 470                 475                 480

Ser Lys Pro Lys Gly Ser Val Arg Ala Pro Gln Val Tyr Val Leu Pro
                485                 490                 495

Pro Pro Glu Glu Glu Met Thr Lys Lys Gln Val Thr Leu Thr Cys Met
            500                 505                 510

Val Thr Asp Phe Met Pro Glu Asp Ile Tyr Val Glu Trp Thr Asn Asn
        515                 520                 525

Gly Lys Thr Glu Leu Asn Tyr Lys Asn Thr Glu Pro Val Leu Asp Ser
    530                 535                 540

Asp Gly Ser Tyr Phe Met Tyr Ser Lys Leu Arg Val Glu Lys Lys Asn
545                 550                 555                 560

Trp Val Glu Arg Asn Ser Tyr Ser Cys Ser Val Val His Glu Gly Leu
                565                 570                 575

His Asn His His Thr Thr Lys Ser Phe Ser Arg Thr Pro Gly Lys Gly
            580                 585                 590

Gly Gly Gly Ser Gly Gly Gly Gly Ser Gly Tyr Ile Pro Glu Ala Pro
        595                 600                 605

Arg Asp Gly Gln Ala Tyr Val Arg Lys Asp Gly Glu Trp Val Leu Leu
```

```
    610                 615                 620

Ser Thr Phe Leu
625


<210> SEQ ID NO 63
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gly Trp Ser Cys Ile Ile Leu Phe Leu Val Ala Thr Ala Thr Gly
1               5                   10                  15

Val His Ser Gln Thr Ser Lys Leu Leu Thr Met Gln Ser Ser Val Thr
            20                  25                  30

Val Gln Glu Gly Leu Cys Val His Val Pro Cys Ser Phe Ser Tyr Pro
        35                  40                  45

Ser His Gly Trp Ile Tyr Pro Gly Pro Val Val His Gly Tyr Trp Phe
    50                  55                  60

Arg Glu Gly Ala Asn Thr Asp Gln Asp Ala Pro Val Ala Thr Asn Asn
65                  70                  75                  80

Pro Ala Arg Ala Val Trp Glu Glu Thr Arg Asp Arg Phe His Leu Leu
                85                  90                  95

Gly Asp Pro His Thr Lys Asn Cys Thr Leu Ser Ile Arg Asp Ala Arg
            100                 105                 110

Arg Ser Asp Ala Gly Arg Tyr Phe Phe Arg Met Glu Lys Gly Ser Ile
        115                 120                 125

Lys Trp Asn Tyr Lys His His Arg Leu Ser Val Asn Val Thr Ala Leu
    130                 135                 140

Thr His Arg Pro Asn Ile Leu Ile Pro Gly Thr Leu Glu Ser Gly Cys
145                 150                 155                 160

Pro Gln Asn Leu Thr Cys Ser Val Pro Trp Ala Cys Glu Gln Gly Thr
                165                 170                 175

Pro Pro Met Ile Ser Trp Ile Gly Thr Ser Val Ser Pro Leu Asp Pro
            180                 185                 190

Ser Thr Thr Arg Ser Ser Val Leu Thr Leu Ile Pro Gln Pro Gln Asp
        195                 200                 205

His Gly Thr Ser Leu Thr Cys Gln Val Thr Phe Pro Gly Ala Ser Val
    210                 215                 220

Thr Thr Asn Lys Thr Val His Leu Asn Val Ser Tyr Pro Pro Gln Asn
225                 230                 235                 240

Leu Thr Met Thr Val Phe Gln Gly Asp Gly Thr Val Ser Thr Val Leu
                245                 250                 255

Gly Asn Gly Ser Ser Leu Ser Leu Pro Glu Gly Gln Ser Leu Arg Leu
            260                 265                 270

Val Cys Ala Val Asp Ala Val Asp Ser Asn Pro Pro Ala Arg Leu Ser
        275                 280                 285

Leu Ser Trp Arg Gly Leu Thr Leu Cys Pro Ser Gln Pro Ser Asn Pro
    290                 295                 300

Gly Val Leu Glu Leu Pro Trp Val His Leu Arg Asp Ala Ala Glu Phe
305                 310                 315                 320

Thr Cys Arg Ala Gln Asn Pro Leu Gly Ser Gln Gln Val Tyr Leu Asn
                325                 330                 335
```

-continued

```
Val Ser Leu Gln Ser Lys Ala Thr Ser Gly Val Thr Gln Gly Gly Gly
            340                 345                 350

Gly Gly Ser Gly Gly Gly Gly Ser Gly Tyr Ile Pro Glu Ala Pro Arg
        355                 360                 365

Asp Gly Gln Ala Tyr Val Arg Lys Asp Gly Glu Trp Val Leu Leu Ser
    370                 375                 380

Thr Phe Leu Glu Pro Arg Gly Pro Thr Ile Lys Pro Cys Pro Pro Cys
385                 390                 395                 400

Lys Cys Pro Ala Pro Asn Leu Leu Gly Gly Pro Ser Val Phe Ile Phe
                405                 410                 415

Pro Pro Lys Ile Lys Asp Val Leu Met Ile Ser Leu Ser Pro Ile Val
            420                 425                 430

Thr Cys Val Val Val Asp Val Ser Glu Asp Asp Pro Asp Val Gln Ile
        435                 440                 445

Ser Trp Phe Val Asn Asn Val Glu Val His Thr Ala Gln Thr Gln Thr
    450                 455                 460

His Arg Glu Asp Tyr Asn Ser Thr Leu Arg Val Val Ser Ala Leu Pro
465                 470                 475                 480

Ile Gln His Gln Asp Trp Met Ser Gly Lys Glu Phe Lys Cys Lys Val
                485                 490                 495

Asn Asn Lys Asp Leu Pro Ala Pro Ile Glu Arg Thr Ile Ser Lys Pro
            500                 505                 510

Lys Gly Ser Val Arg Ala Pro Gln Val Tyr Val Leu Pro Pro Pro Glu
        515                 520                 525

Glu Glu Met Thr Lys Lys Gln Val Thr Leu Thr Cys Met Val Thr Asp
    530                 535                 540

Phe Met Pro Glu Asp Ile Tyr Val Glu Trp Thr Asn Asn Gly Lys Thr
545                 550                 555                 560

Glu Leu Asn Tyr Lys Asn Thr Glu Pro Val Leu Asp Ser Asp Gly Ser
                565                 570                 575

Tyr Phe Met Tyr Ser Lys Leu Arg Val Glu Lys Lys Asn Trp Val Glu
            580                 585                 590

Arg Asn Ser Tyr Ser Cys Ser Val Val His Glu Gly Leu His Asn His
        595                 600                 605

His Thr Thr Lys Ser Phe Ser Arg Thr Pro Gly Lys
    610                 615                 620


<210> SEQ ID NO 64
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Gly Trp Ser Cys Ile Ile Leu Phe Leu Val Ala Thr Ala Thr Gly
1               5                   10                  15

Val His Ser Gln Thr Ser Lys Leu Leu Thr Met Gln Ser Ser Val Thr
            20                  25                  30

Val Gln Glu Gly Leu Cys Val His Val Pro Cys Ser Phe Ser Tyr Pro
        35                  40                  45

Ser His Gly Trp Ile Tyr Pro Gly Pro Val Val His Gly Tyr Trp Phe
    50                  55                  60

Arg Glu Gly Ala Asn Thr Asp Gln Asp Ala Pro Val Ala Thr Asn Asn
65                  70                  75                  80
```

-continued

```
Pro Ala Arg Ala Val Trp Glu Glu Thr Arg Asp Arg Phe His Leu Leu
                85                  90                  95

Gly Asp Pro His Thr Lys Asn Cys Thr Leu Ser Ile Arg Asp Ala Arg
            100                 105                 110

Arg Ser Asp Ala Gly Arg Tyr Phe Phe Arg Met Glu Lys Gly Ser Ile
        115                 120                 125

Lys Trp Asn Tyr Lys His His Arg Leu Ser Val Asn Val Thr Ala Leu
    130                 135                 140

Thr His Arg Pro Asn Ile Leu Ile Pro Gly Thr Leu Glu Ser Gly Cys
145                 150                 155                 160

Pro Gln Asn Leu Thr Cys Ser Val Pro Trp Ala Cys Glu Gln Gly Thr
                165                 170                 175

Pro Pro Met Ile Ser Trp Ile Gly Thr Ser Val Ser Pro Leu Asp Pro
            180                 185                 190

Ser Thr Thr Arg Ser Ser Val Leu Thr Leu Ile Pro Gln Pro Gln Asp
        195                 200                 205

His Gly Thr Ser Leu Thr Cys Gln Val Thr Phe Pro Gly Ala Ser Val
    210                 215                 220

Thr Thr Asn Lys Thr Val His Leu Asn Val Ser Tyr Pro Pro Gln Asn
225                 230                 235                 240

Leu Thr Met Thr Val Phe Gln Gly Asp Gly Thr Val Ser Thr Val Leu
                245                 250                 255

Gly Asn Gly Ser Ser Leu Ser Leu Pro Glu Gly Gln Ser Leu Arg Leu
            260                 265                 270

Val Cys Ala Val Asp Ala Val Asp Ser Asn Pro Pro Ala Arg Leu Ser
        275                 280                 285

Leu Ser Trp Arg Gly Leu Thr Leu Cys Pro Ser Gln Pro Ser Asn Pro
    290                 295                 300

Gly Val Leu Glu Leu Pro Trp Val His Leu Arg Asp Ala Ala Glu Phe
305                 310                 315                 320

Thr Cys Arg Ala Gln Asn Pro Leu Gly Ser Gln Gln Val Tyr Leu Asn
                325                 330                 335

Val Ser Leu Gln Ser Lys Ala Thr Ser Gly Val Thr Gln Gly Glu Pro
            340                 345                 350

Arg Gly Pro Thr Ile Lys Pro Cys Pro Pro Cys Lys Cys Pro Ala Pro
        355                 360                 365

Asn Leu Leu Gly Gly Pro Ser Val Phe Ile Phe Pro Pro Lys Ile Lys
    370                 375                 380

Asp Val Leu Met Ile Ser Leu Ser Pro Ile Val Thr Cys Val Val Val
385                 390                 395                 400

Asp Val Ser Glu Asp Asp Pro Asp Val Gln Ile Ser Trp Phe Val Asn
                405                 410                 415

Asn Val Glu Val His Thr Ala Gln Thr Gln Thr His Arg Glu Asp Tyr
            420                 425                 430

Asn Ser Thr Leu Arg Val Val Ser Ala Leu Pro Ile Gln His Gln Asp
        435                 440                 445

Trp Met Ser Gly Lys Glu Phe Lys Cys Lys Val Asn Asn Lys Asp Leu
    450                 455                 460

Pro Ala Pro Ile Glu Arg Thr Ile Ser Lys Pro Lys Gly Ser Val Arg
465                 470                 475                 480

Ala Pro Gln Val Tyr Val Leu Pro Pro Pro Glu Glu Glu Met Thr Lys
                485                 490                 495
```

```
Lys Gln Val Thr Leu Thr Cys Met Val Thr Asp Phe Met Pro Glu Asp
            500                 505                 510

Ile Tyr Val Glu Trp Thr Asn Asn Gly Lys Thr Glu Leu Asn Tyr Lys
        515                 520                 525

Asn Thr Glu Pro Val Leu Asp Ser Asp Gly Ser Tyr Phe Met Tyr Ser
    530                 535                 540

Lys Leu Arg Val Glu Lys Lys Asn Trp Val Glu Arg Asn Ser Tyr Ser
545                 550                 555                 560

Cys Ser Val Val His Glu Gly Leu His Asn His His Thr Thr Lys Ser
                565                 570                 575

Phe Ser Arg Thr Pro Gly Lys Gly Gly Gly Gly Ser Gly Gly Gly Gly
            580                 585                 590

Ser Gly Tyr Ile Pro Glu Ala Pro Arg Asp Gly Gln Ala Tyr Val Arg
        595                 600                 605

Lys Asp Gly Glu Trp Val Leu Leu Ser Thr Phe Leu
    610                 615                 620


<210> SEQ ID NO 65
<211> LENGTH: 212
<212> TYPE: PRT
<213> ORGANISM: Homo sapiens

<400> SEQUENCE: 65

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30

Trp Ile Tyr Pro Gly Pro Val Val His Gly Tyr Trp Phe Arg Glu Gly
        35                  40                  45

Ala Asn Thr Asp Gln Asp Ala Pro Val Ala Thr Asn Asn Pro Ala Arg
    50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
    130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His
    210


<210> SEQ ID NO 66
<211> LENGTH: 331
<212> TYPE: PRT
<213> ORGANISM: Homo sapiens
```

<400> SEQUENCE: 66

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30

Trp Ile Tyr Pro Gly Pro Val Val His Gly Tyr Trp Phe Arg Glu Gly
        35                  40                  45

Ala Asn Thr Asp Gln Asp Ala Pro Val Ala Thr Asn Asn Pro Ala Arg
    50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
    130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro Pro Gln Asn Leu Thr Met
    210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
                245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
        275                 280                 285

Glu Leu Pro Trp Val His Leu Arg Asp Ala Ala Glu Phe Thr Cys Arg
    290                 295                 300

Ala Gln Asn Pro Leu Gly Ser Gln Gln Val Tyr Leu Asn Val Ser Leu
305                 310                 315                 320

Gln Ser Lys Ala Thr Ser Gly Val Thr Gln Gly
                325                 330

<210> SEQ ID NO 67
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Gly Trp Ser Cys Ile Ile Leu Phe Leu Val Ala Thr Ala Thr Gly
1               5                   10                  15

-continued

```
Val His Ser Gln Thr Ser Lys Leu Leu Thr Met Gln Ser Ser Val Thr
            20                  25                  30

Val Gln Glu Gly Leu Cys Val His Val Pro Cys Ser Phe Ser Tyr Pro
        35                  40                  45

Ser His Gly Trp Ile Tyr Pro Gly Pro Val Val His Gly Tyr Trp Phe
    50                  55                  60

Arg Glu Gly Ala Asn Thr Asp Gln Asp Ala Pro Val Ala Thr Asn Asn
65                  70                  75                  80

Pro Ala Arg Ala Val Trp Glu Glu Thr Arg Asp Arg Phe His Leu Leu
                85                  90                  95

Gly Asp Pro His Thr Lys Asn Cys Thr Leu Ser Ile Arg Asp Ala Arg
            100                 105                 110

Arg Ser Asp Ala Gly Arg Tyr Phe Phe Arg Met Glu Lys Gly Ser Ile
        115                 120                 125

Lys Trp Asn Tyr Lys His His Arg Leu Ser Val Asn Val Thr Ala Leu
    130                 135                 140

Thr His Arg Pro Asn Ile Leu Ile Pro Gly Thr Leu Glu Ser Gly Ser
145                 150                 155                 160

Pro Gln Asn Leu Thr Cys Ser Val Pro Trp Ala Cys Glu Gln Gly Thr
                165                 170                 175

Pro Pro Met Ile Ser Trp Ile Gly Thr Ser Val Ser Pro Leu Asp Pro
            180                 185                 190

Ser Thr Thr Arg Ser Ser Val Leu Thr Leu Ile Pro Gln Pro Gln Asp
        195                 200                 205

His Gly Thr Ser Leu Thr Cys Gln Val Thr Phe Pro Gly Ala Ser Val
    210                 215                 220

Thr Thr Asn Lys Thr Val His Leu Asn Val Ser Tyr Pro Pro Gln Asn
225                 230                 235                 240

Leu Thr Met Thr Val Phe Gln Gly Asp Gly Thr Val Ser Thr Val Leu
                245                 250                 255

Gly Asn Gly Ser Ser Leu Ser Leu Pro Glu Gly Gln Ser Leu Arg Leu
            260                 265                 270

Val Cys Ala Val Asp Ala Val Asp Ser Asn Pro Pro Ala Arg Leu Ser
        275                 280                 285

Leu Ser Trp Arg Gly Leu Thr Leu Tyr Pro Ser Gln Pro Ser Asn Pro
    290                 295                 300

Gly Val Leu Glu Leu Pro Trp Val His Leu Arg Asp Ala Ala Glu Phe
305                 310                 315                 320

Thr Cys Arg Ala Gln Asn Pro Leu Gly Ser Gln Gln Val Tyr Leu Asn
                325                 330                 335

Val Ser Leu Gln Ser Lys Ala Thr Ser Gly Val Thr Gln Gly Gly Tyr
            340                 345                 350

Ile Pro Glu Ala Pro Arg Asp Gly Gln Ala Tyr Val Arg Lys Asp Gly
        355                 360                 365

Glu Trp Val Leu Leu Ser Thr Phe Leu Glu Pro Arg Gly Pro Thr Ile
    370                 375                 380

Lys Pro Cys Pro Pro Cys Lys Cys Pro Ala Pro Asn Leu Leu Gly Gly
385                 390                 395                 400

Pro Ser Val Phe Ile Phe Pro Pro Lys Ile Lys Asp Val Leu Met Ile
                405                 410                 415

Ser Leu Ser Pro Ile Val Thr Cys Val Val Val Asp Val Ser Glu Asp
            420                 425                 430
```

```
Asp Pro Asp Val Gln Ile Ser Trp Phe Val Asn Asn Val Glu Val His
        435                 440                 445

Thr Ala Gln Thr Gln Thr His Arg Glu Asp Tyr Asn Ser Thr Leu Arg
    450                 455                 460

Val Val Ser Ala Leu Pro Ile Gln His Gln Asp Trp Met Ser Gly Lys
465                 470                 475                 480

Glu Phe Lys Cys Lys Val Asn Asn Lys Asp Leu Pro Ala Pro Ile Glu
                485                 490                 495

Arg Thr Ile Ser Lys Pro Lys Gly Ser Val Arg Ala Pro Gln Val Tyr
            500                 505                 510

Val Leu Pro Pro Pro Glu Glu Glu Met Thr Lys Lys Gln Val Thr Leu
        515                 520                 525

Thr Cys Met Val Thr Asp Phe Met Pro Glu Asp Ile Tyr Val Glu Trp
    530                 535                 540

Thr Asn Asn Gly Lys Thr Glu Leu Asn Tyr Lys Asn Thr Glu Pro Val
545                 550                 555                 560

Leu Asp Ser Asp Gly Ser Tyr Phe Met Tyr Ser Lys Leu Arg Val Glu
                565                 570                 575

Lys Lys Asn Trp Val Glu Arg Asn Ser Tyr Ser Cys Ser Val Val His
            580                 585                 590

Glu Gly Leu His Asn His His Thr Thr Lys Ser Phe Ser Arg Thr Pro
        595                 600                 605

Gly Lys
    610


<210> SEQ ID NO 68
<211> LENGTH: 1833
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

atgggatgga gctgtatcat cctcttcttg gtagcaacag ctacaggtgt acactcccag     60

accagcaagc tgctgaccat gcagagcagc gtgaccgtgc aggagggcct gtgcgtgcat    120

gtgccctgca gcttcagcta ccccagccac ggctggatct accccggtcc cgtagtgcac    180

ggctactggt tcagggaggg cgccaacacc gaccaggacg ctcccgtggc aaccaacaac    240

cccgccaggg ccgtgtggga ggagaccagg gacaggttcc acctgctggg cgacccccac    300

accaagaact gcaccctgag catcagggac gccaggagga gcgacgccgg caggtacttc    360

ttcaggatgg agaaggggtc tatcaagtgg aactacaagc accaccggct gagcgtgaat    420

gtgaccgccc tgacccaccg gcccaatatc ctcatccccg gcaccctgga gagcggcagc    480

ccccagaatc ttacctgcag cgtaccctgg gcctgcgagc agggcacccc tccaatgatc    540

agctggatcg gcaccagcgt gagccccctg gaccctagta ccaccaggag cagcgtgctg    600

accctgatcc cccagcccca ggaccacgga accagcctga cctgccaggt gaccttcccc    660

ggagccagcg taaccaccaa caagaccgtg cacctgaacg tgagctaccc accccaaaac    720

ctgaccatga ccgtgttcca gggcgacggc acggtgagca ccgtactggg caacggcagc    780

tctctgagcc tgcccgaggg ccagagcttg cggctggtct gcgccgtgga tgctgtggac    840

agcaaccctc ccgccaggct gagcctgagc tggaggggcc tgaccctgta ccccagccag    900

cccagcaatc ccggcgtgct ggagctgccc tgggttcacc tgagggacgc tgccgagttc    960
```

-continued

```
acatgtaggg cccagaaccc cctgggctct cagcaggtgt acctgaacgt gtctcttcag   1020

agtaaggcca ccagcggcgt gacccaagga ggctatatcc ccgaggctcc tagagatggc   1080

caggcctatg ttcggaagga tggcgaatgg gtgctgctga gcaccttcct tgaacctcga   1140

gggcctacca tcaagccctg tcctccatgc aagtgccccg ctcctaatct gctcggaggc   1200

cccagcgtgt tcatcttccc acctaagatc aaggacgtgc tgatgatctc tctgagcccc   1260

atcgtgacct gcgtggtggt ggatgtgtcc gaggacgatc ccgatgtgca gatcagttgg   1320

ttcgtgaaca acgtggaagt gcacacagcc cagacacaga cccacagaga ggactacaac   1380

agcaccctga gagtggtgtc tgccctgcct atccagcacc aggattggat gagcggcaaa   1440

gaattcaagt gcaaagtgaa caacaaggac ctgcctgctc ctatcgagcg gaccatctct   1500

aagcctaagg gctctgttag agcccctcag gtgtacgtgc tgcctcctcc agaggaagag   1560

atgaccaaga aacaagtgac cctgacctgc atggtcaccg acttcatgcc cgaggacatc   1620

tacgtggaat ggaccaacaa cggcaagacc gagctgaact acaagaacac cgagcctgtg   1680

ctggacagcg acggcagcta cttcatgtac tccaagctgc gcgtggaaaa gaagaactgg   1740

gtcgagcgga acagctacag ctgctctgtg gtgcacgagg gcctgcacaa tcaccacacc   1800

accaagagct tcagccgtac gcctggaaag tag                                1833
```

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

```
Gly Gly Gly Gly Ser Gly Gly Gly Gly Ser
1               5                   10
```

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(15)
<223> OTHER INFORMATION: This sequence may encompass 1-5 “Gly Gly Pro” repeating units

<400> SEQUENCE: 70

```
Gly Gly Pro Gly Gly Pro Gly Gly Pro Gly Gly Pro Gly Gly Pro
1               5                   10                  15
```

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(25)
<223> OTHER INFORMATION: This sequence may encompass 1-5 “Gly Gly Gly Gly Ser” repeating units

<400> SEQUENCE: 71

-continued

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gly Gly Gly Ser Gly Gly Gly Gly Ser Gly Gly Gly Gly Ser
1               5                   10                  15


<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met Gly Trp Ser Cys Ile Ile Leu Phe Leu Val Ala Thr Ala Thr Gly
1               5                   10                  15

Val His Ser
```

MULTIMERIC PROTEINS FOR DETECTING A CARBOHYDRATE AND/OR TREATING A SIGLEC-MEDIATED DISORDER

This application is a § 371 National Stage of International (PCT) Patent Application Serial No. PCT/US2019/036161, filed Jun. 7, 2019, which claims priority to and the benefit of U.S. Provisional Patent Application No. 62/681,849, filed on Jun. 7, 2018, and U.S. Provisional Patent Application 62/755,285, filed Nov. 2, 2018; the contents of each of which are hereby incorporated by reference in their entirety.

SEQUENCE LISTING

The instant application contains a Sequence Listing which has been filed electronically in ASCII format and is hereby incorporated by reference in its entirety. Said ASCII copy, created on Aug. 10, 2021, is named PAL-008_SL.txt and is 270,332 bytes in size.

FIELD OF THE INVENTION

The invention relates generally to methods and compositions for detecting a carbohydrate, e.g., a Siglec ligand, and to methods for treating a Siglec-mediated disorder.

BACKGROUND

Siglecs (Sialic acid-binding immunoglobulin-type lectins) are cell surface proteins that bind sialic acid. Siglecs comprise a lectin family of surface receptors that bind to sialoglycans and are predominantly expressed on cells of the hematopoietic system in a manner dependent on cell type and differentiation. Siglecs are Type I transmembrane proteins where the amino terminus is located in the extracellular space and the carboxy terminus is located in the cytosol. Each Siglec contains an N-terminal V-set immunoglobulin-like domain (Ig domain) that acts as the binding receptor for sialic acid. Siglecs are lectins, and are categorized into the group of I-type lectins because the lectin domain is an immunoglobulin fold. All Siglecs extend from the cell surface by means of intervening C2-set domains which have no binding activity. Siglecs differ in the number of these C2-set domains. As these proteins contain Ig domains, they are members of the Immunoglobulin superfamily (IgSF).

There are at least 14 different mammalian Siglecs, which together provide an array of different functions based on cell surface receptor-ligand interactions. These receptor-glycan interactions can mediate, among other things, cell adhesion and cell signaling. Although sialic acid is ubiquitously expressed, typically at the terminal position of glycoproteins and lipids, only very specific, distinct sialoglycan structures are recognized by individual Siglecs, depending on identity and linkage to subterminal carbohydrate moieties.

A growing body of evidence supports roles for glycans, and sialoglycans in particular, at various pathophysiological steps of tumor progression. Glycans regulate tumor proliferation, invasion, hematogenous metastasis and angiogenesis (Fuster et al. (2005) Nat. Rev. Cancer 5(7):526-42). The sialylation of cell surface glycoconjugates is frequently altered in cancers, resulting in the expression of sialylated tumor-associated carbohydrate antigens that are specific markers for this disease. Because sialylated glycans are involved in many biological processes, their expression by tumor cells is often associated with increased aggressiveness and metastatic potential of the tumors.

However, the heterogeneity of Siglec ligands causes difficulties in developing detection reagents (e.g., antibodies) specific to a particular ligand. Such detection reagents would be useful for many purposes, including as part of a biomarker strategy to classify cancer type based on the expression of specific Siglec ligand(s). Accordingly, there is a need in the art for improved Siglec detection methods and reagents.

SUMMARY OF THE INVENTION

The invention is based, in part, upon the discovery of recombinant polypeptides that can be used to detect a Siglec ligand, e.g., in a sample of interest, and/or treat a Siglec-mediated disorder in a subject in need thereof. In certain embodiments, recombinant polypeptides are associated (non-covalently and/or covalently) to produce a multimeric protein that is used to detect a Siglec ligand and/or treat a Siglec-mediated disorder in a subject in need thereof.

In one aspect, the invention provides an isolated polypeptide comprising a lectin domain, a trimerization domain, and a dimerization domain. In certain embodiments, the lectin domain, the trimerization domain, and the dimerization domain are covalently linked together in an N- to C-terminal orientation. In certain embodiments, the lectin domain, the dimerization domain, and the trimerization domain are covalently linked together in an N- to C-terminal orientation. For example, in certain embodiments, the polypeptide further comprises a linker. In certain other embodiments, the polypeptide further comprises a linker between the lectin domain and the trimerization domain, and in certain other embodiments, the polypeptide further comprises a linker between the dimerization domain and the trimerization domain.

In another aspect, the invention provides an isolated polypeptide comprising a first lectin domain, a second lectin domain, and a dimerization domain. In certain embodiments, the first lectin domain and the second lectin domain are identical. In certain embodiments, the first lectin domain, the second lectin domain, and the dimerization domain are covalently linked together in an N- to C-terminal orientation. In certain embodiments, the first lectin domain, the dimerization domain, and the second lectin domain are covalently linked together in an N- to C-terminal orientation.

In certain embodiments of the above aspects, the lectin domain comprises a Siglec sialic acid binding V-set immunoglobulin-like domain or a variant thereof. In certain embodiments, the lectin domain comprises a Siglec extracellular domain or a variant thereof. The Siglec from which the Siglec sialic acid binding V-set immunoglobulin-like domain or extracellular domain is derived can be a mammalian Siglec, such as a human, monkey, dog, rat, or mouse Siglec.

In certain embodiments, the Siglec is a human Siglec. In certain embodiments, the Siglec can be Siglec-1, Siglec-2, Siglec-3, Siglec-4, Siglec-5, Siglec-6, Siglec-7, Siglec-8, Siglec-9, Siglec-10, Siglec-11, Siglec-12, Siglec-14 or Siglec-15. In certain embodiments, the Siglec can be Siglec-3, Siglec-5, Siglec-6, Siglec-7, Siglec-8, Siglec-9, Siglec-10, or Siglec-11. In certain embodiments, the Siglec can be Siglec-3, Siglec-7, or Siglec-9. In certain embodiments, the Siglec can be Siglec-7 or Siglec-9. In certain embodiments, the lectin domain comprises SEQ ID NO: 1, SEQ ID NO: 2, SEQ ID NO: 43, or SEQ ID NO: 44, or SEQ ID NO: 51. In certain embodiments, the lectin domain comprises SEQ ID NO: 3, SEQ ID NO: 4, SEQ ID NO: 13, SEQ ID NO: 14, SEQ ID NO: 52, SEQ ID NO: 65, or SEQ ID NO: 66.

In certain embodiments, the Siglec is a mouse Siglec. The mouse Siglec can be, for example, SigE, SigF, SigG, or SigF.

In certain embodiments, the lectin domain comprises a C-type lectin domain. The C-type lectin can be, for example, CLEC1A, CLEC1B, CLEC2A, CLEC2B, CD69 (CLEC2C), CLEC2D, CLEC2L, CLEC3A, CLEC3B, CLEC4A, CLEC4C, CLEC4D, CLEC4E, CLEC4F, CLEC4G, ASGR1 (CLEC4H1), ASGR2 (CLEC4H2), FCER2 (CLEC4J), CD207 (CLEC4K), CD209 (CLEC4L), CLEC4M, CLEC5A, CLEC6A, CLEC7A, OLR1 (CLEC8A), CLEC9A, CLEC10A, CLEC11A, CLEC12A, CLEC12B, CD302 (CLEC13A), LY75 (CLEC13B), PLA2R1 (CLEC13C), MRC1 (CLEC13D), MRC2 (CLEC13E), CLEC14A, CLEC16A, CLEC17A, KLRA1, KLRB1 (CLEC5B), KLRC1, KLRC2, KLRC3, KLRC4, KLRD1, KLRF1 (CLEC5C), KLRG1 (CLEC15A), KLRG2 (CLEC15B), or KLRK1. In certain embodiments, the C-type lectin is selected from CLEC4A, CLEC12A, and CLEC12B.

In certain embodiments, the trimerization domain is a natural trimerization domain or a synthetic trimerization domain. In certain embodiments, the trimerization domain is selected from a T4 phage fibritin (foldon), clathrin, heat shock factor 1, collagen, hemagglutinin, GCN4, GCN4-based isoleucine zipper, and coiled-coil peptide trimerization domain. In certain embodiments, the trimerization domain is selected from a GCN4-based isoleucine zipper and T4 phage fibritin (foldon) trimerization domain. In certain embodiments, the trimerization domain is a T4 phage fibritin (foldon) trimerization domain, such as SEQ ID NO: 5.

In certain embodiments, the dimerization domain is a natural dimerization domain or a synthetic dimerization domain. In certain embodiments, the dimerization domain is selected from an immunoglobulin Fc domain, leucine zipper-based, coiled-coil-based, and helix-based dimerization domain. In certain embodiments, the dimerization domain is an immunoglobulin Fc domain, such as a mouse or human immunoglobulin Fc domain. In certain embodiments, the immunoglobulin Fc domain is a mouse IgG2a immunoglobulin Fc domain, such as a mouse IgG2a immunoglobulin Fc domain comprising SEQ ID NO: 6. In certain embodiments, the linker comprises SEQ ID NO: 69.

In certain embodiments, the polypeptide comprises SEQ ID NO: 7 or SEQ ID NO: 8. In certain embodiments, the polypeptide comprises SEQ ID NO: 9, SEQ ID NO: 10, SEQ ID NO: 11, SEQ ID NO: 12, SEQ ID NO: 53, SEQ ID NO: 55, SEQ ID NO: 57, SEQ ID NO: 59, SEQ ID NO: 60, SEQ ID NO: 61, SEQ ID NO: 62, SEQ ID NO: 63, SEQ ID NO: 64, or SEQ ID NO: 67.

In another aspect, the invention relates to a multimeric protein comprising a polypeptide as disclosed herein. In certain embodiments, the multimeric protein is a dimer, trimer, hexamer, or dodecamer. In certain embodiments, the multimeric protein is a hexamer. In certain embodiments, the multimeric protein comprises six separate polypeptides as described herein complexed to produce a hexameric protein. In certain embodiments, the multimeric protein comprises two separate polypeptides dimerized via each dimerization domain of each polypeptide (e.g., via a covalent bond or non-covalent association) to produce a dimeric protein.

In certain embodiments, the multimeric protein binds a carbohydrate ligand with a KD of 0.01 nM to 100 nM, as measured by surface plasmon resonance or bio-layer interferometry. In certain embodiments, the KD is 10 nM, 1 nM, 0.1 nM, or lower. In certain embodiments, the KD is 1 nM, 0.1 nM or lower. In certain embodiments, the carbohydrate ligand is a Siglec ligand. In certain embodiments, the Siglec ligand is selected from a Siglec-1, Siglec-2, Siglec-3, Siglec-4, Siglec-5, Siglec-6, Siglec-7, Siglec-8, Siglec-9, Siglec-10, Siglec-11, Siglec-12, Siglec-14 and Siglec-15 ligand. In certain embodiments, the Siglec ligand is selected from a Siglec-3, Siglec-5, Siglec-6, Siglec-7, Siglec-8, Siglec-9, Siglec-10, and Siglec-11 ligand. In certain embodiments, the Siglec ligand is selected from a Siglec 3, Siglec-7, and Siglec-9 ligand. In certain embodiments, the Siglec ligand is selected from a Siglec-7 and Siglec-9 ligand.

In certain embodiments, the Siglec ligand is selected from α2,3-linked sialic acid, α2,6-linked sialic acid, sialyl Lewis X, NeuAcα2-3Galβ1-4Glc, NeuAcα2-3Galβ1-4GlcNAc, NeuAcα2-3Galβ1-3GlcNAc, NeuAcα2-3Galβ1-3GalNAc, NeuGcα2-3Galβ1-4GlcNAc, NeuGcα2-3Galβ1-3GlcNAc, NeuAcα2-6Galβ1-4Glc, NeuAcα2-6Galβ1-4GlcNAc, NeuAcα2-6GalNAc, Galβ1-3(NeuAcα2-6)GalNAc, NeuGcα2-6Galβ1-4Glc, NeuGcα2-6Galβ1-4GlcNAc, NeuGcα2-6GalNAc, NeuAcα2-8NeuAcα2-3Galβ1-4Glc, NeuAcα2-6Galβ1-4GlcNAc, NeuAcα2-3Galβ1-4[Fucα1-3]GlcNAc, NeuAcα2-6Galβ1-4GlcNAc6S, NeuAcα2-3Galβ1-4GalNAc, NeuAcα2-8NeuAc, NeuAcα2-3GalβSβ1-4GlcNAcα2-3Fuc, and NeuAcα2-3Galβ1-4GlcNAc6Sα2-3Fuc (where S stands for sulfate). In certain embodiments, the Siglec ligand is selected from α2,3-linked sialic acid, α2,6-linked sialic acid, and sialyl Lewis X.

In another aspect, the invention provides a multimeric protein comprising two polypeptides, wherein each polypeptide comprises, in an N-terminal to C-terminal direction, a first Siglec-7 sialic acid binding V-set immunoglobulin-like domain, a first Siglec-7 C2-set domain, a second Siglec-7 sialic acid binding V-set immunoglobulin-like domain, a second Siglec-7 C2-set domain, and an Fc domain, and wherein the two polypeptides are dimerized (e.g., via one or more covalent bonds) at their Fc domains.

In another aspect, the invention provides a multimeric protein comprising two polypeptides, wherein each polypeptide comprises, in an N-terminal to C-terminal direction, a first Siglec-7 sialic acid binding V-set immunoglobulin-like domain, a first Siglec-7 C2-set domain, a second Siglec-7 C2-set domain, an Fc domain, a second Siglec-7 sialic acid binding V-set immunoglobulin-like domain, a third Siglec-7 C2-set domain, and a fourth Siglec-7 C2-set domain, wherein the two polypeptides are dimerized at their Fc domains (e.g., via one or more covalent bonds).

In another aspect, the invention provides a multimeric protein comprising six polypeptides, wherein each polypeptide comprises, in an N-terminal to C-terminal direction, a first Siglec-7 sialic acid binding V-set immunoglobulin-like domain, a first Siglec-7 C2-set domain, a second Siglec-7 C2-set domain, a T4 phage fibritin (foldon) trimerization domain, and an Fc domain, and wherein: a) the first, second and third polypeptides are trimerized at their respective trimerization domains; b) the fourth, fifth, and sixth polypeptides are trimerized at their respective trimerization domains; c) the first and second polypeptides are dimerized at their respective Fc domains (e.g., via one or more covalent bonds); d) the third and fourth polypeptides are dimerized at their respective Fc domains (e.g., via one or more covalent bonds); and e) the fifth and sixth polypeptides are dimerized at their respective Fc domains (e.g., via one or more covalent bonds).

In another aspect, the invention provides a multimeric protein comprising six polypeptides, wherein each polypeptide comprises, in an N-terminal to C-terminal direction, a first Siglec-7 sialic acid binding V-set immunoglobulin-like domain, a first Siglec-7 C2-set domain, a second Siglec-7 C2-set domain, an Fc domain, and a T4 phage fibritin (foldon) trimerization domain, and wherein: a) the first, second and third polypeptides are trimerized at their respective trimerization domains; b) the fourth, fifth, and sixth polypeptides are trimerized at their respective trimerization domains; c) the first and second polypeptides are dimerized (e.g., covalently linked) at their respective Fc domains; d) the third and fourth polypeptides are dimerized (e.g., covalently linked) at their respective Fc domains; and e) the fifth and sixth polypeptides are dimerized (e.g., covalently linked) at their respective Fc domains.

In another aspect, the invention provides a multimeric protein comprising two polypeptides, wherein each polypeptide comprises, in an N-terminal to C-terminal direction, a first Siglec-9 sialic acid binding V-set immunoglobulin-like domain, a first Siglec-9 C2-set domain, a first linker, a second Siglec-9 sialic acid binding V-set immunoglobulin-like domain, a second Siglec-9 C2-set domain, and an Fc domain, and wherein the two polypeptides are dimerized at their Fc domains (e.g., via one or more covalent bonds).

In another aspect, the invention provides a multimeric protein comprising two polypeptides, wherein each polypeptide comprises, in an N-terminal to C-terminal direction, a first Siglec-9 sialic acid binding V-set immunoglobulin-like domain, a first Siglec-9 C2-set domain, a second Siglec-9 C2-set domain, an Fc domain, a second Siglec-9 sialic acid binding V-set immunoglobulin-like domain, a third Siglec-9 C2-set domain, and a fourth Siglec-9 C2-set domain, wherein the two polypeptides are dimerized at their Fc domains (e.g., via one or more covalent bonds).

In another aspect, the invention provides a multimeric protein comprising six polypeptides, wherein each polypeptide comprises, in an N-terminal to C-terminal direction, a first Siglec-9 sialic acid binding V-set immunoglobulin-like domain, a first Siglec-9 C2-set domain, a second Siglec-9 C2-set domain, a T4 phage fibritin (foldon) trimerization domain, and an Fc domain, and wherein: a) the first, second and third polypeptides are trimerized at their respective trimerization domains; b) the fourth, fifth, and sixth polypeptides are trimerized at their respective trimerization domains; c) the first and second polypeptides are dimerized at their respective Fc domains (e.g., via one or more covalent bonds); d) the third and fourth polypeptides are dimerized at their respective Fc domains (e.g., via one or more covalent bonds); and e) the fifth and sixth polypeptides are dimerized at their respective Fc domains (e.g., via one or more covalent bonds).

In another aspect, the invention provides a multimeric protein comprising six polypeptides, wherein each polypeptide comprises, in an N-terminal to C-terminal direction, a first Siglec-9 sialic acid binding V-set immunoglobulin-like domain, a first Siglec-9 C2-set domain, a second Siglec-9 C2-set domain, an Fc domain, and a T4 phage fibritin (foldon) trimerization domain, and wherein: a) the first, second and third polypeptides are trimerized at their respective trimerization domains; b) the fourth, fifth, and sixth polypeptides are trimerized at their respective trimerization domains; c) the first and second polypeptides are dimerized (e.g., covalently linked) at their respective Fc domains; d) the third and fourth polypeptides are dimerized (e.g., covalently linked) at their respective Fc domains; and e) the fifth and sixth polypeptides are dimerized (e.g., covalently linked) at their respective Fc domains.

In another aspect, the invention provides a multimeric protein comprising two polypeptides, wherein each polypeptide comprises, in an N-terminal to C-terminal direction, a first Siglec-3 sialic acid binding V-set immunoglobulin-like domain, a first Siglec-3 C2-set domain, a first linker, a second Siglec-3 sialic acid binding V-set immunoglobulin-like domain, a second Siglec-3 C2-set domain, and an Fc domain, and wherein the two polypeptides are dimerized (e.g., covalently linked) at their Fc domains.

In another aspect, the invention provides a multimeric protein comprising two polypeptides, wherein each polypeptide comprises, in an N-terminal to C-terminal direction, a first Siglec-3 sialic acid binding V-set immunoglobulin-like domain, a first Siglec-3 C2-set domain, an Fc domain, a second Siglec-3 sialic acid binding V-set immunoglobulin-like domain, and a second Siglec-3 C2-set domain, wherein the two polypeptides are dimerized (e.g., covalently linked) at their Fc domains.

In another aspect, the invention provides a multimeric protein comprising six polypeptides, wherein each polypeptide comprises, in an N-terminal to C-terminal direction, a Siglec-3 sialic acid binding V-set immunoglobulin-like domain, a Siglec-3 C2-set domain, an Fc domain, and a T4 phage fibritin (foldon) trimerization domain, and wherein: a) the first, second and third polypeptides are trimerized at their respective trimerization domains; b) the fourth, fifth, and sixth polypeptides are trimerized at their respective trimerization domains; c) the first and second polypeptides are dimerized (e.g., covalently linked) at their respective Fc domains; d) the third and fourth polypeptides are dimerized (e.g., covalently linked) at their respective Fc domains; and e) the fifth and sixth polypeptides are dimerized (e.g., covalently linked) at their respective Fc domains.

In certain embodiments, the multimeric protein has been treated with a sialidase to reduce the sialic acid content of the protein. In certain embodiments, the multimeric protein that has been treated with a sialidase contains less than 50%, 40%, 30%, 20%, 10%, 5%, 4%, 3%, 2%, or 1% of the sialic acid content of a similar or identical multimeric protein that has not been treated with the sialidase.

In another aspect, the invention relates to a pharmaceutical composition comprising a multimeric protein as described herein.

In another aspect, the invention relates to a method of treating a Siglec-mediated disorder (e.g., a cancer or an inflammatory disorder) in a subject in need thereof, the method comprising administering to the subject an effective amount of the multimeric protein or the pharmaceutical composition described herein thereby to treat the Siglec-mediated disorder in the subject.

In another aspect, the invention relates to a method of detecting a carbohydrate in a sample. The method includes contacting the sample with a multimeric protein described herein under conditions to permit the multimeric protein to form a multimeric protein-carbohydrate complex, if the carbohydrate is present in the sample and detecting the presence of the complex, if any.

In another aspect, the invention relates to a method of detecting a carbohydrate in a subject with cancer. The method includes contacting a sample from the subject with the multimeric protein described herein under conditions to permit the multimeric protein to form a multimeric protein-carbohydrate complex, if the carbohydrate is present in the sample and detecting the presence of the complex, if any. In certain embodiments, the carbohydrate is a Siglec ligand.

In another aspect, the invention relates to a method of identifying a subject with cancer likely to respond to treatment with a Siglec inhibitor. The method includes contacting a sample from the subject with the multimeric protein described herein under conditions to permit the multimeric protein to form a multimeric protein-Siglec ligand complex, if the Siglec ligand is present in the sample and detecting the presence of the complex, if any, wherein the presence of a complex is indicative that the subject will respond to treatment with a Siglec inhibitor.

In another aspect, the invention relates to a method of treating cancer in a subject in need thereof, the method comprising administering to the subject an effective amount of a Siglec inhibitor, thereby to treat the cancer in the subject, wherein the cancer has been identified as comprising cancerous cells that express one or more ligands of the Siglec by a method described herein. In certain embodiments, the Siglec ligand is a Siglec-3, Siglec-5, Siglec-6, Siglec-7, Siglec-8, Siglec-9, Siglec-10, or Siglec-11 ligand. In certain embodiments, the Siglec ligand is a Siglec-7 or Siglec-9 ligand. In certain embodiments, the Siglec ligand is selected from α2,3-linked sialic acid, α2,6-linked sialic acid, sialyl Lewis X, NeuAcα2-3Galβ1-4Glc, NeuAcα2-3Galβ1-4GlcNAc, NeuAcα2-3Galβ1-3GlcNAc, NeuAcα2-3Galβ1-3GalNAc, NeuGcα2-3Galβ1-4GlcNAc, NeuGcα2-3Galβ1-3GlcNAc, NeuAcα2-6Galβ1-4Glc, NeuAcα2-6Galβ1-4GlcNAc, NeuAcα2-6GalNAc, Galβ1-3(NeuAcα2-6)GalNAc, NeuGcα2-6Galβ1-4Glc, NeuGcα2-6Galβ1-4GlcNAc, NeuGcα2-6GalNAc, NeuAcα2-8NeuAcα2-3Galβ1-4Glc, NeuAcα2-6Galβ1-4GlcNAc, NeuAcα2-3Galβ1-4[Fucα1-3]GlcNAc, NeuAcα2-6Galβ1-4GlcNAc6S, NeuAcα2-3Galβ1-4GalNAc, NeuAcα2-8NeuAc, NeuAcα2-3GalβSβ1-4GlcNAcα2-3Fuc, and NeuAcα2-3Galβ1-4GlcNAc6Sα2-3Fuc (where S stands for sulfate). In certain embodiments, the Siglec ligand is selected from α2,3-linked sialic acid, α2,6-linked sialic acid, and sialyl Lewis X.

In certain embodiments, the Siglec inhibitor is an anti-Siglec antibody. The anti-Siglec antibody can be, for example, an anti-Siglec-3 antibody, anti-Siglec-5 antibody, anti-Siglec-6 antibody, anti-Siglec-7 antibody, anti-Siglec-8 antibody, anti-Siglec-9 antibody, anti-Siglec-10 antibody, or anti-Siglec-11 antibody. In certain embodiments, the anti-Siglec antibody is an anti-Siglec-3 antibody, an anti-Siglec-7 antibody, or anti-Siglec-9 antibody. In certain embodiments, the anti-Siglec antibody is an anti-Siglec-7 antibody or anti-Siglec-9 antibody.

In another aspect, the invention relates to a method of identifying a subject with a cancer or an inflammatory disorder likely to respond to treatment with a Siglec-3 inhibitor (e.g., an anti-Siglec-3 antibody). The method includes contacting a sample from the subject with the multimeric protein described herein under conditions to permit the multimeric protein to form a multimeric protein-Siglec-3 ligand complex, if the Siglec-3 ligand is present in the sample and detecting the presence of the complex, if any, wherein the presence of a complex is indicative that the subject will respond to treatment with a Siglec-3 inhibitor.

In another aspect, the invention relates to a method of identifying a subject with a cancer or an inflammatory disorder likely to respond to treatment with a Siglec-5 inhibitor (e.g., an anti-Siglec-5 antibody). The method includes contacting a sample from the subject with the multimeric protein described herein under conditions to permit the multimeric protein to form a multimeric protein-Siglec-5 ligand complex, if the Siglec-5 ligand is present in the sample and detecting the presence of the complex, if any, wherein the presence of a complex is indicative that the subject will respond to treatment with a Siglec-5 inhibitor.

In another aspect, the invention relates to a method of identifying a subject with a cancer or an inflammatory disorder likely to respond to treatment with a Siglec-6 inhibitor (e.g., an anti-Siglec-6 antibody). The method includes contacting a sample from the subject with the multimeric protein described herein under conditions to permit the multimeric protein to form a multimeric protein-Siglec-6 ligand complex, if the Siglec-6 ligand is present in the sample and detecting the presence of the complex, if any, wherein the presence of a complex is indicative that the subject will respond to treatment with a Siglec-6 inhibitor.

In another aspect, the invention relates to a method of identifying a subject with a cancer or an inflammatory disorder likely to respond to treatment with a Siglec-7 inhibitor (e.g., an anti-Siglec-7 antibody). The method includes contacting a sample from the subject with the multimeric protein described herein (e.g., a multimeric protein comprising a polypeptide comprising SEQ ID NO: 7) under conditions to permit the multimeric protein to form a multimeric protein-Siglec-7 ligand complex, if the Siglec-7 ligand is present in the sample and detecting the presence of the complex, if any, wherein the presence of a complex is indicative that the subject will respond to treatment with a Siglec-7 inhibitor.

In another aspect, the invention relates to a method of identifying a subject with a cancer or an inflammatory disorder likely to respond to treatment with a Siglec-8 inhibitor (e.g., an anti-Siglec-8 antibody). The method includes contacting a sample from the subject with the multimeric protein described herein under conditions to permit the multimeric protein to form a multimeric protein-Siglec-8 ligand complex, if the Siglec-8 ligand is present in the sample and detecting the presence of the complex, if any, wherein the presence of a complex is indicative that the subject will respond to treatment with a Siglec-8 inhibitor.

In another aspect, the invention relates to a method of identifying a subject with a cancer or an inflammatory disorder likely to respond to treatment with a Siglec-9 inhibitor (e.g., an anti-Siglec-9 antibody). The method includes contacting a sample from the subject with the multimeric protein described herein (e.g., a multimeric protein comprising a polypeptide comprising SEQ ID NO: 8) under conditions to permit the multimeric protein to form a multimeric protein-Siglec-9 ligand complex, if the Siglec-9 ligand is present in the sample and detecting the presence of the complex, if any, wherein the presence of a complex is indicative that the subject will respond to treatment with a Siglec-9 inhibitor.

In another aspect, the invention relates to a method of identifying a subject with a cancer or an inflammatory disorder likely to respond to treatment with a Siglec-10 inhibitor (e.g., an anti-Siglec-10 antibody). The method includes contacting a sample from the subject with the multimeric protein described herein under conditions to permit the multimeric protein to form a multimeric protein-Siglec-10 ligand complex, if the Siglec-10 ligand is present in the sample and detecting the presence of the complex, if any, wherein the presence of a complex is indicative that the subject will respond to treatment with a Siglec-10 inhibitor.

In another aspect, the invention relates to a method of identifying a subject with a cancer or an inflammatory disorder likely to respond to treatment with a Siglec-11 inhibitor (e.g., an anti-Siglec-11 antibody). The method includes contacting a sample from the subject with the multimeric protein described herein under conditions to permit the multimeric protein to form a multimeric protein-Siglec-11 ligand complex, if the Siglec-11 ligand is present in the sample and detecting the presence of the complex, if any, wherein the presence of a complex is indicative that the subject will respond to treatment with a Siglec-11 inhibitor.

In another aspect, the invention relates to a method of treating a cancer or an inflammatory disorder in a subject in need thereof, the method comprising administering to the subject an effective amount of a Siglec-3 inhibitor (e.g., an anti-Siglec-3 antibody), thereby to treat the cancer in the subject, wherein the cancer has been identified as comprising cancerous cells that express a Siglec-3 ligand by a method described herein.

In another aspect, the invention relates to a method of treating a cancer or an inflammatory disorder in a subject in need thereof, the method comprising administering to the subject an effective amount of a Siglec-5 inhibitor (e.g., an anti-Siglec-5 antibody), thereby to treat the cancer in the subject, wherein the cancer has been identified as comprising cancerous cells that express a Siglec-5 ligand by a method described herein.

In another aspect, the invention relates to a method of treating a cancer or an inflammatory disorder in a subject in need thereof, the method comprising administering to the subject an effective amount of a Siglec-6 inhibitor (e.g., an anti-Siglec-6 antibody), thereby to treat the cancer in the subject, wherein the cancer has been identified as comprising cancerous cells that express a Siglec-6 ligand by a method described herein.

In another aspect, the invention relates to a method of treating a cancer or an inflammatory disorder in a subject in need thereof, the method comprising administering to the subject an effective amount of a Siglec-7 inhibitor (e.g., an anti-Siglec-7 antibody), thereby to treat the cancer in the subject, wherein the cancer has been identified as comprising cancerous cells that express a Siglec-7 ligand by a method described herein.

In another aspect, the invention relates to a method of treating a cancer or an inflammatory disorder in a subject in need thereof, the method comprising administering to the subject an effective amount of a Siglec-8 inhibitor (e.g., an anti-Siglec-8 antibody), thereby to treat the cancer in the subject, wherein the cancer has been identified as comprising cancerous cells that express a Siglec-8 ligand by a method described herein.

In another aspect, the invention relates to a method of treating a cancer or an inflammatory disorder in a subject in need thereof, the method comprising administering to the subject an effective amount of a Siglec-9 inhibitor (e.g., an anti-Siglec-9 antibody), thereby to treat the cancer in the subject, wherein the cancer has been identified as comprising cancerous cells that express a Siglec-9 ligand by a method described herein.

In another aspect, the invention relates to a method of treating a cancer or an inflammatory disorder in a subject in need thereof, the method comprising administering to the subject an effective amount of a Siglec-10 inhibitor (e.g., an anti-Siglec-10 antibody), thereby to treat the cancer in the subject, wherein the cancer has been identified as comprising cancerous cells that express a Siglec-10 ligand by a method described herein.

In another aspect, the invention relates to a method of treating a cancer or an inflammatory disorder in a subject in need thereof, the method comprising administering to the subject an effective amount of a Siglec-11 inhibitor (e.g., an anti-Siglec-11 antibody), thereby to treat the cancer in the subject, wherein the cancer has been identified as comprising cancerous cells that express a Siglec-11 ligand by a method described herein.

In certain embodiments, the sample is selected from a tissue sample, a body fluid sample, or a cell sample. In certain embodiments, the cancer is an epithelial cancer. In certain embodiments, the epithelial cancer is endometrial cancer, ovarian cancer, cervical cancer, vulvar cancer, uterine cancer, fallopian tube cancer, breast cancer, prostate cancer, lung cancer, pancreatic cancer, urinary cancer, bladder cancer, head and neck cancer, oral cancer or liver cancer.

These and other aspects and features of the invention are described in the following detailed description and claims.

DESCRIPTION OF THE DRAWINGS

The invention can be more completely understood with reference to the following drawings.

FIG. 15 depicts representative IHC staining of serial sections of paraffin embedded human tumor biopsy slides with Siglec-7 hydra (Hydra-7; left), and Siglec-9 hydra (Hydra-9; right). The accompanying H-Score is also shown.

FIG. 24 provides a chart showing that pretreating Hydra 9 constructs with VC sialidase improves yield (e.g., from 24% to 55% for WT in one experiment, or from 27% to 65% in another experiment).

DETAILED DESCRIPTION

Figures 1, 1A, 1B, 1C, 1D:
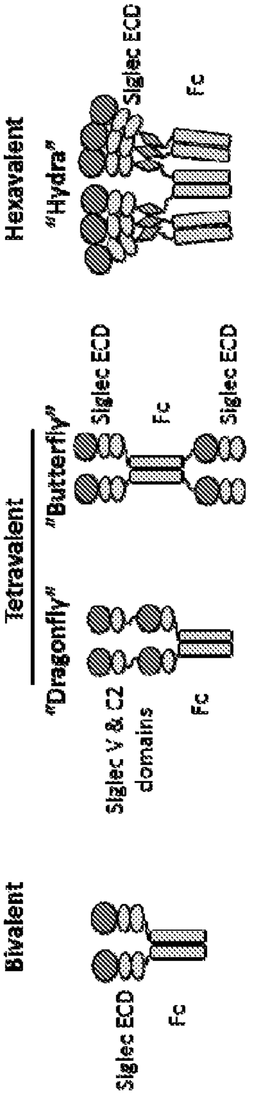
FIG. 1 depicts various exemplary recombinant protein configurations, where
FIG. 1A depicts a dimeric and bivalent protein configuration referred to as "dimer.
"FIG. 1B depicts a dimeric and tetravalent protein configuration referred to as "dragonfly.
" FIG. 1C depicts a dimeric and tetravalent protein configuration referred to as "butterfly.
" and FIG. 1D depicts a hexameric and hexavalent protein configuration referred to as "hydra."

The invention is based, in part, upon the discovery of recombinant polypeptides that can be used to detect a Siglec ligand, e.g., in a sample of interest, and/or treat a Siglec-mediated disorder in a subject in need thereof. In certain embodiments, recombinant polypeptides are associated (non-covalently and/or covalently) to produce a multimeric protein that can be used to detect a Siglec ligand, e.g., in a sample of interest, and/or treat a Siglec-mediated disorder in a subject in need thereof.

I. Siglecs and Siglec Biology

Siglecs (Sialic acid-binding immunoglobulin-type lectins) are cell surface proteins that bind sialic acid. Siglecs comprise a lectin family of surface receptors that bind to sialoglycans and are predominantly expressed on cells of the hematopoietic system in a manner dependent on cell type and differentiation. There are at least 14 different mammalian Siglecs, which together provide an array of different functions based on cell surface receptor-ligand interactions. These receptor-glycan interactions can mediate, among other things, cell adhesion and cell signaling. Although sialic acid is ubiquitously expressed, typically at the terminal position of glycoproteins and lipids, only very specific, distinct sialoglycan structures are recognized by individual Siglecs, depending on identity and linkage to subterminal carbohydrate moieties.

Siglecs are Type I transmembrane proteins where the amino terminus is located in the extracellular space and the carboxy terminus is located in the cytosol. Each Siglec contains an N-terminal V-set immunoglobulin-like domain (Ig domain) that acts as the binding receptor for sialic acid. Siglecs are lectins, and are categorized into the group of I-type lectins because the lectin domain is an immunoglobulin fold. All Siglecs extend from the cell surface by means of intervening C2-set domains which have no binding activity. Siglecs differ in the number of these C2-set domains. As these proteins contain Ig domains, they are members of the Immunoglobulin superfamily (IgSF).

Most Siglecs, and in particular the CD33-like Siglecs, contain immunoreceptor tyrosine-based inhibitory motifs (ITIMs) in their cytoplasmic domains. These act to down-regulate signaling pathways involving phosphorylation, such as those induced by immunoreceptor tyrosine-based activation motifs (ITAMs).

Due to their ITIM-containing cytoplasmic domains, most CD33-like Siglecs interfere with cellular signaling, thereby inhibiting immune cell activation. Once bound to their ligands, these Siglecs recruit inhibitory proteins such as SHP phosphatases via their ITIM domains. The tyrosine contained within the ITIM becomes phosphorylated upon ligand binding and acts as a docking site for SH2 domain-containing proteins like SHP phosphatases. This leads to de-phosphorylation of cellular proteins, and down-regulating activating signaling pathways.

Siglecs have been attractive therapeutic targets because of their cell type-specific expression patterns, endocytic properties, high expression on certain lymphomas/leukemias, and ability to modulate receptor signaling. To date, Siglec-targeting based therapies have involved antibody- and glycan-based strategies that directly target tumor cells. Several antibody-based therapies directly targeting Siglecs on the surface of malignant cells currently are undergoing clinical evaluation and continue to be developed for the treatment of lymphoma/leukemia and autoimmune disease (Angata et al. (2015) Trends in Pharmacological Sciences, 36(10): 645-660).

A growing body of evidence supports roles for glycans, and sialoglycans in particular, at various pathophysiological steps of tumor progression. Glycans regulate tumor proliferation, invasion, haematogenous metastasis and angiogenesis (Fuster et al. (2005) Nat. Rev. Cancer 5(7):526-42). The sialylation of cell surface glycoconjugates is frequently altered in cancers, resulting in the expression of sialylated tumor-associated carbohydrate antigens that are specific markers for this disease. Because sialylated glycans are involved in many biological processes, their expression by tumor cells is often associated with increased aggressiveness and metastatic potential of the tumors.

An amino acid sequence of an exemplary human Siglec-1 protein is provided in SEQ ID NO: 15 (NCBI Reference Sequence: NP_075556.1) and a DNA sequence encoding an exemplary human Siglec-1 protein is provided in SEQ ID NO: 16 (NCBI Reference Sequence: NM_023068.3). An amino acid sequence of an exemplary human Siglec-2 protein is provided in SEQ ID NO: 17 (NCBI Reference Sequence: NP_001762.2) and a DNA sequence encoding an exemplary human Siglec-2 protein is provided in SEQ ID NO: 18 (NCBI Reference Sequence: NM_001771.3). An amino acid sequence of an exemplary human Siglec-3 protein is provided in SEQ ID NO: 19 (NCBI Reference Sequence: NP_001763.3) and a DNA sequence encoding an exemplary human Siglec-3 protein is provided in SEQ ID NO: 20 (NCBI Reference Sequence: NM_001772.3). An amino acid sequence of an exemplary human Siglec-4 protein is provided in SEQ ID NO: 21 (NCBI Reference Sequence: NP_002352.1) and a DNA sequence encoding an exemplary human Siglec-4 protein is provided in SEQ ID NO: 22 (NCBI Reference Sequence: NM_002361.3). An amino acid sequence of an exemplary human Siglec-5 protein is provided in SEQ ID NO: 23 (NCBI Reference Sequence: NP_003821.1) and a DNA sequence encoding an exemplary human Siglec-5 protein is provided in SEQ ID NO: 24 (NCBI Reference Sequence: NM_003830). An amino acid sequence of an exemplary human Siglec-6 protein is provided in SEQ ID NO: 25 (NCBI Reference Sequence: NP_001236.4) and a DNA sequence encoding an exemplary human Siglec-6 protein is provided in SEQ ID NO: 26 (NCBI Reference Sequence: NM_198845.5). An amino acid sequence of an exemplary human Siglec-7 protein is provided in SEQ ID NO: 27 (NCBI Reference Sequence: NP_055200.1) and a DNA sequence encoding an exemplary human Siglec-7 protein is provided in SEQ ID NO: 28 (NCBI Reference Sequence: NM_014385.3). An amino acid sequence of an exemplary human Siglec-8 protein is provided in SEQ ID NO: 29 (NCBI Reference Sequence: NP_055257.2) and a DNA sequence encoding an exemplary human Siglec-8 protein is provided in SEQ ID NO: 30 (NCBI Reference Sequence: NM_014442.2). An amino acid sequence of an exemplary human Siglec-9 protein is provided in SEQ ID NO: 31 (NCBI Reference Sequence: NP_055256.1) and a DNA sequence encoding an exemplary human Siglec-9 protein is provided in SEQ ID NO: 32 (NCBI Reference Sequence: NM_014441.2). An amino acid sequence of an exemplary human Siglec-10 protein is provided in SEQ ID NO: 33 (NCBI Reference Sequence: NP_149121.2) and a DNA sequence encoding an exemplary human Siglec-10 protein is provided in SEQ ID NO: 34 (NCBI Reference Sequence: NM_033130.4). An amino acid sequence of an exemplary human Siglec-11 protein is provided in SEQ ID NO: 35 (NCBI Reference Sequence: NP_443116.2) and a DNA sequence encoding an exemplary human Siglec-11 protein is provided in SEQ ID NO: 36 (NCBI Reference Sequence: NM_052884.2). An amino acid sequence of an exemplary human Siglec-12 protein is provided in SEQ ID NO: 37 (NCBI Reference Sequence: NP_443729.1) and a DNA sequence encoding an exemplary human Siglec-12 protein is provided in SEQ ID NO: 38 (NCBI Reference Sequence: NM_053003.3). An amino acid sequence of an exemplary human Siglec-14 protein is provided in SEQ ID NO: 39 (NCBI Reference Sequence: NP_001092082.1) and a DNA sequence encoding an exemplary human Siglec-14 protein is provided in SEQ ID NO: 40 (NCBI Reference Sequence: NM_001098612.1).

An amino acid sequence of an exemplary human Siglec-15 protein is provided in SEQ ID NO: 41 (NCBI Reference Sequence: NP_998767.1) and a DNA sequence encoding an exemplary human Siglec-15 protein is provided in SEQ ID NO: 42 (NCBI Reference Sequence: NM_213602.2).

II. Polypeptides

The instant disclosure provides an isolated polypeptide comprising one or more lectin domains, one or more dimerization domains, and/or one or more trimerization domains. The lectin, dimerization and/or trimerization domain(s) can be linked together (e.g., covalently linked) in any orientation. The lectin, dimerization and/or trimerization domain(s) can be linked directly together, or indirectly, e.g., by a linker.

For example, a polypeptide may comprise a lectin domain, a trimerization domain, and a dimerization domain. In certain embodiments, the lectin domain, the trimerization domain, and the dimerization domain are covalently linked together in an N- to C-terminal orientation.

A polypeptide may comprise a first lectin domain, a second lectin domain, and a dimerization domain. In certain embodiments, the first lectin domain and the second lectin domain are identical. In certain embodiments, the first lectin domain, the second lectin domain, and the dimerization domain are covalently linked together in an N- to C-terminal orientation. In certain embodiments, the first lectin domain, the dimerization domain, and the second lectin domain are covalently linked together in an N- to C-terminal orientation.

In certain embodiments, the polypeptide comprises the amino acid sequence of SEQ ID NO: 7 or SEQ ID NO: 8, or an amino acid sequence having 80%, 85%, 86%, 87%, 88%, 89%, 90%, 91%, 92%, 93%, 94%, 95%, 96%, 97%, 98%, or 99% sequence identity to the amino acid sequence of SEQ ID NO: 7 or SEQ ID NO: 8. In certain embodiments, the polypeptide comprises the amino acid sequence of SEQ ID NO: 9, SEQ ID NO: 10, SEQ ID NO: 11, or SEQ ID NO: 12, or an amino acid sequence having 80%, 85%, 86%, 87%, 88%, 89%, 90%, 91%, 92%, 93%, 94%, 95%, 96%, 97%, 98%, or 99% sequence identity to the amino acid sequence of SEQ ID NO: 9, SEQ ID NO: 10, SEQ ID NO: 11, or SEQ ID NO: 12.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36, 290-300; Altschul et al., (1997) Nucleic Acids Res. 25:3389-3402, incorporated by reference) are tailored for sequence similarity searching. For a discussion of basic issues in searching sequence databases see Altschul et al., (1994) Nature Genetics 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: —G, Cost to open gap [Integer]: default=5 for nucleotides/11 for proteins; —E, Cost to extend gap [Integer]: default=2 for nucleotides/1 for proteins; —q, Penalty for nucleotide mismatch [Integer]: default=−3; —r, reward for nucleotide match [Integer]: default=1; —e, expect value [Real]: default=10; —W, wordsize [Integer]: default=11 for nucleotides/28 for megablast/3 for proteins; —y, Dropoff (X) for blast extensions in bits: default=20 for blastn/7 for others; —X, X dropoff value for gapped alignment (in bits): default=15 for all programs, not applicable to blastn; and —Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

a. Lectin Domains

As used herein, a lectin domain refers to a sequence of amino acids capable of binding to a carbohydrate. Lectin domains typically are derived from a lectin protein (lectin). Lectins fall into distinct families depending upon structure, and include calnexin family lectins, C-type lectins, P-type lectins, I-type lectins (including Siglecs), R-type lectins, galectins, F-box lectins, ficolins, chitinase-like lectins, F-type lectins, and intelectins. Lectin domains suitable for use herein can be derived from mannose binding lectins such as Concanavalin A (ConA), Lentil lectin (LCH), and snowdrop lectin (GNA); galactose/N-acetylgalactosamine binding lectins such as Ricin or *Ricinus communis* Agglutinin or RCE120 (RCA), peanut agglutinin (PNA), Jacalin (AIL), and Hairy vetch lectin (VVL); N-Acetylaglucosamine binding lectins such as Wheat Germ Agglutinin (WGA); N-acetylaneuraminic acid binding lectins such as Elderberry lectin (SNA), *Maackia amurensis* leukoagglutinin (MAL), and *Maackia amurensis* hemoagglutinin (MAH); and fucose binding lectins such as *Ulex europaeus* agglutinin (UEA) and *Aleuria aurantia* lectin (AAL).

In certain embodiments, the lectin domain comprises a lectin domain from a Siglec protein. Siglecs are cell surface transmembrane receptors comprised of 2-17 extracellular domains. For example, a lectin domain can comprise a Siglec sialic acid binding V-set immunoglobulin-like domain or a variant thereof and/or a Siglec extracellular domain or a variant thereof. In certain embodiments, a variant of a Siglec sialic acid binding V-set immunoglobulin-like domain or a variant of a Siglec extracellular domain is a Siglec sialic acid binding V-set immunoglobulin-like domain or a Siglec extracellular domain having one or more amino acid changes as compared to a wild-type counterpart, but retaining at least 20% binding affinity, at least 30% binding affinity, at least 40% binding affinity, at least 50% binding affinity, at least 60% binding affinity, at least 70% binding affinity, at least 80% binding affinity, at least 90% binding affinity, at least 95% binding affinity, or at least 100% binding affinity as compared to the wild-type counterpart. The Siglec from which the Siglec sialic acid binding V-set immunoglobulin-like domain or extracellular domain is derived can be a mammalian Siglec, such as a human, monkey, dog, rat, or mouse Siglec.

In certain embodiments, the Siglec is a human Siglec. In certain embodiments, the Siglec can be Siglec-1, Siglec-2, Siglec-3, Siglec-4, Siglec-5, Siglec-6, Siglec-7, Siglec-8, Siglec-9, Siglec-10, Siglec-11, Siglec-12, Siglec-14 or Siglec-15. In certain embodiments, the Siglec can be Siglec-3, Siglec-5, Siglec-6, Siglec-7, Siglec-8, Siglec-9, Siglec-10, or Siglec-11. In certain embodiments, the Siglec can be Siglec-7 or Siglec-9.

In certain embodiments, the lectin domain comprises a Siglec-1 V-set immunoglobulin-like domain, e.g., amino acid residues 21-136 of SEQ ID NO: 15. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 21-136 of SEQ ID NO: 15. In certain embodiments, the lectin domain comprises a Siglec-1 extracellular domain, e.g., amino acid residues 20-1642 of SEQ ID NO: 15. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 20-1642 of SEQ ID NO: 15.

In certain embodiments, the lectin domain comprises a Siglec-2 V-set immunoglobulin-like domain, e.g., amino acid residues 24-122 of SEQ ID NO: 17. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 24-122 of SEQ ID NO: 17. In certain embodiments, the lectin domain comprises a Siglec-2 extracellular domain, e.g., amino acid residues 20-688 of SEQ ID NO: 17. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 20-688 of SEQ ID NO: 17.

In certain embodiments, the lectin domain comprises a Siglec-3 V-set immunoglobulin-like domain, e.g., amino acid residues 23-139 of SEQ ID NO: 19. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 23-139 of SEQ ID NO: 19. In certain embodiments, the lectin domain comprises a Siglec-3 extracellular domain, e.g., amino acid residues 18-260 of SEQ ID NO: 19. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 18-260 of SEQ ID NO: 19.

In certain embodiments, the lectin domain comprises a Siglec-4 V-set immunoglobulin-like domain, e.g., amino acid residues 22-139 of SEQ ID NO: 21. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 22-139 of SEQ ID NO: 21. In certain embodiments, the lectin domain comprises a Siglec-4 extracellular domain, e.g., amino acid residues 20-157 of SEQ ID NO: 21. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 20-157 of SEQ ID NO: 21.

In certain embodiments, the lectin domain comprises a Siglec-5 V-set immunoglobulin-like domain, e.g., amino acid residues 21-140 of SEQ ID NO: 23. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 21-140 of SEQ ID NO: 23. In certain embodiments, the lectin domain comprises a Siglec-5 extracellular domain, e.g., amino acid residues 17-442 of SEQ ID NO: 23. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 17-442 of SEQ ID NO: 23.

In certain embodiments, the lectin domain comprises a Siglec-6 V-set immunoglobulin-like domain, e.g., amino acid residues 31-141 of SEQ ID NO: 25. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 31-141 of SEQ ID NO: 25. In certain embodiments, the lectin domain comprises a Siglec-6 extracellular domain, e.g., amino acid residues 27-348 of SEQ ID NO: 25. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 27-348 of SEQ ID NO: 25.

In certain embodiments, the lectin domain comprises a Siglec-7 V-set immunoglobulin-like domain, e.g., amino acid residues 26-144 of SEQ ID NO: 27, amino acid residues 31-122 of SEQ ID NO: 27, SEQ ID NO: 1, or SEQ ID NO: 43. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 26-144 of SEQ ID NO: 27, amino acid residues 31-122 of SEQ ID NO: 27, SEQ ID NO: 1, or SEQ ID NO: 43. In certain embodiments, the lectin domain comprises a Siglec-7 V-Set immunoglobulin-like domain and 1 Siglec-7 C2-Set domain, e.g., SEQ ID NO: 3. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to SEQ ID NO: 3. In certain embodiments, the lectin domain comprises a Siglec-7 extracellular domain, e.g., a Siglec-7 V-Set immunoglobulin-like domain and 2 Siglec-7 C2-Set domains, e.g., amino acid residues 19-357 of SEQ ID NO: 27 or SEQ ID NO: 13. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 19-357 of SEQ ID NO: 27 or SEQ ID NO: 13.

In certain embodiments, the lectin domain comprises a Siglec-8 V-set immunoglobulin-like domain, e.g., amino acid residues 27-151 of SEQ ID NO: 29. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 27-151 of SEQ ID NO: 29. In certain embodiments, the lectin domain comprises a Siglec-8 extracellular domain, e.g., amino acid residues 17-364 of SEQ ID NO: 29. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 17-364 of SEQ ID NO: 29.

In certain embodiments, the lectin domain comprises a Siglec-9 V-set immunoglobulin-like domain, e.g., amino acid residues 23-144 of SEQ ID NO: 31, amino acid residues 23-140 of SEQ ID NO: 31, SEQ ID NO: 2, or SEQ ID NO: 44. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 23-144 of SEQ ID NO: 31, amino acid residues 23-140 of SEQ ID NO: 31, SEQ ID NO: 2, or SEQ ID NO: 44. In certain embodiments, the lectin domain comprises a Siglec-9 V-Set immunoglobulin-like domain and 1 Siglec-9 C2-Set domain, e.g., SEQ ID NO: 4. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to SEQ ID NO: 4. In certain embodiments, the lectin domain comprises a Siglec-9 extracellular domain, e.g., a Siglec-9 V-Set immunoglobulin-like domain and 2 Siglec-9 C2-Set domains, e.g., amino acid residues 18-348 of SEQ ID NO: 31 or SEQ ID NO: 14. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 18-348 of SEQ ID NO: 31 or SEQ ID NO: 14.

In certain embodiments, the lectin domain comprises a Siglec-10 V-set immunoglobulin-like domain, e.g., amino acid residues 23-140 of SEQ ID NO: 33. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 23-140 of SEQ ID NO: 33. In certain embodiments, the lectin domain comprises a Siglec-10 extracellular domain, e.g., amino acid residues 17-551 of SEQ ID NO: 33. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 17-551 of SEQ ID NO: 33.

In certain embodiments, the lectin domain comprises a Siglec-11 V-set immunoglobulin-like domain, e.g., amino acid residues 34-153 of SEQ ID NO: 35. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 34-153 of SEQ ID NO: 35. In certain embodiments, the lectin domain comprises a Siglec-11 extracellular domain, e.g., amino acid residues 28-562 of SEQ ID NO: 35. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 28-562 of SEQ ID NO: 35.

In certain embodiments, the lectin domain comprises a Siglec-12 V-set immunoglobulin-like domain, e.g., amino acid residues 24-142 of SEQ ID NO: 37. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 24-142 of SEQ ID NO: 37. In certain embodiments, the lectin domain comprises a Siglec-12 extracellular domain, e.g., amino acid residues 19-482 of SEQ ID NO: 37. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 19-482 of SEQ ID NO: 37.

In certain embodiments, the lectin domain comprises a Siglec-14 V-set immunoglobulin-like domain, e.g., amino acid residues 21-140 of SEQ ID NO: 39. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 21-140 of SEQ ID NO: 39. In certain embodiments, the lectin domain comprises a Siglec-14 extracellular domain, e.g., amino acid residues 17-359 of SEQ ID NO: 39. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 17-359 of SEQ ID NO: 39.

In certain embodiments, the lectin domain comprises a Siglec-15 V-set immunoglobulin-like domain, e.g., amino acid residues 44-150 of SEQ ID NO: 41. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 44-150 of SEQ ID NO: 41. In certain embodiments, the lectin domain comprises a Siglec-15 extracellular domain, e.g., amino acid residues 20-264 of SEQ ID NO: 41. In certain embodiments, the lectin domain comprises an amino acid sequence having 80%, 85%, 86%, 87%, 88%, 89%, 90%, 91%, 92%, 93%, 94%, 95%, 96%, 97%, 98%, or 99% sequence identity to amino acid residues 20-264 of SEQ ID NO: 41. In certain embodiments, the lectin domain comprises a Siglec-3 V-Set immunoglobulin-like domain, e.g., SEQ ID NO: 51, a Siglec-7 V-Set immunoglobulin-like domain, e.g., SEQ ID NO: 1 or SEQ ID NO: 43, or a Siglec-9 V-Set immunoglobulin-like domain, e.g., SEQ ID NO: 2 or SEQ ID NO: 44. In certain embodiments, the lectin domain comprises a Siglec-3 V-Set immunoglobulin-like domain and 1 Siglec-3 C2-Set domain, e.g., SEQ ID NO: 52. In certain embodiments, the lectin domain comprises a Siglec-7 V-Set immunoglobulin-like domain and 1 Siglec-7 C2-Set domain, e.g., SEQ ID NO: 3. In certain embodiments, the lectin domain comprises a Siglec-9 V-Set immunoglobulin-like domain and 1 Siglec-9 C2-Set domain, e.g., SEQ ID NO: 4. In certain embodiments, the lectin domain comprises a Siglec-7 V-Set immunoglobulin-like domain and 2 Siglec-7 C2-Set domains, e.g., SEQ ID NO: 13. In certain embodiments, the lectin domain comprises a Siglec-9 V-Set immunoglobulin-like domain and 2 Siglec-9 C2-Set domains, e.g., SEQ ID NO: 14.

In certain embodiments, the lectin domain comprises a substitution of at least one wild-type cysteine residue. For example, in certain embodiments, the lectin domain is from human Siglec-9, and the lectin domain comprises a substitution of a cysteine residue at a position corresponding to position 141 of wild-type human Siglec-9, e.g., the cysteine residue at a position corresponding to position 141 of wild-type human Siglec-9 is substituted by serine (C141S). In certain embodiments, the lectin domain is from human Siglec-9, and the lectin domain comprises a substitution of a cysteine residue at a position corresponding to position 278 of wild-type human Siglec-9, e.g., the cysteine residue at a position corresponding to position 278 of wild-type human Siglec-9 is substituted by threonine (C278T).

In certain embodiments, the Siglec is a mouse Siglec. The mouse Siglec can be, for example, SigE, SigF, SigG, or SigF.

In certain embodiments, the lectin domain comprises a C-type lectin domain. The C-type lectin can be, for example, CLEC1A, CLEC1B, CLEC2A, CLEC2B, CD69 (CLEC2C), CLEC2D, CLEC2L, CLEC3A, CLEC3B, CLEC4A, CLEC4C, CLEC4D, CLEC4E, CLEC4F, CLEC4G, ASGR1 (CLEC4H1), ASGR2 (CLEC4H2), FCER2 (CLEC4J), CD207 (CLEC4K), CD209 (CLEC4L), CLEC4M, CLEC5A, CLEC6A, CLEC7A, OLR1 (CLEC8A), CLEC9A, CLEC10A, CLEC11A, CLEC12A, CLEC12B, CD302 (CLEC13A), LY75 (CLEC13B), PLA2R1 (CLEC13C), MRC1 (CLEC13D), MRC2 (CLEC13E), CLEC14A, CLEC16A, CLEC17A, KLRA1, KLRB1 (CLEC5B), KLRC1, KLRC2, KLRC3, KLRC4, KLRD1, KLRF1 (CLEC5C), KLRG1 (CLEC15A), KLRG2 (CLEC15B), or KLRK1. In certain embodiments, the C-type lectin is selected from CLEC4A, CLEC12A, and CLEC12B.

b. Dimerization Domains

As used herein, a dimer refers to complex of two monomers (two monomeric subunits), and a dimerization domain refers to a sequence of amino acids that mediates or otherwise facilitates covalent and/or non-covalent association or interaction between two monomers in a dimer. Accordingly, a dimer may comprise a first dimerization domain that binds preferentially to a second dimerization domain A dimer may be a homodimer, wherein the two monomer subunits are identical, or a heterodimer, wherein the two monomer subunits are different. Similarly, a dimerization domain may be a homodimerization domain, wherein the homodimerization domain binds preferentially to an identical second dimerization domain, or a heterodimerization domain, wherein the heterodimerization domain binds preferentially to a different second dimerization domain.

The terms "bind preferentially," or "binds specifically" as used in connection with a domain refers to a domain that binds and/or associates (i) more stably, (ii) more rapidly, (iii) with stronger affinity, (iv) with greater duration, or (v) or a combination of any two or more of (i)-(iv), with a particular target molecule (e.g., a protein, carbohydrate, glycoprotein, or glycolipid) than it does with a molecule other than the target molecule. For example, a first dimerization domain that specifically or preferentially binds a second dimerization domain is a first dimerization domain that binds a second dimerization domain, e.g., with stronger affinity, avidity, more readily, and/or with greater duration than it binds a different domain. The first dimerization domain may have affinity for the second dimerization domain of about 100 nM, 50 nM, 20 nM, 15 nM, 10 nM, 9 nM, 8 nM, 7 nM, 6 nM, 5 nM, 4 nM, 3 nM, 2 nM, 1 nM, 0.5 nM, 0.1 nM, or 0.01 nM, or stronger, as determined by surface plasmon resonance. For example, the first dimerization domain may have an affinity for the second dimerization domain within the range from about 0.01 nM to about 100 nM, from about 0.1 nM to about 100 nM, or from about 1 nM to about 100 nM. It is understood that a domain that binds preferentially to a first target molecule may or may not preferentially bind to a second target. As such, "preferential binding" does not necessarily require (although it can include) exclusive binding.

In certain embodiments, the dimerization domain is a natural dimerization domain or a synthetic dimerization domain. In certain embodiments, the dimerization domain is selected from an immunoglobulin Fc domain, leucine zipper-based, coiled-coil-based, and helix-based dimerization domain.

In certain embodiments, the dimerization domain is an immunoglobulin Fc domain (also referred to herein as an Fc domain), such as a mouse or human immunoglobulin Fc domain. As used herein, unless otherwise indicated, the term "immunoglobulin Fc domain" refers to a fragment of an immunoglobulin heavy chain constant region which, either alone or in combination with a second immunoglobulin Fc domain, is capable of binding to an Fc receptor. An immunoglobulin Fc domain may include, e.g., immunoglobulin CH2 and CH3 domains. An immunoglobulin Fc domain may include, e.g., immunoglobulin CH2 and CH3 domains and an immunoglobulin hinge region. Boundaries between immunoglobulin hinge regions, CH2, and CH3 domains are well known in the art, and can be found, e.g., in the PROSITE database (available on the world wide web at prosite.expasy.org).

In certain embodiments, the immunoglobulin Fc domain is a human immunoglobulin Fc domain, e.g., a human IgG1, IgG2, IgG3, IgG4, IgM, IgA1, IgA2, IgD, or IgE Fc domain. In certain embodiments, the immunoglobulin Fc domain is an Fc domain that binds the FcγRIIB1 or FcγRIIB2 Fc receptor. In certain embodiments, the immunoglobulin Fc domain is a mouse immunoglobulin Fc domain, e.g., a mouse IgG1, IgG2a, IgG2b, IgG2c, IgM, IgA, IgD, or IgE Fc domain. In certain embodiments, the immunoglobulin Fc domain is a mouse IgG2a immunoglobulin Fc domain, such as a mouse IgG2a immunoglobulin Fc domain comprising SEQ ID NO: 6.

c. Trimerization Domain

As used herein, a trimer refers to a complex of three monomers (three monomeric subunits), and a trimerization domain refers to a sequence of amino acids that mediates or otherwise facilitates covalent and/or non-covalent association or interaction between three monomers in a trimer. Accordingly, a trimer may comprise a first trimerization domain that binds preferentially to a second trimerization domain and a third trimerization domain. A trimer may be a homotrimer, wherein the three monomer subunits are identical, or a heterotrimer, wherein the three monomer subunits are different. Similarly, a trimerization domain may be a homotrimerization domain, wherein the homotrimerization domain binds preferentially to an identical second and third trimerization domain, or a heterotrimerization domain, wherein the heterotrimerization domain binds preferentially to a different second or third trimerization domain.

In certain embodiments, the trimerization domain is a natural trimerization domain or a synthetic trimerization domain. In certain embodiments, the trimerization domain is selected from a T4 phage fibritin (foldon), clathrin, heat shock factor 1, collagen, hemagglutinin, GCN4, GCN4-based isoleucine zipper, and coiled-coil peptide trimerization domain. In certain embodiments, the trimerization domain is selected from a GCN4-based isoleucine zipper and T4 phage fibritin (foldon) trimerization domain. In certain embodiments, the trimerization domain is a T4 phage fibritin (foldon) trimerization domain, such as SEQ ID NO: 5.

d. Linkers

In certain embodiments, the lectin, dimerization and/or trimerization domains are linked or fused directly together to form the polypeptide. In other embodiments, the lectin, dimerization and/or trimerization domains can be covalently linked together by one or more intervening linker sequences.

The linker may couple, with one or more natural amino acids, lectin, dimerization and/or trimerization domains, where the amino acid (for example, a cysteine amino acid) may be introduced by site-directed mutagenesis. The linker may include one or more unnatural amino acids. It is contemplated that, in certain circumstances, a linker containing for example, one or more sulfhydryl reactive groups (e.g., a maleimide) may covalently link a cysteine in the lectin, dimerization and/or trimerization domains that is a naturally occurring cysteine residue or is the product of site-specific mutagenesis.

The linker may be a cleavable linker or a non-cleavable linker. Optionally or in addition, the linker may be a flexible linker or an inflexible linker.

The linker should be a length sufficiently long to allow the lectin, dimerization and/or trimerization domains to be linked without steric hindrance from one another and sufficiently short to retain the intended activity of the polypeptide. The linker preferably is sufficiently hydrophilic to avoid or minimize instability of the polypeptide. The linker preferably is sufficiently hydrophilic to avoid or minimize insolubility of the polypeptide. The linker should be sufficiently stable in vivo (e.g., it is not cleaved by serum, enzymes, etc.) to permit the fusion protein to be operative in vivo.

The linker may be from about 1 angstroms (Å) to about 150 Å in length, or from about 1 Å to about 120 Å in length, or from about 5 Å to about 110 Å in length, or from about 10 Å to about 100 Å in length. The linker may be greater than about 2, 3, 4, 5, 6, 7, 8, 9, 10, 11, 12, 13, 14, 15, 16, 17, 18, 19, 20, 25, 27, 30 or greater angstroms in length and/or less than about 110, 100, 90, 85, 80, 75, 70, 65, 60, 55, 50, 45, 43, 42, 41, 40, 39, 38, 37, 36, 35, 34, 33, 32, 31, or fewer A in length. Furthermore, the linker may be about 5, 10, 15, 20, 25, 30, 35, 40, 45, 50, 55, 60, 65, 70, 75, 80, 85, 90, 95, 100, 110, and 120 Å in length.

In certain embodiments, the linker comprises a polypeptide linker that connects or fuses the lectin, dimerization and/or trimerization domains of the polypeptide. For example, it is contemplated that a gene encoding a lectin domain linked directly or indirectly (for example, via an amino acid containing linker) to an dimerization and/or trimerization domain can be created and expressed using conventional recombinant DNA technologies. For example, the amino terminus of a lectin domain can be linked to the carboxy terminus of a dimerization or trimerization domain. When a linker is employed, the linker preferably contains hydrophilic amino acid residues, such as Gln, Ser, Gly, Glu, Pro, His and Arg. In certain embodiments, the linker is a peptide containing 1-25 amino acid residues, 1-20 amino acid residues, 2-15 amino acid residues, 3-10 amino acid residues, 3-7 amino acid residues, 4-25 amino acid residues, 4-20 amino acid residues, 4-15 amino acid residues, 4-10 amino acid residues, 5-25 amino acid residues, 5-20 amino acid residues, 5-15 amino acid residues, or 5-10 amino acid residues. Exemplary linkers include glycine and serine-rich linkers, e.g., $(GlyGlyPro)_n$, (SEQ ID NO: 70), or $(GlyGlyGlyGlySer)_n$, (SEQ ID NO: 71), where n is 1-5. In certain embodiments, the linker is $(GlyGlyGlyGlySer)_3$ (SEQ ID NO: 72). In certain embodiments, the linker is $(Gly_4Ser)_2$ (SEQ ID NO: 69). Additional exemplary linker sequences are disclosed, e.g., in George et al. (2003) Protein Engineering 15:871-879, and U.S. Pat. Nos. 5,482,858 and 5,525,491.

e. Multimeric Proteins

In another aspect, the invention relates to a multimeric protein comprising a polypeptide as disclosed herein. In certain embodiments, the multimeric protein is a dimer, trimer, hexamer, or dodecamer. In certain embodiments, the multimeric protein is a hexamer. In certain embodiments, the multimeric protein comprises six separate polypeptides as described herein complexed to produce a hexameric protein. In certain embodiments, the multimeric protein comprises two separate polypeptides dimerized via each dimerization domain of each polypeptide to produce a dimeric protein.

In certain embodiments, the multimeric protein binds a carbohydrate ligand with a KD of 0.01 nM to 100 nM, as measured by surface plasmon resonance or bio-layer interferometry. In certain embodiments, the KD is 10 nM, 1 nM, 0.1 nM or lower. In certain embodiments, the KD is 1 nM, 0.1 nM or lower. In certain embodiments, the carbohydrate ligand is a Siglec ligand. In certain embodiments, the Siglec ligand is selected from a Siglec-1, Siglec-2, Siglec-3, Siglec-4, Siglec-5, Siglec-6, Siglec-7, Siglec-8, Siglec-9, Siglec-10, Siglec-11, Siglec-12, Siglec-14 and Siglec-15 ligand. In certain embodiments, the Siglec ligand is selected from a Siglec-3, Siglec-5, Siglec-6, Siglec-7, Siglec-8, Siglec-9, Siglec-10, and Siglec-11 ligand. In certain embodiments, the Siglec ligand is selected from a Siglec-7 and Siglec-9 ligand. In certain embodiments, the Siglec ligand is selected from α2,3-linked sialic acid, α2,6-linked sialic acid, sialyl Lewis X, NeuAcα2-3Galβ1-4Glc, NeuAcα2-3Galβ1-4GlcNAc, NeuAcα2-3Galβ1-3GlcNAc, NeuAcα2-3Galβ1-3GalNAc, NeuGcα2-3Galβ1-4GlcNAc, NeuGcα2-3Galβ1-3GlcNAc, NeuAcα2-6Galβ1-4Glc, NeuAcα2-6Galβ1-4GlcNAc, NeuAcα2-6GalNAc, Galβ1-3(NeuAcα2-6)GalNAc, NeuGcα2-6Galβ1-4Glc, NeuGcα2-6Galβ1-4GlcNAc, NeuGcα2-6GalNAc, NeuAcα2-8NeuAcα2-3Galβ1-4Glc, NeuAcα2-6Galβ1-4GlcNAc, NeuAcα2-3Galβ1-4[Fucα1-3]GlcNAc, NeuAcα2-6Galβ1-4GlcNAc6S, NeuAcα2-3Galβ1-4GalNAc, NeuAcα2-8NeuAc, NeuAcα2-3GalβSβ1-4GlcNAcα2-3Fuc, and NeuAcα2-3Galβ1-4GlcNAc6Sα2-3Fuc (where S stands for sulfate). In certain embodiments, the Siglec ligand is selected from α2,3-linked sialic acid, α2,6-linked sialic acid, and sialyl Lewis X.

In another aspect, the invention provides a multimeric protein comprising two polypeptides, wherein each polypeptide comprises, in an N-terminal to C-terminal direction, a first Siglec-based sialic acid binding V-set immunoglobulin-like domain, a first Siglec-based C2-set domain, a second Siglec-based sialic acid binding V-set immunoglobulin-like domain, a second Siglec-based C2-set domain, and an Fc domain. The two polypeptides can be dimerized at their Fc domains (covalently and/or non-covalently). In certain embodiments, each polypeptide comprises a linker between the first Siglec-based C2-set domain and the second Siglec-based sialic acid binding V-set immunoglobulin-like domain.

In another aspect, the invention provides a multimeric protein comprising two polypeptides, wherein each polypeptide comprises, in an N-terminal to C-terminal direction, a first Siglec-based sialic acid binding V-set immunoglobulin-like domain, a first Siglec-based C2-set domain, a second Siglec-based C2-set domain, an Fc domain, a second Siglec-based sialic acid binding V-set immunoglobulin-like domain, a third Siglec-based C2-set domain, and a fourth Siglec-based C2-set domain. The two polypeptides can be dimerized at their Fc domains (covalently and/or non-covalently). In certain embodiments, each polypeptide comprises a linker between the Fc domain and the second Siglec-based sialic acid binding V-set immunoglobulin-like domain.

In another aspect, the invention provides a multimeric protein comprising six polypeptides, wherein each polypeptide comprises, in an N-terminal to C-terminal direction, a first Siglec-based sialic acid binding V-set immunoglobulin-like domain, a first Siglec-based C2-set domain, a second Siglec-based C2-set domain, a trimerization domain (e.g., a T4 phage fibritin (foldon) trimerization domain), and an Fc domain A linker optionally may be used in between any of the components of the polypeptide. In certain embodiments, a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising six polypeptides, wherein each polypeptide comprises, in an N-terminal to C-terminal direction, a first sialic acid binding V-set immunoglobulin-like domain, one or more C2-set domains, optionally a linker, a T4 phage fibritin (foldon) trimerization domain, and an Fc domain. In certain embodiments, a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising six polypeptides, wherein each polypeptide comprises, in an N-terminal to C-terminal direction, a first sialic acid binding V-set immunoglobulin-like domain, one or more (e.g., one or two) C2-set domain, an Fc domain, optionally a linker, a T4 phage fibritin (foldon) trimerization domain. A linker optionally may be used in between any of the components of the polypeptide. In certain embodiments, a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising two polypeptides, wherein each polypeptide comprises, in an N-terminal to C-terminal direction, a first Siglec-3 sialic acid binding V-set immunoglobulin-like domain, a first Siglec-3 C2-set domain, a second Siglec-3 sialic acid binding V-set immunoglobulin-like domain, a second Siglec-3 C2-set domain, and an Fc domain, and wherein the two polypeptides are dimerized at their Fc domains (covalently and/or non-covalently). In certain embodiments, each polypeptide comprises a linker between the first Siglec-3 C2-set domain and the second Siglec-3 sialic acid binding V-set immunoglobulin-like domain.

In another aspect, the invention provides a multimeric protein comprising two polypeptides, wherein each polypeptide comprises, in an N-terminal to C-terminal direction, a first Siglec-3 sialic acid binding V-set immunoglobulin-like domain, a first Siglec-3 C2-set domain, a second Siglec-3 C2-set domain, an Fc domain, a second Siglec-3 sialic acid binding V-set immunoglobulin-like domain, a third Siglec-3 C2-set domain, and a fourth Siglec-3 C2-set domain, wherein the two polypeptides are dimerized at their Fc domains (covalently and/or non-covalently). In certain embodiments, each polypeptide comprises a linker between the Fc domain and the second Siglec-3 sialic acid binding V-set immunoglobulin-like domain.

In another aspect, the invention provides a multimeric protein comprising six polypeptides, wherein each polypeptide comprises, in an N-terminal to C-terminal direction, a first Siglec-3 sialic acid binding V-set immunoglobulin-like domain, a first Siglec-3 C2-set domain, a T4 phage fibritin (foldon) trimerization domain, and an Fc domain, and wherein: a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising six polypeptides, wherein each polypeptide comprises, in an N-terminal to C-terminal direction, a first Siglec-3 sialic acid binding V-set immunoglobulin-like domain, a Siglec-3 C2-set domain, optionally a linker, a T4 phage fibritin (foldon) trimerization domain, and an Fc domain, and wherein: a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising six polypeptides, wherein each polypeptide comprises, in an N-terminal to C-terminal direction, a first Siglec-3 sialic acid binding V-set immunoglobulin-like domain, a Siglec-3 C2-set domain, an Fc domain, optionally a linker, a T4 phage fibritin (foldon) trimerization domain, and wherein: a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising two polypeptides, wherein each polypeptide comprises, in an N-terminal to C-terminal direction, a first Siglec-7 sialic acid binding V-set immunoglobulin-like domain, a first Siglec-7 C2-set domain, a second Siglec-7 sialic acid binding V-set immunoglobulin-like domain, a second Siglec-7 C2-set domain, and an Fc domain, and wherein the two polypeptides are dimerized at their Fc domains (covalently and/or non-covalently). In certain embodiments, each polypeptide comprises a linker between the first Siglec-7 C2-set domain and the second Siglec-7 sialic acid binding V-set immunoglobulin-like domain.

In another aspect, the invention provides a multimeric protein comprising two polypeptides, wherein each polypeptide comprises, in an N-terminal to C-terminal direction, a first Siglec-7 sialic acid binding V-set immunoglobulin-like domain, a first Siglec-7 C2-set domain, a second Siglec-7 C2-set domain, an Fc domain, a second Siglec-7 sialic acid binding V-set immunoglobulin-like domain, a third Siglec-7 C2-set domain, and a fourth Siglec-7 C2-set domain, wherein the two polypeptides are dimerized at their Fc domains (covalently and/or non-covalently). In certain embodiments, each polypeptide comprises a linker between the Fc domain and the second Siglec-7 sialic acid binding V-set immunoglobulin-like domain.

In another aspect, the invention provides a multimeric protein comprising six polypeptides, wherein each polypeptide comprises, in an N-terminal to C-terminal direction, a first Siglec-7 sialic acid binding V-set immunoglobulin-like domain, a first Siglec-7 C2-set domain, a second Siglec-7 C2-set domain, a T4 phage fibritin (foldon) trimerization domain, and an Fc domain, and wherein: a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising six polypeptides, wherein each polypeptide comprises, in an N-terminal to C-terminal direction, a first Siglec-7 sialic acid binding V-set immunoglobulin-like domain, one or more (e.g., one or two) Siglec-7 C2-set domain(s), an Fc domain, optionally a linker, a T4 phage fibritin (foldon) trimerization domain, and wherein: a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising two polypeptides, wherein each polypeptide comprises, in an N-terminal to C-terminal direction, a first Siglec-9 sialic acid binding V-set immunoglobulin-like domain, a first Siglec-9 C2-set domain, a second Siglec-9 sialic acid binding V-set immunoglobulin-like domain, a second Siglec-9 C2-set domain, and an Fc domain, and wherein the two polypeptides are dimerized at their Fc domains (covalently and/or non-covalently). In certain embodiments, each polypeptide comprises a linker between the first Siglec-9 C2-set domain and the second Siglec-9 sialic acid binding V-set immunoglobulin-like domain.

In another aspect, the invention provides a multimeric protein comprising two polypeptides, wherein each polypeptide comprises, in an N-terminal to C-terminal direction, a first Siglec-9 sialic acid binding V-set immunoglobulin-like domain, a first Siglec-9 C2-set domain, a second Siglec-9 C2-set domain, an Fc domain, a second Siglec-9 sialic acid binding V-set immunoglobulin-like domain, a third Siglec-9 C2-set domain, and a fourth Siglec-9 C2-set domain, wherein the two polypeptides are dimerized at their Fc domains (covalently and/or non-covalently). In certain embodiments, each polypeptide comprises a linker between the Fc domain and the second Siglec-9 sialic acid binding V-set immunoglobulin-like domain.

In another aspect, the invention provides a multimeric protein comprising six polypeptides, wherein each polypeptide comprises, in an N-terminal to C-terminal direction, a first Siglec-9 sialic acid binding V-set immunoglobulin-like domain, a first Siglec-9 C2-set domain, a second Siglec-9 C2-set domain, a T4 phage fibritin (foldon) trimerization domain, and an Fc domain, and wherein: a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In another aspect, the invention provides a multimeric protein comprising six polypeptides, wherein each polypeptide comprises, in an N-terminal to C-terminal direction, a first Siglec-9 sialic acid binding V-set immunoglobulin-like domain, one or more (e.g., one or two) Siglec-9 C2-set domain(s), a one or more (e.g., one or two) Fc domains, optionally a linker, a T4 phage fibritin (foldon) trimerization domain, and wherein: a) the first, second and third polypeptides are trimerized at their respective trimerization domains (covalently and/or non-covalently); b) the fourth, fifth, and sixth polypeptides are trimerized at their respective trimerization domains (covalently and/or non-covalently); c) the first and second polypeptides are dimerized at their respective Fc domains (covalently and/or non-covalently); d) the third and fourth polypeptides are dimerized at their respective Fc domains (covalently and/or non-covalently); and e) the fifth and sixth polypeptides are dimerized at their respective Fc domains (covalently and/or non-covalently).

In certain embodiments, the multimeric protein comprises a polypeptide comprising SEQ ID NO: 7 or SEQ ID NO: 8. In certain embodiments, multimeric protein comprises a polypeptide comprising SEQ ID NO: 9, SEQ ID NO: 10, SEQ ID NO: 11, SEQ ID NO: 12, SEQ ID NO: 53, SEQ ID NO: 55, SEQ ID NO: 57, SEQ ID NO: 59, SEQ ID NO: 60, SEQ ID NO: 61, SEQ ID NO:

62, SEQ ID NO: 63, SEQ ID NO: 64, or SEQ ID NO: 67, or an amino acid sequence having 80%, 85%, 86%, 87%, 88%, 89%, 90%, 91%, 92%, 93%, 94%, 95%, 96%, 97%, 98%, or 99% sequence identity thereto. In certain embodiments, the multimeric protein comprises a polypeptide comprising SEQ ID NO: 53, SEQ ID NO: 55, SEQ ID NO: 57, SEQ ID NO: 59, SEQ ID NO: 60, SEQ ID NO: 61, SEQ ID NO: 62, SEQ ID NO: 63, SEQ ID NO: 64, or SEQ ID NO: 67 wherein the first 19 amino acids (MGWSCIILFL-VATATGVHS (SEQ ID NO: 73), a leader sequence) are not present.

II. Methods of Making a Polypeptide and/or Multimeric Protein

Methods for producing polypeptides and/or multimeric proteins, e.g., those disclosed herein, antibodies, or antibody conjugates, e.g., those disclosed herein, are known in the art.

For example, DNA molecules encoding lectin domains, dimerization domains, and/or trimerization domains can be synthesized chemically or by recombinant DNA methodologies. For example, the sequences of the lectin domains, dimerization domains, and/or trimerization domains can be synthesized or cloned from libraries by conventional hybridization techniques or polymerase chain reaction (PCR) techniques, using the appropriate synthetic nucleic acid primers. The resulting DNA molecules encoding the lectin domains, dimerization domains, and/or trimerization domains of interest can be ligated to other appropriate nucleotide sequences, including, for example, expression control sequences to produce conventional gene expression constructs (i.e., expression vectors) encoding the desired antibodies. Production of defined gene constructs is within routine skill in the art.

Nucleic acids encoding desired recombinant polypeptides can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the polypeptides comprising the lectin domains, dimerization domains, and/or trimerization domains.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an antibody or portion thereof, the expression vector optionally contains sequences encoding all or part of a constant region, enabling an entire, or a part of, a heavy or light chain to be expressed. The gene construct can be introduced into eukaryotic host cells using conventional techniques.

The host cells express a polypeptide comprising a lectin domains, dimerization domains, and/or trimerization domains s, or portions thereof. In some embodiments involving multimeric proteins, a host cell is transfected with a single vector expressing a polypeptide expressing a lectin domain, dimerization domain, and/or trimerization domain. In some embodiments, a host cell is co-transfected with more than one expression vector (e.g., each encoding a different polypeptide), which, when expressed, will form a multimeric protein.

DNA encoding a polypeptide comprising a lectin domain, dimerization domain, and/or trimerization domain can be assembled using PCR by overlap extension, and cloned into an expression vector, e.g., pCEP (Invitrogen). An expression vector encoding a polypeptide comprising a lectin domain, dimerization domain, and/or trimerization domain can be transfected into a host cell, e.g., using ExpiFectamine (Invitrogen). A polypeptide comprising a lectin domain, dimerization domain, and/or trimerization domain can be produced by growing (culturing) a host cell, e.g., an Expi293 cell, transfected with an expression vector encoding such a polypeptide, under conditions that permit expression of the polypeptide, e.g., for 6 days post transfection. Following expression, the polypeptide can be harvested and purified or isolated (i.e., recovered) using techniques known in the art, e.g., affinity tags such as glutathione-S-transferase (GST) or histidine tags or by protein A resin.

In certain embodiments, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In certain embodiments, the polypeptide and/or multimeric protein can be treated with a sialidase to improve expression, stability, recovery, and/or binding affinity to sialic acid. Sialidases suitable for use herein include *Vibrio Cholerae* (VC) sialidase or *Arthrobacter Ureafaciens* sialidase. In certain embodiments, recovery is improved by at least 25%, 50%, 75%, 100%, 150%, 200%, 500% as compared to a polypeptide and/or multimeric protein that has not been treated by a sialidase. In certain embodiments, recovery is improved from between about 25% to about 500%, for example, from between about 25% to about 200%, from about 25% to about 150%, from about 25 to about 75%, from about 25% to about 50%, from about 50% to about 500%, from about 50% to about 200%, from about 50% to about 150%, from about 50% to about 100%, from about 50% to about 75%, from about 75% to about 500%, from about 75% to about 200%, from about 75% to about 150%, from about 75% to about 100%, from about 100% to about 500%, from about 100% to about 200%, from about 100% to about 150%, from about 150% to about 500%, from about 150% to about 200% or from about 200% to about 500% as compared to a polypeptide and/or multimeric protein that has not been treated by a sialidase.

In certain embodiments, binding affinity (e.g., to a sialic acid) is increased by at least about 25% to about 500%, for example, from about 25% to about 200%, from about 25% to about 150%, from about 25 to about 75%, from about 25% to about 50%, from about 50% to about 500%, from about 50% to about 200%, from about 50% to about 150%, from about 50% to about 100%, from about 50% to about 75%, from about 75% to about 500%, from about 75% to about 200%, from about 75% to about 150%, from about 75% to about 100%, from about 100% to about 500%, from about 100% to about 200%, from about 100% to about 150%, from about 150% to about 500%, from about 150% to about 200% or from about 200% to about 500% as compared to a polypeptide and/or multimeric protein that has not been treated by a sialidase. Binding affinity can be measured by any method known in the art, including for example, FACS analysis, Octet binding analysis, or glycan array.

In certain embodiments, the multimeric protein that has been treated with a sialidase contains less than 50%, 40%, 30%, 20%, 10%, 5%, 4%, 3%, 2%, or 1% of the sialic acid content of a similar or identical multimeric protein that has not been treated with the sialidase.

III. Pharmaceutical Compositions

For therapeutic use, a polypeptide and/or multimeric protein preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (See Remington's Pharmaceutical Sciences, 18th ed. (Mack Publishing Company, 1990).

In certain embodiments, a pharmaceutical composition may contain nanoparticles, e.g., polymeric nanoparticles, liposomes, or micelles (See Anselmo et al. (2016) Bioeng. Transl. Med. 1: 10-29).

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semi-permeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (−)-3-hydroxybutyric acid. Sustained release compositions may also include liposomes that can be prepared by any of several methods known in the art.

Pharmaceutical compositions containing a polypeptide and/or a multimeric protein disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. A preferred route of administration is IV infusion. Useful formulations can be prepared by methods known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. Administration will generally be parenteral administration. In a preferred embodiment, the pharmaceutical composition is administered subcutaneously and in an even more preferred embodiment intravenously.

Preparations for parenteral administration include sterile aqueous or non-aqueous solutions, suspensions, and emulsions.

Generally, a therapeutically effective amount of active component, for example, a polypeptide and/or multimeric protein, is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life, and the disease being treated. Exemplary dosing frequencies are once per day, once per week and once every two weeks. A preferred route of administration is parenteral, e.g., intravenous infusion. In certain embodiments, a polypeptide and/or multimeric protein is lyophilized, and then reconstituted in buffered saline, at the time of administration.

IV. Detection Methods

The compositions and methods disclosed herein can be used to detect a carbohydrate, e.g., a Siglec ligand, in a sample, e.g., a sample from a subject. The carbohydrate can be detected in tissue, body fluid and/or cell samples from subjects of interest using techniques known in the art. The body fluid sample can be, for example, blood, serum or plasma. The tissue sample can be, for example, tumor tissue. The cell sample can be, for example, a cancer cell sample. It is understood that the tumor tissue or any of the samples may be preserved or processed using techniques known in the art, e.g., formalin-fixed, paraffin-embedded sections.

The invention provides a method of detecting the presence and/or quantifying the amount of a carbohydrate, e.g., a Siglec ligand, in a sample, e.g., a body fluid sample, tissue sample, and/or cell sample, from a subject, e.g., a human. The method comprises combining the sample with any one of the multimeric proteins described herein, and detecting the presence and/or quantifying the amount of complex comprising the multimeric protein and the carbohydrate, e.g., a Siglec ligand, if the carbohydrate is present in the sample.

The invention also provides a method of identifying a subject with a cancer or an inflammatory disorder likely to be responsive to treatment with a Siglec inhibitor, e.g., an anti-Siglec antibody. The method comprises combining a sample, e.g., a body fluid sample, tissue sample, and/or cell sample, from a subject, e.g., a human, with any one of the multimeric proteins described herein, and detecting the presence and/or quantifying the amount of complex comprising the multimeric protein and the carbohydrate, e.g., a Siglec ligand, if the carbohydrate is present in the sample. The presence of a complex is indicative that the subject will respond to treatment with a Siglec inhibitor.

In certain embodiments, the Siglec ligand is selected from a Siglec-1, Siglec-2, Siglec-3, Siglec-4, Siglec-5, Siglec-6, Siglec-7, Siglec-8, Siglec-9, Siglec-10, Siglec-11, Siglec-12, Siglec-14 and Siglec-15 ligand. In certain embodiments, the Siglec ligand is selected from a Siglec-3, Siglec-5, Siglec-6, Siglec-7, Siglec-8, Siglec-9, Siglec-10, and Siglec-11 ligand. In certain embodiments, the Siglec ligand is selected from a Siglec-7 and Siglec-9 ligand. In certain embodiments, the Siglec ligand is selected from α2,3-linked sialic acid, α2,6-linked sialic acid, sialyl Lewis X, NeuAcα2-3Galβ1-4Glc, NeuAcα2-3Galβ1-4GlcNAc, NeuAcα2-3Galβ1-3GlcNAc, NeuAcα2-3Galβ1-3GalNAc, NeuGcα2-3Galβ1-4GlcNAc, NeuGcα2-3Galβ1-3GlcNAc, NeuAcα2-6Galβ1-4Glc, NeuAcα2-6Galβ1-4GlcNAc, NeuAcα2-6GalNAc, Galβ1-3(NeuAcα2-6)GalNAc, NeuGcα2-6Galβ1-4Glc, NeuGcα2-6Galβ1-4GlcNAc, NeuGcα2-6GalNAc, NeuAcα2-8NeuAcα2-3Galβ1-4Glc, NeuAcα2-6Galβ1-4GlcNAc, NeuAcα2-3Galβ1-4[Fucα1-3]GlcNAc, NeuAcα2-6Galβ1-4GlcNAc6S, NeuAcα2-3Galβ1-4GalNAc, NeuAcα2-8NeuAc, NeuAcα2-3GalβSβ1-4GlcNAcα2-3Fuc, and NeuAcα2-3Galβ1-4GlcNAc6Sα2-3Fuc (where S stands for sulfate). In certain embodiments, the Siglec ligand is selected from α2,3-linked sialic acid, α2,6-linked sialic acid, and sialyl Lewis X.

In certain embodiments, the Siglec inhibitor is an anti-Siglec antibody. The anti-Siglec antibody can be, for example, an anti-Siglec-3 antibody, anti-Siglec-5 antibody, anti-Siglec-6 antibody, anti-Siglec-7 antibody, anti-Siglec-8 antibody, anti-Siglec-9 antibody, anti-Siglec-10 antibody, or anti-Siglec-11 antibody. In certain embodiments, the anti-Siglec antibody is an anti-Siglec-3 antibody, an anti-Siglec-7 antibody, or anti-Siglec-9 antibody. In certain embodiments, the anti-Siglec antibody is an anti-Siglec-7 antibody or anti-Siglec-9 antibody.

The invention also relates to a method of identifying a subject with a cancer or an inflammatory disorder likely to respond to treatment with a Siglec-3 inhibitor (e.g., an anti-Siglec-3 antibody). The method includes contacting a sample from the subject with the multimeric protein described herein under conditions to permit the multimeric protein to form a multimeric protein-Siglec-3 ligand complex, if the Siglec-3 ligand is present in the sample and detecting the presence and/or amount of the complex, if any, wherein the presence and/or amount of a complex is indicative that the subject will respond to treatment with a Siglec-3 inhibitor.

The invention also relates to a method of identifying a subject with a cancer or an inflammatory disorder likely to respond to treatment with a Siglec-5 inhibitor (e.g., an anti-Siglec-5 antibody). The method includes contacting a sample from the subject with the multimeric protein described herein under conditions to permit the multimeric protein to form a multimeric protein-Siglec-5 ligand complex, if the Siglec-5 ligand is present in the sample and detecting the presence and/or amount of the complex, if any, wherein the presence and/or amount of a complex is indicative that the subject will respond to treatment with a Siglec-5 inhibitor.

The invention also relates to a method of identifying a subject with a cancer or an inflammatory disorder likely to respond to treatment with a Siglec-6 inhibitor (e.g., an anti-Siglec-6 antibody). The method includes contacting a sample from the subject with the multimeric protein described herein under conditions to permit the multimeric protein to form a multimeric protein-Siglec-6 ligand complex, if the Siglec-6 ligand is present in the sample and detecting the presence and/or amount of the complex, if any, wherein the presence and/or amount of a complex is indicative that the subject will respond to treatment with a Siglec-6 inhibitor.

The invention also relates to a method of identifying a subject with a cancer or an inflammatory disorder likely to respond to treatment with a Siglec-7 inhibitor (e.g., an anti-Siglec-7 antibody). The method includes contacting a sample from the subject with the multimeric protein described herein (e.g., a multimeric protein comprising a polypeptide comprising SEQ ID NO: 7) under conditions to permit the multimeric protein to form a multimeric protein-Siglec-7 ligand complex, if the Siglec-7 ligand is present in the sample and detecting the presence and/or amount of the complex, if any, wherein the presence and/or amount of a complex is indicative that the subject will respond to treatment with a Siglec-7 inhibitor.

The invention also relates to a method of identifying a subject with a cancer or an inflammatory disorder likely to respond to treatment with a Siglec-8 inhibitor (e.g., an anti-Siglec-8 antibody). The method includes contacting a sample from the subject with the multimeric protein described herein under conditions to permit the multimeric protein to form a multimeric protein-Siglec-8 ligand complex, if the Siglec-8 ligand is present in the sample and detecting the presence and/or amount of the complex, if any, wherein the presence and/or amount of a complex is indicative that the subject will respond to treatment with a Siglec-8 inhibitor.

The invention also relates to a method of identifying a subject with a cancer or an inflammatory disorder likely to respond to treatment with a Siglec-9 inhibitor (e.g., an anti-Siglec-9 antibody). The method includes contacting a sample from the subject with the multimeric protein described herein (e.g., a multimeric protein comprising a polypeptide comprising SEQ ID NO: 8) under conditions to permit the multimeric protein to form a multimeric protein-Siglec-9 ligand complex, if the Siglec-9 ligand is present in the sample and detecting the presence and/or amount of the complex, if any, wherein the presence and/or amount of a complex is indicative that the subject will respond to treatment with a Siglec-9 inhibitor.

The invention also relates to a method of identifying a subject with a cancer or an inflammatory disorder likely to respond to treatment with a Siglec-10 inhibitor (e.g., an anti-Siglec-10 antibody). The method includes contacting a sample from the subject with the multimeric protein described herein under conditions to permit the multimeric protein to form a multimeric protein-Siglec-10 ligand complex, if the Siglec-10 ligand is present in the sample and detecting the presence and/or amount of the complex, if any, wherein the presence and/or amount of a complex is indicative that the subject will respond to treatment with a Siglec-10 inhibitor.

The invention also relates to a method of identifying a subject with a cancer or an inflammatory disorder likely to respond to treatment with a Siglec-11 inhibitor (e.g., an anti-Siglec-11 antibody). The method includes contacting a sample from the subject with the multimeric protein described herein under conditions to permit the multimeric protein to form a multimeric protein-Siglec-11 ligand complex, if the Siglec-11 ligand is present in the sample and detecting the presence and/or amount of the complex, if any, wherein the presence and/or amount of a complex is indicative that the subject will respond to treatment with a Siglec-11 inhibitor.

It is contemplated that the presence and/or amount of a multimeric protein-carbohydrate e.g., Siglec ligand, complex can be detected and/or measured using a variety of techniques known in the art. In one approach, the multimeric protein can be coupled to a detectable label, for example, a radiolabel, a fluorescent label, a visual label, an enzyme label, or other conventional detectable labels useful in diagnostic or prognostic assays. Alternatively, the presence and/or amount of a multimeric protein carbohydrate, e.g., Siglec ligand, complex can be detected and/or using a secondary reagent, e.g., a reagent that binds to the multimeric protein, e.g., an antibody, labeled, for example, with a detectable label, for example, a radiolabel, a fluorescent label, a visual label, an enzyme label, or other conventional detectable labels useful in diagnostic or prognostic assays.

V. Therapeutic Uses

The compositions and methods disclosed herein can be used to treat a Siglec-mediated disorder in a subject. As used herein, the term "Siglec-mediated disorder" refers to a disorder that is mediated, enhanced or otherwise facilitated by a Siglec molecule, for example, by an interaction between a Siglec molecule and a Siglec ligand.

Examples of Siglec-mediated disorders include, for example, cancers, inflammatory disorders, and autoimmune disorders.

The invention provides a method of treating a Siglec-mediated disorder in a subject in need thereof. The method comprises administering to the subject an effective amount of a recombinant polypeptide and/or multimeric protein, either alone or in a combination with another therapeutic agent to treat the Siglec-mediated disorder in the subject. In certain embodiments, the Siglec-mediated disorder is a Siglec-1, Siglec-2, Siglec-3, Siglec-4, Siglec-5, Siglec-6, Siglec-7, Siglec-8, Siglec-9, Siglec-10, Siglec-11, Siglec-12, Siglec-14 or a Siglec-15 mediated disorder. In certain embodiments, the Siglec-mediated disorder is a Siglec-3, Siglec-5, Siglec-6, Siglec-7, Siglec-8, Siglec-9, Siglec-10, or Siglec-11 mediated disorder.

The term "effective amount" as used herein refers to the amount of an active agent (e.g., recombinant polypeptide and/or multimeric protein according to the present invention) sufficient to effect beneficial or desired results. An effective amount can be administered in one or more administrations, applications or dosages and is not intended to be limited to a particular formulation or administration route.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. In certain embodiments, a method or composition described herein, is administered in combination with one or more additional therapies, e.g., an IDO inhibitor, or an immune checkpoint inhibitor, for example, a PD-1 inhibitor, PD-L1 inhibitor, CTLA-4 inhibitor, adenosine A2A receptor inhibitor, B7-H3 inhibitor, B7-H4 inhibitor, BTLA inhibitor, MR inhibitor, LAG3 inhibitor, TEVI-3 inhibitor, VISTA inhibitor or TIGIT inhibitor.

In another aspect, the invention relates to a method of treating cancer in a subject in need thereof, the method comprising administering to the subject an effective amount of a Siglec inhibitor, thereby to treat the cancer in the subject, wherein the cancer has been identified as comprising cancerous cells that express one or more ligands of the Siglec by a method described herein.

In certain embodiments, the Siglec ligand is a Siglec-3, Siglec-5, Siglec-6, Siglec-7, Siglec-8, Siglec-9, Siglec-10, or Siglec-11 ligand. In certain embodiments, the Siglec ligand is a Siglec-7 or Siglec-9 ligand. In certain embodiments, the Siglec ligand is selected from α2,3-linked sialic acid, α2,6-linked sialic acid, sialyl Lewis X, NeuAcα2-3Galβ1-4Glc, NeuAcα2-3Galβ1-4GlcNAc, NeuAcα2-3Galβ1-3GlcNAc, NeuAcα2-3Galβ1-3GalNAc, NeuGcα2-3Galβ1-4GlcNAc, NeuGcα2-3Galβ1-3GlcNAc, NeuAcα2-6Galβ1-4Glc, NeuAcα2-6Galβ1-4GlcNAc, NeuAcα2-6GalNAc, Galβ1-3(NeuAcα2-6)GalNAc, NeuGcα2-6Galβ1-4Glc, NeuGcα2-6Galβ1-4GlcNAc, NeuGcα2-6GalNAc, NeuAcα2-8NeuAcα2-3Galβ1-4Glc, NeuAcα2-6Galβ1-4GlcNAc, NeuAcα2-3Galβ1-4[Fucα1-3]GlcNAc, NeuAcα2-6Galβ1-4GlcNAc6S, NeuAcα2-3Galβ1-4GalNAc, NeuAcα2-8NeuAc, NeuAcα2-3GalβSβ1-4GlcNAcα2-3Fuc, and NeuAcα2-3Galβ1-4GlcNAc6Sα2-3Fuc (where S stands for sulfate). In certain embodiments, the Siglec ligand is selected from α2,3-linked sialic acid, α2,6-linked sialic acid, and sialyl Lewis X.

In certain embodiments, the Siglec inhibitor is an anti-Siglec antibody. The anti-Siglec antibody can be, for example, an anti-Siglec-3 antibody, anti-Siglec-5 antibody, anti-Siglec-6 antibody, anti-Siglec-7 antibody, anti-Siglec-8 antibody, anti-Siglec-9 antibody, anti-Siglec-10 antibody, or anti-Siglec-11 antibody. In certain embodiments, the anti-Siglec antibody is an anti-Siglec-7 antibody or anti-Siglec-9 antibody.

In another aspect, the invention relates to a method of treating cancer in a subject in need thereof, the method comprising administering to the subject an effective amount of a Siglec-3 inhibitor (e.g., an anti-Siglec-3 antibody), thereby to treat the cancer in the subject, wherein the cancer has been identified as comprising cancerous cells that express a Siglec-3 ligand by a method described herein.

In another aspect, the invention relates to a method of treating cancer in a subject in need thereof, the method comprising administering to the subject an effective amount of a Siglec-5 inhibitor (e.g., an anti-Siglec-5 antibody), thereby to treat the cancer in the subject, wherein the cancer has been identified as comprising cancerous cells that express a Siglec-5 ligand by a method described herein.

In another aspect, the invention relates to a method of treating cancer in a subject in need thereof, the method comprising administering to the subject an effective amount of a Siglec-6 inhibitor (e.g., an anti-Siglec-6 antibody), thereby to treat the cancer in the subject, wherein the cancer has been identified as comprising cancerous cells that express a Siglec-6 ligand by a method described herein.

In another aspect, the invention relates to a method of treating cancer in a subject in need thereof, the method comprising administering to the subject an effective amount of a Siglec-7 inhibitor (e.g., an anti-Siglec-7 antibody), thereby to treat the cancer in the subject, wherein the cancer has been identified as comprising cancerous cells that express a Siglec-7 ligand by a method described herein.

In another aspect, the invention relates to a method of treating cancer in a subject in need thereof, the method comprising administering to the subject an effective amount of a Siglec-8 inhibitor (e.g., an anti-Siglec-8 antibody), thereby to treat the cancer in the subject, wherein the cancer has been identified as comprising cancerous cells that express a Siglec-8 ligand by a method described herein.

In another aspect, the invention relates to a method of treating cancer in a subject in need thereof, the method comprising administering to the subject an effective amount of a Siglec-9 inhibitor (e.g., an anti-Siglec-9 antibody), thereby to treat the cancer in the subject, wherein the cancer has been identified as comprising cancerous cells that express a Siglec-9 ligand by a method described herein.

In another aspect, the invention relates to a method of treating cancer in a subject in need thereof, the method comprising administering to the subject an effective amount of a Siglec-10 inhibitor (e.g., an anti-Siglec-10 antibody), thereby to treat the cancer in the subject, wherein the cancer has been identified as comprising cancerous cells that express a Siglec-10 ligand by a method described herein.

In another aspect, the invention relates to a method of treating cancer in a subject in need thereof, the method comprising administering to the subject an effective amount of a Siglec-11 inhibitor (e.g., an anti-Siglec-11 antibody), thereby to treat the cancer in the subject, wherein the cancer has been identified as comprising cancerous cells that express a Siglec-11 ligand by a method described herein.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments the cancer is an epithelial cancer, e.g., an epithelial cancer that upregulates the expression of sialylated glycans. Exemplary epithelial cancers include, but are not limited to, endometrial cancer, colon cancer, ovarian cancer, cervical cancer, vulvar cancer, uterine cancer or fallopian tube cancer, breast cancer, prostate cancer, lung cancer, pancreatic cancer, urinary cancer, bladder cancer, head and neck cancer, oral cancer and liver cancer. Epithelial cancers also include carcinomas, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, baso squamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum. In certain embodiments, the epithelial cancer is endometrial cancer, ovarian cancer, cervical cancer, vulvar cancer, uterine cancer, fallopian tube cancer, breast cancer, prostate cancer, lung cancer, pancreatic cancer, urinary cancer, bladder cancer, head and neck cancer, oral cancer or liver cancer.

In certain embodiments, the cancer is breast cancer. In certain embodiments, the cancer is an adenocarcinoma. In certain embodiments, the cancer is a metastatic cancer. In certain embodiments, the cancer is a refractory cancer.

Exemplary inflammatory disorders include chronic inflammatory disorders (e.g., rheumatoid arthritis, asthma, chronic peptic ulcer, tuberculosis, periodontitis, ulcerative colitis and Crohn's disease, sinusitis, and active hepatitis) and acute inflammatory disorders (e.g., acute bronchitis, acute appendicitis, dermatitis, tonsillitis, infective meningitis and sinusitis). Exemplary autoimmune disorders include type 1 diabetes, rheumatoid arthritis (RA), psoriasis/psoriatic arthritis, multiple sclerosis, systemic lupus erythematosus (lupus), inflammatory bowel disease, Addison's disease, Graves' disease, Sjögren's syndrome, Hashimoto's thyroiditis, myasthenia gravis, vasculitis, pernicious anemia, and Celiac disease.

In certain embodiments of a disclosed method of treating an inflammatory disorder in a subject comprising administering to the subject an effective amount of a recombinant polypeptide and/or multimeric protein of the invention, the recombinant polypeptide and/or multimeric protein comprises an Fc domain that binds the FcγRIIB1 or FcγRIIB2 Fc receptor.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1

This example describes the construction of various Siglec binding constructs, including a dimeric and tetravalent construct referred to as "dragonfly" (see FIG. 1B), a dimeric and tetravalent construct referred to as "butterfly" (see FIG. 1C) and a hexameric and hexavalent construct referred to as "hydra" (see FIG. 1D), and their ability to selectively bind sialic acid ligands. The constructs contained a lectin domain derived from either human Siglec-7 or Siglec-9.

As shown in FIG. 1B, the dragonfly construct was created by fusing two repeats of a truncated human Siglec extracellular domain (ECD), which contained the N-terminal V-set immunoglobulin-like domain and one C2-set domain to the N-terminus of an Fc domain Dimerization via the Fc domain created a tetravalent construct containing four lectin domains.

As shown in FIG. 1C, the butterfly construct was created by fusing a Siglec ECD, which contained a Siglec N-terminal V-set immunoglobulin-like domain and two C2-set domains, to both the N-terminus and the C-terminus of an Fc domain Dimerization via the Fc domain created a tetravalent construct containing four lectin domains.

As shown in FIG. 1D, the hydra construct was created by fusing a Siglec ECD, which contained a Siglec N-terminal V-set immunoglobulin-like domain and two C2-set domains, to the N-terminus of a trimerization domain (foldon), followed by an Fc domain Dimerization via the Fc domain and trimerization by the foldon domain created a hexavalent construct containing six lectin domains.

As shown in FIG. 1A, a Siglec dimer was created by fusing a Siglec ECD, which contained a Siglec N-terminal V-set immunoglobulin-like domain and two C2-set domains, to the N-terminus of an Fc domain. Dimerization via the Fc domain created a bivalent construct containing two lectin domains.

Briefly, all constructs were prepared as follows. DNA encoding the relevant domains was assembled using PCR by overlap extension, and cloned into a mammalian expression vector, pCEP (Invitrogen). Expi293 cells were transiently transfected with the expression vector using ExpiFectamine (Invitrogen) according to the manufacturer's instructions. Supernatants were harvested 6 days post-transfection. Proteins were purified using protein A resin (Repligen) according to the manufacturer's instructions.

Figure 2A:
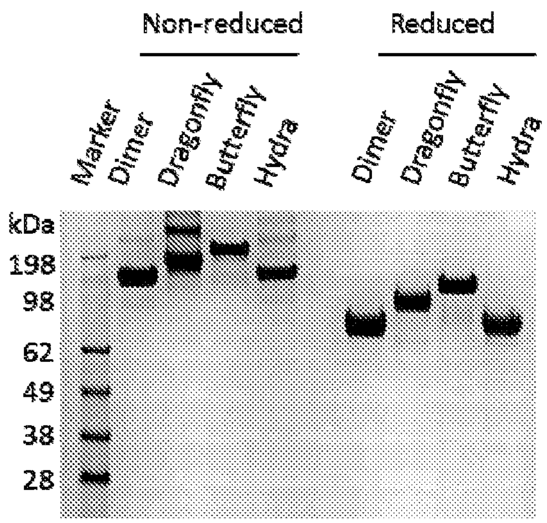
FIG. 2A is a series of sodium dodecyl sulfate polyacrylamide gel electrophoresis ("SDS-PAGE") gels depicting Siglec-7 dimer, dragonfly, butterfly, and hydra. Each gel shows the purified protein under non-reducing (non-red) and reducing (red) conditions.
Figure 2B:
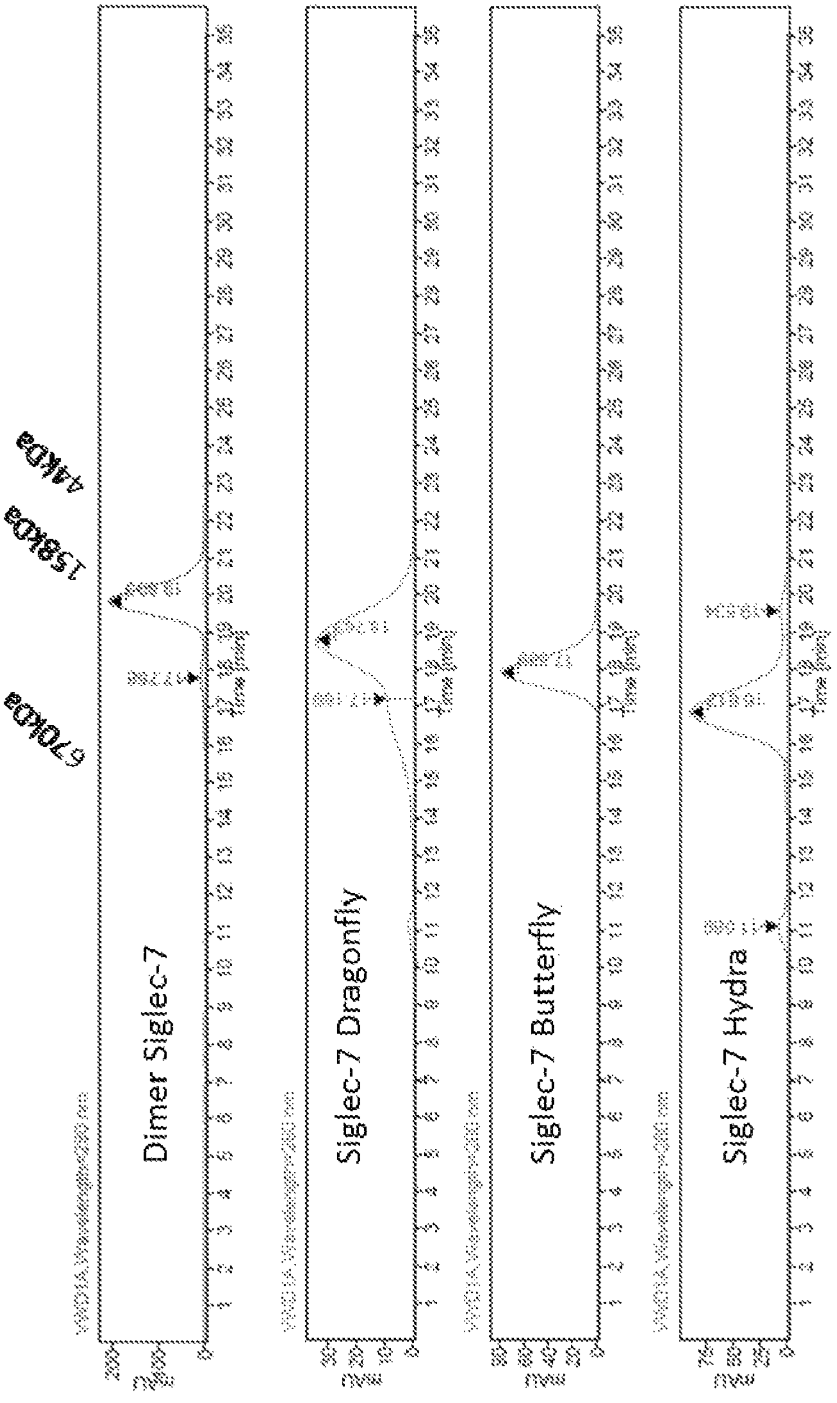
FIG. 2B is a series of size exclusion chromatography high-performance liquid chromatography ("SEC-HPLC") plots depicting Siglec-7 dimer, dragonfly, butterfly, and hydra. Each plot shows absorbance at 280 nM. Retention times for 670 kDa, 158 kDa, and 44 kDa molecular weight standards are indicated.

Siglec-7 hydra (amino acid sequence SEQ ID NO: 7 encoded by nucleic acid sequence SEQ ID NO: 46), dragonfly (amino acid sequence SEQ ID NO: 9 encoded by nucleic acid sequence SEQ ID NO: 47), butterfly (amino acid sequence SEQ ID NO: 11 encoded by nucleic acid sequence SEQ ID NO: 48), and dimer (amino acid sequence SEQ ID NO: 49 encoded by nucleic acid sequence SEQ ID NO: 50) were expressed, purified and characterized using sodium dodecylsulfate polyacrylamide gel electrophoresis (SDS-PAGE). As shown in FIG. 2A, all four proteins have high purity (>95%) and migrated at expected apparent molecular weights (MW) under denatured, non-reducing and reducing conditions. The assembly of multimeric Siglec-7 hydra, dragonfly, butterfly, and dimer was characterized using size exclusion chromatography (SEC-HPLC). As shown in FIG. 2B, Siglec-7 hydra assembled into a multimeric molecule and had a retention time corresponding to a MW≥400 kDa. Siglec-7 dimer, dragonfly, and butterfly had later retention times than Siglec-7 hydra, consistent with an expected smaller MW.

Figure 3A:
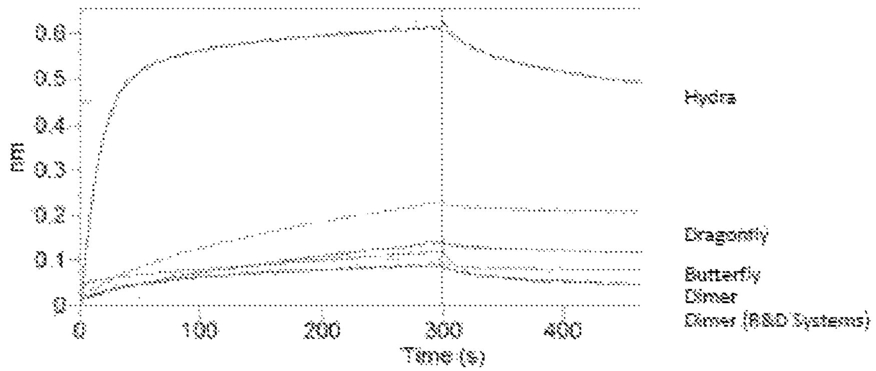
FIG. 3A is a line graph showing binding of Siglec-7 hydra, dragonfly, butterfly, and dimer to sialic acid polymer as determined by Octet binding analysis. A commercially available Siglec-7 dimer (R&D systems) was used as a control.
Figure 3B:
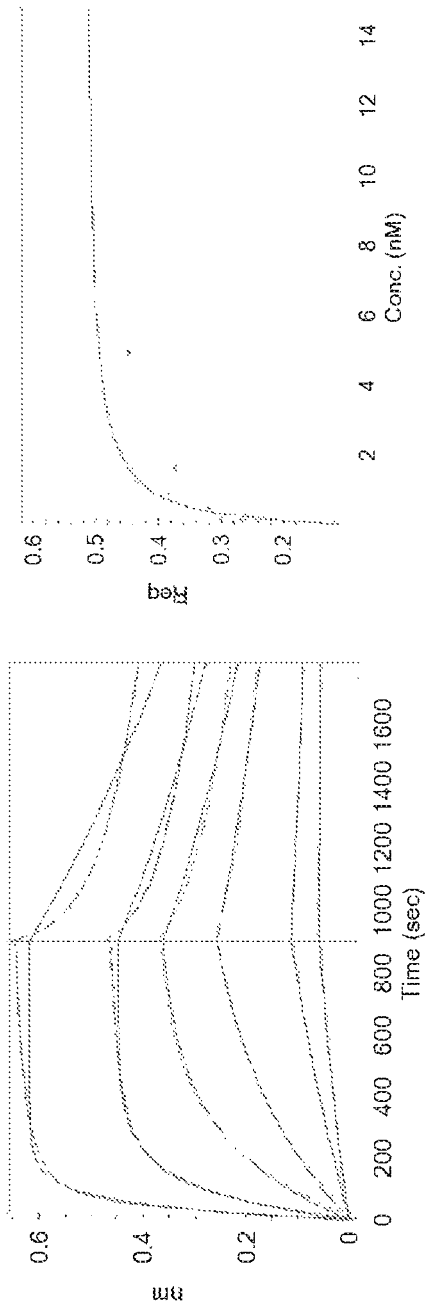
FIG. 3B is a line graph showing kinetics of Siglec-7 hydra binding as determined by Octet binding analysis. Siglec-7 hydra had an apparent binding affinity of 0.1±0.025 nM.

The relative binding affinities of Siglec-7 hydra, dragonfly, butterfly, and dimer were determined. A commercially available Siglec-7 dimer (R&D Systems) was also included as a control. An Octet binding analysis was performed by capturing biotinylated sialic-acid polymer, Neu5Acα2-3Galb1-4(Fucα1-3) (6-H503) GlcNAcb-PAA-biotin (Glycotech #01-095), using streptavidin-coated Octet biosensors. Following a baseline step of 100s in PBS buffer containing 0.1% BSA and 0.02% Tween20, the biosensors with captured ligand were then submerged in wells containing 100 nM of Siglec-7 hydra, Siglec-7 dragonfly, Siglec-7 butterfly, or Siglec-7 dimer for 5 minutes, followed by 3 minutes of dissociation time in PBS buffer containing 0.1% BSA and 0.02% Tween20. As shown in FIG. 3A, Siglec-7 hydra bound to the sialic acid polymer with a higher signal than that of Siglec-7 dragonfly, butterfly, or dimer. Since Siglec-7 hydra had the highest binding signal of the constructs tested, the binding kinetics of Siglec-7 hydra were determined. The binding kinetics were assayed as described above except with Siglec-7 hydra at concentrations of 44 nM to 67 pM (with 1:3 dilutions) and association and dissociation times of 15 minutes. As shown in FIG. 3B, Siglec-7 hydra bound to the sialic-acid polymer with an apparent binding affinity of 0.1±0.025 nM.

Figure 3C:
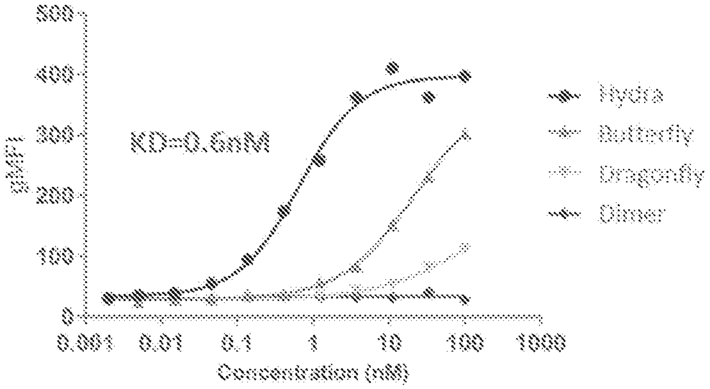
FIG. 3C is a line graph showing binding of Siglec-7 hydra, dragonfly, butterfly, and dimer to sialic acid glycan-expressing T47D cancer cells as measured by fluorescence-activated cell sorting ("FACS").

FACS binding analysis was also performed using T47D breast cancer cells, which express endogenous sialic acid Siglec ligands. Cells were incubated with Siglec-7 hydra, dragonfly, butterfly, and dimer at concentrations of 100 nM to 1.7 pM (with 1:3 dilutions). Bound Siglec-7 constructs on the cell surface were detected using a Alexa488 labeled anti-Fc secondary antibody (Invitrogen) and a flow cytometer. As shown in FIG. 3C, Siglec-7 hydra bound to sialic-acid expressing T47D cancer cells with an apparent affinity of 0.6 nM. This apparent affinity was at least 100 fold higher than the apparent affinity for Siglec-7 dragonfly, butterfly, or dimer.

Together, these results show that Siglec-7 hydra, Siglec-7 dragonfly, and Siglec-7 butterfly bind to Siglec-7 ligands with a higher apparent affinity than Siglec-7 dimer, with the highest apparent affinity for Siglec-7 hydra.

Figure 4A:
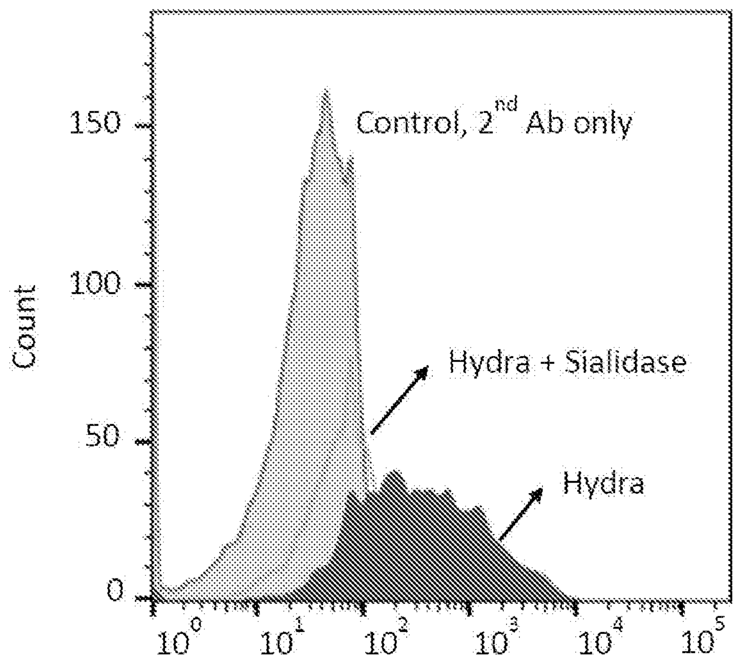
FIG. 4A is a plot showing binding of Siglec-7 hydra to T47D cells with or without sialidase treatment as determined by FACS.

The specificity of Siglec-7 hydra for sialic acid was demonstrated by conducting binding experiments with T47D cells treated with sialidase to remove sialic acid on the cell surface. T47D cells were treated with 125 nM bacterial (*Vibrio cholerae*) sialidase at 37° C. for 1.5 hours. Untreated T47D cells were included as a positive control. Siglec-7 hydra binding was assayed by FACS as described above. As shown in FIG. 4A, sialidase treatment abolished binding of Siglec-7 hydra to T47D cells. These results show that Siglec-7 hydra binding to cells was mediated by sialic acid-recognition.

Figure 4B:
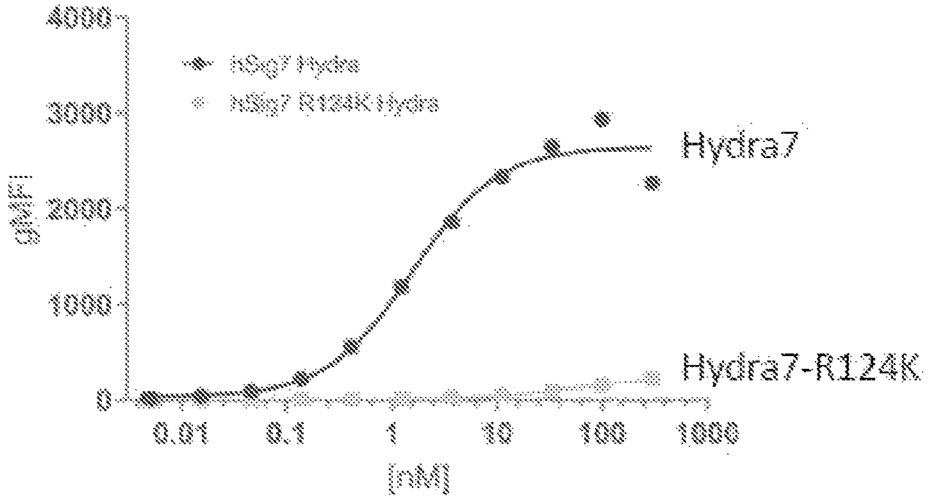
FIG. 4B is a line graph showing binding of Siglec-7 hydra and Siglec-7 R124K hydra to T47D cells as determined by FACS.
Figure 4C:
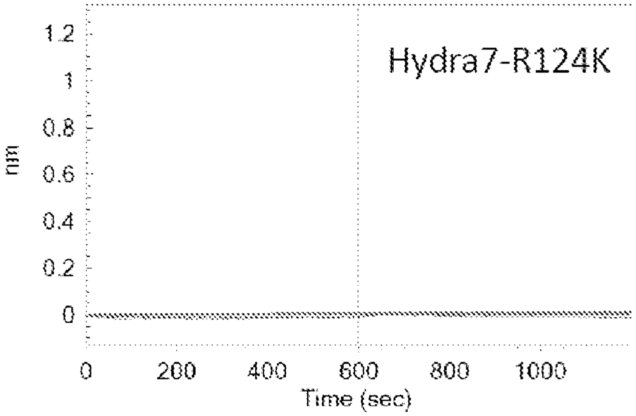
FIG. 4C is line graph showing binding of Siglec-7 hydra and Siglec-7 R124K hydra to sialic acid polymer as determined by Octet.
Figure 4C:
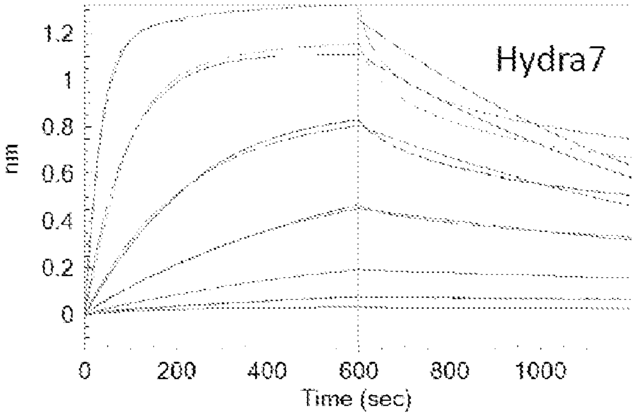

Selective binding of Siglec-7 hydra was further confirmed by substituting a critical ligand-binding arginine residue (R124) with a lysine (R124K) to generate a loss-of-binding Siglec-7 hydra mutant. FACS binding and Octet binding analyses were performed as described above. As shown in FIG. 4B and FIG. 4C, the R124K substitution substantially reduced binding to T47D cells and sialic-acid polymer as compared to the wild type Siglec-7 hydra.

Together, these results show that Siglec-7 hydra binding is mediated by sialic acid-recognition.

Figure 5A:
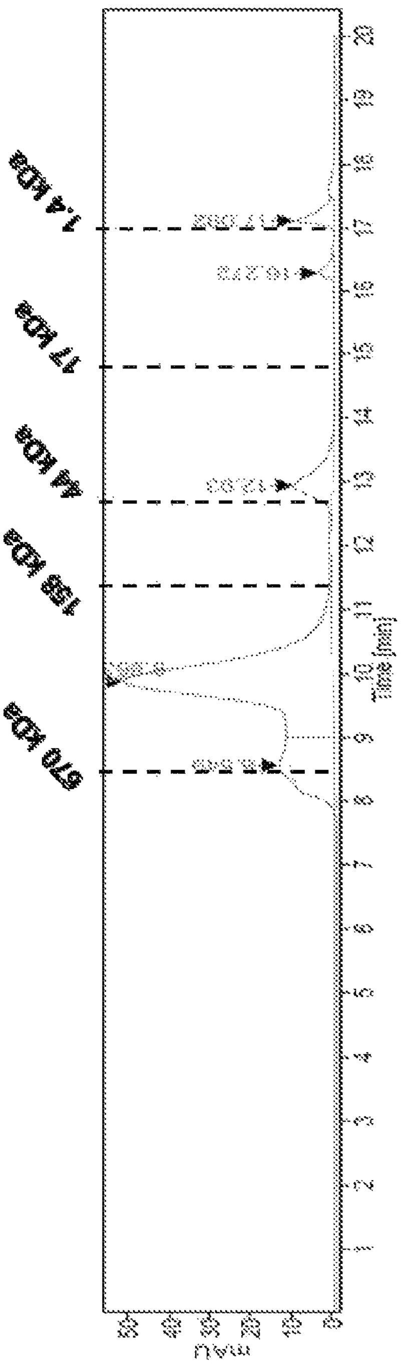
FIG. 5A is a SEC-HPLC plot depicting Siglec-9 hydra. The plot shows absorbance at 280 nM. Retention times for 670 kDa, 158 kDa, 44 kDa, 17 kDa, and 1.4 kDa molecular weight standards are indicated.

Siglec-9 hydra (amino acid sequence SEQ ID NO: 8 encoded by nucleic acid sequence SEQ ID NO: 45) was expressed, purified, and characterized using SEC-HPLC. As shown in FIG. 5A, Siglec-9 hydra assembled into a heterogeneous multimeric molecule with a MW≥300 kDa and multiple peaks in SEC-HPLC. The heterogeneity of Siglec-9 hydra may be a result of dimerization of the Siglec-9 ECD domain.

Figure 5B:
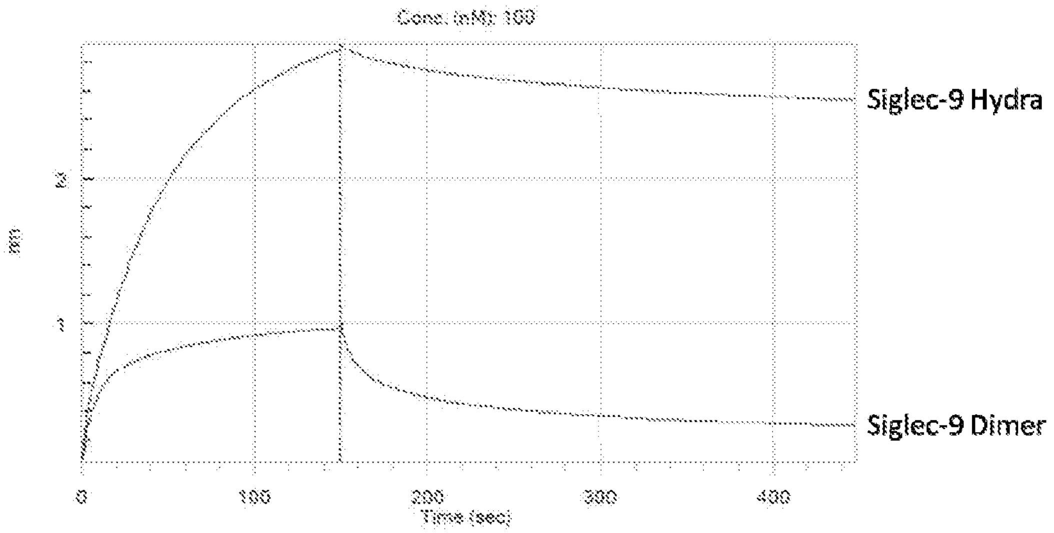
FIG. 5B is a line graph showing binding of Siglec-9 hydra and dimer as determined by Octet binding analysis.
Figure 5C:
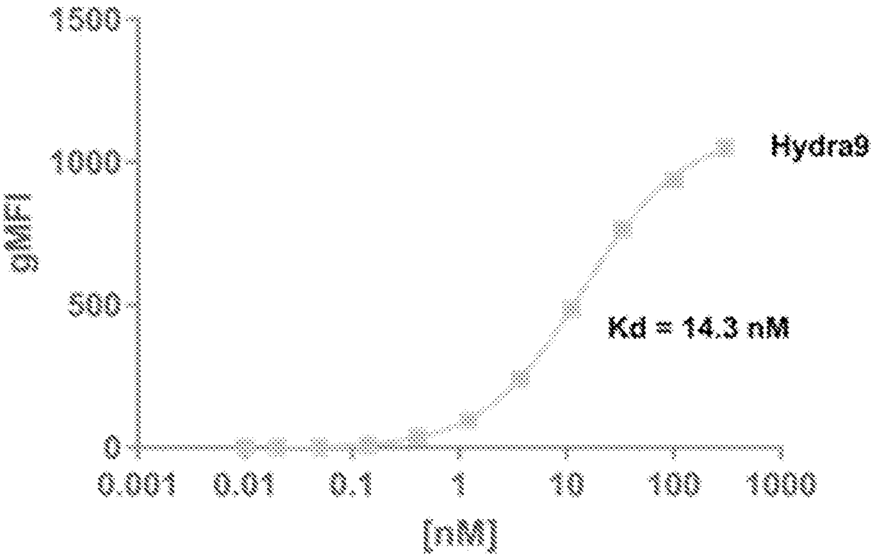
FIG. 5C is a line graph showing binding of Siglec-9 hydra to sialic acid glycan expressing HT-29 breast cancer cells as measured by FACS.

An Octet binding analysis was performed as described above to determine the relative binding affinities of Siglec-9 hydra and Siglec-9 dimer. As shown in FIG. 5B, Siglec-9 hydra bound to a sialic acid polymer with a higher signal than that of dimer construct. FACS binding analysis was also performed using HT-29 breast cancer cells, as described above. As shown in FIG. 5C, Siglec-9 hydra bound to sialic-acid expressing HT-29 cancer cells with an apparent affinity of 14.3 nM. Together, these results show that Siglec-9 hydra binds to Siglec-9 ligands with a higher apparent affinity than Siglec-9 dimer.

Figure 5D:
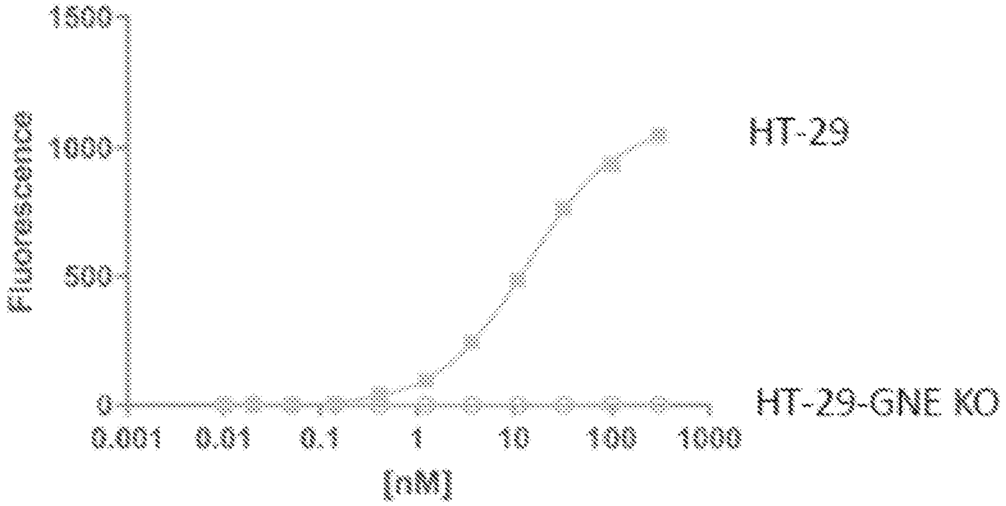
FIG. 5D is a line graph showing binding of Siglec-9 hydra to HT-29 UDP-N-acetylglucosamine-2-epimerase knockout ("HT-29 GNE KO") cells as measured by FACS.
Figure 6A:
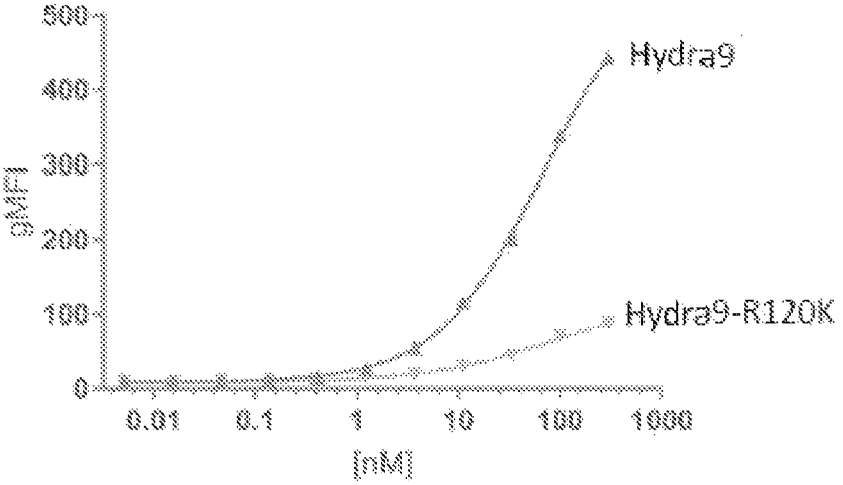
FIG. 6A is a line graph showing binding of Siglec-9 hydra and Siglec-9 R120K hydra to K562 cells as determined by FACS.
Figure 6B:
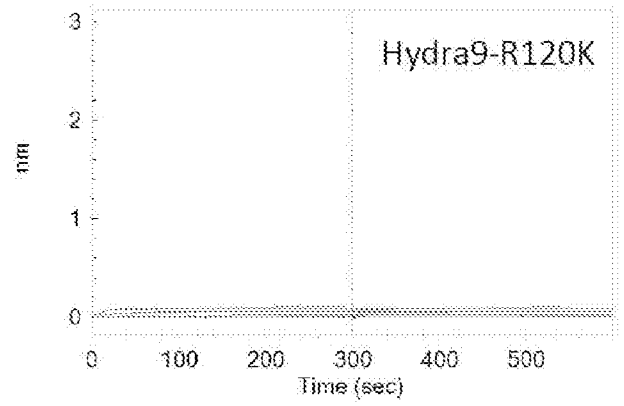
FIG. 6B is line graph showing binding of Siglec-9 hydra and Siglec-9 R120K hydra to sialic acid polymer as determined by Octet.
Figure 6B:
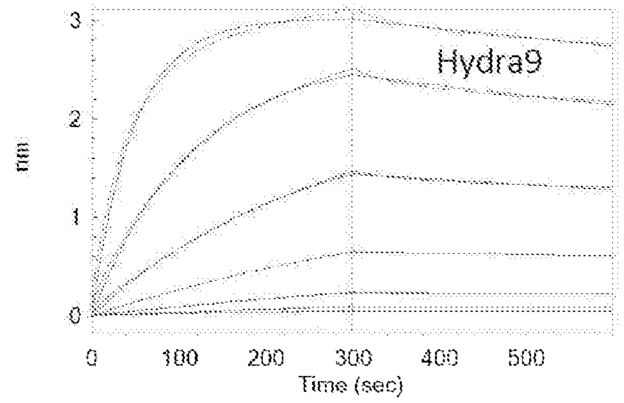
Figure 7A:
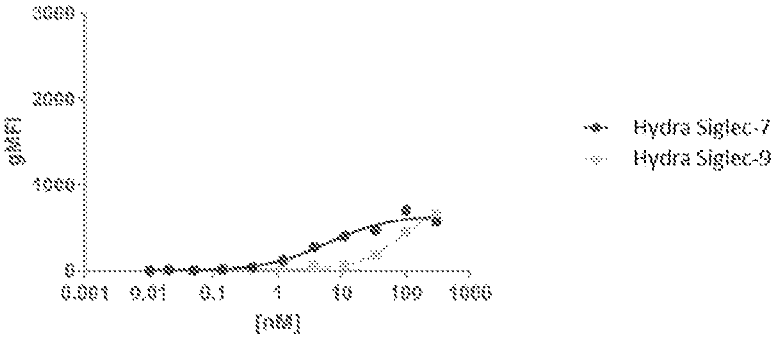
FIG. 7A is a line graph depicting Siglec-7 hydra and Siglec-9 hydra binding to T47D breast cancer cells as measured by FACS.
Figure 7B:
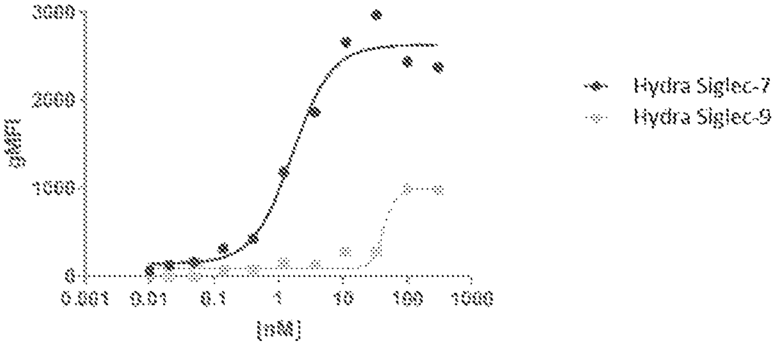
FIG. 7B is a line graph depicting Siglec-7 hydra and Siglec-9 hydra binding to K562 myelogenous leukemia cells as measured by FACS.
Figure 7C:
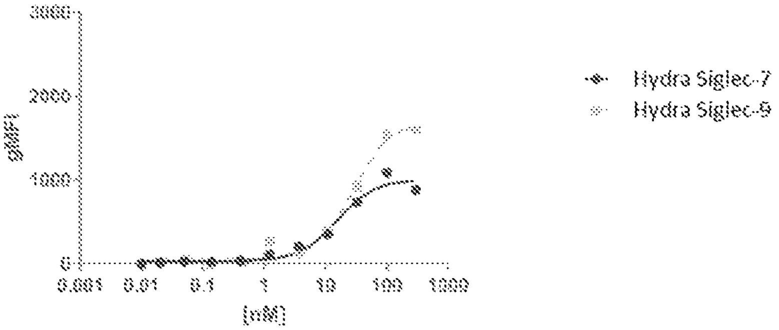
FIG. 7C is a line graph depicting Siglec-7 hydra and Siglec-9 hydra binding to BT-20 breast cancer cells as measured by FACS.
Figure 7D:
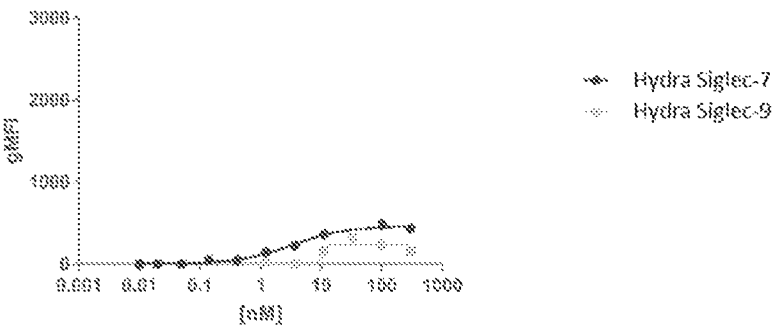
FIG. 7D is a line graph depicting Siglec-7 hydra and Siglec-9 hydra binding to EMT6 breast cancer cells as measured by FACS.
Figure 7E:
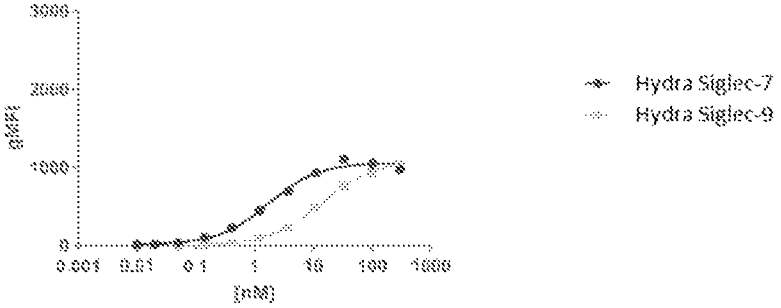
FIG. 7E is a line graph depicting Siglec-7 hydra and Siglec-9 hydra binding to HT-29 colon cancer cells as measured by FACS.
Figure 7F:
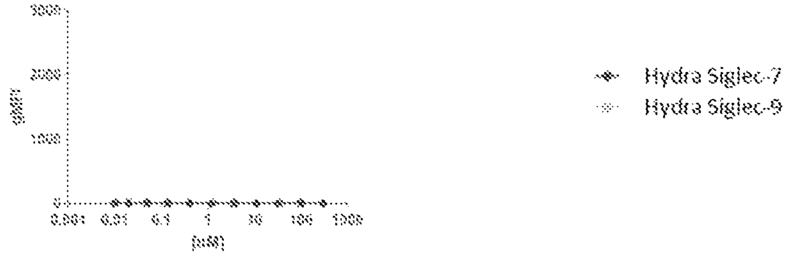
FIG. 7F is a line graph depicting Siglec-7 hydra and Siglec-9 hydra binding to HT-29 GNE KO cells as measured by FACS.
Figure 7G:
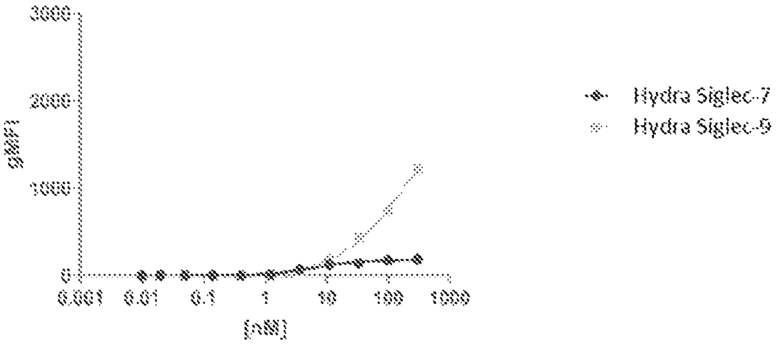
FIG. 7G is a line graph depicting Siglec-7 hydra and Siglec-9 hydra binding to A549 lung cancer cells. as measured by FACS.
Figure 7H:
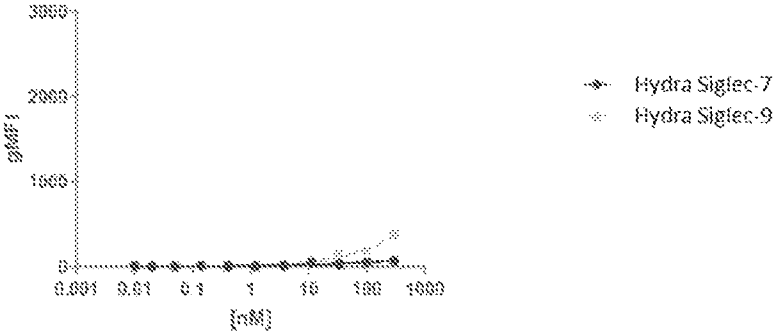
FIG. 7H is a line graph depicting Siglec-7 hydra and Siglec-9 hydra binding to A549 GNE KO cells as measured by FACS.

The specificity of Siglec-9 hydra for sialic acid was demonstrated by conducting binding experiments with engineered HT-29 cells which are deficient for UDP-N-acetylglucosamine-2-epimerase (GNE). GNE is the rate-limiting enzyme for sialic acid biosynthesis, and accordingly, GNE-deficient HT-29 cells (HT-29 GNE KO) don't present sialic acid Siglec ligands. Wild-type HT-29 cells were included as positive controls. As shown in FIG. 5D, Siglec-9 hydra did not bind to the HT-29 GNE KO cells Selective binding of Siglec-9 hydra was further confirmed by substituting a critical ligand-binding arginine residue (R120) with a lysine (R120K) to generate a loss-of-binding Siglec-9 hydra mutant. Binding of Siglec-9 hydra to K562 cells (which are reported to express Siglec ligands) was assayed by FACS, as described above, and binding of Siglec-9 hydra to sialic acid polymer was assayed by Octet, as described above. As shown in FIG. 6A and FIG. 6B, the R120K substitution substantially reduced binding to K562 cells and sialic-acid polymer as compared to the wild type Siglec-9 hydra.

Together, these results show that Siglec-9 hydra binding is mediated by sialic acid-recognition.

Example 2

This Example describes the binding activity of Siglec-7 and Siglec-9 hydra constructs in cell and tissue samples.

Cancer cells, including T47D breast cancer cells, K562 myelogenous leukemia cells, BT20 breast cancer cells, EMT6 breast cancer cells, HT-29 colon cancer cells (both wild type and GNE KO), and A549 lung cancer cells (both wild type and GNE KO) were incubated with Siglec-7 hydra or Siglec-9 hydra. Cancer cells and Siglec hydra (at 1:3 serial dilutions starting at 300 nM) were incubated in PBS at 4° C. for 30 mins, after which cells were washed and Siglec hydra binding was assayed by FACS as described in Example 1.

As shown in FIGS. 7A-H, different expression levels of Siglec-ligands (as measured by Siglec hydra binding) were observed on T47D breast cancer cells, K562 myelogenous leukemia cells, BT20 breast cancer cells, EMT6 breast cancer cells, HT-29 colon cancer cells, and A549 lung cancer cells. As expected, the A549 and HT-29 GNE KO knockout cells displayed little or no Siglec-7 or Siglec-9 hydra binding.

Siglec-7 and -9 ligand expression profiles observed by hydra binding were compared with those previously observed in Jandus et al. (2014) J. Clin. Invest., 124:1810-1820 by comparing the geometric mean fluorescence intensities of ligand staining. Siglec-7 and -9 ligand expression profiles observed by staining with Siglec-7 hydra and Siglec-9 hydra, respectively, were consistent with the results in Jandus et al. For example, Jandus et al. found that K562 cells had about 3-fold higher expression of Siglec-7 ligand than Siglec-9 ligand, A549 cells had about 4-fold higher expression of Siglec-9 ligand that Siglec-7 ligand, Siglec-7 ligand expression was higher for K562 cells than A549 cells, and Siglec-9 ligand expression was comparable between A549 and K562 cells. Hydra staining showed the same expression profiles for K562 cells and A549 cells.

Siglec-9 hydra was used to determine Siglec-9 ligand expression in primary breast cancer and melanoma tumor tissue samples and corresponding non-cancerous tissue samples from different donors.

Tissue samples were embedded in paraffin and sectioned at 5 μm. Sections were mounted onto positively-charged slides (Fisher). Slides were baked at 60° C., dry heat, for at least 1-hour prior to use. Tissue sections were de-waxed using standard conditions and organic solvents (four 5 minute incubations with 100% xylene) and an alcohol series (2 minute incubations with each of 100%, 70%, and 30% ethanol), descending to distilled water to sufficiently hydrate the tissues and allow proper binding of the primary antibody and other detection reagents. Antigen retrieval was performed after tissue sections were dewaxed using a steam heat induced epitope recovery with BioGenix buffer (Citra Plus Buffer, pH 7.1, BioGenix, Cat #HK081-20K) without Proteinase K digestion using a commercial steamer (20 minutes above 97° C.) as a heat source. Immunohistochemistry was performed on a Bond Rx autostainer (Leica Biosystems) with enzyme treatment (1:1000) using standard protocols. Siglec-9 hydra at 1:1000 dilution was incubated with slides and detected by secondary antibody goat anti-mouse IgG2a (Thermofisher Cat #P131983). Bond Polymer Refine Detection (Leica Biosystems) was used according to manufacturer's protocol. Sections were then counterstained with hematoxycilin, dehydrated and coverslipped using a TissueTek-Prisma and Coverslipper (Sakura). Whole slide scanning (40×) was performed on an Aperio AT2 (Leica Biosystems).

Figure 8A:
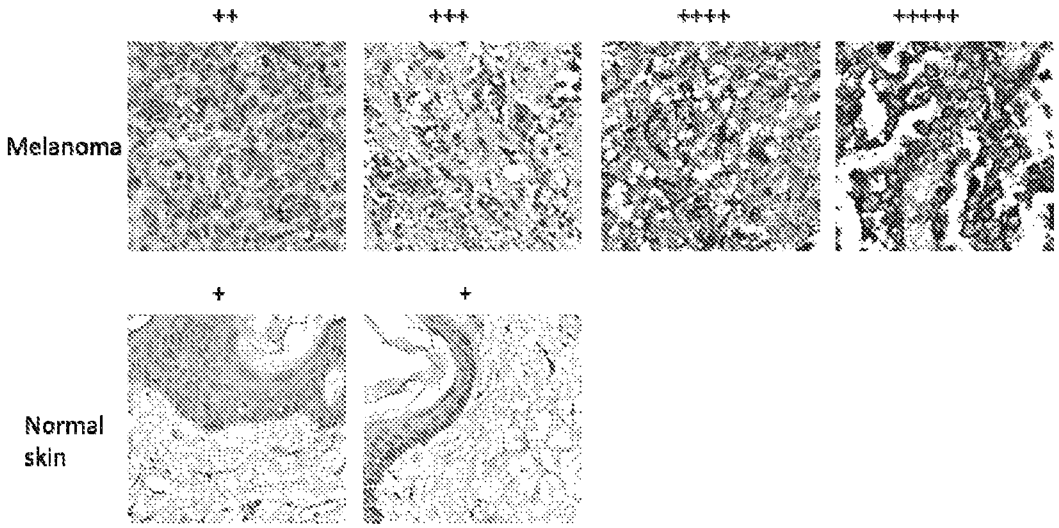
FIG. 8A depicts images of melanoma tumor tissue samples, and corresponding non-cancerous tissue samples, stained for Siglec-9 ligands by immunohistochemistry using Siglec-9 hydra as described in Example 2.
Figure 8B:
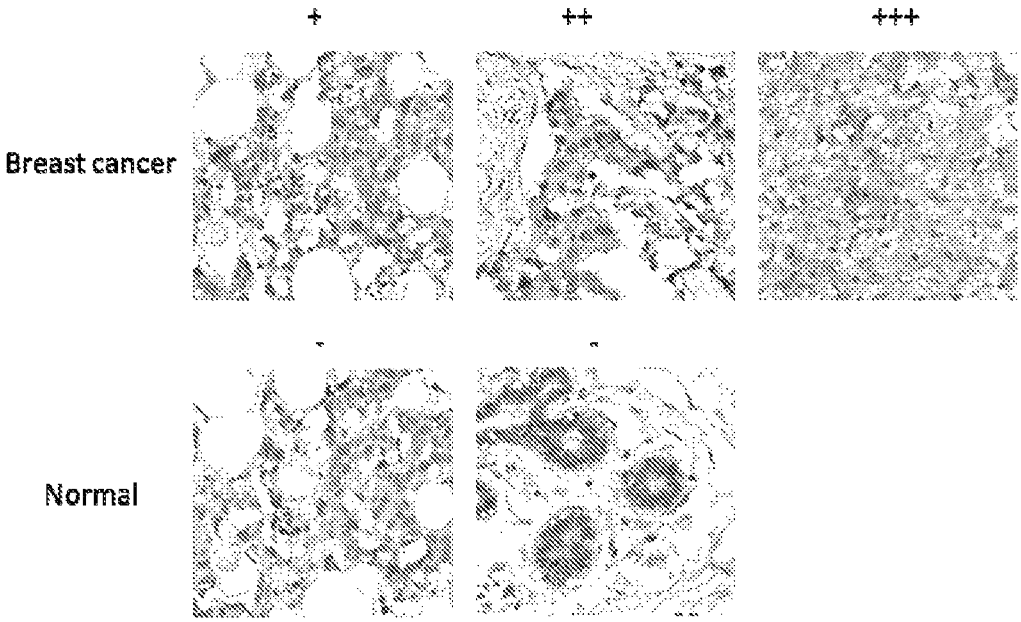
FIG. 8B depicts images of breast cancer tumor tissue samples, and corresponding non-cancerous tissue samples, stained for Siglec-9 ligands by immunohistochemistry using Siglec-9 hydra as described in Example 2. Staining signals were qualitatively classified into six groups denoted −, +, ++, +++, ++++, and +++++, with − indicating negative staining, and + to +++++ indicating increasingly strong staining.

As shown in FIGS. 8A and 8B, melanoma and breast cancer tumor tissue samples had higher staining than corresponding non-cancerous tissue samples Staining signals were qualitatively classified into six groups denoted −, +, ++, +++, ++++, and +++++, with − indicating negative staining, and + to +++++ indicating increasingly strong staining. Melanoma samples had staining ranging from ++ to +++++, while non-cancerous skin tissue samples had staining of +. Breast cancer samples had staining ranging from + to +++, while non-cancerous breast tissue samples had staining of −. Together, these results show that Siglec-9 ligand expression varies between melanoma and breast cancer tumors, and that Siglec-9 ligand expression is upregulated in each of melanoma and breast cancer tumors relative to non-cancerous tissue.

Example 3

This Example describes the binding activity of Siglec-7 and Siglec-9 hydra constructs against a series of glycan arrays available from Z Biotech (Aurora, CO). Binding of hydra constructs to the arrays was assayed as follows:

(1) arrays were blocked with blocking buffer (Z Biotech) for 1 hour;
(2) arrays were washed with the indicated buffer twice briefly (100 μL per well);
(3) Siglec-7 and Siglec-9 hydra in the indicated buffer were applied and incubated for 2 hours;
(4) arrays were washed with washing buffer (Z Biotech);
(5) 10 μg/ml anti-mouse IgG-Cy3 (fCy3 AffiniPure Goat Anti-Mouse IgG (Whole IgG), Fcγ Fragment Specific) was applied;
(6) arrays were washed with washing Buffer (Z Biotech); and
(7) arrays were scanned with a microarray scanner at 532 nm wavelength.

Figure 9:
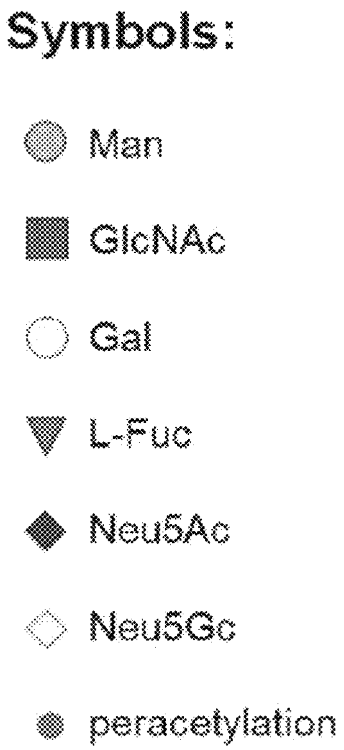
FIG. 9 depicts glycan structures in the 100 N-glycan array (Z Biotech, Colorado) used in binding assays described in Example 3.
Figure 9:
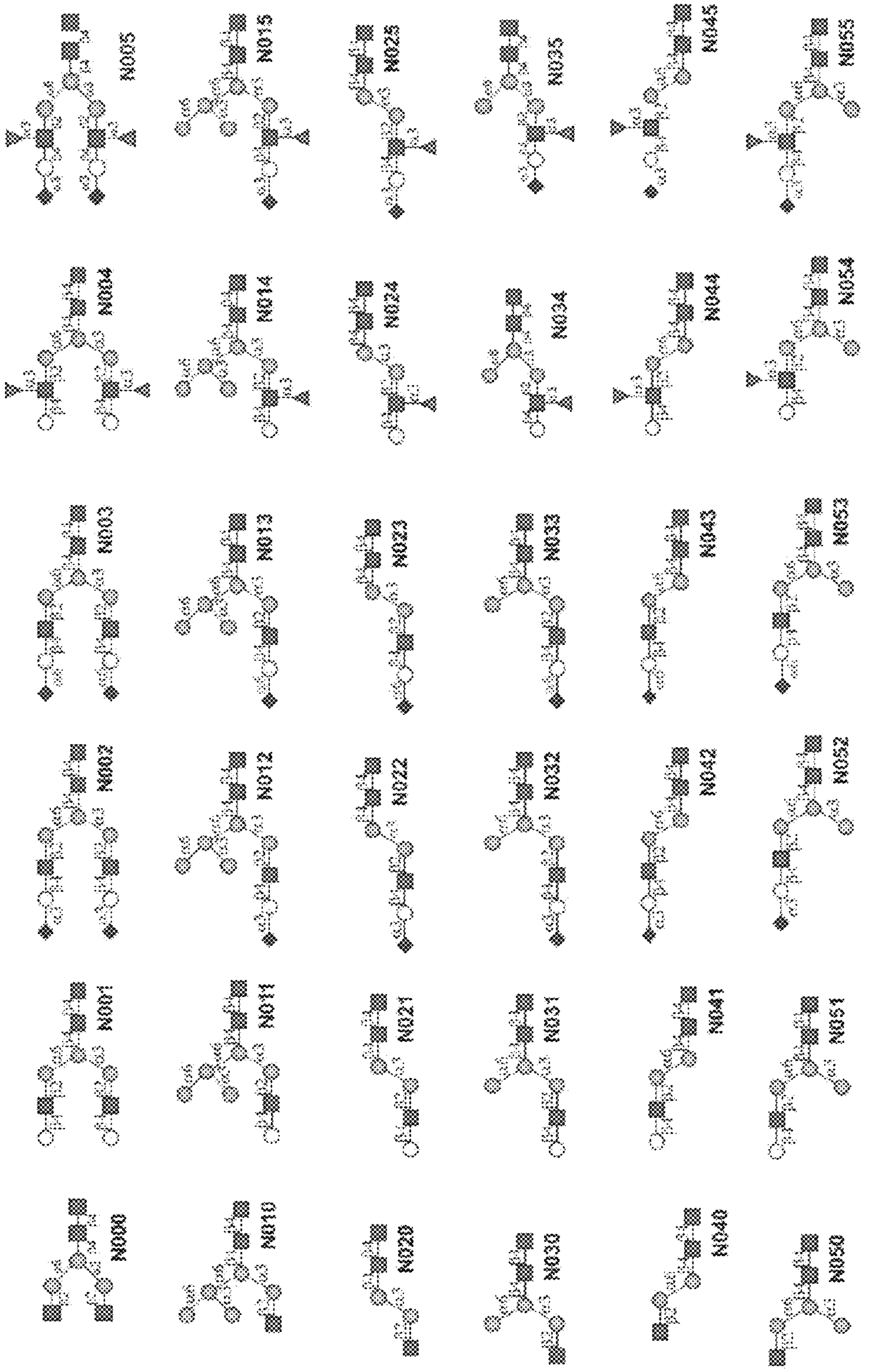
Figure 9:
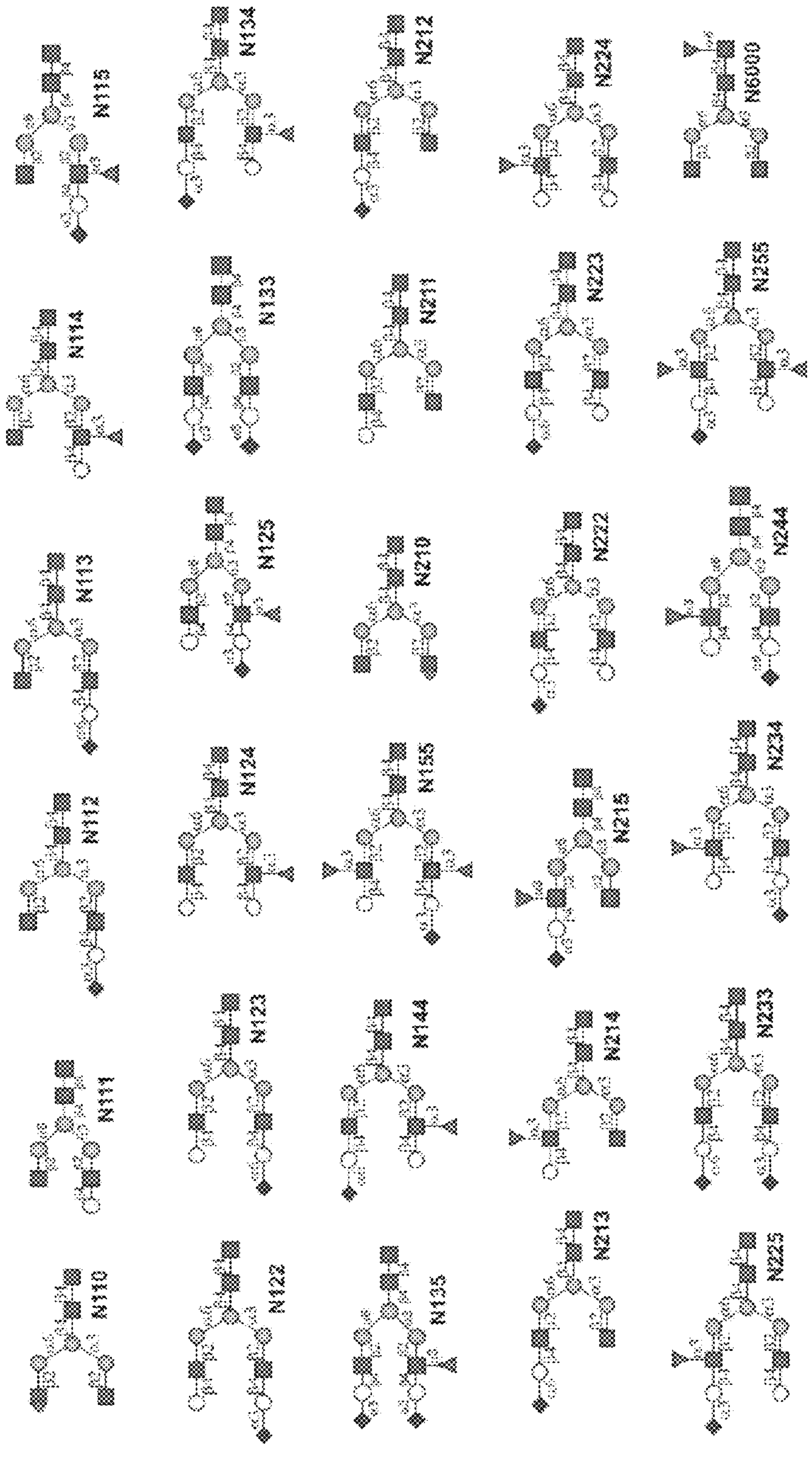
Figure 9:
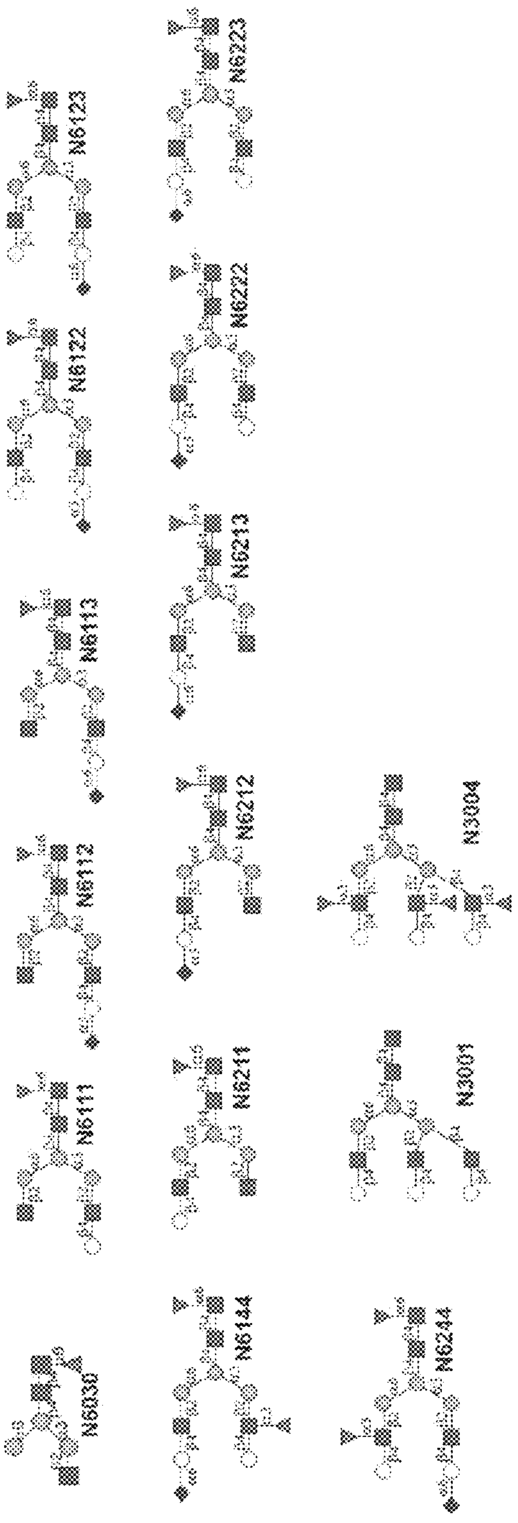
Figure 9:
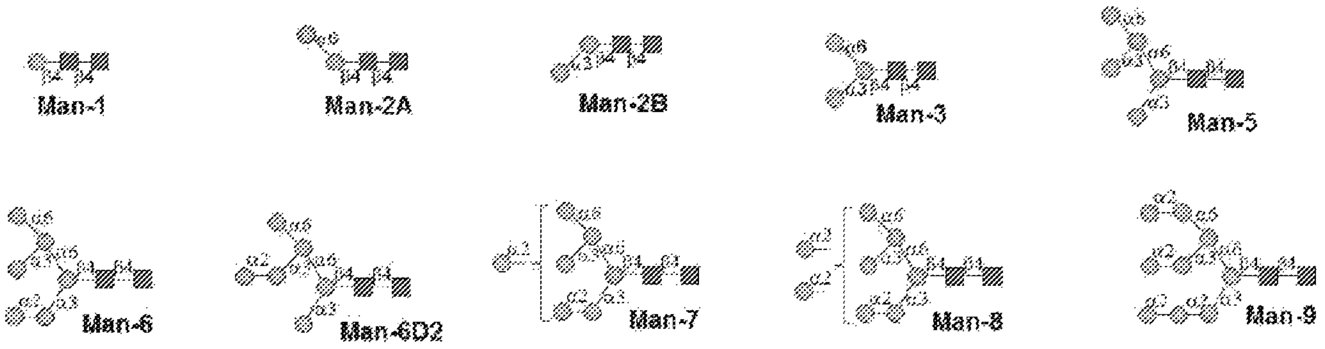
Figure 9:
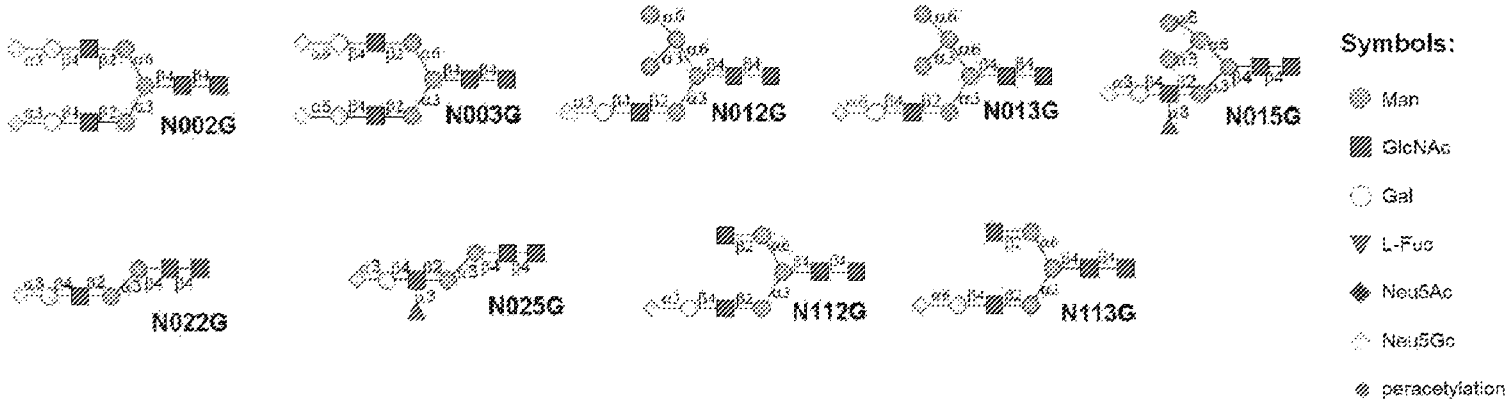
Figure 10:
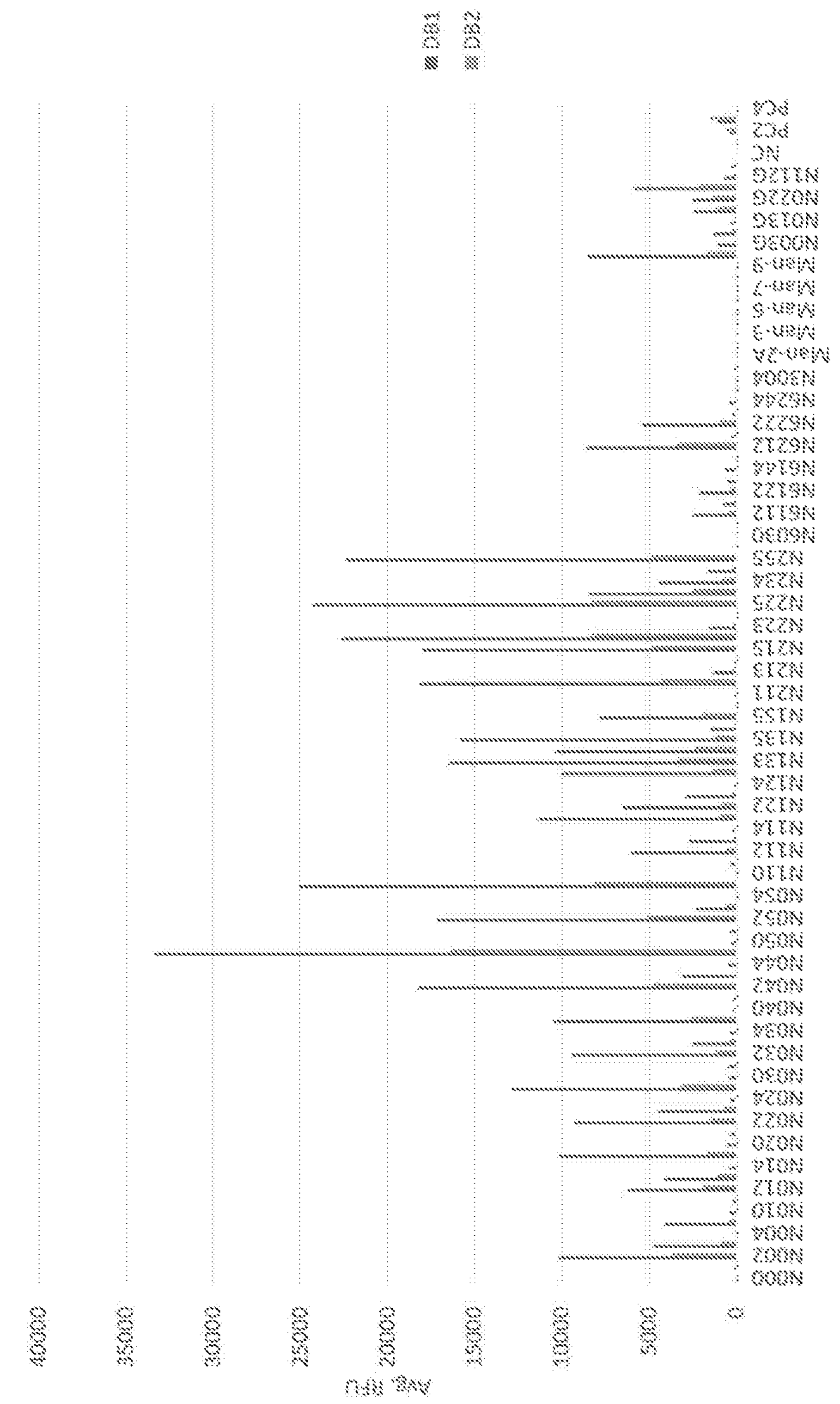
FIG. 10 depicts binding of Siglec-9 hydra the 100 N-glycan array shown in FIG. 9. Binding was determined in two different buffers: DB1 (50 mM sodium phosphate buffer (pH 5.8)); and DB2 (25 mM sodium acetate (pH 6.0)). Siglec-9 hydra bound glycan structures containing α2,3 and α2,6 sialic acid linkages.

FIG. 9 is the key to a 100 N-Glycan Array (Z Biotech, Colorado) used in binding assays. FIG. 10 depicts Siglec-9 hydra binding to the 100 N-Glycan array at 4 nM in buffers DB1 and DB2. Siglec-9 hydra bound glycan structures containing α2,3 and α2,6 sialic acid linkages.

Figure 11:
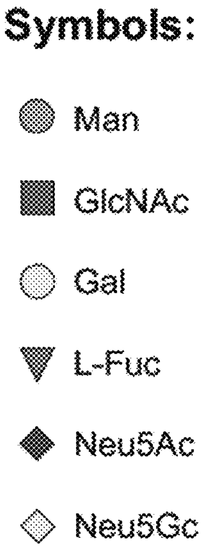
FIG. 11 depicts glycan structures in the Neu5Ac/Neu5Gc glycan array (Z Biotech, Colorado) used in binding assays described in Example 3.
Figure 11:
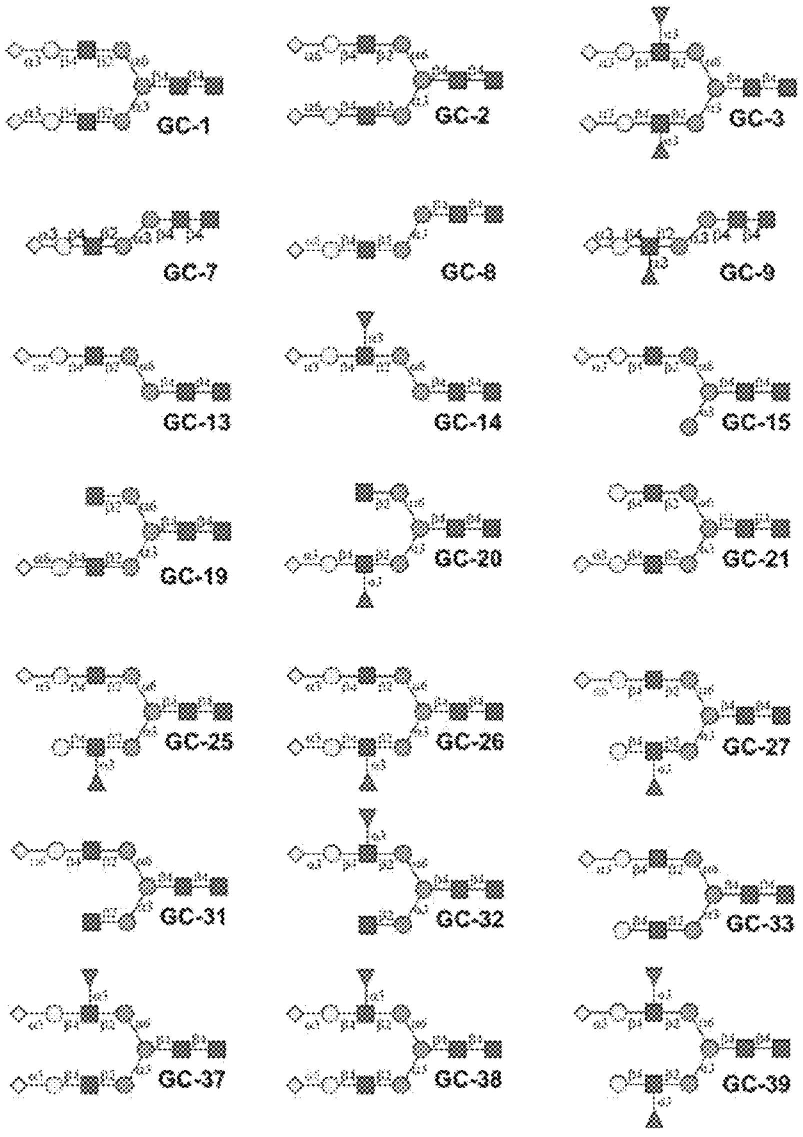
Figure 11:
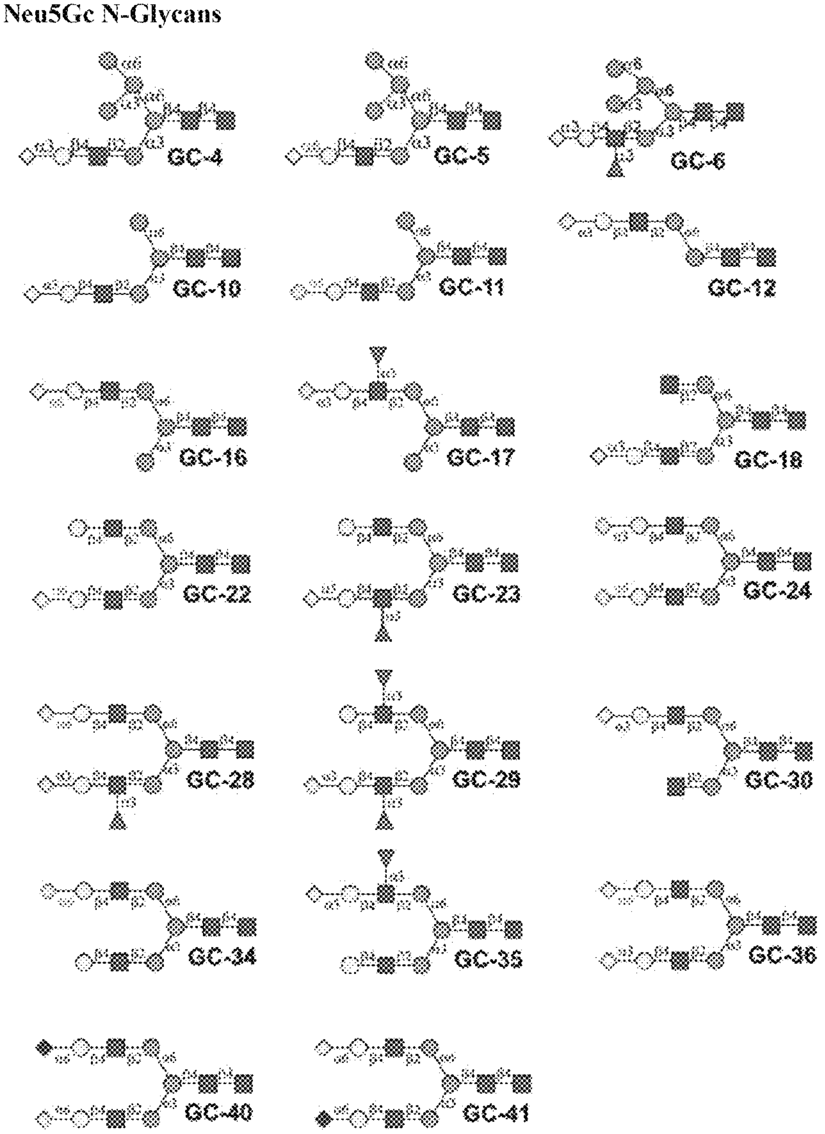
Figure 11:
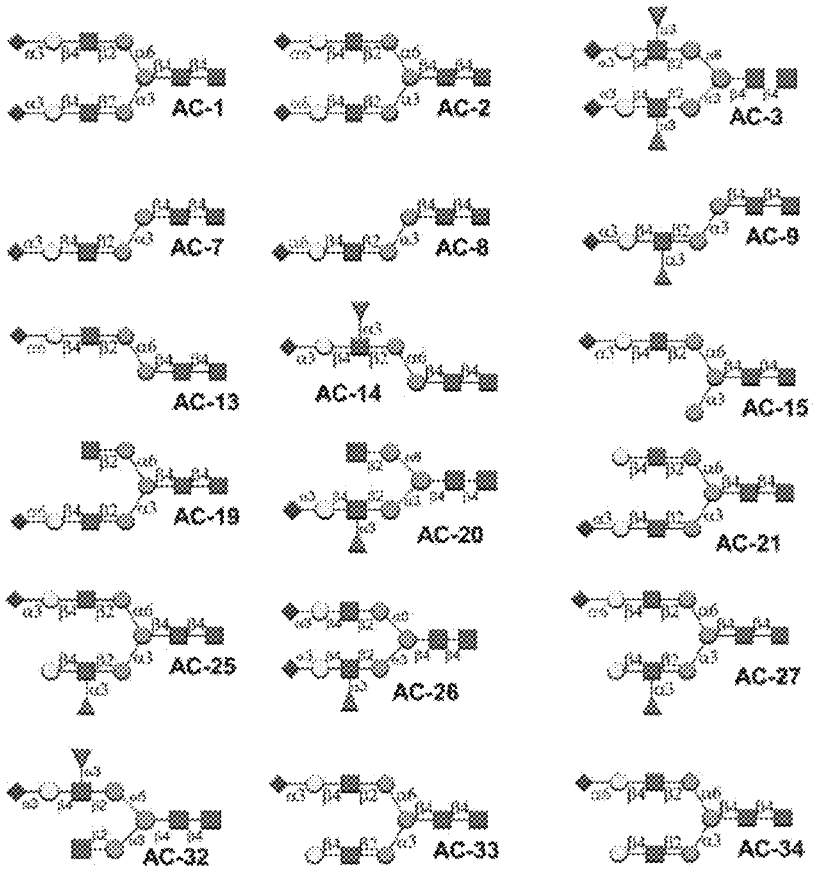
Figure 11:
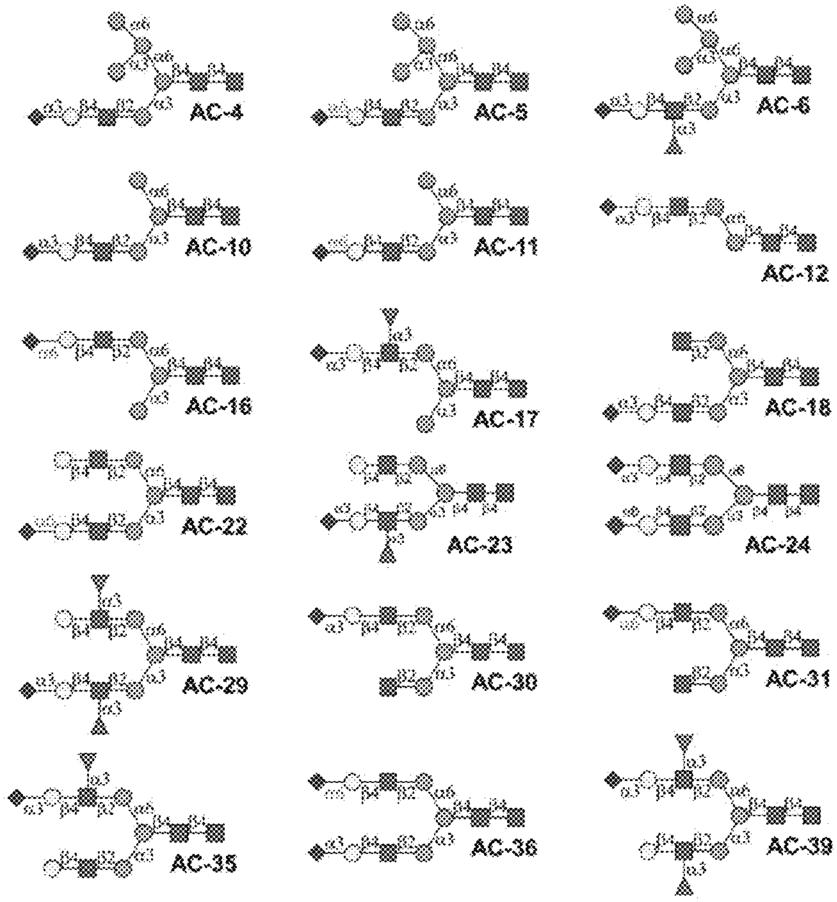
Figure 12:
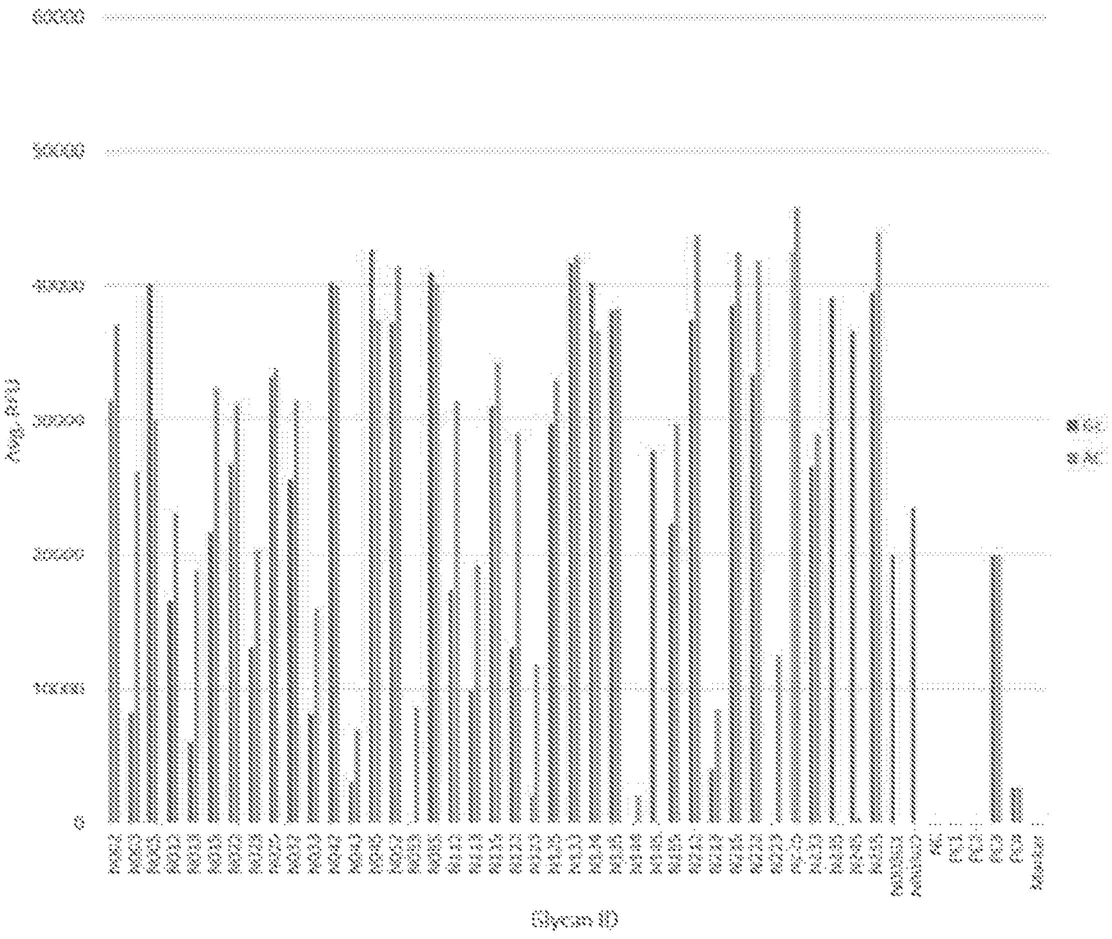
FIG. 12 depicts binding of Siglec-9 hydra to the Neu5Ac/Neu5Gc glycan array shown in FIG. 11. Binding was determined in 50 mM sodium phosphate buffer (pH 5.8). Siglec-9 hydra bound glycan structures containing α2,3 and α2,6 sialic acid linkages.

FIG. 11 is the key to a Neu5Ac/Neu5Gc Glycan Array (Z Biotech, Colorado) used in binding assays. FIG. 12 depicts Siglec-9 hydra binding to the Neu5Ac/Neu5Gc Glycan array at 4 nM in 50 mM sodium phosphate buffer (pH 5.8). Siglec-9 hydra again bound glycan structures containing α2,3 and α2,6 sialic acid linkages.

Figure 13:
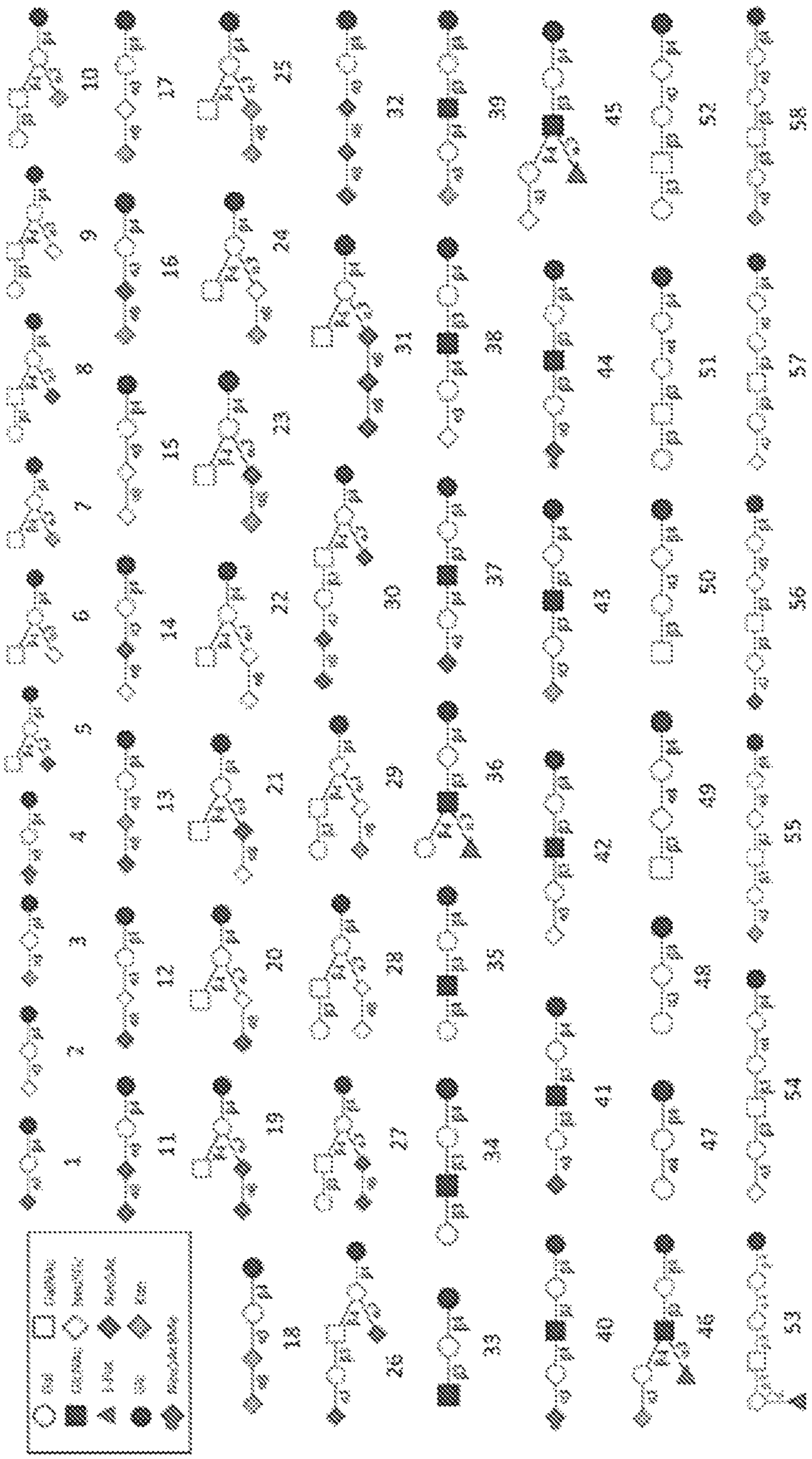
FIG. 13 depicts glycan structures in the glycosphingolipid glycan array (Z Biotech, Colorado) used in binding assays described in Example 3.
Figure 14:
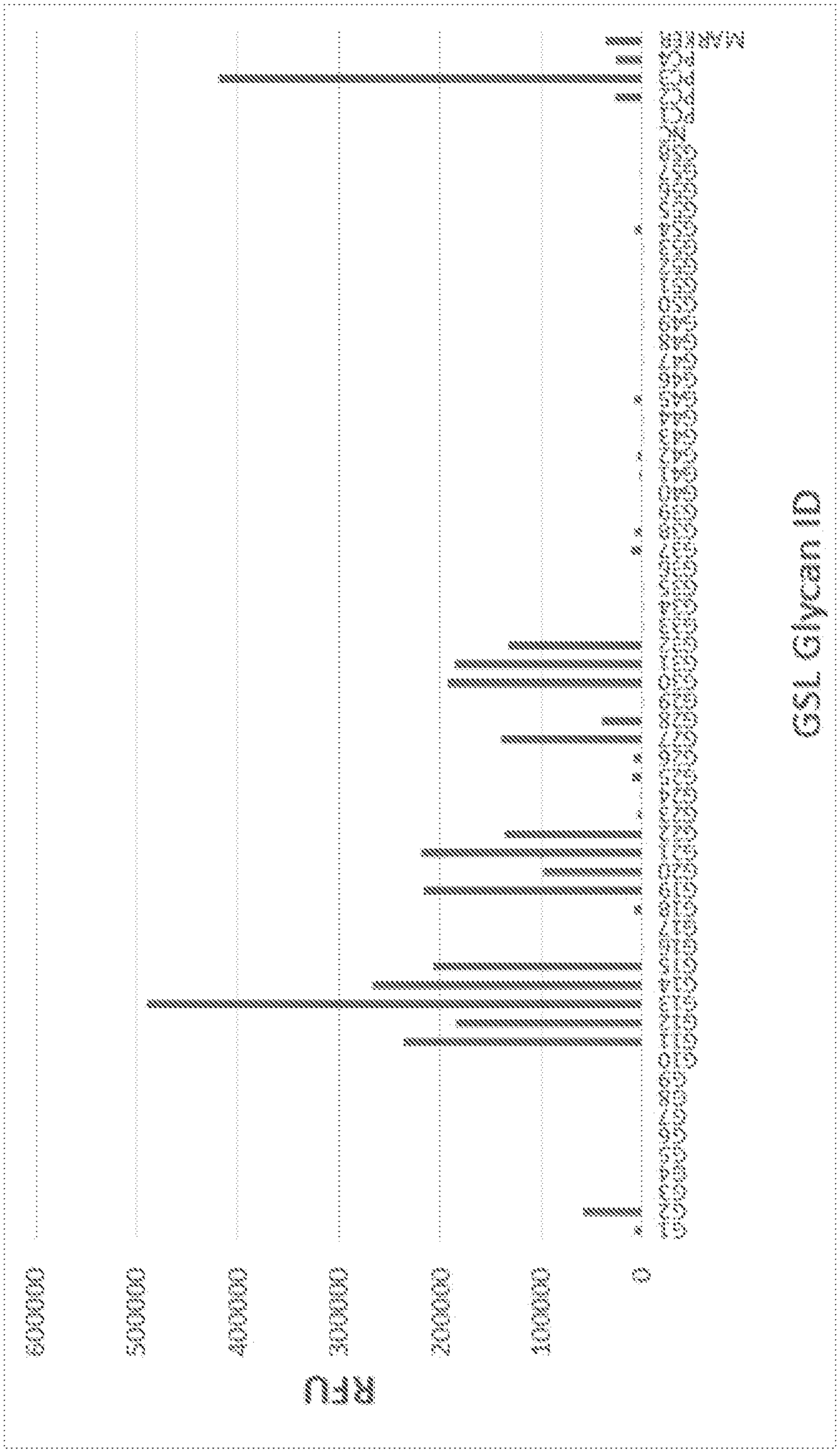
FIG. 14 depicts binding of Siglec-7 hydra to the glycosphingolipid glycan array shown in FIG. 13. Binding was determined in 50 mM sodium phosphate buffer (pH 5.8). Siglec-7 hydra bound G11, G12, G13, G14, G15, G18, G19, G20, G21, G22, G23, G25, G27, G28, G30, G31, and G32 glycan structures, each of which contain α2,8 sialic acid linkages. In addition, Siglec-7 hydra bound G1, G2, G26, G37, G38, and G48 glycan structures, each of which contain α2,3 sialic acid linkages.

FIG. 13 is the key to a Glycosphingolipid Glycan Array (Z Biotech, Colorado) used in binding assays. FIG. 14 depicts Siglec-7 hydra binding to the Glycosphingolipid Glycan array at 20 nM in 50 mM sodium phosphate buffer (pH 5.8). Siglec-7 hydra bound glycan structures G11, G12, G13, G14, G15, G18, G19, G20, G21, G22, G27, G28, G30, G31, and G32, which contain α2,8 sialic acid linkages. In addition, Siglec-7 hydra bound glycan structures G1, G2, G26, and G38, which contain α2,3 sialic acid linkages.

This example demonstrates that Siglec-9 hydra binds α2,3 and α2,6 linked sialic acid containing glycans, and Siglec-7 hydra binds α2,8 linked disialic acid and certain α2,3 linked sialic acid containing glycans.

Example 4

This Example describes the binding activity of Siglec-7 and Siglec-9 hydra constructs against formalin-fixed, paraffin-embedded (FFPE) human tissues.

In brief, immunohistochemistry (IHC) assays were conducted as follows:

(1) FFPE tissue blocks were cut at 4-5 μm thickness and sections were mounted onto positively-charged, capillary gap glass slides (Fisher, 22-230-900). The slides were baked (60° C., dry heat) prior to use.
(2) Tissue sections were de-waxed using organic solvents (xylene, 100%, four changes) and an alcohol series (100%, 70%, 30% ethanol) descending to distilled water to sufficiently hydrate the tissues and allow proper binding of Siglec-7 hydra, Siglec-9 hydra, or other reagents.
(3) Antigen retrieval was performed after tissue sections were dewaxed. A steam heat induced epitope recovery (SHIER) solution that was drawn into the capillary gap formed between paired microscope slides with a commercial steamer (20 minutes above 97° C.) as a heat source, as described in Ladner et al. (2000) CANCER RES. 60: 3493-3503.
(4) Samples were tested by IHC according to the general procedure outlined in TABLE 1 using the TechMate instrumentation platform and the MIP ENV program (which does not include enzymatic digestion with Proteinase K to further expose the epitope). Sequential detection of the primary detection reagent was employed during IHC with a high level of specificity for the Siglec-ligand. The location of Siglec-7 hydra or Siglec-9 hydra was ultimately visualized by the application of a colorimetric chromogen (DAB; GBI Labs, C09-100) that precipitates a discrete insoluble reaction product at the site of ligand in the presence horseradish peroxidase polymer (HRP polymer, Agilent Dako, K4001). Nuclei were counterstained using hematoxylin (blue stain; QML-SB, 100005) to assess cell and tissue morphology.

TABLE 1

| TechMate Sequence | Reagent - Incubation Time |
|---|---|
| 1 | Hydrogen peroxide block - 3 × 2.5 minutes |
| 2 | Siglec-7 hydra (0.35 μg/ml) or Siglec-9 hydra (0.5 μg/ml) - 1 hour |
| 3 | Conjugated horseradish peroxide (HRP) polymer - 30 minutes |
| 4 | DAB chromagen - 3 × 5 minutes |
| 5 | Hematoxylin counterstain - 1 minute |

(5) Slides were unpaired, rinsed in distilled water, dehydrated in an alcohol series (70%, 95%, 100% ethanol) and in organic solvent (xylene, 100%, four changes), then permanently coverslipped, using CytoSeal (Thermo Scientific, 8312-4, 8310-4), for interpretation and storage. Slides were examined under a microscope to assess staining.

SHIER 7 (Citra Plus, pH 7.1, BioGenex, HK081-20K) solution was used for unmasking the epitopes in the FFPE tissues. After heat induced epitope retrieval, the process steps were automated using a TechMate Instrument (Roche Diagnostics) running QML workmate software v3.96. This automated platform uses a capillary gap process for all reagent changes, up to and including counterstaining, and intervening buffer washes. All steps were carried out at room temperature (25° C.).

Reagent Manufacturing Buffer (RMB, from QML-SB) with Goat Serum (QML-SB, 300003) was used to prepare working dilutions of Siglec-7 hydra (final working concentration of 0.35 μg/ml), Siglec-9 hydra (final working concentration of 0.5 μg/ml), and mouse IgG2a negative control antibody. Target recognition for Siglec-7 hydra or Siglec-9 hydra at the site of ligand-primary detection reagent interaction in FFPE sections used a monovalent EnVision-Plus HRP kit from Dako (K4001) designed for detection of mouse primary antibodies.

All pathology analysis and scoring was performed by a board-certified pathologist. Siglec-7 hydra and Siglec-9 hydra were reactive in a subset of tumor and normal cells. Reactivity was primarily localized at the plasma membrane, but staining was also observed in the cytoplasm (diffuse, granular, or loculated) and in the nucleus. The guidelines used for scoring bound Siglec-7 hydra or Siglec-9 hydra, respectively, as detected by IHC in formalin-fixed, paraffin-embedded (FFPE) tumor samples were as described below.

Siglec-7 hydra or Siglec-9 hydra staining was scored semi-quantitatively by a board-certified pathologist for full or partial plasma membrane expression. Full or partial plasma membrane staining includes epi-plasma membrane signal that is extracellular, accumulated between cells, or membrane-associated. For Siglec-7 hydra or Siglec-9 hydra staining, the main components to scoring are percentages at differential intensities, H-Scores, and Percent Scores (as described below). For colorectal samples, definitive apical plasma membrane staining of tumor cells was scored. Apical staining in tumor cells that appeared to be mucin (not Siglec-7 ligand or Siglec-9 ligand) was not scored. When Siglec-7 hydra or Siglec-9 hydra staining was present as diffuse cytoplasmic staining, it was uniformly expressed throughout the tumor and was assigned an overall average intensity score using a relative scale from 0-3. On this scale, 0 indicates no diffuse cytoplasmic staining present, 1 represents weak diffuse cytoplasmic staining, 2 represents moderate diffuse cytoplasmic staining, and 3 represents strong diffuse cytoplasmic staining. In addition, cytoplasmic Siglec-7 hydra and Siglec-9 hydra staining can appear "loculated." The loculated pattern was observed as pockets of dark staining within the cytoplasm that are consistent with Golgi bodies. A separate score for the presence or absence of a loculated cytoplasmic staining pattern is provided as a "Yes" or "No" (Y/N). Cytoplasmic Siglec-7 hydra or Siglec-9 hydra staining can also appear "granular," with small pin-points of dark staining within the cytoplasm that are consistent with endoplasmic reticulum (ER). Such staining was not assigned an individual score as it is generally universally observed throughout all tumors. If cytoplasmic granules line up beneath the plasma membrane, they were included in the score for plasma membrane staining. Siglec-7 hydra or Siglec-9 hydra staining was occasionally observed in tumor cell nuclei (generally 1+). When scoring tumor tissues, scoring excludes any surrounding staining in stroma, areas of non-tumor, and adjacent normal tissue.

To gain a full understanding of Siglec-7 hydra or Siglec-9 hydra staining at the plasma membrane of tumor cells across cancer indications, both standard Percent Score and H-Score approaches were used to capture the pattern of reactivity observed. Both approaches require recording the percentage of tumor cells with Siglec-7 hydra or Siglec-9 hydra plasma membrane staining at a corresponding differential intensity a four-point scale semi-quantitative (0, 1+, 2+, 3+). On this scale: 0=null, negative or non-specific staining, 1+=low or weak staining, 2+=medium or moderate staining, and 3+=high or strong staining.

Percent Scores were calculated by summing the percentages of intensities at either ≥1+, ≥2+ or ≥3+. The Percent Score ≥1+=(% at 1+)+(% at 2+)+(% at 3+), the Percent Score ≥2+=(% at 2+)+(% at 3+), and the Percent Score ≥3+=(% at 3+). Thus, scores ranged from 0 to 100.

H-Scores were calculated by summing the percentage of cells with intensity of expression (brown staining) multiplied by their corresponding differential intensity on a four-point semi-quantitative scale (0, 1+, 2+, 3+). The H-Score=[(% at <1)x0]+[(% at 1+)x1]+[(% at 2+)x2]+[(% at 3+)x3]. Thus, scores ranged from 0 to 300.

Figure 15A:
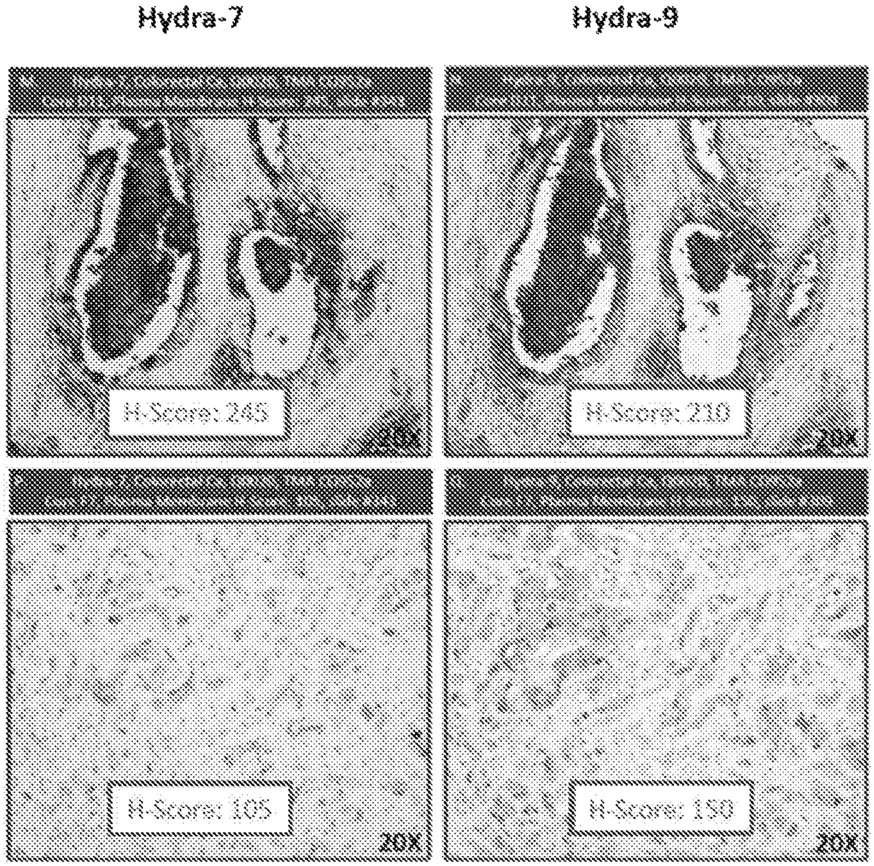
FIGS. 15A and 15B depict staining of independent colorectal cancer samples with a range of H-Scores.
Figure 15B:
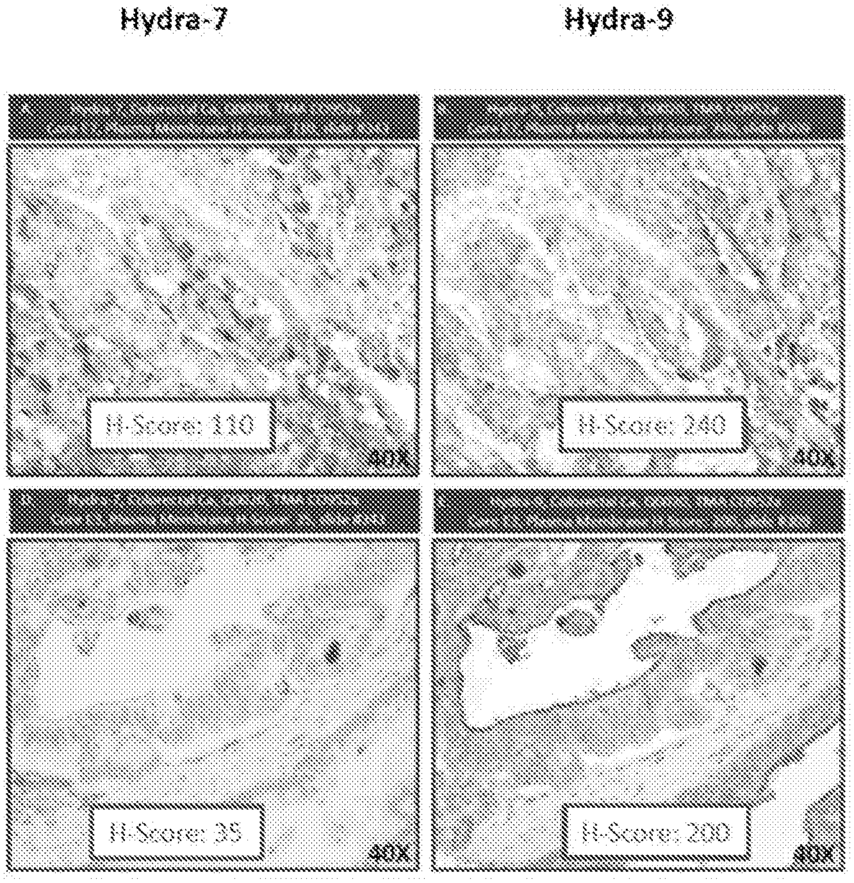
Figure 15C:
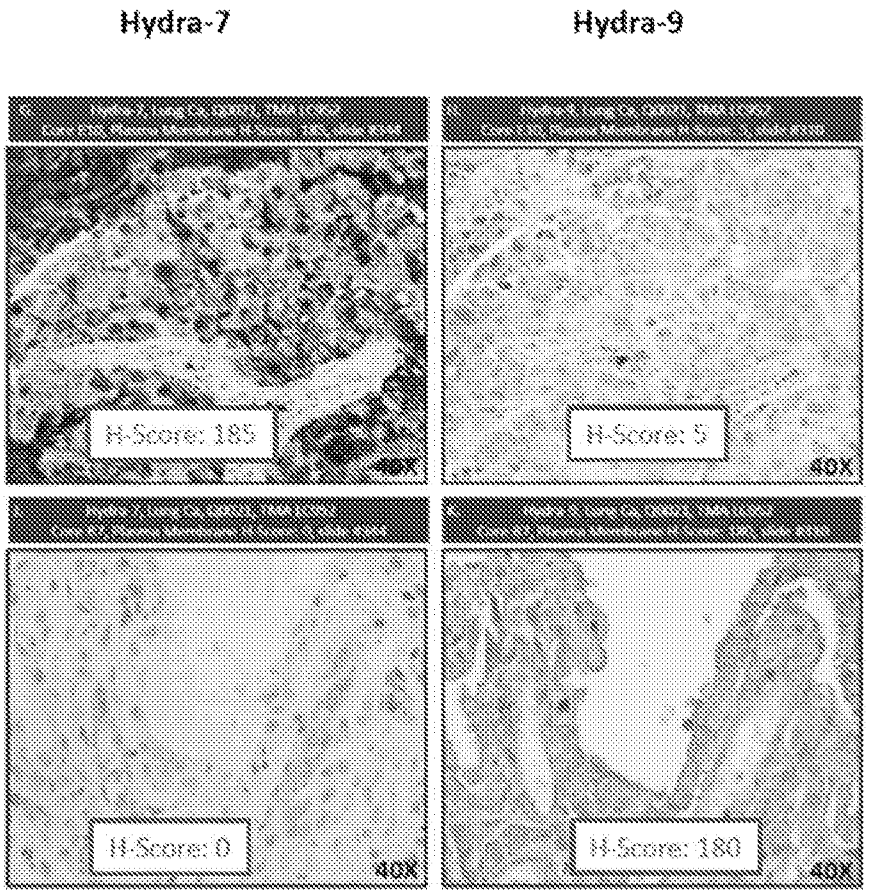
FIG. 15C depicts staining of independent lung cancer samples, with a range of H-Scores.

FIG. 15 depicts representative IHC staining of serial sections of various paraffin embedded human tumor biopsy slides with Siglec-7 hydra (left) or Siglec-9 hydra (right) with an accompanying H-Score. FIGS. 15A and 15B demonstrate a range of H-Scores for staining of independent colorectal cancer samples while FIG. 15C demonstrates a range of H-Scores for staining of independent lung cancer samples.

Example 5

This Example describes staining of tumor micro arrays (TMAs) with Siglec-7 hydra, Siglec-9 hydra, or a biotinylated *Maackia Amurensis* lectin (MAL II; Cat #B-1265 from Vector Labs, Burlingame, CA).

Figure 16:
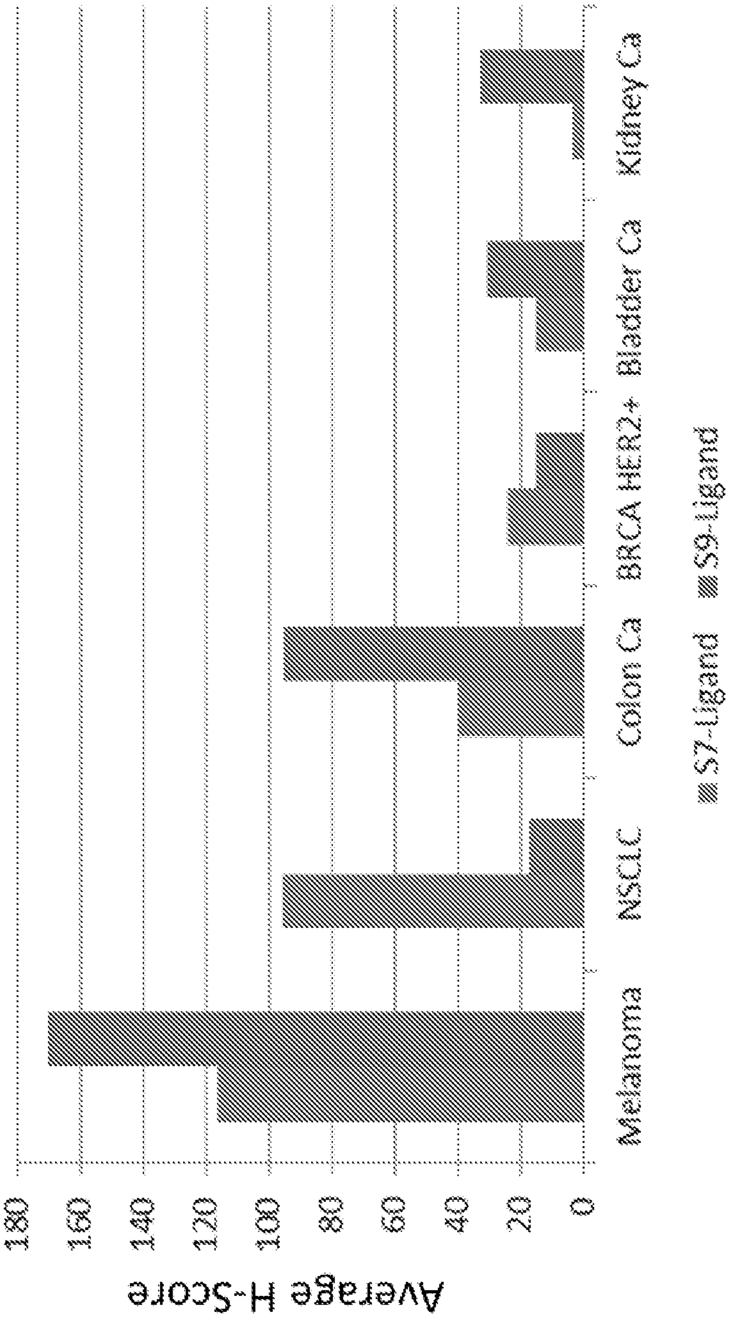
FIG. 16 depicts a comparison of Siglec-7 hydra (S7-Ligand), Siglec-9 hydra (S9-Ligand) and MAL II IHC staining by average H-Score across the indicated cancers.

FIG. 16 depicts a comparison of Siglec-7 hydra (S7-Ligand), and Siglec-9 hydra (S9-Ligand) staining by average H-Score across the indicated cancers (melanoma, non-small cell lung cancer (NSCLC), colon cancer, HER2+ breast cancer (BRCA), bladder cancer, and kidney cancer).

Example 6

Figure 17:
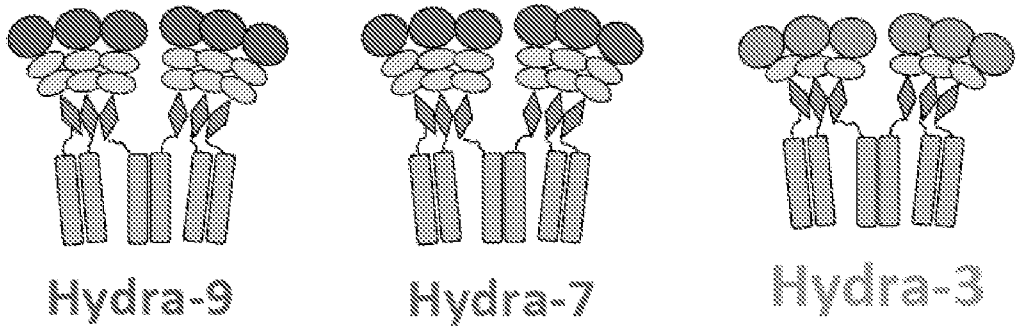
FIG. 17 depicts schematics of certain exemplary hydra configurations. A Version 1.0 construct is shown for Hydra-9, which has a Siglec-9 ECD, Hydra-7, which has a Siglec-7 ECD, and Hydra 3, which has a Siglec-3 ECD. Version 1.0 constructs comprise 6 polypeptides, each polypeptides comprising a Siglec ECD (circles represent V-set domains, ovals represent C2-set domains), trimerization (foldon) domain (diamonds), and Fc domain (wavy line and rectangle) in an N to C terminal direction. A Version 2.0 construct is shown for Hydra-3, which has a Siglec-3 ECD. Version 2.0 constructs comprise 6 polypeptides, each having a Siglec ECD, Fc domain, and a trimerization (foldon) domain in an N to C terminal direction.
Figure 17:
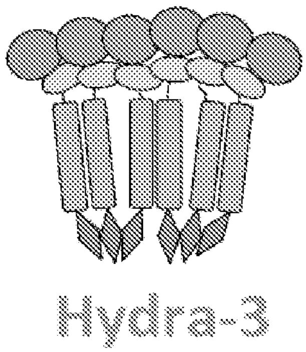

This example describes the construction and binding activity of a Hydra 3 construct. Various Siglec-3 hydra ("Hydra 3") were designed and expressed. FIG. 17 depicts a Hydra-3 Version 1.0 construct comprising 6 polypeptides, each polypeptides comprising a Siglec-3 ECD (circles represent V-set domains, ovals represent C2-set domains), trimerization (foldon) domain (diamonds), and Fc domain (wavy line and rectangle) in an N to C terminal direction. A Hydra-3 Version 2.0 construct comprises a Siglec-3 ECD, Fc domain, and a trimerization (foldon) domain in an N to C terminal direction. A Version 1.1 was also created that was identical to Version 1.0 but included a $(Gly_4Ser)_2$ (SEQ ID NO: 69) linker between the Siglec ECD and the foldon domain. Dimerization via the Fc domain and trimerization by the foldon domain created a hexavalent construct containing six lectin domains.

It is understood that Versions 1.0, 1.1, and 2.0 can be constructed for any of the lectin binding domains as described herein.

Hydra 3 v1.0, Hydra 3 v1.1, and Hydra 3 v2.0 constructs were expressed, purified, and characterized using SEC-HPLC. The amino acid sequence of Hydra 3 v1.0 is provided as SEQ ID NO: 53, which is encoded by nucleic acid sequence SEQ ID NO: 54). The amino acid sequence of Hydra 3 v1.1 is provided as SEQ ID NO: 55, which is encoded by the nucleic acid sequence SEQ ID NO: 56). The amino acid sequence of Hydra 3 v2.0 is provide as SEQ ID NO: 57, which is encoded by the nucleic acid sequence SEQ ID NO: 58).

Figure 18:
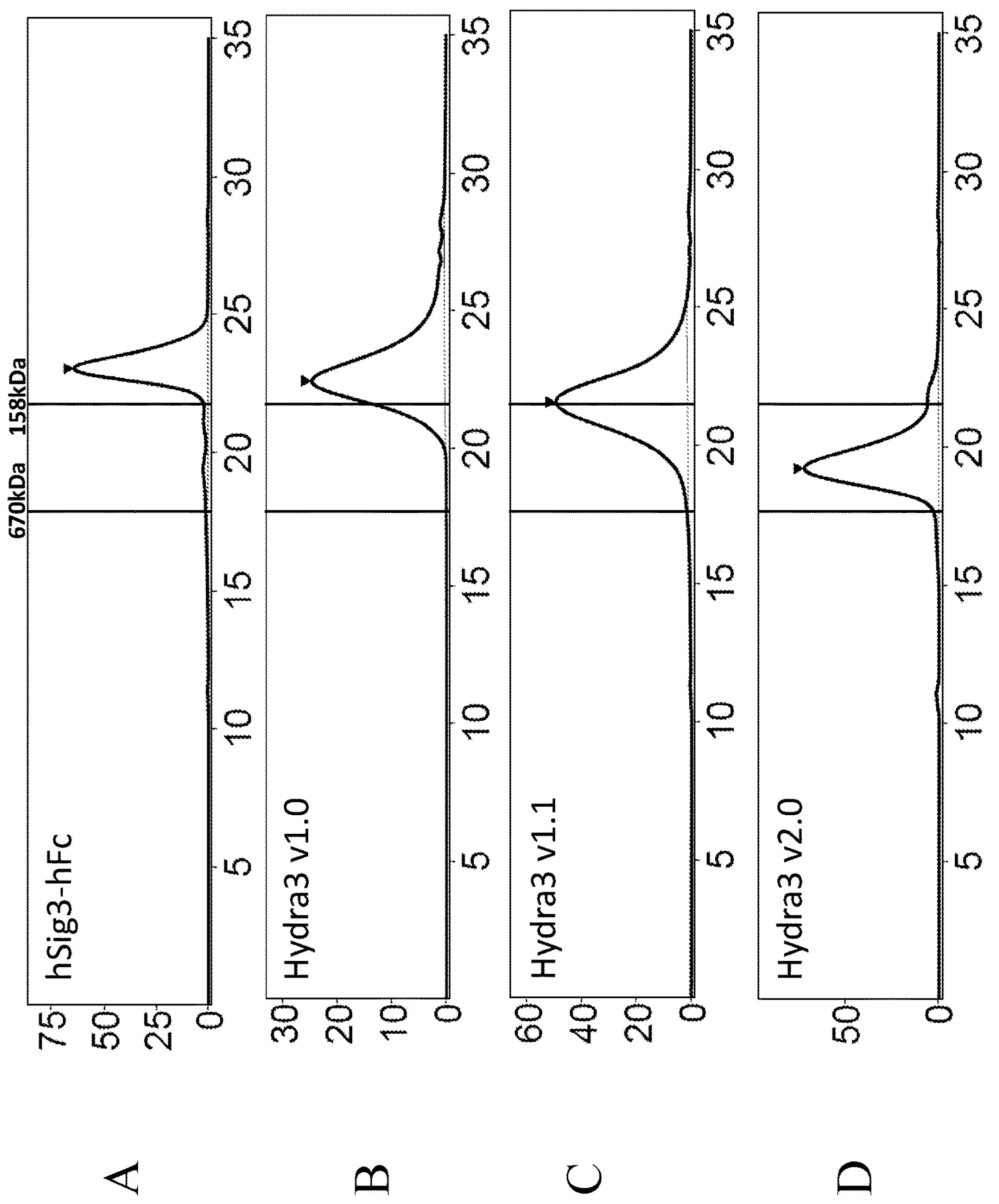
FIGS. 18A-D provides SEC chromatograms of various Hydra 3 Versions (Hydra 3 Version 1.0, "Sig3 Hydra" (FIG. 18B); Hydra 3 Version 1.1 (FIG. 18C); Hydra 3 Version 2.0 (FIG. 18D)) compared to an FC dimer of Siglec-3 (Sig3, FIG. 18A). The expected molecular weight (MW) of Hydra 3 Version 2.0 is 340 kD. The retention time of MW standards of 670 kD and 158 kD is also shown.

As shown in FIG. 18B, Hydra 3 v1.0 assembled into a multimeric molecule with a MW<300 kDa and a size comparative to human Sig3-hIgG1Fc dimer (FIG. 18A) via SEC-HPLC. Without wishing to be bound by the theory, it is contemplated that the size of Hydra 3 v1.0 may be a result of the dimerization of two Siglec-3 ECD domains. As shown in FIG. 18C, Hydra 3 v1.1 assembled into a multimeric molecule with a MW<300 kDa indicating that adding a linker between Siglec-3 ECD and Foldon domain did not produce a molecule with the predicted MW of a Hydra 3. As shown in FIG. 18D, Hydra 3 v2.0 assembled into a multimeric molecule with a MW≥300 kDa, indicating that placement of the Foldon domain c-terminal to the Fc domain produced a molecule with the predicted MW of a Hydra 3. Hydra 3 v2.0 was used in the following experiments.

Figure 19:
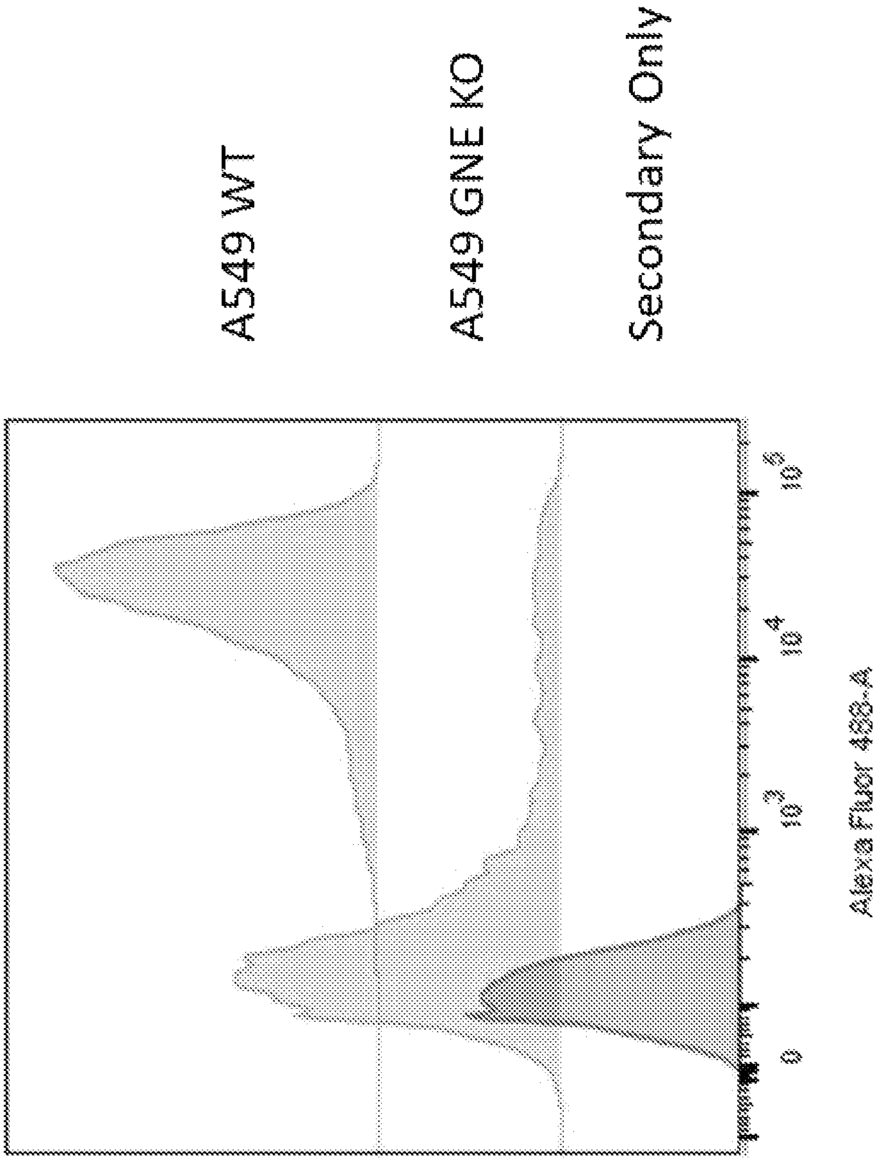
FIG. 19 depicts a FACS binding analysis showing sialic acid dependent staining of A549 cells by Hydra 3 as compared to A549 with a GNE Knock Out ("GNE KO," strain that does not present sialic acid).

The specificity of Hydra 3 for sialic acid was demonstrated by conducting binding experiments with engineered A549 cells that are deficient for UDP-N-acetylglucosamine-2-epimerase (GNE). GNE is the rate-limiting enzyme for sialic acid biosynthesis, and as a result, GNE-deficient A549 cells (A549 GNE KO) do not present significant amounts of sialic acid Siglec ligands. Wild-type A549 cells were included as positive controls. As shown in FIG. 19, Hydra 3 binds minimally to the A549 GNE KO cells.

Figure 20A:
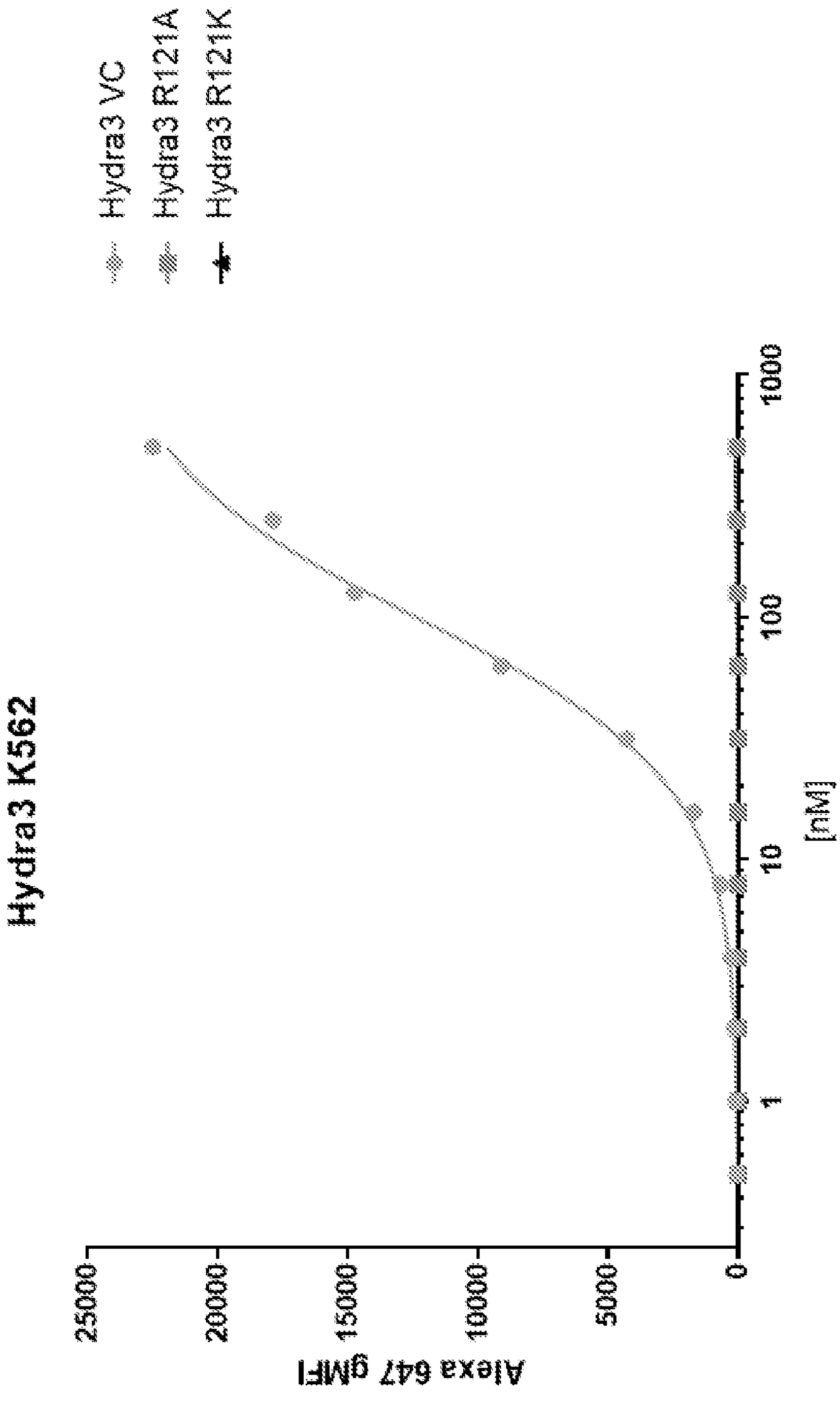
FIG. 20A depicts a binding curve showing the binding of Hydra 3 to sialic acid-expressing K562 cancer cells as compared to Hydra 3-loss of binding (LOB) mutations R121K and R121A.
Figure 20B:
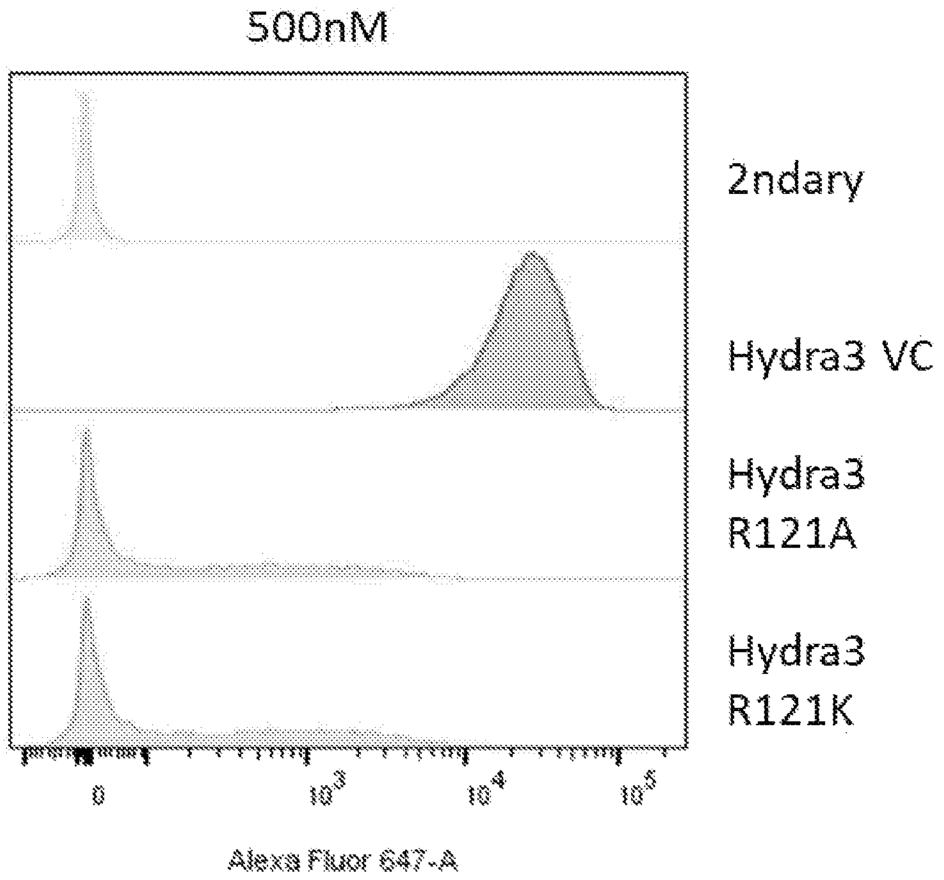
FIG. 20B depicts a FACS binding analysis showing sialic acid dependent staining of K562 cell surface ligands Hydra 3 as compared to Hydra 3-loss of binding (LOB) mutations R121K and R121A. The term "2ndary" represents the negative control.

FACS binding analysis was performed using K562 CML cells, as described above. As shown in FIG. 20A, Hydra 3 bound to sialic-acid expressing K562 cancer cells with a nM apparent affinity. Selective binding of Hydra 3 was further confirmed by substituting a critical ligand-binding arginine residue (R121) with a lysine (R121K) or an alanine (R121A) to generate loss-of-binding Hydra 3 mutants (Hydra 3 LOB). FACS binding analyses was performed as described above. As shown in FIG. 20A and FIG. 20B, the R121K and R121A substitution substantially reduced binding to K562 cells as compared to the wild type Hydra 3.

Together, these results show that Hydra 3 binding is mediated by sialic acid-recognition.

Example 7

This example shows the creation of a Hydra 9 double mutant construct that aggregates less than a wild-type version of Hydra 9.

Figure 21:
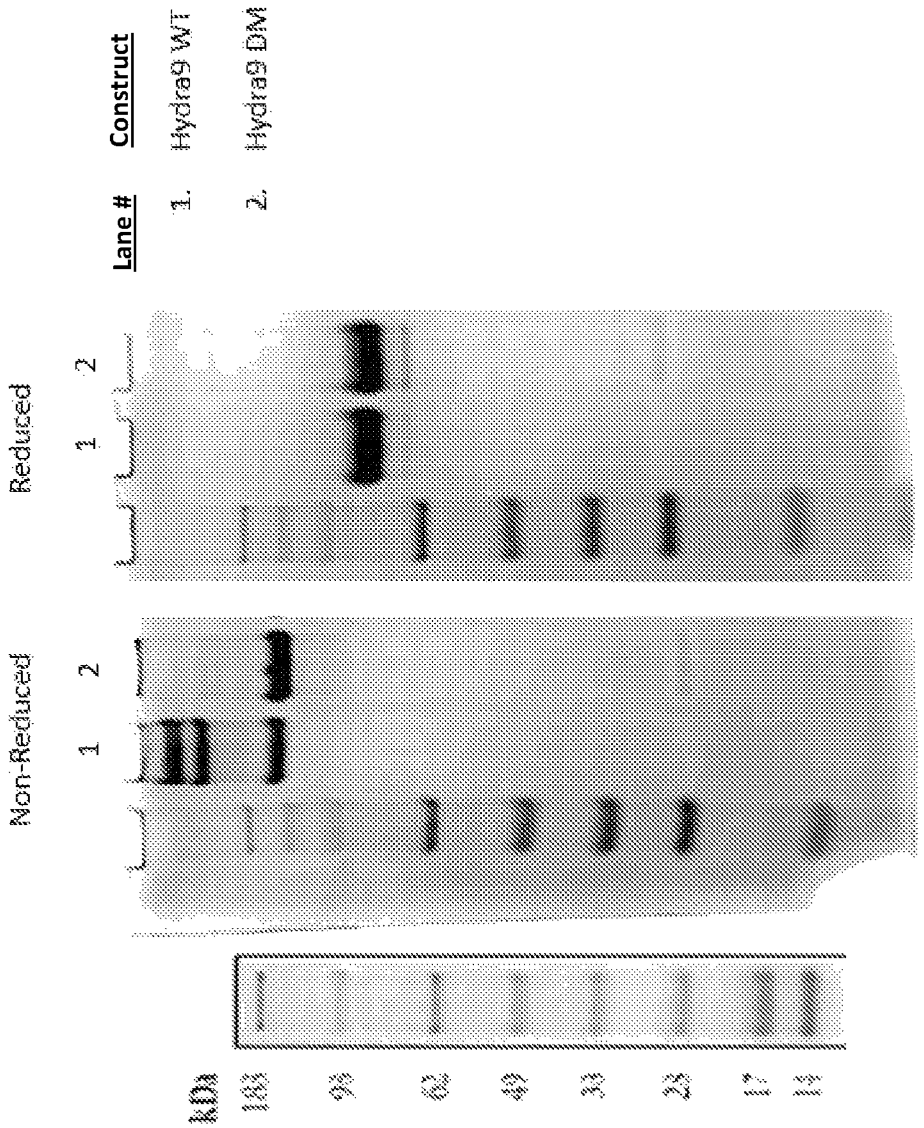
FIG. 21 depicts two SDS-PAGE gels, a non-reducing gel and a reducing gel. The WT Hydra 9 construct aggregates (see higher MW structures at the top of the non-reducing gel). A double mutant (DM) form of the Hydra 9 construct (C141S and C278Y) that removes two cysteine residues show less aggregation.
Figure 22:
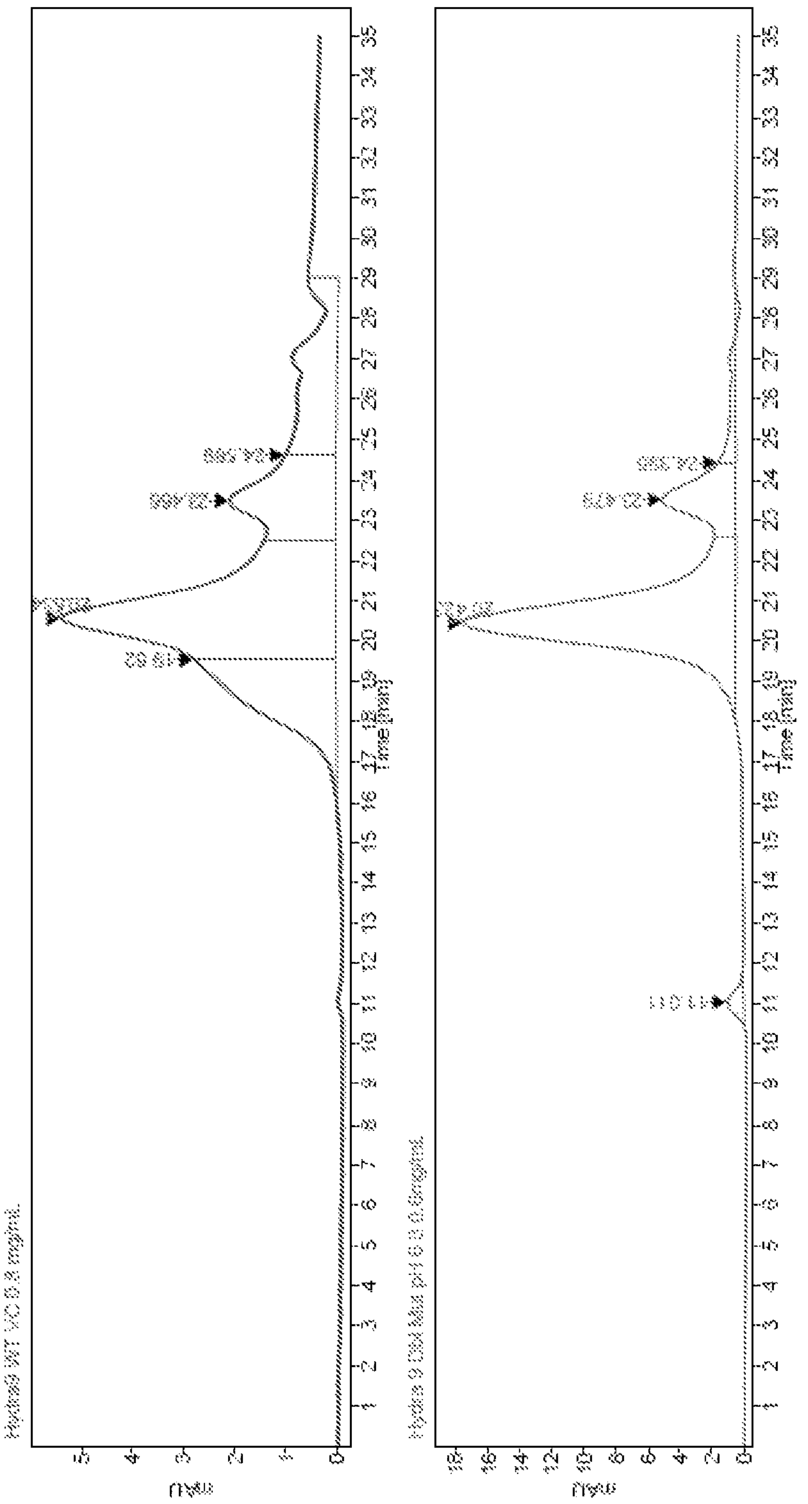
FIG. 22 depicts an SEC chromatogram showing that the WT form of Hydra 9 shows additional higher MW structures as compared to the Hydra 9 double mutant (DM) construct (comprising C141S and C278Y mutations), suggesting that the WT form exhibits more aggregation than the DM.

Hydra 9 Wild Type (WT) was created as described in Example 1, and a double mutant version was created having mutations at C141S and C278Y ("Hydra 9 Double Mutant (DM)"). As shown in FIG. 21, Hydra 9 WT appears to have more cysteine coupled aggregates compared to Hydra 9 DM as shown by the non-reduced lanes. FIG. 22 shows that Hydra 9 WT has more aggregates via SEC when compared to Hydra 9 DM.

Example 8

This examples shows that treatment of Hydra constructs with a sialidase can improve stability and/or yield recovery of the constructs.

Figure 23:
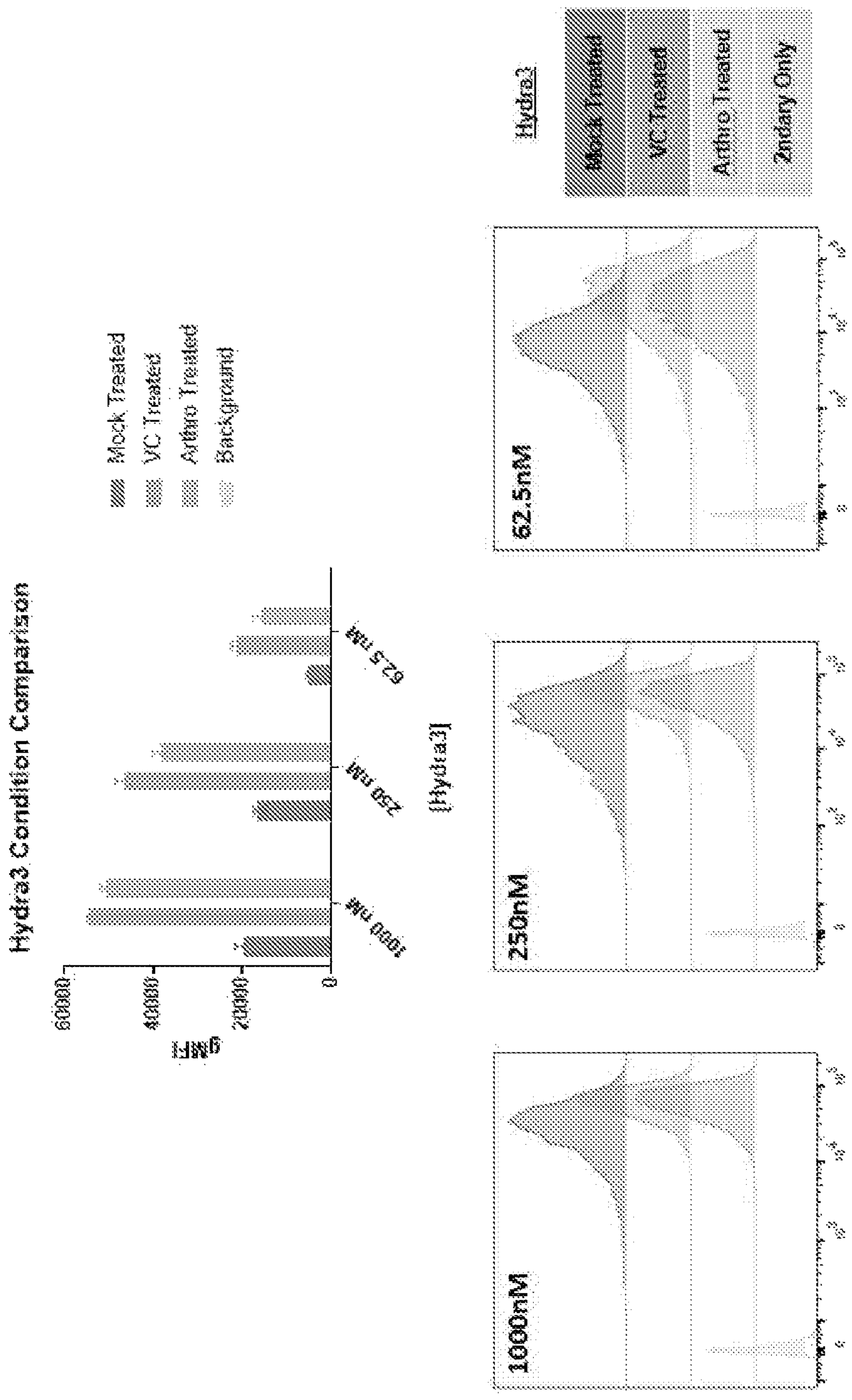
FIG. 23 depicts three FACS curve diagrams and corresponding bar graphs showing that sialidase pre-treatment (using *Vibrio Cholerae* (VC) sialidase or *Arthrobacter ureafaciens* (Arthro) sialidase) of Hydra 3 increases binding to K562 cell surface ligands.

Hydra 3 or Hydra 9-containing supernatant was loaded onto Protein A resin and washed thoroughly with PBS. This resin was resuspended in a 50% slurry with 50 mM Hepes pH6.8+50 mM NaCl and either *Vibrio Cholerae* (VC) or *Arthrobacter Ureafaciens* sialidase was added to suspension. This was incubated for 3 hours at room temperature. Mock treatment was the suspension of resin in 50 mM Hepes pH6.8+50 mM NaCl only. After incubation, another wash was performed with 50 mM Hepes pH6.8+50 mM NaCl and then Hydra 3 or Hydra 9 was eluted with 1M Arginine pH3.9. As shown in FIG. 23, K562 cells were stained with these constructs and analyzed by flow cytometry. The sialidase pre-treated Hydra 3 constructs showed significant increase of binding to K562 cells when compared to mock treated Hydra 3. In FIG. 24, the yield recoveries were compared for Hydra 9 WT, Hydra 9 WT LOB, and Hydra 9 DM with or without pretreatment with a sialidase. The removal of sialic acids from the Hydra 9 construct appeared to result in an increase in stability and/or yield recovery.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

SEQUENCE LISTING

SEQ ID NO: 1
```
YSLTMQSSVTVQEGMCVHVRCSFSYPVDSQT
DSDPVHGYWFRAGNDISWKAPVATNNPAWAV
QEETRDRFHLLGDPQTKNCTLSIRDARMSDA
GRYFFRMEKGNIKWNYKYDQLSVNVT
```

SEQ ID NO: 2
```
LTMQSSVTVQEGLCVHVPCSFSYPSHGWIYP
GPVVHGYWFREGANTDQDAPVATNNPARAVW
EETRDRFHLLGDPHTKNCTLSIRDARRSDAG
RYFFRMEKGSIKWNYKHHRLSVNVTALTH
```

SEQ ID NO: 3
```
QKSNRKDYSLTMQSSVTVQEGMCVHVRCSFS
YPVDSQTDSDPVHGYWFRAGNDISWKAPVAT
NNPAWAVQEETRDRFHLLGDPQTKNCTLSIR
DARMSDAGRYFFRMEKGNIKWNYKYDQLSVN
VTALTHRPNILIPGTLESGCFQNLTCSVPWA
CEQGTPPMISWMGTSVSPLHPSTTRSSVLTL
IPQPQHHGTSLTCQVTLPGAGVTTNRTIQLN
VSYP
```

SEQ ID NO: 4
```
QTSKLLTMQSSVTVQEGLCVHVPCSFSYPSH
GWIYPGPVVHGYWFREGANTDQDAPVATNNP
ARAVWEETRDRFHLLGDPHTKNCTLSIRDAR
RSDAGRYFFRMEKGSIKWNYKHHRLSVNVTA
LTHRPNILIPGTLESGCPQNLTCSVPWACEQ
GTPPMISWIGTSVSPLDPSTTRSSVLTLIPQ
PQDHGTSLTCQVTFPGASVTTNKTVHLNVSY
P
```

SEQ ID NO: 5
```
GYIPEAPRDGQAYVRKDGEWVLLSTFL
```

SEQ ID NO: 6
```
EPRGPTIKPCPPCKCPAPNLLGGPSVFIFPP
KIKDVLMISLSPIVTCVVVDVSEDDPDVQIS
WFVNNVEVHTAQTQTHREDYNSTLRVVSALP
IQHQDWMSGKEFKCKVNNKDLPAPIERTISK
PKGSVRAPQVYVLPPPEEEMTKKQVTLTCMV
TDFMPEDIYVEWTNNGKTELNYKNTEPVLDS
DGSYFMYSKLRVEKKNWVERNSYSCSVVHEG
LHNHHTTKSFSRTPGK
```

SEQ ID NO: 7
```
QKSNRKDYSLTMQSSVTVQEGMCVHVRCSFS
YPVDSQTDSDPVHGYWFRAGNDISWKAPVAT
NNPAWAVQEETRDRFHLLGDPQTKNCTLSIR
DARMSDAGRYFFRMEKGNIKWNYKYDQLSVN
```

-continued

VTALTHRPNILIPGTLESGCFQNLTCSVPWA
CEQGTPPMISWMGTSVSPLHPSTTRSSVLTL
IPQPQHHGTSLTCQVTLPGAGVTTNRTIQLN
VSYPPQNLTVTVFQGEGTASTALGNSSSLSV
LEGQSLRLVCAVDSNPPARLSWTWRSLTLYP
SQPSNPLVLELQVHLGDEGEFTCRAQNSLGS
QHVSLNLSLQQEYTGKMRPVSGVLLGAVGGY
IPEAPRDGQAYVRKDGEWVLLSTFLEPRGPT
IKPCPPCKCPAPNLLGGPSVFIFPPKIKDVL
MISLSPIVTCVVVDVSEDDPDVQISWFVNNV
EVHTAQTQTHREDYNSTLRVVSALPIQHQDW
MSGKEFKCKVNNKDLPAPIERTISKPKGSVR
APQVYVLPPPEEEMTKKQVTLTCMVTDFMPE
DIYVEWTNNGKTELNYKNTEPVLDSDGSYFM
YSKLRVEKKNWVERNSYSCSVVHEGLHNHHT
TKSFSRTPGK

SEQ ID NO: 8

QTSKLLTMQSSVTVQEGLCVHVPCSFSYPSH
GWIYPGPVVHGYWFREGANTDQDAPVATNNP
ARAVWEETRDRFHLLGDPHTKNCTLSIRDAR
RSDAGRYFFRMEKGSIKWNYKHHRLSVNVTA
LTHRPNILIPGTLESGCPQNLTCSVPWACEQ
GTPPMISWIGTSVSPLDPSTTRSSVLTLIPQ
PQDHGTSLTCQVTFPGASVTTNKTVHLNVSY
PPQNLTMTVFQGDGTVSTVLGNGSSLSLPEG
QSLRLVCAVDAVDSNPPARLSLSWRGLTLCP
SQPSNPGVLELPWVHLRDAAEFTCRAQNPLG
SQQVYLNVSLQSKATSGVTQGGYIPEAPRDG
QAYVRKDGEWVLLSTFLEPRGPTIKPCPPCK
CPAPNLLGGPSVFIFPPKIKDVLMISLSPIV
TCVVVDVSEDDPDVQISWFVNNVEVHTAQTQ
THREDYNSTLRVVSALPIQHQDWMSGKEFKC
KVNNKDLPAPIERTISKPKGSVRAPQVYVLP
PPEEEMTKKQVTLTCMVTDFMPEDIYVEWTN
NGKTELNYKNTEPVLDSDGSYFMYSKLRVEK
KNWVERNSYSCSVVHEGLHNHHTTKSFSRTP
GK

SEQ ID NO: 9

QKSNRKDYSLTMQSSVTVQEGMCVHVRCSFS
YPVDSQTDSDPVHGYWFRAGNDISWKAPVAT
NNPAWAVQEETRDRFHLLGDPQTKNCTLSIR

-continued

DARMSDAGRYFFRMEKGNIKWNYKYDQLSVN
VTALTHRPNILIPGTLESGCFQNLTCSVPWA
CEQGTPPMISWMGTSVSPLHPSTTRSSVLTL
IPQPQHHGTSLTCQVTLPGAGVTTNRTIQLN
VSYPGGGGSGGGGSGGGGSQKSNRKDYSLTM
QSSVTVQEGMCVHVRCSFSYPVDSQTDSDPV
HGYWFRAGNDISWKAPVATNNPAWAVQEETR
DRFHLLGDPQTKNCTLSIRDARMSDAGRYFF
RMEKGNIKWNYKYDQLSVNVTALTHRPNILI
PGTLESGCFQNLTCSVPWACEQGTPPMISWM
GTSVSPLHPSTTRSSVLTLIPQPQHHGTSLT
CQVTLPGAGVTTNRTIQLNVSYPEPRGPTIK
PCPPCKCPAPNLLGGPSVFIFPPKIKDVLMI
SLSPIVTCVVVDVSEDDPDVQISWFVNNVEV
HTAQTQTHREDYNSTLRVVSALPIQHQDWMS
GKEFKCKVNNKDLPAPIERTISKPKGSVRAP
QVYVLPPPEEEMTKKQVTLTCMVTDFMPEDI
YVEWTNNGKTELNYKNTEPVLDSDGSYFMYS
KLRVEKKNWVERNSYSCSVVHEGLHNHHTTK
SFSRTPGK

SEQ ID NO: 10

QTSKLLTMQSSVTVQEGLCVHVPCSFSYPSH
GWIYPGPVVHGYWFREGANTDQDAPVATNNP
ARAVWEETRDRFHLLGDPHTKNCTLSIRDAR
RSDAGRYFFRMEKGSIKWNYKHHRLSVNVTA
LTHRPNILIPGTLESGCPQNLTCSVPWACEQ
GTPPMISWIGTSVSPLDPSTTRSSVLTLIPQ
PQDHGTSLTCQVTFPGASVTTNKTVHLNVSY
PGGGGSGGGGSGGGGSQTSKLLTMQSSVTVQ
EGLCVHVPCSFSYPSHGWIYPGPVVHGYWFR
EGANTDQDAPVATNNPARAVWEETRDRFHLL
GDPHTKNCTLSIRDARRSDAGRYFFRMEKGS
IKWNYKHHRLSVNVTALTHRPNILIPGTLES
GCPQNLTCSVPWACEQGTPPMISWIGTSVSP
LDPSTTRSSVLTLIPQPQDHGTSLTCQVTFP
GASVTTNKTVHLNVSYPEPRGPTIKPCPPCK
CPAPNLLGGPSVFIFPPKIKDVLMISLSPIV
TCVVVDVSEDDPDVQISWFVNNVEVHTAQTQ
THREDYNSTLRVVSALPIQHQDWMSGKEFKC
KVNNKDLPAPIERTISKPKGSVRAPQVYVLP
PPEEEMTKKQVTLTCMVTDFMPEDIYVEWTN

-continued

NGKTELNYKNTEPVLDSDGSYFMYSKLRVEK
KNWVERNSYSCSVVHEGLHNHHTTKSFSRTP
GK

SEQ ID NO: 11

QKSNRKDYSLTMQSSVTVQEGMCVHVRCSFS
YPVDSQTDSDPVHGYWFRAGNDISWKAPVAT
NNPAWAVQEETRDRFHLLGDPQTKNCTLSIR
DARMSDAGRYFFRMEKGNIKWNYKYDQLSVN
VTALTHRPNILIPGTLESGCFQNLTCSVPWA
CEQGTPPMISWMGTSVSPLHPSTTRSSVLTL
IPQPQHHGTSLTCQVTLPGAGVTTNRTIQLN
VSYPPQNLTVTVFQGEGTASTALGNSSSLSV
LEGQSLRLVCAVDSNPPARLSWTWRSLTLYP
SQPSNPLVLELQVHLGDEGEFTCRAQNSLGS
QHVSLNLSLQQEYTGKMRPVSGVLLGAVGEP
RGPTIKPCPPCKCPAPNLLGGPSVFIFPPKI
KDVLMISLSPIVTCVVVDVSEDDPDVQISWF
VNNVEVHTAQTQTHREDYNSTLRVVSALPIQ
HQDWMSGKEFKCKVNNKDLPAPIERTISKPK
GSVRAPQVYVLPPPEEEMTKKQVTLTCMVTD
FMPEDIYVEWTNNGKTELNYKNTEPVLDSDG
SYFMYSKLRVEKKNWVERNSYSCSVVHEGLH
NHHTTKSFSRTPGKGGGGSGGGGSGGGGSQK
SNRKDYSLTMQSSVTVQEGMCVHVRCSFSYP
VDSQTDSDPVHGYWFRAGNDISWKAPVATNN
PAWAVQEETRDRFHLLGDPQTKNCTLSIRDA
RMSDAGRYFFRMEKGNIKWNYKYDQLSVNVT
ALTHRPNILIPGTLESGCFQNLTCSVPWACE
QGTPPMISWMGTSVSPLHPSTTRSSVLTLIP
QPQHHGTSLTCQVTLPGAGVTTNRTIQLNVS
YPPQNLTVTVFQGEGTASTALGNSSSLSVLE
GQSLRLVCAVDSNPPARLSWTWRSLTLYPSQ
PSNPLVLELQVHLGDEGEFTCRAQNSLGSQH
VSLNLSLQQEYTGKMRPVSGVLLGAVG

SEQ ID NO: 12

QTSKLLTMQSSVTVQEGLCVHVPCSFSYPSH
GWIYPGPVVHGYWFREGANTDQDAPVATNNP
ARAVWEETRDRFHLLGDPHTKNCTLSIRDAR
RSDAGRYFFRMEKGSIKWNYKHHRLSVNVTA
LTHRPNILIPGTLESGCPQNLTCSVPWACEQ
GTPPMISWIGTSVSPLDPSTTRSSVLTLIPQ
PQDHGTSLTCQVTFPGASVTTNKTVHLNVSY

-continued

PPQNLTMTVFQGDGTVSTVLGNGSSLSLPEG
QSLRLVCAVDAVDSNPPARLSLSWRGLTLCP
SQPSNPGVLELPWVHLRDAAEFTCRAQNPLG
SQQVYLNVSLQSKATSGVTQGEPRGPTIKPC
PPCKCPAPNLLGGPSVFIFPPKIKDVLMISL
SPIVTCVVVDVSEDDPDVQISWFVNNVEVHT
AQTQTHREDYNSTLRVVSALPIQHQDWMSGK
EFKCKVNNKDLPAPIERTISKPKGSVRAPQV
YVLPPPEEEMTKKQVTLTCMVTDFMPEDIYV
EWTNNGKTELNYKNTEPVLDSDGSYFMYSKL
RVEKKNWVERNSYSCSVVHEGLHNHHTTKSF
SRTPGKGGGGSGGGGSGGGGSQTSKLLTMQS
SVTVQEGLCVHVPCSFSYPSHGWIYPGPVVH
GYWFREGANTDQDAPVATNNPARAVWEETRD
RFHLLGDPHTKNCTLSIRDARRSDAGRYFFR
MEKGSIKWNYKHHRLSVNVTALTHRPNILIP
GTLESGCPQNLTCSVPWACEQGTPPMISWIG
TSVSPLDPSTTRSSVLTLIPQPQDHGTSLTC
QVTFPGASVTTNKTVHLNVSYPPQNLTMTVF
QGDGTVSTVLGNGSSLSLPEGQSLRLVCAVD
AVDSNPPARLSLSWRGLTLCPSQPSNPGVLE
LPWVHLRDAAEFTCRAQNPLGSQQVYLNVSL
QSKATSGVTQG

SEQ ID NO: 13

QKSNRKDYSLTMQSSVTVQEGMCVHVRCSFS
YPVDSQTDSDPVHGYWFRAGNDISWKAPVAT
NNPAWAVQEETRDRFHLLGDPQTKNCTLSIR
DARMSDAGRYFFRMEKGNIKWNYKYDQLSVN
VTALTHRPNILIPGTLESGCFQNLTCSVPWA
CEQGTPPMISWMGTSVSPLHPSTTRSSVLTL
IPQPQHHGTSLTCQVTLPGAGVTTNRTIQLN
VSYPPQNLTVTVFQGEGTASTALGNSSSLSV
LEGQSLRLVCAVDSNPPARLSWTWRSLTLYP
SQPSNPLVLELQVHLGDEGEFTCRAQNSLGS
QHVSLNLSLQQEYTGKMRPVSGVLLGAVG

SEQ ID NO: 14

QTSKLLTMQSSVTVQEGLCVHVPCSFSYPSH
GWIYPGPVVHGYWFREGANTDQDAPVATNNP
ARAVWEETRDRFHLLGDPHTKNCTLSIRDAR
RSDAGRYFFRMEKGSIKWNYKHHRLSVNVTA
LTHRPNILIPGTLESGCPQNLTCSVPWACEQ

-continued

GTPPMISWIGTSVSPLDPSTTRSSVLTLIPQ
PQDHGTSLTCQVTFPGASVTTNKTVHLNVSY
PPQNLTMTVFQGDGTVSTVLGNGSSLSLPEG
QSLRLVCAVDAVDSNPPARLSLSWRGLTLCP
SQPSNPGVLELPWVHLRDAAEFTCRAQNPLG
SQQVYLNVSLQSKATSGVTQG

SEQ ID NO: 15

MGFLPKLLLLASFFPAGQASWGVSSPQDVQG
VKGSCLLIPCIFSFPADVEVPDGITAIWYYD
YSGQRQVVSHSADPKLVEARFRGRTEFMGNP
EHRVCNLLLKDLQPEDSGSYNFRFEISEVNR
WSDVKGTLVTVTEEPRVPTIASPVELLEGTE
VDFNCSTPYVCLQEQVRLQWQGQDPARSVTF
NSQKFEPTGVGHLETLHMAMSWQDHGRILRC
QLSVANHRAQSEIHLQVKYAPKGVKILLSPS
GRNILPGELVTLTCQVNSSYPAVSSIKWLKD
GVRLQTKTGVLHLPQAAWSDAGVYTCQAENG
VGSLVSPPISLHIFMAEVQVSPAGPILENQT
VTLVCNTPNEAPSDLRYSWYKNHVLLEDAHS
HTLRLHLATRADTGFYFCEVQNVHGSERSGP
VSVVVNHPPLTPVLTAFLETQAGLVGILHCS
VVSEPLATLVLSHGGHILASTSGDSDHSPRF
SGTSGPNSLRLEIRDLEETDSGEYKCSATNS
LGNATSTLDFHANAARLLISPAAEVVEGQAV
TLSCRSGLSPTPDARFSWYLNGALLHEGPGS
SLLLPAASSTDAGSYHCRARDGHSASGPSSP
AVLTVLYPPRQPTFTTRLDLDAAGAGAGRRG
LLLCRVDSDPPARLQLLHKDRVVATSLPSGG
GCSTCGGCSPRMKVTKAPNLLRVEIHNPLLE
EEGLYLCEASNALGNASTSATFNGQATVLAI
APSHTLQEGTEANLTCNVSREAAGSPANFSW
FRNGVLWAQGPLETVTLLPVARTDAALYACR
ILTEAGAQLSTPVLLSVLYPPDRPKLSALLD
MGQGHMALFICTVDSRPLALLALFHGEHLLA
TSLGPQVPSHGRFQAKAEANSLKLEVRELGL
GDSGSYRCEATNVLGSSNTSLFFQVRGAWVQ
VSPSPELQEGQAVVLSCQVHTGVPEGTSYRW
YRDGQPLQESTSATLRFAAITLTQAGAYHCQ
AQAPGSATTSLAAPISLHVSYAPRHVTLTTL
MDTGPGRLGLLLCRVDSDPPAQLRLLHGDRL
VASTLQGVGGPEGSSPRLHVAVAPNTLRLEI

-continued

HGAMLEDEGVYICEASNTLGQASASADFDAQ
AVNVQVWPGATVREGQLVNLTCLVWTTHPAQ
LTYTWYQDGQQRLDAHSIPLPNVTVRDATSY
RCGVGPPGRAPRLSRPITLDVLYAPRNLRLT
YLLESHGGQLALVLCTVDSRPPAQLALSHAG
RLLASSTAASVPNTLRLELRGPQPRDEGFYS
CSARSPLGQANTSLELRLEGVRVILAPEAAV
PEGAPITVTCADPAAHAPTLYTWYHNGRWLQ
EGPAASLSFLVATRAHAGAYSCQAQDAQGTR
SSRPAALQVLYAPQDAVLSSFRDSRARSMAV
IQCTVDSEPPAELALSHDGKVLATSSGVHSL
ASGTGHVQVARNALRLQVQDVPAGDDTYVCT
AQNLLGSISTIGRLQVEGARVVAEPGLDVPE
GAALNLSCRLLGGPGPVGNSTFAWFWNDRRL
HAEPVPTLAFTHVARAQAGMYHCLAELPTGA
AASAPVMLRVLYPPKTPTMMVFVEPEGGLRG
ILDCRVDSEPLASLTLHLGSRLVASSQPQGA
PAEPHIHVLASPNALRVDIEALRPSDQGEYI
CSASNVLGSASTSTYFGVRALHRLHQFQQLL
WVLGLLVGLLLLLLGLGACYTWRRRRVCKQS
MGENSVEMAFQKETTQLIDPDAATCETSTCA
PPLG

SEQ ID NO: 16

ATGGGCTTCTTGCCCAAGCTTCTCCTCCTGG
CCTCATTCTTCCCAGCAGGCCAGGCCTCATG
GGGCGTCTCCAGTCCCCAGGACGTGCAGGGT
GTGAAGGGGTCTTGCCTGCTTATCCCCTGCA
TCTTCAGCTTCCCTGCCGACGTGGAGGTGCC
CGACGGCATCACGGCCATCTGGTACTACGAC
TACTCGGGCCAGCGGCAGGTGGTGAGCCACT
CGGCGGACCCCAAGCTGGTGGAGGCCCGCTT
CCGCGGCCGCACCGAGTTCATGGGGAACCCC
GAGCACAGGGTGTGCAACCTGCTGCTGAAGG
ACCTGCAGCCCGAGGACTCTGGTTCCTACAA
CTTCCGCTTCGAGATCAGTGAGGTCAACCGC
TGGTCAGATGTGAAAGGCACCTTGGTCACAG
TAACAGAGGAGCCCAGGGTGCCCACCATTGC
CTCCCCGGTGGAGCTTCTCGAGGGCACAGAG
GTGGACTTCAACTGCTCCACTCCCTACGTAT
GCCTGCAGGAGCAGGTCAGACTGCAGTGGCA
AGGCCAGGACCCTGCTCGCTCTGTCACCTTC

-continued

AACAGCCAGAAGTTTGAGCCCACCGGCGTCG

GCCACCTGGAGACCCTCCACATGGCCATGTC

CTGGCAGGACCACGGCCGGATCCTGCGCTGC

CAGCTCTCCGTGGCCAATCACAGGGCTCAGA

GCGAGATTCACCTCCAAGTGAAGTATGCCCC

CAAGGGTGTGAAGATCCTCCTCAGCCCCTCG

GGGAGGAACATCCTTCCAGGTGAGCTGGTCA

CACTCACCTGCCAGGTGAACAGCAGCTACCC

TGCAGTCAGTTCCATTAAGTGGCTCAAGGAT

GGGGTACGCCTCCAAACCAAGACTGGTGTGC

TGCACCTGCCCCAGGCAGCCTGGAGCGATGC

TGGCGTCTACACCTGCCAAGCTGAGAACGGC

GTGGGCTCTTTGGTCTCACCCCCCATCAGCC

TCCACATCTTCATGGCTGAGGTCCAGGTGAG

CCCAGCAGGTCCCATCCTGGAGAACCAGACA

GTGACACTAGTCTGCAACACACCCAATGAGG

CACCCAGTGATCTCCGCTACAGCTGGTACAA

GAACCATGTCCTGCTGGAGGATGCCCACTCC

CATACCCTCCGGCTGCACTTGGCCACTAGGG

CTGATACTGGCTTCTACTTCTGTGAGGTGCA

GAACGTCCATGGCAGCGAGCGCTCGGGCCCT

GTCAGCGTGGTAGTCAACCACCCGCCTCTCA

CTCCAGTCCTGACAGCCTTCCTGGAGACCCA

GGCGGGACTTGTGGGCATCCTTCACTGCTCT

GTGGTCAGTGAGCCCCTGGCCACACTGGTGC

TGTCACATGGGGGTCATATCCTGGCCTCCAC

CTCCGGGGACAGTGATCACAGCCCACGCTTC

AGTGGTACCTCTGGTCCCAACTCCCTGCGCC

TGGAGATCCGAGACCTGGAGGAAACTGACAG

TGGGGAGTACAAGTGCTCAGCCACCAACTCC

CTTGGAAATGCAACCTCCACCCTGGACTTCC

ATGCCAATGCCGCCCGTCTCCTCATCAGCCC

GGCAGCCGAGGTGGTGGAAGGACAGGCAGTG

ACACTGAGCTGCAGAAGCGGCCTAAGCCCCA

CACCTGATGCCCGCTTCTCCTGGTACCTGAA

TGGAGCCCTGCTTCACGAGGGTCCCGGCAGC

AGCCTCCTGCTCCCCGCGGCCTCCAGCACTG

ACGCCGGCTCATACCACTGCCGGGCCCGGGA

CGGCCACAGTGCCAGTGGCCCCTCTTCGCCA

GCTGTTCTCACTGTGCTCTACCCCCCTCGAC

-continued

AACCAACATTCACCACCAGGCTGGACCTTGA

TGCCGCTGGGGCCGGGGCTGGACGGCGAGGC

CTCCTTTTGTGCCGTGTGGACAGCGACCCCC

CCGCCAGGCTGCAGCTGCTCCACAAGGACCG

TGTTGTGGCCACTTCCCTGCCATCAGGGGGT

GGCTGCAGCACCTGTGGGGGCTGTTCCCCAC

GCATGAAGGTCACCAAAGCCCCCAACTTGCT

GCGTGTGGAGATTCACAACCCTTTGCTGGAA

GAGGAGGGCTTGTACCTCTGTGAGGCCAGCA

ATGCCCTGGGCAACGCCTCCACCTCAGCCAC

CTTCAATGGCCAGGCCACTGTCCTGGCCATT

GCACCATCACACACACTTCAGGAGGGCACAG

AAGCCAACTTGACTTGCAACGTGAGCCGGGA

AGCTGCTGGCAGCCCTGCTAACTTCTCCTGG

TTCCGAAATGGGGTGCTGTGGGCCCAGGGTC

CCCTGGAGACCGTGACACTGCTGCCCGTGGC

CAGAACTGATGCTGCCCTTTACGCCTGCCGC

ATCCTGACTGAGGCTGGTGCCCAGCTCTCCA

CTCCCGTGCTCCTGAGTGTACTCTATCCCCC

GGACCGTCCAAAGCTGTCAGCCCTCCTAGAC

ATGGGCCAGGGCCACATGGCTCTGTTCATCT

GCACTGTGGACAGCCGCCCCCTGGCCTTGCT

GGCCTTGTTCCATGGGGAGCACCTCCTGGCC

ACCAGCCTGGGTCCCCAGGTCCCATCCCATG

GTCGGTTCCAGGCTAAAGCTGAGGCCAACTC

CCTGAAGTTAGAGGTCCGAGAACTGGGCCTT

GGGGACTCTGGCAGCTACCGCTGTGAGGCCA

CAAATGTTCTTGGATCATCCAACACCTCACT

CTTCTTCCAGGTCCGAGGAGCCTGGGTCCAG

GTGTCACCATCACCTGAGCTCCAAGAGGGCC

AGGCTGTGGTCCTGAGCTGCCAGGTACACAC

AGGAGTCCCAGAGGGGACCTCATATCGTTGG

TATCGGGATGGCCAGCCCCTCCAGGAGTCGA

CCTCGGCCACGCTCCGCTTTGCAGCCATAAC

TTTGACACAAGCTGGGGCCTATCATTGCCAA

GCCCAGGCCCCAGGCTCAGCCACCACGAGCC

TAGCTGCACCCATCAGCCTCCACGTGTCCTA

TGCCCCACGCCACGTCACACTCACTACCCTG

ATGGACACAGGCCCTGGACGACTGGGCCTCC

TCCTGTGCCGTGTGGACAGTGACCCTCCGGC

CCAGCTGCGGCTGCTCCACGGGGATCGCCTT

-continued

GTGGCCTCCACCCTACAAGGTGTGGGGGGAC
CCGAAGGCAGCTCTCCCAGGCTGCATGTGGC
TGTGGCCCCCAACACACTGCGTCTGGAGATC
CACGGGGCTATGCTGGAGGATGAGGGTGTCT
ATATCTGTGAGGCCTCCAACACCCTGGGCCA
GGCCTCGGCCTCAGCTGACTTCGACGCTCAA
GCTGTGAATGTGCAGGTGTGGCCCGGGGCTA
CCGTGCGGGAGGGGCAGCTGGTGAACCTGAC
CTGCCTTGTGTGGACCACTCACCCGGCCCAG
CTCACCTACACATGGTACCAGGATGGGCAGC
AGCGCCTGGATGCCCACTCCATCCCCCTGCC
CAACGTCACAGTCAGGGATGCCACCTCCTAC
CGCTGCGGTGTGGGCCCCCCTGGTCGGGCAC
CCCGCCTCTCCAGACCTATCACCTTGGACGT
CCTCTACGCGCCCCGCAACCTGCGCCTGACC
TACCTCCTGGAGAGCCATGGCGGGCAGCTGG
CCCTGGTACTGTGCACTGTGGACAGCCGCCC
GCCCGCCCAGCTGGCCCTCAGCCACGCCGGT
CGCCTCTTGGCCTCCTCGACAGCAGCCTCTG
TCCCCAACACCCTGCGCCTGGAGCTGCGAGG
GCCACAGCCCAGGGATGAGGGTTTCTACAGC
TGCTCTGCCCGCAGCCCTCTGGGCCAGGCCA
ACACGTCCCTGGAGCTGCGGCTGGAGGGTGT
GCGGGTGATCCTGGCTCCGGAGGCTGCCGTG
CCTGAAGGTGCCCCCATCACAGTGACCTGTG
CGGACCCTGCTGCCCACGCACCCACACTCTA
TACTTGGTACCACAACGGTCGTTGGCTGCAG
GAGGGTCCAGCTGCCTCACTCTCATTCCTGG
TGGCCACGCGGGCTCATGCAGGCGCCTACTC
TTGCCAGGCCCAGGATGCCCAGGGCACCCGC
AGCTCCCGTCCTGCTGCCCTGCAAGTCCTCT
ATGCCCCTCAGGACGCTGTCCTGTCCTCCTT
CCGGGACTCCAGGGCCAGATCCATGGCTGTG
ATACAGTGCACTGTGGACAGTGAGCCACCTG
CTGAGCTGGCCCTATCTCATGATGGCAAGGT
GCTGGCCACGAGCAGCGGGGTCCACAGCTTG
GCATCAGGGACAGGCCATGTCCAGGTGGCCC
GAAACGCCCTACGGCTGCAGGTGCAAGATGT
GCCTGCAGGTGATGACACCTATGTTTGCACA
GCCCAAAACTTGCTGGGCTCAATCAGCACCA

-continued

TCGGGCGGTTGCAGGTAGAAGGTGCACGCGT
GGTGGCAGAGCCTGGCCTGGACGTGCCTGAG
GGCGCTGCCCTGAACCTCAGCTGCCGCCTCC
TGGGTGGCCCTGGGCCTGTGGGCAACTCCAC
CTTTGCATGGTTCTGGAATGACCGGCGGCTG
CACGCGGAGCCTGTGCCCACTCTCGCCTTCA
CCCACGTGGCTCGTGCTCAAGCTGGGATGTA
CCACTGCCTGGCTGAGCTCCCCACTGGGGCT
GCTGCCTCTGCTCCAGTCATGCTCCGTGTGC
TCTACCCTCCCAAGACGCCCACCATGATGGT
CTTCGTGGAGCCTGAGGGTGGCCTCCGGGGC
ATCCTGGATTGCCGAGTGGACAGCGAGCCGC
TCGCCAGCCTGACTCTCCACCTTGGCAGTCG
ACTGGTGGCCTCCAGTCAGCCCCAGGGTGCT
CCTGCAGAGCCACACATCCATGTCCTGGCTT
CCCCCAATGCCCTGAGGGTGGACATCGAGGC
GCTGAGGCCCAGCGACCAAGGGGAATACATC
TGTTCTGCCTCAAATGTCCTGGGCTCTGCCT
CTACCTCCACCTACTTTGGGGTCAGAGCCCT
GCACCGCCTGCATCAGTTCCAGCAGCTGCTC
TGGGTCCTGGGACTGCTGGTGGGCCTCCTGC
TCCTGCTGTTGGGCCTGGGGGCCTGCTACAC
CTGGAGAAGGAGGCGTGTTTGTAAGCAGAGC
ATGGGCGAGAATTCGGTGGAGATGGCTTTTC
AGAAAGAGACCACGCAGCTCATTGATCCTGA
TGCAGCCACATGTGAGACCTCAACCTGTGCC
CCACCCCTGGGCTGACCAGTGGTGTTGCCTG
CCCTCCGGAGGAGAAAGTGGCCAGAATCTGT
GATGACTCCAGCCTATGAATGTGAATGAGGC

AGTGTTGAGTCCTGCCCGCCTCTACGAAAAC
AGCTCTGTGACATCTGACTTTTTATGACCTG
GCCCCAAGCCTCTTGCCCCCCCAAAAATGGG
TGGTGAGAGGTCTGCCCAGGAGGGTGTTGAC
CCTGGAGGACACTGAAGAGCACTGAGCTGAT
CTCGCTCTCTCTTCTCTGGATCTCCTCCCTT
CTCTCCATTTCTCCCTCAAAGGAAGCCCTGC
CCTTTCACATCCTTCTCCTCGAAAGTCACCC
TGGACTTTGGTTGGATTGCAGCATCCTGCAT
CCTCAGAGGCTCACCAAGGCATTCTGTATTC
AACAGAGTATCAGTCAGCCTGCTCTAACAAG

-continued

AGACCAAATACAGTGACTTCAACATGATAGA

ATTTTATTTTTCTCTCCCACGCTAGTCTGGC

TGTTACGATGGTTTATGATGTTGGGGCTCAG

GATCCTTCTATCTTCCTTTTCTCTATCCCTA

AAATGATGCCTTTGATTGTGAGGCTCACCAT

GGCCCCGCTTTGTCCACATGCCCTCCAGCCA

GAAGAAGGAAGAGTGGAGGTAGAAGCACACC

CATGCCCATGGTGGACGCAACTCAGAAGCTG

CACAGGACTTTTCCACTCACTTCCCATTGGC

TGGAGTATTGTCACATGGCTACTGCAAGCTA

CAAGGGAGACTGGGAAATGTAGTTTTTATTT

TGAGTCCAGAGGACATTTGGAATTGGACTTC

CAAAGGACTCCCAACTGTGAGCTCATCCCTG

AGACTTTTGACATTGTTGGGAATGCCACCAG

CAGGCCATGTTTTGTCTCAGTGCCCATCTAC

TGAGGGCCAGGGTGTGCCCCTGGCCATTCTG

GTTGTGGGCTTCCTGGAAGAGGTGATCACTC

TCACACTAAGACTGAGGAAATAAAAAAGGTT

TGGTGTTTTCCTAGGGAGAGAGCATGCCAGG

CAGTGGAGTTGCCTAAGCAGACATCCTTGTG

CCAGATTTGGCCCCTGAAAGAAGAGATGCCC

TCATTCCCACCACCACCCCCCCTACCCCCAG

GGACTGGGTACTACCTTACTGGCCCTTACAA

GAGTGGAGGGCAGACACAGATGTTGTCAGCA

TCCTTATTCCTGCTCCAGATGCATCTCTGTT

CATGACTGTGTGAGCTCCTGTCCTTTTCCTG

GAGACCCTGTGTCGGGCTGTTAAAGAGAATG

AGTTACCAAGAAGGAATGACGTGCCCCTGCG

AATCAGGGACCAACAGGAGAGAGCTCTTGAG

TGGGCTAGTGACTCCCCCTGCAGCCTGGTGG

AGATGGTGTGAGGAGCGAAGAGCCCTCTGCT

CTAGGATTTGGGTTGAAAAACAGAGAGAGAA

GTGGGGAGTTGCCACAGGAGCTAACACGCTG

GGAGGCAGTTGGGGGCGGGTGAACTTTGTGT

AGCCGAGGCCGCACCCTCCCTCATTCCAGGC

TCATTCATTTTCATGCTCCATTGCCAGACTC

TTGCTGGGAGCCCGTCCAGAATGTCCTCCCA

ATAAAACTCCATCCTATGACGCAAAAAAAAA

AAAAAAAAA

SEQ ID NO: 17

MHLLGPWLLLLVLEYLAFSDSSKWVFEHPET

-continued

LYAWEGACVWIPCTYRALDGDLESFILFHNP

EYNKNTSKFDGTRLYESTKDGKVPSEQKRVQ

FLGDKNKNCTLSIHPVHLNDSGQLGLRMESK

TEKWMERIHLNVSERPFPPHIQLPPEIQESQ

EVTLTCLLNFSCYGYPIQLQWLLEGVPMRQA

AVTSTSLTIKSVFTRSELKFSPQWSHHGKIV

TCQLQDADGKFLSNDTVQLNVKHTPKLEIKV

TPSDAIVREGDSVTMTCEVSSSNPEYTTVSW

LKDGTSLKKQNTFTLNLREVTKDQSGKYCCQ

VSNDVGPGRSEEVFLQVQYAPEPSTVQILHS

PAVEGSQVEFLCMSLANPLPTNYTWYHNGKE

MQGRTEEKVHIPKILPWHAGTYSCVAENILG

TGQRGPGAELDVQYPPKKVTTVIQNPMPIRE

GDTVTLSCNYNSSNPSVTRYEWKPHGAWEEP

SLGVLKIQNVGWDNTTIACAACNSWCSWASP

VALNVQYAPRDVRVRKIKPLSEIHSGNSVSL

QCDFSSSHPKEVQFFWEKNGRLLGKESQLNF

DSISPEDAGSYSCWVNNSIGQTASKAWTLEV

LYAPRRLRVSMSPGDQVMEGKSATLTCESDA

NPPVSHYTWFDWNNQSLPYHSQKLRLEPVKV

QHSGAYWCQGTNSVGKGRSPLSTLTVYYSPE

TIGRRVAVGLGSCLAILILAICGLKLQRRWK

RTQSQQGLQENSSGQSFFVRNKKVRRAPLSE

GPHSLGCYNPMMEDGISYTTLRFPEMNIPRT

GDAESSEMQRPPPDCDDTVTYSALHKRQVGD

YENVIPDFPEDEGIHYSELIQFGVGERPQAQ

ENVDYVILKH

SEQ ID NO: 18

ATGCATCTCCTCGGCCCCTGGCTCCTGCTCC

TGGTTCTAGAATACTTGGCTTTCTCTGACTC

AAGTAAATGGGTTTTTGAGCACCCTGAAACC

CTCTACGCCTGGGAGGGGGCCTGCGTCTGGA

TCCCCTGCACCTACAGAGCCCTAGATGGTGA

CCTGGAAAGCTTCATCCTGTTCCACAATCCT

GAGTATAACAAGAACACCTCGAAGTTTGATG

GGACAAGACTCTATGAAAGCACAAAGGATGG

GAAGGTTCCTTCTGAGCAGAAAAGGGTGCAA

TTCCTGGGAGACAAGAATAAGAACTGCACAC

TGAGTATCCACCCGGTGCACCTCAATGACAG

TGGTCAGCTGGGGCTGAGGATGGAGTCCAAG

ACTGAGAAATGGATGGAACGAATACACCTCA

-continued

ATGTCTCTGAAAGGCCTTTTCCACCTCATAT
CCAGCTCCCTCCAGAAATTCAAGAGTCCCAG
GAAGTCACTCTGACCTGCTTGCTGAATTTCT
CCTGCTATGGGTATCCGATCCAATTGCAGTG
GCTCCTAGAGGGGGTTCCAATGAGGCAGGCT
GCTGTCACCTCGACCTCCTTGACCATCAAGT
CTGTCTTCACCCGGAGCGAGCTCAAGTTCTC
CCCACAGTGGAGTCACCATGGGAAGATTGTG
ACCTGCCAGCTTCAGGATGCAGATGGGAAGT
TCCTCTCCAATGACACGGTGCAGCTGAACGT
GAAGCACACCCCGAAGTTGGAGATCAAGGTC
ACTCCCAGTGATGCCATAGTGAGGGAGGGGG
ACTCTGTGACCATGACCTGCGAGGTCAGCAG
CAGCAACCCGGAGTACACGACGGTATCCTGG
CTCAAGGATGGGACCTCGCTGAAGAAGCAGA
ATACATTCACGCTAAACCTGCGCGAAGTGAC
CAAGGACCAGAGTGGGAAGTACTGCTGTCAG
GTCTCCAATGACGTGGGCCCGGGAAGGTCGG
AAGAAGTGTTCCTGCAAGTGCAGTATGCCCC
GGAACCTTCCACGGTTCAGATCCTCCACTCA
CCGGCTGTGGAGGGAAGTCAAGTCGAGTTTC
TTTGCATGTCACTGGCCAATCCTCTTCCAAC
AAATTACACGTGGTACCACAATGGGAAAGAA
ATGCAGGGAAGGACAGAGGAGAAAGTCCACA
TCCCAAAGATCCTCCCCTGGCACGCTGGGAC
TTATTCCTGTGTGGCAGAAAACATTCTTGGT
ACTGGACAGAGGGGCCCGGGAGCTGAGCTGG
ATGTCCAGTATCCTCCCAAGAAGGTGACCAC
AGTGATTCAAAACCCCATGCCGATTCGAGAA
GGAGACACAGTGACCCTTTCCTGTAACTACA
ATTCCAGTAACCCCAGTGTTACCCGGTATGA
ATGGAAACCCCATGGCGCCTGGGAGGAGCCA
TCGCTTGGGGTGCTGAAGATCCAAAACGTTG
GCTGGGACAACACAACCATCGCCTGCGCAGC
TTGTAATAGTTGGTGCTCGTGGGCCTCCCCT
GTCGCCCTGAATGTCCAGTATGCCCCCCGAG
ACGTGAGGGTCCGGAAAATCAAGCCCCTTTC
CGAGATTCACTCTGGAAACTCGGTCAGCCTC
CAATGTGACTTCTCAAGCAGCCACCCCAAAG
AAGTCCAGTTCTTCTGGGAGAAAAATGGCAG
GCTTCTGGGGAAAGAAAGCCAGCTGAATTTT

-continued

GACTCCATCTCCCCAGAAGATGCTGGGAGTT
ACAGCTGCTGGGTGAACAACTCCATAGGACA
GACAGCGTCCAAGGCCTGGACACTTGAAGTG
CTGTATGCACCCAGGAGGCTGCGTGTGTCCA
TGAGCCCGGGGGACCAAGTGATGGAGGGGAA
GAGTGCAACCCTGACCTGTGAGAGCGACGCC
AACCCTCCCGTCTCCCACTACACCTGGTTTG
ACTGGAATAACCAAAGCCTCCCCTACCACAG
CCAGAAGCTGAGATTGGAGCCGGTGAAGGTC
CAGCACTCGGGTGCCTACTGGTGCCAGGGGA
CCAACAGTGTGGGCAAGGGCCGTTCGCCTCT
CAGCACCCTCACCGTCTACTATAGCCCGGAG
ACCATCGGCAGGCGAGTGGCTGTGGGACTCG
GGTCCTGCCTCGCCATCCTCATCCTGGCAAT
CTGTGGGCTCAAGCTCCAGCGACGTTGGAAG
AGGACACAGAGCCAGCAGGGGCTTCAGGAGA
ATTCCAGCGGCCAGAGCTTCTTTGTGAGGAA
TAAAAAGGTTAGAAGGGCCCCCCTCTCTGAA
GGCCCCCACTCCCTGGGATGCTACAATCCAA
TGATGGAAGATGGCATTAGCTACACCACCCT
GCGCTTTCCCGAGATGAACATACCACGAACT
GGAGATGCAGAGTCCTCAGAGATGCAGAGAC
CTCCCCCGGACTGCGATGACACGGTCACTTA
TTCAGCATTGCACAAGCGCCAAGTGGGCGAC
TATGAGAACGTCATTCCAGATTTTCCAGAAG
ATGAGGGGATTCATTACTCAGAGCTGATCCA
GTTTGGGGTCGGGGAGCGGCCTCAGGCACAA
GAAAATGTGGACTATGTGATCCTCAAACATT
GA

SEQ ID NO: 19

MPLLLLLPLLWAGALAMDPNFWLQVQESVTV
QEGLCVLVPCTFFHPIPYYDKNSPVHGYWFR
EGAIISRDSPVATNKLDQEVQEETQGRFRLL
GDPSRNNCSLSIVDARRRDNGSYFFRKERGS
TKYSYKSPQLSVHVTDLTHRPKILIPGTLEP
GHSKNLTCSVSWACEQGTPPIFSWLSAAPTS
LGPRTTHSSVLIITPRPQDHGTNLTCQVKFA
GAGVTTERTIQLNVTYVPQNPTTGIFPGDGS
GKQETRAGWHGAIGGAGVTALLALCLCLIFF
IVKTHRRKAARTAVGRNDTHPTTGSASPKH

-continued

QKKSKLHGPTETSSCSGAAPTVEMDEELHYA

SLNFHGMNPSKDTSTEYSEVRTQ

SEQ ID NO: 20

TCTGCTCACACAGGAAGCCCTGGAAGCTGCT

TCCTCAGACATGCCGCTGCTGCTACTGCTGC

CCCTGCTGTGGGCAGGGGCCCTGGCTATGGA

TCCAAATTTCTGGCTGCAAGTGCAGGAGTCA

GTGACGGTACAGGAGGGTTTGTGCGTCCTCG

TGCCCTGCACTTTCTTCCATCCCATACCCTA

CTACGACAAGAACTCCCCAGTTCATGGTTAC

TGGTTCCGGGAAGGAGCCATTATATCCAGGG

ACTCTCCAGTGGCCACAAACAAGCTAGATCA

AGAAGTACAGGAGGAGACTCAGGGCAGATTC

CGCCTCCTTGGGGATCCCAGTAGGAACAACT

GCTCCCTGAGCATCGTAGACGCCAGGAGGAG

GGATAATGGTTCATACTTCTTTCGGATGGAG

AGAGGAAGTACCAAATACAGTTACAAATCTC

CCCAGCTCTCTGTGCATGTGACAGACTTGAC

CCACAGGCCCAAAATCCTCATCCCTGGCACT

CTAGAACCCGGCCACTCCAAAAACCTGACCT

GCTCTGTGTCCTGGGCCTGTGAGCAGGGAAC

ACCCCCGATCTTCTCCTGGTTGTCAGCTGCC

CCCACCTCCCTGGGCCCCAGGACTACTCACT

CCTCGGTGCTCATAATCACCCCACGGCCCCA

GGACCACGGCACCAACCTGACCTGTCAGGTG

AAGTTCGCTGGAGCTGGTGTGACTACGGAGA

GAACCATCCAGCTCAACGTCACCTATGTTCC

ACAGAACCCAACAACTGGTATCTTTCCAGGA

GATGGCTCAGGGAAACAAGAGACCAGAGCAG

GAGTGGTTCATGGGGCCATTGGAGGAGCTGG

TGTTACAGCCCTGCTCGCTCTTTGTCTCTGC

CTCATCTTCTTCATAGTGAAGACCCACAGGA

GGAAAGCAGCCAGGACAGCAGTGGGCAGGAA

TCACACCCACCCTACCACAGGGTCAGCCTCC

CCCAAACACCAGAAGAAGTCCAAGTTACATG

GCCCCACTGAAACCTCAAGCTGTTCAGGTGC

CGCCCCTACTGTGGAGATGGATGAGGAGCTG

CATTATGCTTCCCTCAACTTTCATGGGATGA

ATCCTTCCAAGGACACCTCCACCGAATACTC

AGAGGTCAGGACCCAGTGAGGAACCCACAAG

AGCATCAGGCTCAGCTAGAAGATCCACATCC

-continued

TCTACAGGTCGGGGACCAAAGGCTGATTCTT

GGAGATTTAACACCCCACAGGCAATGGGTTT

ATAGACATTATGTGAGTTTCCTGCTATATTA

ACATCATCTTAGACTTTGCAAGCAGAGAGTC

GTGGAATCAAATCTGTCCTCTTTCATTTGCT

AAGTGTATGATGTCACACAAGCTCCTTAACC

TTCCATGTCTCCATTTTCTTCTCTGTGAAGT

AGGTATAAGAAGTCCTATCTCATAGGGATGC

TGTGAGCATTAAATAAAGGTACACATGGAAA

ACACCAGTC

SEQ ID NO: 21

MIFLTALPLFWIMISASRGGHWGAWMPSSIS

AFEGTCVSIPCRFDFPDELRPAVVHGVWYFN

SPYPKNYPPVVFKSRTQVVHESFQGRSRLLG

DLGLRNCTLLLSNVSPELGGKYYFRGDLGGY

NQYTFSEHSVLDIVNTPNIVVPPEVVAGTEV

EVSCKVPDNCPELRPELSWLGHEGLGEPAVL

GRLREDEGTWVQVSLLHFVPTREANGHRLGC

QASFPNTTLQFEGYASMDVKYPPVIVEMNSS

VEAIEGSHVSLLCGADSNPPPLLTWMRDGTV

LREAVAESLLLELEEVTPAEDGVYACLAENA

YGQDNRTVGLSVMYAPWKPTVNGTMVAVEGE

TVSILCSTQSNPDPILTIFKEKQILSTVIYE

SELQLELPAVSPEDDGEYWCVAENQYGQRAT

AFNLSVEFAPVLLLESHCAAARDTVQCLCVV

KSNPEPSVAFELPSRNVTVNESEREFVYSER

SGLVLTSILTLRCQAQAPPRVICTARNLYCA

KSLELPFQGAHRLMWAKIGPVGAVVAFAILI

AIVCYITQTRRKKNVTESPSFSAGDNPPVLF

SSDFRISGAPEKYESERRLGSERRLLGLRGE

PPELDLSYSHSDLGKRPTKDSYTLTEELAEY

AEIRVK

SEQ ID NO: 22

ATGATATTCCTCACGGCACTGCCTCTGTTCT

GGATTATGATTTCAGCCTCCCGAGGGGGTCA

CTGGGGTGCCTGGATGCCCTCGTCCATCTCG

GCCTTCGAAGGCACGTGCGTCTCCATCCCCT

GCCGCTTTGACTTCCCGGATGAGCTGCGGCC

CGCTGTGGTGCATGGTCTCTGGTACTTCAAT

AGCCCCTACCCCAAGAACTACCCCCCGGTGG

TCTTCAAGTCGCGCACCCAAGTAGTCCACGA

-continued

GAGCTTCCAGGGCCGCAGCCGCCTCCTGGGG
GACCTGGGCCTGCGAAACTGCACCCTCCTGC
TCAGCAACGTCAGCCCCGAGCTGGGCGGGAA
GTACTACTTCCGTGGGGACCTGGGCGGCTAC
AACCAGTACACCTTCTCAGAGCACAGCGTCC
TGGATATCGTCAACACCCCCAACATCGTGCT
GCCCCCAGAGGTGGTGGCAGGCACGGAGGTG
GAGGTCAGCTGCATGGTGCCGGACAACTGCC
CAGAGCTGCGCCCTGAGCTGAGCTGGCTGGG
CCACGAGGGGCTGGGGGAGCCCGCTGTGCTG
GGCCGGCTGCGGGAGGACGAGGGCACCTGGG
TGCAGGTGTCACTGCTGCACTTCGTGCCCAC
GAGGGAGGCCAACGGCCACAGGCTGGGCTGC
CAGGCCTCCTTCCCCAACACCACCCTGCAGT
TCGAGGGCTACGCCAGCATGGACGTCAAGTA
CCCCCCGGTGATTGTGGAGATGAACTCCTCG
GTGGAGGCCATCGAGGGCTCCCACGTGAGCC
TGCTCTGTGGGGCTGACAGCAACCCCCCGCC
GCTGCTGACCTGGATGCGGGACGGGACAGTC
CTCCGGGAGGCGGTGGCCGAGAGCCTGCTCC
TGGAGCTGGAGGAGGTGACCCCCGCCGAAGA
CGGCGTCTATGCCTGCCTGGCCGAGAATGCC
TATGGCCAGGACAACCGCACCGTGGGGCTCA
GTGTCATGTATGCACCCTGGAAGCCAACAGT
GAACGGGACAATGGTGGCCGTAGAGGGGGAG
ACGGTCTCTATCTTGTGCTCCACACAGAGCA
ACCCGGACCCTATTCTCACCATCTTCAAGGA
GAAGCAGATCCTGTCCACGGTCATCTACGAG
AGCGAGCTGCAGCTGGAGCTGCCGGCCGTGT
CACCCGAGGATGATGGAGAGTACTGGTGTGT
GGCTGAGAACCAGTATGGCCAGAGGGCCACC
GCCTTCAACCTGTCTGTGGAGTTCGCCCCTG
TGCTCCTCCTGGAGTCCCACTGCGCGGCAGC
CCGAGACACGGTGCAGTGCCTGTGCGTGGTG
AAGTCCAACCCGGAGCCGTCCGTGGCCTTTG
AGCTGCCATCGCGCAATGTGACCGTGAACGA
GAGCGAGCGGGAGTTCGTGTACTCGGAGCGC
AGCGGCCTCGTGCTCACCAGCATCCTCACGC
TGCGGGGGCAGGCCCAGGCCCCGCCCCGCGT
CATCTGCACCGCGAGGAACCTCTATGGCGCC
AAGAGCCTGGAGCTGCCCTTCCAGGGAGCCC

-continued

ATCGACTGATGTGGGCCAAGATCGGGCCTGT
GGGCGCCGTGGTCGCCTTTGCCATCCTGATT
GCCATCGTCTGCTACATTACCCAGACACGCA
GGAAAAAGAACGTGACAGAGAGCCCCAGCTT
CTCGGCAGGGGACAACCCTCCCGTCCTGTTC
AGCAGCGACTTCCGCATCTCTGGGGCACCAC
AGAAGTACGAGAGCGACAGGCGCCTGGGATC
TGAGAGGAGGCTGCTGGGCCTTCGGGGTGAG
CCCCCAGAGCTGGACCTGAGCTATTCTCACT
CGGACCTGGGGAAACGGCCCACCAAGGACAG
CTACACGCTGACGGAGGAGCTAGCTCAGTAT
GCTGAAATCCGGGTCAAGTGA

SEQ ID NO: 23

MLPLLLLPLLWGGSLQEKPVYELQVQKSVTV
QEGLCVLVPCSFSYPWRSWYSSPPLYVYWFR
DGEIPYYAEVVATNNPDRRVKPETQGRFRLL
GDVQKKNCSLSIGDARMEDTGSYFFRVERGR
DVKYSYQQNKLNLEVTALIEKPDIHFLEPLE
SGRPTRLSCSLPGSCEAGPP1TFSWTGNALS
PLDPETTRSSELTLTPRPEDHGTNLTCQMKR
QGAQVTTERTVQLNVSYAPQTITIFRNGIAL
EILQNTSYLPVLEGQALRLLCDAPSNPPAHL
SWFQGSPALNATPISNTGILELRRVRSAEEG
GFTCRAQHPLGFLQIFLNLSVYSLPQLLGPS
CSWEAEGLHCRCSFRARPAPSLCWRLEEKPL
EGNSSQGSFKVNSSSACPWANSSLILHGGLS
SDLKVSCKAWNIYGSQSGSVLLLQGRSNLCT
GVVPAALGGAGVMALLCICLCLIFFLIVKAR
RKQAAGRPEKMDDEDPIMGTITSGSRKKPWP
DSPGDQASPPGDAPPLEEQKELHYASLSFSE
MKSREPKDQEAPSTTEYSEIKTSK

SEQ ID NO: 24

GTGCGCGTCCACAGCTCTCACTCACCCTCCG
GCTTCCTGTCGGGGCTTTCTCAGCCCCACCC
CACGTTTGGACATTTGGAGCATTTCCTTCCC
TGACAGCCGGACCTGGGACTGGGCTGGGGCC
CTGGCGGATGGAGACATGCTGCCCCTGCTGC
TGCTGCCCCTGCTGTGGGGGGGGTCCCTGCA
GGAGAAGCCAGTGTACGAGCTGCAAGTGCAG
AAGTCGGTGACGGTGCAGGAGGGCCTGTGCG
TCCTTGTGCCCTGCTCCTTCTCTTACCCCTG

-continued

GAGATCCTGGTATTCCTCTCCCCCACTCTAC
GTCTACTGGTTCCGGGACGGGGAGATCCCAT
ACTACGCTGAGGTTGTGGCCACAAACAACCC
AGACAGAAGAGTGAAGCCAGAGACCCAGGGC
CGATTCCGCCTCCTTGGGGATGTCCAGAAGA
AGAACTGCTCCCTGAGCATCGGAGATGCCAG
AATGGAGGACACGGGAAGCTATTTCTTCCGC
GTGGAGAGAGGAAGGGATGTAAAATATAGCT
ACCAACAGAATAAGCTGAACTTGGAGGTGAC
AGCCCTGATAGAGAAACCCGACATCCACTTT
CTGGAGCCTCTGGAGTCCGGCCGCCCCACAA
GGCTGAGCTGCAGCCTTCCAGGATCCTGTGA
AGCGGGACCACCTCTCACATTCTCCTGGACG
GGGAATGCCCTCAGCCCCCTGGACCCCGAGA
CCACCCGCTCCTCGGAGCTCACCCTCACCCC
CAGGCCCGAGGACCATGGCACCAACCTCACC
TGTCAGATGAAACGCCAAGGAGCTCAGGTGA
CCACGGAGAGAACTGTCCAGCTCAATGTCTC
CTATGCTCCACACACCATCACCATCTTCAGG
AACGGCATAGCCCTAGAGATCCTGCAAAACA
CCTCATACCTTCCGGTCCTGGAGGGCCAGGC
TCTGCGGCTGCTCTGTCATGCTCCCAGCAAC
CCCCCTGCACACCTGAGCTGGTTCCAGGGCT
CCCCTGCCCTGAACGCCACCCCCATCTCCAA
TACCGGGATCTTGGAGCTTCGTCGAGTAAGG
TCTGCAGAAGAAGGAGGCTTCACCTGCCGCG
CTCAGCACCCGCTGGGCTTCCTGCAAATTTT
TCTGAATCTCTCAGTTTACTCCCTCCCACAG
TTGCTGGGCCCCTCCTGCTCCTGGGAGGCTG
AGGGTCTGCACTGCAGATGCTCCTTTCGAGC
CCGGCCGGCCCCCTCCCTGTGCTGGCGGCTT
GAGGAGAAGCCGCTGGAGGGGAACAGCAGCC
AGGGCTCATTCAAGGTCAACTCCAGCTCAGC
TGGGCCCTGGGCCAACAGCTCCCTGATCCTC
CACGGGGGGCTCAGCTCCGACCTCAAAGTCA
GCTGCAAGGCCTGGAACATCTATGGGTCCCA
GAGCGGCTCTGTCCTGCTGCTGCAAGGGAGA
TCGAACCTCGGGACAGGAGTGGTTCCTGCAG
CCCTTGGTGGTGCTGGTGTCATGGCCCTGCT
CTGTATCTGTCTGTGCCTCATCTTCTTTTTA
ATAGTGAAAGCCCGCAGGAAGCAAGCAGCTG

-continued

GGAGACCAGAGAAAATGGATGATGAAGACCC
CATTATGGGTACCATCACCTCGGGTTCCAGG
AAGAAGCCCTGGCCAGACAGCCCCGGAGATC
AAGCATCTCCTCCTGGGGATGCCCCTCCCTT
GGAAGAACAAAAGGAGCTCCATTATGCCTCC
CTTAGTTTTTCTGAGATGAAGTCGAGGGAGC
CTAAGGACCAGGAGGCCCCAAGCACCACGGA
GTACTCGGAGATCAAGACAAGCAAGTGAGGA
TTTGCCCAGAGTTCAGTCCTGGCTGGAGGAG
CCACAGCCTGTCTGGGGGAAAGGACAAGTCA
GGGACCACTTGCTGAAGCACGAAGAGCCCTT
GTGGCAATGTTAACATTAACTGATGTTTAAG
TGCTCCAAGCAGATGGAATTAGAGAGGTGGG
CTCAAATCTAGGCCCTGGCACTGTCATCAAG
CAATTCACTGCATCCCTCTGTGCCTCAGTTT
CCCATTCTGTAAATCACAGATCATGCATGCT
ACCTCAAAGGTTGTTGTGAACATTAAAGAAA
TCAACACATGGAAATCAACCAACATGGGTCC
TGGAACAGGGCGTTGTCCTCAGTGCTTTCTG
GTCTCTCTTCCTTGAATAGAAAGGTCCTGCT
GGCAAGTTCTCTCAAGGCTGGGGATGACCAG
GCACAAAAAACAGGGCAGCAATATGTTGGTG
TCACTCCC
CTTCCCAAAACTCTTCGAAGACTCCCTAGGA
AAGACCAGCCCCTCAGCCTGGCACTTGGTTC
ATGATGTGGGATCTTATATCCTTGCCAGAGT
CATATCTTTGCCCACTTTTACCTGCAATCCT
TGCATCATATTCCTTTGGCTCCAGTCCTTCA
TTTATGAGACCCATAGGAATCCTTCCAACAG
CCAAAGAGTTGAGTCTAACTCTTTCCTGCCC
AAACCCATTCACGGCCCCCTGGCCTTAGACA
ATATATCACAAGCATCTCCCCTGACACATAA
AGTC

SEQ ID NO: 25

MQGAQEASASEMLPLLLPLLWAGALAQERRF
QLEGPESLTVQEGLCVLVPCRLPTTLPASYY
GYGYWFLEGADVPVATNDPDEEVQEETRGRF
HLLWDPRRKNCSLSIRDARRRDNAAYFFRLK
SKWMKYGYTSSKLSVRVMALTHRPNISIPGT
LESGHPSNLTCSVPWVCEQCTPPIFSWMSAA
PTSLGPRTTQSSVLTITPRPQDHSTNLTCQV

-continued

TFPGAGVTMERTIQLNVSYAPQKVAISIFQG

NSAAFKILQNTSSLPVLEGQALRLLCDADGN

PPAHLSWFQGFPALNATPISNTGVLELPQVG

SAEEGDFTCRAQHPLGSLQISLSLFVHWKPE

GRAGGVLGAVWGASITTLVFLCVCFIFRVKT

RRKKAAQPVQNTDDVNPVMVSGSRGHQHQFQ

TGIVSDHPAEAGPISEDEQELHYAVLHFHKV

QPQEPKVTDTEYSEIKIHK

SEQ ID NO: 26

GCGGGACACAGTCTCTTCTCCTCTGCTCTTC

TTTGGGCAGGTCTCTGGGTCTCAAAGTTTCC

GTCTGCTCTGTGCAGAGGGAGTGGAGCTCCG

AGGGCTTGTGGCTTCGCAGTTCCTCTTCTGT

GAACAGCCGAGATCACGCGCTCCTCCCCAGC

CACCCGTTCCTCCCCGCAGTCCTTCCCCTCC

ACTCCCTTCCCCTTCTCTGCTCATGCAGGGA

GCCCAGGAAGCCTCCGCCTCAGAGATGCTAC

CGCTGCTGCTGCCCCTGCTGTGGGCAGGGGC

CCTGGCTCAGGAGCGGAGATTCCAGCTGGAG

GGGCCAGAGTCACTGACGGTGCAGGAGGGTC

TGTGCGTCCTCGTACCCTGCAGATTGCCCAC

TACCCTTCCAGCCTCGTACTATGGTTATGGC

TACTGGTTCCTGGAAGGGGCTGATGTTCCAG

TGGCCACAAACGACCCAGACGAAGAAGTGCA

GGAGGAGACCCGGGGCCGATTCCACCTCCTC

TGGGATCCCAGAAGGAAGAACTGCTCCCTGA

GCATCAGAGATGCCCGGAGGAGGGACAATGC

TGCATACTTCTTTCGGTTGAAGTCCAAATGG

ATGAAATACGGTTATACATCTTCCAAGCTCT

CTGTGCGTGTGATGGCCCTGACCCACAGGCC

CAACATCTCCATCCCAGGGACCCTGGAGTCT

GGCCATCCCAGCAATCTGACCTGCTCTGTGC

CCTGGGTCTGTGAGCAGGGGACGCCCCCCAT

CTTCTCCTGGATGTCAGCTGCCCCCACCTCC

CTGGGCCCCAGGACCACCCAGTCCTCGGTGC

TCACAATCACCCCACGGCCCCAGGACCACAG

CACCAACCTCACCTGTCAGGTGACGTTCCCT

GGAGCCGGTGTGACCATGGAGAGAACCATCC

AGCTCAATGTCTCCTCCTTCAAAATCCTGCA

AAACACCTCGTCCCTCCCTGTCCTGGAGGGC

CAGGCTCTGCGGCTGCTCTGTGATGCTGACG

-continued

GCAACCCCCCTGCACACCTGAGCTGGTTCCA

GGGCTTCCCCGCCCTGAACGCCACCCCCATC

TCCAATACCGGGGTCCTGGAGCTGCCTCAAG

TAGGGTCTGCAGAAGAAGGAGATTTCACCTG

CCGTGCTCAGCATCCTCTGGGCTCCCTGCAA

ATCTCTCTGAGTCTCTTTGTGCATTGGAAAC

CAGAAGGCAGGGCTGGTGGTGTCCTGGGAGC

AGTCTGGGGAGCTAGCATCACAACCCTGGTT

TTCCTCTGTGTTTGCTTCATCTTCAGAGTGA

AGACTAGAAGGAAGAAAGCAGCCCAGCCAGT

GCAAAACACGGATGATGTGAACCCCGTCATG

GTCTCAGGCTCCAGGGGTCATCAGCACCAGT

TCCAGACAGGCATAGTTTCAGACCACCCTGC

TGAGGCTGGCCCCATCTCAGAAGATGAGCAG

GAGCTCCACTACGCTGTCCTACACTTCCACA

AGGTGCAACCTCAGGAACCAAAGGTCACCGA

CACTGAGTACTCAGAAATCAAGATACACAAG

TGAGGAATTGTCCAAAGCCATAACCTTGATT

GGAGAGAACATGGTACCTCTCAGTGTATTGG

TTACTAGGGCTGCCACAGCAATGTACCACAA

ACCGAGTGACATAAACACAGAACTTTATTTT

CGTATAGTTTCAGATGTTAGAGGTCTGAGAA

CAAGGTGTTATCAGGGTTGGTCCCTTCTAAG

GCCTCTCTTGTTGGCTTGTAGATGGCTGTCT

CCTCCTTGTGTCTTCACATGGTCTTTCCTCT

GAGTGTGTTTGTGTCCTAATCTTCTCTTCTT

ATAAAGACACTAGTCATATTGGATTAGGGCC

TCCCCATGACCTAATTTAAATAAATTAACTA

TTTAAAGACCCTCCAAATACAGTAACCTTCT

GAGATATTGAGATTTAGGACTTCCAACATAT

GAATTTTAGAAGGGAACAATTTAGCCCATAA

CACTGTGTCCAATTCTTTTAAAATTAATGTT

TTTGTTGTAAATGGACTATATAAATACCTTC

GTATATATGGCAGACCACAGGACTTCTGTCC

AAGAGAACTGAGTTCAACTCCATCTATGCCA

GCTATTGAGCAAGTCGCTTTATGTCCCTGCT

CTGTAAGGCAGGGAAATAATTTCCATCTAAC

CAGATTATTGTGAAAGGTCAAAGAAAGCATA

CAGCTAACATACAGCTTTGTTAGCTGTAAAA

-continued

CAGCTAACAAAGGCCCTGACACAAAGGTTTT

CATAAAGT

CTGTATATTTTTGTAAATGAATGCCTTGTAT

CTGGCTTTGGCTAGCTTTTTTTTTTTTTTTT

TTTTTCTGAGATGGAGTCTTGCTGTATCTCC

CAGGCTGGAGTGCAGTGGTGCGATCTTGGCT

CAGTGCAAGCTTCGCCCCCTGGGTTCACACC

ATTCTCCTGCCTCAGCCTCCCAAGTAGCTGG

GACTACAGGCACCCACCACCACACCCGGCTA

ATTTTTTGTATTTTTAGTAGAGACGGGGTTT

CACCGTGTTAGCCAGGATGGTCTTGATCTCC

TGACCTCGTGATCTGCCCTCCTCGGCCTCCC

AAAGTGCTGAGATTACAGGCATGAGCCACCG

CACCCGGCTTTGATTAGCTGTTTTAACAGAC

GGTTTCTGCTGGCAATTTCTTCTAAGGCTGA

AAAGGAGTAGGCCCAGAGGCCACAGCACCAG

GTGTCTGTGTCACCCCCTGTTCAGAACTCTT

CACGACTCCCCAAAATAAGGTTTCCATCCAT

CATCTTTCTGCTCAAGGCTCTCTACATGATC

TTGTCCATCCAGATTTCCCCAGATCAATTCC

TCACCAGTCACCAATACCCCATGTCCATTTC

CACAGCTTCCTCTTACAAATCCCAGTCTCCA

CTATTCCAGTGAAATTGAAGAAAGCATTTAA

TGAAGACCAACTATTAAGGAAAATTCTTAAG

AGTAGCCATGAAAAATAAAAAGATAGATTAC

ACTTAAAAGACCACAGTTAGCAGTGGCTCAC

GCCTGTAATCCCAGCACTTTGGGAGGCTGAG

GTGGGTGGATCACTGGAGGTCAGGAGTTCGA

GACTGGTCTGGCCAACATGGTGAAACCCCAT

CTCTACTAAAATACAAAAATTAGCTCGGTGT

GGTGGCACTTGCCTGTAATCCCAGGTACTTC

TGCAGGTTGAAGCAGGAGAATTGCTTGAACC

TGGGAGGTGGAGGTTGAAGTGAGCTGAGATT

GCATCACTGCACTCCAGCCTGGGCAACAGAG

CGAGACTCCAACTCAGAAAAAGCAAAACAAA

ACAAACAAACAAGCAAAAAACCACAATTAGA

CTGACAGCTGACTTTTTTAGGAGCAATATTG

GAAGGCTAAATGCAATAGAAAGATGTCTTTG

ATGGCTTAAGAGAAATAAATGTTGTTTTAGA

AAGCCTACTCAATGAAAACACATTTTAAGAC

-continued

TGAAAGTGAAATATAGATATTTTAAGGAAAA

CCAAAATATGTGAGTGTTAATAAAGAAAAGA

TTTCTCAAATAAATTCTAAAACATATAATTC

AGGTATTAGGAAAGTGATCCCAGATTAGATT

TTTGAGATCCAAAAAAAATGAAAACCTAGGA

AAGTAGCAAATATGTGAGCAAAATGAAACAA

ATACTTGTTGTAAAAATGATGGTTTGTAGAG

GGGTCAAACATCAAATGTAATATTGAAATAC

CAATATTATATAGCCCAGAAACTATAATAAC

ATAAAGTTCAGAAGAGTGTAAATAGAATTTA

TATTACATAAAGTCTTTATATTTTTCCAGAG

AAAATTAAATGTTATGATGAATGTTAAAAAA

AAAAAAAAAAAAAAAAAAAAAAAAA

SEQ ID NO: 27

MLLLLLLPLLWGRERVEGQKSNRKDYSLTMQ

SSVTVQEGMCVHVRCSFSYPVDSQTDSDPVH

GYWFRAGNDISWKAPVATNNPAWAVQEETRD

RFHLLGDPQTKNCTLSIRDARMSDAGRYFFR

MEKGNIKWNYKYDQLSVNVTALTHRPNILIP

GTLESGCFQNLTCSVPWACEQGTPPMISWMG

TSVSPLHPSTTRSSVLTLIPQPQHHGTSLTC

QVTLPGAGVTTNRTIQLNVSYPPQNLTVTVF

QGEGTASTALGNSSSLSVLEGQSLRLVCAVD

SNPPARLSWTWRSLTLYPSQPSNPLVLELQV

HLGDEGEFTCRAQNSLGSQHVSLNLSLQQEY

TGKMRPVSGVLLGAVGGAGATALVFLSFCVI

FIVVRSCRKKSARPAADVGDIGMKDANTIRG

SASQGNLTESWADDNPRHHGLAAHSSGEERE

IQYAPLSFHKGEPQDLSGQEATNNEYSEIKI

PK

SEQ ID NO: 28

GCAGTTCCTGAGAGAAGAACCCTGAGGAACA

GACGTTCCCTCGCGGCCCTGGCACCTCCAAC

CCCAGATATGCTGCTGCTGCTGCTGCTGCCC

CTGCTCTGGGGGAGGGAGAGGGTGGAAGGAC

AGAAGAGTAACCGGAAGGATTACTCGCTGAC

GATGCAGAGTTCCGTGACCGTGCAAGAGGGC

ATGTGTGTCCATGTGCGCTGCTCCTTCTCCT

ACCCAGTGGACAGCCAGACTGACTCTGACCC

AGTTCATGGCTACTGGTTCCGGGCAGGGAAT

GATATAAGCTGGAAGGCTCCAGTGGCCACAA

ACAACCCAGCTTGGGCAGTGCAGGAGGAAAC

-continued

TCGGGACCGATTCCACCTCCTTGGGGACCCA
CAGACCAAAAATTGCACCCTGAGCATCAGAG
ATGCCAGAATGAGTGATGCGGGGAGATACTT
CTTTCGTATGGAGAAAGGAAATATAAAATGG
AATTATAAATATGACCAGCTCTCTGTGAACG
TGACAGCCTTGACCCACAGGCCCAACATCCT
TATCCCCGGTACCCTGGAGTCTGGCTGCTTC
CAGAATCTGACCTGCTCTGTGCCCTGGGCCT
GTGAGCAGGGGACGCCCCCTATGATCTCCTG
GATGGGGACCTCTGTGTCCCCCCTGCACCCC
TCCACCACCCGCTCCTCAGTGCTCACCCTCA
TCCCACAGCCCCAGCACCACGGCACCAGCCT
CACCTGTCAGGTGACCTTGCCTGGGGCCGGC
GTGACCACGAACAGGACCATCCAACTCAATG
TGTCCTACCCTCCTCAGAACTTGACTGTGAC
TGTCTTCCAAGGAGAAGGCACAGCATCCACA
GCTCTGGGGAACAGCTCATCTCTTTCAGTCC
TAGAGGGCCAGTCTCTGCGCTTGGTCTGTGC
TGTTGACAGCAATCCCCCTGCCAGGCTGAGC
TGGACCTGGAGGAGTCTGACCCTGTACCCCT
CACAGCCCTCAAACCCTCTGGTACTGGAGCT
GCAAGTGCACCTGGGGGATGAAGGGGAATTC
ACCTGTCGAGCTCAGAACTCTCTGGGTTCCC
AGCACGTTTCCCTGAACCTCTCCCTGCAACA
GGAGTACACAGGCAAAATGAGGCCTGTATCA
GGAGTGTTGCTGGGGGCGGTCGGGGGAGCTG
GAGCCACAGCCCTGGTCTTCCTCTCCTTCTG
TGTCATCTTCATTGTAGTGAGGTCCTGCAGG
AAGAAATCGGCAAGGCCAGCAGCGGACGTGG
GAGACATAGGCATGAAGGATGCAAACACCAT
CAGGGGCTCAGCCTCTCAGGGTAACCTGACT
GAGTCCTGGGCAGATGATAACCCCCGACACC
ATGGCCTGGCTGCCCACTCCTCAGGGGAGGA
AAGAGAGATCCAGTATGCACCCCTCAGCTTT
CATAAGGGGGAGCCTCAGGACCTATCAGGAC
AAGAAGCCACCAACAATGAGTACTCAGAGAT
CAAGATCCCCAAGTAAGAAAATGCAGAGGCT
CGGGCTTGTTTGAGGGTTCACGACCCCTCCA
GCAAAGGAGTCTGAGGCTGATTCCAGTAGAA
TTAGCAGCCCTCAATGCTGTGCAACAAGACA

-continued

TCAGAACTTATTCCTCTTGTCTAACTGAAAA
TGCATGCCTGATGACCAAACTCTCCCTTTCC
CCATCCAATCGGTCCACACTCCCCGCCCTGG
CCTCTGGTACCCACCATTCTCCTCTGTACTT
CTCTAAGGATGACTACTTTAGATTCCGAATA
TAGTGAGATTGTAACGTGAAAAAAAAAAAAA
AA

SEQ ID NO: 29

MLLLLLLLPLLWGTKGMEGDRQYGDGYLLQV
QELVTVQEGLCVHVPCSFSYPQDGWTDSDPV
HGYWFRAGDRPYQDAPVATNNPDREVQAETQ
GRFQLLGDIWSNDCSLSIRDARKRDKGSYFF
RLERGSMKWSYKSQLNYKTKQLSVFVTALTH
RPDILILGTLESGHSRNLTCSVPWACKQGTP
PMISWIGASVSSPGPTTARSSVLTLTPKPQD
HGTSLTCQVTLPGTGVTTTSTVRLDVSYPPW
NLTMTVFQGDATASTALGNGSSLSVLEGQSL
RLVCAVNSNPPARLSWTRGSLTLCPSRSSNP
GLLELPRVHVRDEGEFTCRAQNAQGSQHISL
SLSLQNEGTGTSRPVSQVTLAAVGGAGATAL
AFLSFCIIFIIVRSCRKKSARPAAGVGDTGM
EDAKAIRGSASQGPLTESWKDGNPLKKPPPA
VAPSSGEEGELHYATLSFHKVKPQDPQGQEA
TDSEYSEIKIHKRETAETQACLRNHNPSSKE
VRG

SEQ ID NO: 30

AGTTTCTGAGAGAAGAACCCTGAGGAACAGA
CGTTCCCTGGCGGCCCTGGCGCCTTCAAACC
CAGACATGCTGCTGCTGCTGCTGCTGCTGCC
CCTGCTCTGGGGGACAAAGGGGATGGAGGGA
GACAGACAATATGGGGATGGTTACTTGCTGC
AAGTGCAGGAGCTGGTGACGGTGCAGGAGGG
CCTGTGTGTCCATGTGCCCTGCTCCTTCTCC
TACCCCCAGGATGGCTGGACTGACTCTGACC
CAGTTCATGGCTACTGGTTCCGGGCAGGAGA
CAGACCATACCAAGACGCTCCAGTGGCCACA
AACAACCCAGACAGAGAAGTGCAGGCAGAGA
CCCAGGGCCGATTCCAACTCCTTGGGGACAT
TTGGAGCAACGACTGCTCCCTGAGCATCAGA
GACGCCAGGAAGAGGGATAAGGGGTCATATT
TCTTTCGGCTAGAGAGAGGAAGCATGAAATG
GAGTTACAAATCACAGTTGAATTACAAAACT

-continued

AAGCAGCTGTCTGTGTTTGTGACAGCCCTGA
CCCATAGGCCTGACATCCTCATCCTAGGGAC
CCTAGAGTCTGGCCACTCCAGGAACCTGACC
TGCTCTGTGCCCTGGGCCTGTAAGCAGGGGA
CACCCCCCATGATCTCCTGGATTGGGGCCTC
CGTGTCCTCCCCGGGCCCCACTACTGCCCGC
TCCTCAGTGCTCACCCTTACCCCAAAGCCCC
AGGACCACGGCACCAGCCTCACCTGTCAGGT
GACCTTGCCTGGGACAGGTGTGACCACGACC
AGTACCGTCCGCCTCGATGTGTCCTACCCTC
CTTGGAACTTGACCATGACTGTCTTCCAAGG
AGATGCCACAGCATCCACAGCCCTGGGAAAT
GGCTCATCTCTTTCAGTCCTTGAGGGCCAGT
CTCTGCGCCTGGTCTGTGCTGTCAACAGCAA
TCCCCCTGCCAGGCTGAGCTGGACCCGGGGG
AGCCTGACCCTGTGCCCCTCACGGTCCTCAA
ACCCTGGGCTGCTGGAGCTGCCTCGAGTGCA
CGTGAGGGATGAAGGGGAATTCACCTGCCGA
GCTCAGAACGCTCAGGGCTCCCAGCACATTT
CCCTGAGCCTCTCCCTGCAGAATGAGGGCAC
AGGCACCTCAAGACCTGTATCACAAGTGACA
CTGGCAGCAGTCGGGGGAGCTGGAGCCACAG
CCCTGGCCTTCCTGTCCTTCTGCATCATCTT
CATCATAGTGAGGTCCTGCAGGAAGAAATCG
GCAAGGCCAGCAGCGGGCGTGGGGGATACAG
GCATGGAAGATGCAAAGGCCATCAGGGGCTC
GGCCTCTCAGGGACCCCTGACTGAATCCTGG
AAAGATGGCAACCCCCTGAAGAAGCCTCCCC
CAGCTGTTGCCCCCTCGTCAGGGGAGGAAGG
AGAGCTCCATTATGCAACCCTCAGCTTCCAT
AAAGTGAAGCCTCAGGACCCGCAGGGACAGG
AGGCCACTGACAGTGAATACTCGGAGATCAA
GATCCACAAGCGAGAAACTGCAGAGACTCAG
GCCTGTTTGAGGAATCACAACCCCTCCAGCA
AAGAAGTCAGAGGCTGATTCTCATAGAACAA
GAACCCTCTAGAGCCCCATGCTATGCAGTAG
GTCACCAGGGCTCCCTCCTCCTGTCTAACCA
AAACTTGGACCAATGTCTCCCCTTTCCCCGG
CTACCAGGGACCCATCCCTGCCTCTAGCTTC
TACTACCCACCATTCTCCTCTCGACCTCTCT

-continued

GAGGTTGACTATTTTAGATTCCACATAGAGA
TGAGGTCATGTGGTACTTGCCTCTCTGTGTG
TGGCTCATTTTACACAAAAAAATATCCCCTA
GGTTCATCCATGTTCTCTCAAATGACAGAAT
CAAGCACTGAATATTTTTTTTTCTTTGAGAG
ATGGAGTTTCGCTCTGTTGCCCAGGCTGGAG
TGCAGTGGTTCAATCTCTGCTCACTGCAACC
TCCACCTCCTGGGTTCAAACGATTCTCCTGC
CTCAGCTTCCCAAGTAGCTGGTACTACAGGC
GTGTGTCACCACGCCCAGCTAATTTTTGTAT
TTTTTAGTAGAGACGGGGTTTCACTATAAGT
GGGCCAGGCTAGTCTCAAACTCCTGACCTCA
AGTGATCTGCCTGCCTTGGCCTCCCAAAGTG
CTGGGATTTCAGGCATGAGCCACCGCACCCA
GCTTGCATTGAATATTTTCAAGGAGCTAAAA
GAAGATTTTAAATGGTCTCACAAAAACAGAT
AAATATTT

GCACAGATGGGTGTGCTAATCATTGTGCCTT
GATGGTTCCACGATGTATCCGGGTGTGGAAA
TCTCACTGGGTCTCTCTCAAGGCCACTCGGC
TACTCAGGACAGGGCTGGAATTTAAAGCCTG
TCCGATTCTGAGGTCTCTTCTCTCATCTAGC
ACTGAGTCAAGCAATCAGCAGGCTGGGCACC
CCTTAGCCATAAGTTTTCAGGAAATAAATTC
CTTGAGGGCATTGACTTTTACAAAAGAGGGA
GCAGCAATGGCCTAGAGTCTCAGGAACAAGA
CAGGTGCACTGAGGAGATGAAGGCCGGGACC
CCCTGCCCAACCTGTATGGCGGGTCTGTACT
TATTTTGTTTACCCCCAATTTAAAACGTTTT
TTTTTATTGCAGGTTGTTTGTTTGATATGGT
TTGGCTGTGTCCCCACCCAAATCTTATCTAG
AATTGTAATCAGAATTATAATCCCCATGTGT
TGGGGGAGGGACCTGGTGGGAGGTGATAGGA
TCATGGGGGTGGTTCCCCCATGCTGTTCTGA
TAGTGAGTGAGTTATCACGAGATCTGATGGT
TTTGTAAGTGGTGGTTTCCCCTGCTCTTCTC
TCTTGCCTGCCACCATGTAAGATGTGCCTGG
TTCCCCTTCCGCCATGATTGTAAGTTTCCTG
AGGCCTCCCCCGCCATGTGGAACTGTGAGTC
AATTACACCTCTTTCATTTATAAATTAAAAA
AAAAAAAAAAAAAA

-continued

SEQ ID NO: 31
MLLLLLPLLWGRERAEGQTSKLLTMQSSVTV
QEGLCVHVPCSFSYPSHGWIYPGPVVHGYWF
REGANTDQDAPVATNNPARAVWEETRDRFHL
LGDPHTKNCTLSIRDARRSDAGRYFFRMEKG
SIKWNYKHHRLSVNVTALTHRPNILIPGTLE
SGCPQNLTCSVPWACEQGTPPMISWIGTSVS
PLDPSTTRSSVLTLIPQPQDHGTSLTCQVTF
PGASVTTNKTVHLNVSYPPQNLTMTVFQGDG
TVSTVLGNGSSLSLPEGQSLRLVCAVDAVDS
NPPARLSLSWRGLTLCPSQPSNPGVLELPWV
HLRDAAEFTCRAQNPLGSQQVYLNVSLQSKA
TSGVTQGVVGGAGATALVFLSFCVIFVVVRS
CRKKSARPAAGVGDTGIEDANAVRGSASQGP
LTEPWAEDSPPDQPPPASARSSVGEGELQYA
SLSFQMVKPWDSRGQEATDTEYSEIKIHR

SEQ ID NO: 32
TAGGGCCTCCTCTAAGTCTTGAGCCCGCAGT
TCCTGAGAGAAGAACCCTGAGGAACAGACGT
TCCCTCGCGGCCCTGGCACCTCTAACCCCAG
ACATGCTGCTGCTGCTGCTGCCCCTGCTCTG
GGGGAGGGAGAGGGCGGAAGGACAGACAAGT
AAACTGCTGACGATGCAGAGTTCCGTGACGG
TGCAGGAAGGCCTGTGTGTCCATGTGCCCTG
CTCCTTCTCCTACCCCTCGCATGGCTGGATT
TACCCTGGCCCAGTAGTTCATGGCTACTGGT
TCCGGGAAGGGGCCAATACAGACCAGGATGC
TCCAGTGGCCACAAACAACCCAGCTCGGGCA
GTGTGGGAGGAGACTCGGGACCGATTCCACC
TCCTTGGGGACCCACATACCAAGAATTGCAC
CCTGAGCATCAGAGATGCCAGAAGAAGTGAT
GCGGGGAGATACTTCTTTCGTATGGAGAAAG
GAAGTATAAAATGGAATTATAAACATCACCG
GCTCTCTGTGAATGTGACAGCCTTGACCCAC
AGGCCCAACATCCTCATCCCAGGCACCCTGG
AGTCCGGCTGCCCCCAGAATCTGACCTGCTC
TGTGCCCTGGGCCTGTGAGCAGGGGACACCC
CCTATGATCTCCTGGATAGGGACCTCCGTGT
CCCCCCTGGACCCCTCCACCACCCGCTCCTC
GGTGCTCACCCTCATCCCACAGCCCCAGGAC
CATGGCACCAGCCTCACCTGTCAGGTGACCT

-continued

TCCCTGGGGCCAGCGTGACCACGAACAAGAC
CGTCCATCTCAACGTGTCCTACCCGCCTCAG
AACTTGACCATGACTGTCTTCCAAGGAGACG
GCACAGTATCCACAGTCTTGGGAAATGGCTC
ATCTCTGTCACTCCCAGAGGGCCAGTCTCTG
CGCCTGGTCTGTGCAGTTGATGCAGTTGACA
GCAATCCCCCTGCCAGGCTGAGCCTGAGCTG
GAGAGGCCTGACCCTGTGCCCCTCACAGCCC
TCAAACCCGGGGGTGCTGGAGCTGCCTTGGG
TGCACCTGAGGGATGCAGCTGAATTCACCTG
CAGAGCTCAGAACCCTCTCGGCTCTCAGCAG
GTCTACCTGAACGTCTCCCTGCAGAGCAAAG
CCACATCAGGAGTGACTCAGGGGGTGGTCGG
GGGAGCTGGAGCCACAGCCCTGGTCTTCCTG
TCCTTCTGCGTCATCTTCGTTGTAGTGAGGT
CCTGCAGGAAGAAATCGGCAAGGCCAGCAGC
GGGCGTGGGAGATACGGGCATAGAGGATGCA
AACGCTGTCAGGGGTTCAGCCTCTCAGGGGC
CCCTGACTGAACCTTGGGCAGAAGACAGTCC
CCCAGACCAGCCTCCCCCAGCTTCTGCCCGC
TCCTCAGTGGGGGAAGGAGAGCTCCAGTATG
CATCCCTCAGCTTCCAGATGGTGAAGCCTTG
GGACTCGCGGGGACAGGAGGCCACTGACACC
GAGTACTCGGAGATCAAGATCCACAGATGAG
AAACTGCAGAGACTCACCCTGATTGAGGGAT
CACAGCCCCTCCAGGCAAGGGAGAAGTCAGA
GGCTGATTCTTGTAGAATTAACAGCCCTCAA
CGTGATGAGCTATGATAACACTATGAATTAT
GTGCAGAGTGAAAAGCACACAGGCTTTAGAG
TCAAAGTATCTCAAACCTGAATCCACACTGT
GCCCTCCCTTTTATTTTTTTAACTAAAAGAC
AGACAAATTCCTAAAAAAAAAAAAAAAAAAA
A

SEQ ID NO: 33
MLLPLLLSSLLGGSQAMDGRFWIRVQESVMV
PEGLCISVPCSFSYPRQDWTGSTPAYGYWFK
AVTETTKGAPVATNHQSREVEMSTRGRFQLT
GDPAKGNCSLVIRDAQMQDESQYFFRVERGS
YVRYNFMNDGFFLKVTALTQKPDVYIPETLE
PGQPVTVICVFNWAFEECPPPSFSWTGAALS
SQGTKPTTSHFSVLSFTPRPQDHNTDLTCHV

-continued

DFSRKGVSAQRTVRLRVAYAPRDLVISISRD

NTPALEPQPQGNVPYLEAQKGQFLRLLCAAD

SQPPATLSWVLQNRVLSSSHPWGPRPLGLEL

PGVKAGDSGRYTCRAENRLGSQQRALDLSVQ

YPPENLRVMVSQANRTVLENLGNGTSLPVLE

GQSLCLVCVTHSSPPARLSWTQRGQVLSPSQ

PSDPGVLELPRVQVEHEGEFTCHARHPLGSQ

HVSLSLSVHYSPKLLGPSCSWEAEGLHCSCS

SQASPAPSLRWWLGEELLEGNSSQDSFEVTP

SSAGPWANSSLSLHGGLSSGLRLRCEAWNVH

GAQSGSILQLPDKKGLISTAFSNGAFLGIGI

TALLFLCLALIIMKILPKRRTQTETPRPRFS

RHSTILDYINVVPTAGPLAQKRNQKATPNSP

RTPLPPGAPSPESKKNQKKQYQLPSFPEPKS

STQAPESQESQEELHYATLNFPGVRPRPEAR

MPKGTQADYAEVKFQ

SEQ ID NO: 34

GCCCCCAGGAGACCCAGAGGACAACTGGGCA

AGGTGGGCCGGAGAGTGTGGGGGAAGGCAAA

GGAGTTCTGTGAGCTCAGCGTCTGAAGCTCA

TTTCATGCATCAGGCCCCAGGGCTCAGCTTC

CGCCTTCGGCTTCCCCTTCTGCCAAGAGCCC

TGAGCCACTCACAGCACGACCAGAGAACAGG

CCTGTCTCAGGCAGGCCCTGCGCCTCCTATG

CGGAGATGCTACTGCCACTGCTGCTGTCCTC

GCTGCTGGGCGGGTCCCAGGCTATGGATGGG

AGATTCTGGATACGAGTGCAGGAGTCAGTGA

TGGTGCCGGAGGGCCTGTGCATCTCTGTGCC

CTGCTCTTTCTCCTACCCCCGACAAGACTGG

ACAGGGTCTACCCCAGCTTATGGCTACTGGT

TCAAAGCAGTGACTGAGACAACCAAGGGTGC

TCCTGTGGCCACAAACCACCAGAGTCGAGAG

GTGGAAATGAGCACCCGGGGCCGATTCCAGC

TCACTGGGGATCCCGCCAAGGGGAACTGCTC

CTTGGTGATCAGAGACGCGCAGATGCAGGAT

GAGTCACAGTACTTCTTTCGGGTGGAGAGAG

GAAGCTATGTGAGATATAATTTCATGAACGA

TGGGTTCTTTCTAAAAGTAACAGCCCTGACT

CAGAAGCCTGATGTCTACATCCCCGAGACCC

TGGAGCCCGGGCAGCCGGTGACGGTCATCTG

TGTGTTTAACTGGGCCTTTGAGGAATGTCCA

-continued

CCCCCTTCTTTCTCCTGGACGGGGGCTGCCC

TCTCCTCCCAAGGAACCAAACCAACGACCTC

CCACTTCTCAGTGCTCAGCTTCACGCCCAGA

CCCCAGGACCACAACACCGACCTCACCTGCC

ATGTGGACTTCTCCAGAAAGGGTGTGAGCGC

ACAGAGGACCGTCCGACTCCGTGTGGCCTAT

GCCCCCAGAGACCTTGTTATCAGCATTTCAC

GTGACAACACGCCAGCCCTGGAGCCCCAGCC

CCAGGGAAATGTCCCATACCTGGAAGCCCAA

AAAGGCCAGTTCCTGCGGCTCCTCTGTGCTG

CTGACAGCCAGCCCCCTGCCACACTGAGCTG

GGTCCTGCAGAACAGAGTCCTCTCCTCGTCC

CATCCCTGGGGCCCTAGACCCCTGGGGCTGG

AGCTGCCCGGGGTGAAGGCTGGGGATTCAGG

GCGCTACACCTGCCGAGCGGAGAACAGGCTT

GGCTCCCAGCAGCGAGCCCTGGACCTCTCTG

TGCAGTATCCTCCAGAGAACCTGAGAGTGAT

GGTTTCCCAAGCAAACAGGACAGTCCTGGAA

AACCTTGGGAACGGCACGTCTCTCCCAGTAC

TGGAGGGCCAAAGCCTGTGCCTGGTCTGTGT

CACACACAGCAGCCCCCCAGCCAGGCTGAGC

TGGACCCAGAGGGGACAGGTTCTGAGCCCCT

CCCAGCCCTCAGACCCCGGGGTCCTGGAGCT

GCCTCGGGTTCAAGTGGAGCACGAAGGAGAG

TTCACCTGCCACGCTCGGCACCCACTGGGCT

CCCAGCACGTCTCTCTCAGCCTCTCCGTGCA

CTACTCCCCGAAGCTGCTGGGCCCCTCCTGC

TCCTGGGAGGCTGAGGGTCTGCACTGCAGCT

GCTCCTCCCAGGCCAGCCCGGCCCCCTCTCT

GCGCTGGTGGCTTGGGGAGGAGCTGCTGGAG

GGGAACAGCAGCCAGGACTCCTTCGAGGTCA

CCCCCAGCTCAGCCGGGCCCTGGGCCAACAG

CTCCCTGAGCCTCCATGGAGGGCTCAGCTCC

GGCCTCAGGCTCCGCTGTGAGGCCTGGAACG

TCCATGGGGCCCAGAGTGGATCCATCCTGCA

GCTGCCAGATAAGAAGGGACTCATCTCAACG

GCATTCTCCAACGGAGCGTTTCTGGGAATCG

GCATCACGGCTCTTCTTTTCCTCTGCCTGGC

CCTGATCATCATGAAGATTCTACCGAAGAGA

CGGACTCAGACAGAAACCCCGAGGCCCAGGT

-continued

TCTCCCGGCACAGCACGATCCTGGATTACAT

CAATGTGGTCCCGACGGCTGGCCCCCTGGCT

CAGAAGCGGAATCAGAAAGCCACACCAAACA

GTCCTCGGACCCCTCTTCCACCAGGTGCTCC

CTCCCCAGAATCAAAGAAGAACCAGAAAAAG

CAGTATCAGTTGCCCAGTTTCCCAGAACCCA

AATCATCCACTCAAGCCCCAGAATCCCAGGA

GAGCCAAGAGGAGCTCCATTATGCCACGCTC

AACTTCCC

AGGCGTCAGACCCAGGCCTGAGGCCCGGATG

CCCAAGGGCACCCAGGCGGATTATGCAGAAG

TCAAGTTCCAATGAGGGTCTCTTAGGCTTTA

GGACTGGGACTTCGGCTAGGGAGGAAGGTAG

AGTAAGAGGTTGAAGATAACAGAGTGCAAAG

TTTCCTTCTCTCCCTCTCTCTCTCTCTTTCT

CTCTCTCTCTCTCTTTCTCTCTCTTTTAAAA

AAACATCTGGCCAGGGCACAGTGGCTCACGC

CTGTAATCCCAGCACTTTGGGAGGTTGAGGT

GGGCAGATCGCCTGAGGTCGGGAGTTCGAGA

CCAGCCTGGCCAACTTGGTGAAACCCCGTCT

CTACTAAAAATACAAAAATTAGCTGGGCATG

GTGGCAGGCGCCTGTAATCCTACCTACTTGG

GAAGCTGAGGCAGGAGAATCACTTGAACCTG

GGAGACGGAGGTTGCAGTGAGCCAAGATCAC

ACCATTGCACGCCAGCCTGGGCAACAAAGCG

AGACTCCATCTCAAAAAAAAAATCCTCCAAA

TGGGTTGGGTGTCTGTAATCCCAGCACTTTG

GGAGGCTAAGGTGGGTGGATTGCTTGAGCCC

AGGAGTTCGAGACCAGCCTGGGCAACATGGT

GAAACCCCATCTCTACAAAAAATACAAAACA

TAGCTGGGCTTGGTGGTGTGTGCCTGTAGTC

CCAGCTGTCAGACATTTAAACCAGAGCAACT

CCATCTGGAATAGGAGCTGAATAAAATGAGG

CTGAGACCTACTGGGCTGCATTCTCAGACAG

TGGAGGCATTCTAAGTCACAGGATGAGACAG

GAGGTCCGTACAAGATACAGGTCATAAAGAC

TTTGCTGATAAAACAGATTGCAGTAAAGAAG

CCAACCAAATCCCACCAAAACCAAGTTGGCC

ACGAGAGTGACCTCTGGTCGTCCTCACTGCT

ACACTCCTGACAGCACCATGACAGTTTACAA

ATGCCATGGCAACATCAGGAAGTTACCCGAT

-continued

ATGTCCCAAAAGGGGGGAGGAATGAATAATCC

ACCCCTTGTTTAGCAAATAAGCAAGAAATAA

CCATAAAAGTGGGCAACCAGCAGCTCTAGGC

GCTGCTCTTGTCTATGGAGTAGCCATTCTTT

TGTTCCTTTACTTTCTTAATAAACTTGCTTT

CACCTTAAAAAAA

SEQ ID NO: 35

MVPGQAQPQSPEMLLLPLLLPVLGAGSLNKD

PSYSLQVQRQVPVPEGLCVIVSCNLSYPRDG

WDESTAAYGYWFKGRTSPKTGAPVATNNQSR

EVEMSTRDRFQLTGDPGKGSCSLVIRDAQRE

DEAWYFFRVERGSRVRHSFLSNAFFLKVTAL

TKKPDVYIPETLEPGQPVTVICVFNWAFKKC

PAPSFSWTGAALSPRRTRPSTSHFSVLSFTP

SPQDHDTDLTCHVDFSRKGVSAQRTVRLRVA

YAPKDLIISISHDNTSALELQGNVIYLEVQK

GQFLRLLCAADSQPPATLSWVLQDRVLSSSH

PWGPRTLGLELRGVRAGDSGRYTCRAENRLG

SQQQALDLSVQYPPENLRVMVSQANRTVLEN

LGNGTSLPVLEGQSLRLVCVTHSSPPARLSW

TRWGQTVGPSQPSDPGVLELPPIQMEHEGEF

TCHAQHPLGSQHVSLSLSVHYPPQLLGPSCS

WEAEGLHCSCSSQASPAPSLRWWLGEELLEG

NSSQGSFEVTPSSAGPWANSSLSLHGGLSSG

LRLRCKAWNVHGAQSGSVFQLLPGKLEHGGG

LGLGAALGAGVAALLAFCSCLVVFRVKICRK

EARKRAAAEQDVPSTLGPISQGHQHECSAGS

SQDHPPPGAATYTPGKGEEQELHYASLSFQG

LRLWEPADQEAPSTTEYSEIKIHTGQPLRGP

GFGLQLEREMSGMVPK

SEQ ID NO: 36

CGAGGCTCCTCCTCTGTGGATGGTCACTGCC

CCTCCACCAGGCTTCCTGCTGGAGGAGTTTC

CTTCCCAGCCAGGCCGGCCCAGAAGCCAGAT

GGTCCCGGGACAGGCCCAGCCCCAGAGCCCA

GAGATGCTGCTGCTGCCCCTGCTGCTGCCCG

TGCTGGGGGCGGGGTCCCTGAACAAGGATCC

CAGTTACAGTCTTCAAGTGCAGAGGCAGGTG

CCGGTGCCGGAGGGCCTGTGTGTCATCGTGT

CTTGCAACCTCTCCTACCCCCGGGATGGCTG

GGACGAGTCTACTGCTGCTTATGGCTACTGG

-continued

TTCAAAGGACGGACCAGCCCAAAGACGGGTG
CTCCTGTGGCCACTAACAACCAGAGTCGAGA
GGTGGAAATGAGCACCCGGGACCGATTCCAG
CTCACTGGGGATCCCGGCAAAGGGAGCTGCT
CCTTGGTGATCAGAGACGCGCAGAGGGAGGA
TGAGGCATGGTACTTCTTTCGGGTGGAGAGA
GGAAGCCGTGTGAGACATAGTTTCCTGAGCA
ATGCGTTCTTTCTAAAAGTAACAGCCCTGAC
TAAGAAGCCTGATGTCTACATCCCCGAGACC
CTGGAGCCCGGGCAGCCGGTGACGGTCATCT
GTGTGTTTAACTGGGCTTTCAAGAAATGTCC
AGCCCCTTCTTTCTCCTGGACGGGGGCTGCC
CTCTCCCCTAGAAGAACCAGACCAAGCACCT
CCCACTTCTCAGTGCTCAGCTTCACGCCCAG
CCCCCAGGACCACGACACCGACCTCACCTGC
CATGTGGACTTCTCCAGAAAGGGTGTGAGCG
CACAGAGGACCGTCCGACTCCGTGTGGCCTA
TGCCCCCAAAGACCTTATTATCAGCATTTCA
CATGACAACACGTCAGCCCTGGAACTCCAGG
GAAACGTCATATATCTGGAAGTTCAGAAAGG
CCAGTTCCTGCGGCTCCTCTGTGCTGCTGAC
AGCCAGCCCCCTGCCACGCTGAGCTGGGTCC
TGCAGGACAGAGTCCTCTCCTCGTCCCACCC
CTGGGGCCCCAGAACCCTGGGGCTGGAGCTG
CGTGGGGTAAGGGCCGGGGATTCAGGGCGCT
ACACCTGCCGAGCGGAGAACAGGCTTGGCTC
CCAGCAGCAAGCCCTGGACCTCTCTGTGCAG
TATCCTCCAGAGAACCTGAGAGTGATGGTTT
CCCAAGCAAACAGGACAGTCCTGGAAAACCT
CGGGAACGGCACATCCCTCCCGGTCCTGGAG
GGCCAAAGCCTGCGCCTGGTCTGTGTCACCC
ACAGCAGCCCCCCAGCCAGGCTGAGCTGGAC
CCGGTGGGGACAGACCGTGGGCCCCTCCCAG
CCCTCAGACCCCGGGGTCCTGGAGCTGCCAC
CCATTCAAATGGAGCACGAAGGAGAGTTCAC
CTGCCACGCTCAGCACCCTCTGGGCTCCCAG
CACGTCTCTCTCAGCCTCTCCGTGCACTACC
CTCCACAGCTGCTGGGCCCCTCCTGCTCCTG
GGAGGCTGAGGGTCTGCACTGCAGCTGCTCC
TCCCAGGCCAGCCCGGCCCCCTCTCTGCGCT
GGTGGCTTGGGGAGGAGCTGCTGGAGGGGAA

-continued

CAGCAGTCAGGGCTCCTTCGAGGTCACCCCC
AGCTCAGCCGGGCCCTGGGCCAACAGCTCCC
TGAGCCTCCATGGAGGGCTCAGCTCCGGCCT
CAGGCTCCGCTGTAAGGCCTGGAACGTCCAC
GGGGCCCAGAGTGGCTCTGTCTTCCAGCTGC
TACCAGGGAAGCTGGAGCATGGGGGAGGACT
TGGCCTGGGGGCTGCCCTGGGAGCTGGCGTC
GCTGCCCTGCTCGCTTTCTGTTCCTGCCTTG
TCGTCTTCAGGGTGAAGATCTGCAGGAAGGA
AGCTCGCAAGAGGGCAGCAGCTGAGCAGGAC
GTGCCCTCCACCCTGGGACCCATCTCCCAGG
GTCACCAGCATGAATGCTCGGCAGGCAGCTC
CCAAGACCACCCGCCCCCAGGTGCAGCCACC
TACACCCCGGGGAAGGGGGAAGAGCAGGAGC
TCCACTATGCCTCCCTCAGCTTCCAGGGCCT
GAGGCTCTGGGAGCCTGCGGACCAGGAGGCC
CCCAGCACCACCGAGTACTCGGAGATCAAGA
TCCACACAGGACAGCCCCTGAGGGGCCCAGG
CTTTGGGCTTCAATTGGAGAGGGAGATGTCA
GGGATGGTTCCAAAGTGAAGAGGTCTCCATG
GCAACAGGACACCAGCAAGTGTGTGGGAGTC
GCACTGGT
GTGACGGCCAGAACTGGACTCAGATTTCAGC
CCCATCCCCAATGAAGAGCTTGAGTTTGAAG
ATTATACTTTTTTTGAGACAGGGTCTGACTC
TGTCCTCCAGGCCAGAGTCCAGTGGTGCAAT
CTCAGCTCACTGTAGCCTCAACCTGCCAGGT
TGAAGTGAGCCTCCCATTTCAGCCTCCCAAG
TAGCTGGGACTACAATTGTGAGCCACCATGC
CAGGCTCATTGTTATATTTTTAGTAGAGACA
GGGTTTTGCCATGTTTCCCTGGCTGGTCTCA
GACTCCTGGGCTCAAGCAATCTGCCCGCCTC
TGCCTCCCAAAGTGCTGGGATTACAGACGTG
AGCCACCACAGCTGGCTGAAGATTATACTTT
CAATTCAGAGCGAGTTTGAAGATGACACTTT
GAGGCATCGTGTCTATGGTTCATTACTACAG
AAGCTTCTCTGGATGTGTAAAGCACAGGAAA
CCAGGCAGAGGAGGCACAGGGTGCTCTCCAG
AACGAGAAGCCAGCTCCTGGAGTTGTTTGCT
GCAACTGCCATTCCCCGTTGATGACCATGCT

-continued

CTTCCTTCAGAAGAGGGAGAGTGAGAGGACC
AAGTCCAAGTGGTTCCCATTTGAACATTTAA
AAAAAAAAAAAAGGCTGGGCATGGTGGCTCA
CGCCTGTAATCTCAACACTTTGGGAGGCTGA
AGTGGGTGGATCACAAGTCAGGAGTTCAAGA
CCAGCCTGGGCAAGATGGTGAAACCCCATCT
CTACTAAAAATACAAAAATTAGCCGGGCATG
GTGGCGGGCGCCTAAAATCCCAGCTACTCGG
GAGACTAGGCAGAGAATTGGTTGAACCCGGG
AGGTGGAGGTTGCAGTGAGCCGAGATCGTCC
CACTGCACTCCAGCCTGGGCAACAGAGTGAG
ACTCTGTTTCTAAATAAATAAATGAAAAAAA
AAAAAAAAAAAAA

SEQ ID NO: 37

MLLLLLLLPPLLCGRVGAKEQKDYLLTMQKS
VTVQEGLCVSVLCSFSYPQNGWTASDPVHGY
WFRAGDHVSRNIPVATNNPARAVQEETRDRF
HLLGDPQNKDCTLSIRDTRESDAGTYVFCVE
RGNMKWNYKYDQLSVNVTASQDLLSRYRLEV
PESVTVQEGLCVSVPCSVLYPHYNWTASSPV
YGSWFKEGADIPWDIPVATNTPSGKVQEDTH
GRFLLLGDPQTNNCSLSIRDARKGDSGKYYF
QVERGSRKWNYIYDKLSVHVTALTHMPTFSI
PGTLESGHPRNLTCSVPWACEQGTPPTITWM
GASVSSLDPTITRSSMLSLIPQPQDHGTSLT
CQVTLPGAGVTMTRAVRLNISYPPQNLTMTV
FQGDGTASTTLRNGSALSVLEGQSLHLVCAV
DSNPPARLSWTWGSLTLSPSQSSNLGVLELP
RVHVKDEGEFTCRAQNPLGSQHISLSLSLQN
EYTGKMRPISGVTLGAFGGAGATALVFLYFC
IIFVVVRSCRKKSARPAVGVGDTGMEDANAV
RGSASQGPLIESPADDSPPHHAPPALATPSP
EEGEIQYASLSFHKARPQYPQEQEAIGYEYS
EINIPK

SEQ ID NO: 38

ATGCTACTGCTGCTGCTACTGCTGCCACCCC
TGCTCTGTGGGAGAGTGGGGGCTAAGGAACA
GAAGGATTACCTGCTGACAATGCAGAAGTCC
GTGACGGTGCAGGAGGGCCTGTGTGTCTCTG
TGCTTTGCTCCTTCTCCTACCCCCAAAATGG
CTGGACTGCCTCCGATCCAGTTCATGGCTAC
TGGTTCCGGGCAGGGGACCATGTAAGCCGGA

-continued

ACATTCCAGTGGCCACAAACAACCCAGCTCG
AGCAGTGCAGGAGGAGACTCGGGACCGATTC
CACCTCCTTGGGGACCCACAGAACAAGGATT
GTACCCTGAGCATCAGAGACACCAGAGAGAG
TGATGCAGGGACATACGTCTTTTGTGTAGAG
AGAGGAAATATGAAATGGAATTATAAATATG
ACCAGCTCTCTGTGAATGTGACAGCGTCCCA
GGACCTACTGTCAAGATACAGGCTGGAGGTG
CCAGAGTCGGTGACTGTGCAGGAGGGTCTGT
GTGTCTCTGTGCCCTGCAGTGTCCTTTACCC
CCATTACAACTGGACTGCCTCTAGCCCTGTT
TATGGATCCTGGTTCAAGGAAGGGGCCGATA
TACCATGGGATATTCCAGTGGCCACAAACAC
CCCAAGTGGAAAAGTGCAAGAGGATACCCAC
GGTCGATTCCTCCTCCTTGGGGACCCACAGA
CCAACAACTGCTCCCTGAGCATCAGAGATGC
CAGGAAGGGGGATTCAGGGAAGTACTACTTC
CAGGTGGAGAGAGGAAGCAGGAAATGGAACT
ACATATATGACAAGCTCTCTGTGCATGTGAC
AGCCCTGACTCACATGCCCACCTTCTCCATC
CCGGGGACCCTGGAGTCTGGCCACCCCAGGA
ACCTGACCTGCTCTGTGCCCTGGGCCTGTGA
ACAGGGGACGCCCCCCACGATCACCTGGATG
GGGGCCTCCGTGTCCTCCCTGGACCCCACTA
TCACTCGCTCCTCGATGCTCAGCCTCATCCC
ACAGCCCCAGGACCATGGCACCAGCCTCACC
TGTCAGGTGACCTTGCCTGGGGCCGGCGTGA
CCATGACCAGGGCTGTCCGACTCAACATATC
CTATCCTCCTCAGAACTTGACCATGACTGTC
TTCCAAGGAGATGGCACAGCATCCACAACCT
TGAGGAATGGCTCGGCCCTTTCAGTCCTGGA
GGGCCAGTCCCTGCACCTTGTCTGTGCTGTC
GACAGCAATCCCCCTGCCAGGCTGAGCTGGA
CCTGGGGGAGCCTGACCCTGAGCCCCTCACA
GTCCTCGAACCTTGGGGTGCTGGAGCTGCCT
CGAGTGCATGTGAAGGATGAAGGGGAATTCA
CCTGCCGAGCTCAGAACCCTCTAGGCTCCCA
GCACATTTCCCTGAGCCTCTCCCTGCAAAAC
GAGTACACAGGCAAAATGAGGCCTATATCAG
GAGTGACGCTAGGGGCATTCGGGGGAGCTGG

AGCCACAGCCCTGGTCTTCCTGTACTTCTGC
ATCATCTTCGTTGTAGTGAGGTCCTGCAGGA
AGAAATCGGCAAGGCCAGCAGTGGGCGTGGG
GGATACAGGCATGGAGGACGCAAACGCTGTC
AGGGGCTCAGCCTCTCAGGGACCCCTGATTG
AATCCCCGGCAGATGACAGCCCCCCACACCA
TGCTCCGCCAGCCCTGGCCACCCCCTCCCCA
GAGGAAGGAGAGATCCAGTATGCATCCCTCA
GCTTCCACAAAGCGAGGCCTCAGTACCCACA
GGAACAGGAGGCCATCGGCTATGAGTACTCC
GAGATCAACATCCCCAAGTGA

SEQ ID NO: 39

MLPLLLLPLLWGGSLQEKPVYELQVQKSVTV
QEGLCVLVPCSFSYPWRSWYSSPPLYVYWFR
DGEIPYYAEVVATNNPDRRVKPETQGRFRLL
GDVQKKNCSLSIGDARMEDTGSYFFRVERGR
DVKYSYQQNKLNLEVTALIEKPDIHFLEPLE
SGRPTRLSCSLPGSCEAGPPLTFSWTGNALS
PLDPETTRSSELTLTPRPEDHGTNLTCQVKR
QGAQVTTERTVQLNVSYAPQNLAISIFFRNG
TGTALRILSNGMSVPIQEGQSLFLACTVDSN
PPASLSWFREGKALNPSQTSMSGTLELPNIG
AREGGEFTCRVQHPLGSQHLSFILSVQRSSS
SCICVTEKQQGSWPLVLTLIRGALMGAGFLL
TYGLTWIYYTRCGGPQQSRAERPG

SEQ ID NO: 40

ATGCTGCCCCTGCTGCTGCTGCCCCTGCTGT
GGGGGGGGTCCCTGCAGGAGAAGCCAGTGTA
CGAGCTGCAAGTGCAGAAGTCGGTGACGGTG
CAGGAGGGCCTGTGCGTCCTTGTGCCCTGCT
CCTTCTCTTACCCCTGGAGATCCTGGTATTC
CTCTCCCCCACTCTACGTCTACTGGTTCCGG
GACGGGGAGATCCCATACTACGCTGAGGTTG
TGGCCACAAACAACCCAGACAGAAGAGTGAA
GCCAGAGACCCAGGGCCGATTCCGCCTCCTT
GGGGATGTCCAGAAGAAGAACTGCTCCCTGA
GCATCGGAGATGCCAGAATGGAGGACACGGG
AAGCTATTTCTTCCGCGTGGAGAGAGGAAGG
GATGTAAAATATAGCTACCAACAGAATAAGC
TGAACTTGGAGGTGACAGCCCTGATAGAGAA
ACCCGACATCCACTTTCTGGAGCCTCTGGAG
TCCGGCCGCCCCACAAGGCTGAGCTGCAGCC

TTCCAGGATCCTGTGAAGCGGGACCACCTCT
CACATTCTCCTGGACGGGGAATGCCCTCAGC
CCCCTGGACCCCGAGACCACCCGCTCCTCGG
AGCTCACCCTCACCCCCAGGCCCGAGGACCA
TGGCACCAACCTCACCTGTCAGGTGAAACGC
CAAGGAGCTCAGGTGACCACGGAGAGAACTG
TCCAGCTCAATGTCTCCTATGCTCCACAGAA
CCTCGCCATCAGCATCTTCTTCAGAAATGGC
ACAGGCACAGCCCTGCGGATCCTGAGCAATG
GCATGTCGGTGCCCATCCAGGAGGGCCAGTC
CCTGTTCCTCGCCTGCACAGTTGACAGCAAC
CCCCCTGCCTCACTGAGCTGGTTCCGGGAGG
GAAAAGCCCTCAATCCTTCCCAGACCTCAAT
GTCTGGGACCCTGGAGCTGCCTAACATAGGA
GCTAGAGAGGGAGGGGAATTCACCTGCCGGG
TTCAGCATCCGCTGGGCTCCCAGCACCTGTC
CTTCATCCTTTCTGTGCAGAGAAGCTCCTCT
TCCTGCATATGTGTAACTGAGAAACAGCAGG
GCTCCTGGCCCCTCGTCCTCACCCTGATCAG
GGGGGCTCTCATGGGGGCTGGCTTCCTCCTC
ACCTATGGCCTCACCTGGATCTACTATACCA
GGTGTGGAGGCCCCCAGCAGAGCAGGGCTGA
GAGGCCTGGCTGA

SEQ ID NO: 41

MEKSIWLLACLAWVLPTGSFVRTKIDTTENL
LNTEVHSSPAQRWSMQVPPEVSAEAGDAAVL
PCTFTHPHRHYDGPLTAIWRAGEPYAGPQVF
RCAAARGSELCQTALSLHGRFRLLGNPRRND
LSLRVERLALADDRRYFCRVEFAGDVHDRYE
SRHGVRLHVTAAPRIVNISVLPSPAHAFRAL
CTAEGEPPPALAWSGPALGNSLAAVRSPREG
HGHLVTAELPALTHDGRYTCTAANSLGRSEA
SVYLFRFHGASGASTVALLLGALGFKALLLL
GVLAARAARRRPEHLDTPDTPPRSQAQESNY
ENLSQMNPRSPPATMCSP

SEQ ID NO: 42

ATGGAAAAGTCCATCTGGCTGCTGGCCTGCT
TGGCGTGGGTTCTCCCGACAGGCTCATTTGT
GAGAACTAAAATAGATACTACGGAGAACTTG
CTCAACACAGAGGTGCACAGCTCGCCAGCGC
AGCGCTGGTCCATGCAGGTGCCACCCGAGGT

GAGCGCGGAGGCAGGCGACGCGGCAGTGCTG

CCCTGCACCTTCACGCACCCGCACCGCCACT

ACGACGGGCCGCTGACGGCCATCTGGCGCGC

GGGCGAGCCCTATGCGGGCCCGCAGGTGTTC

CGCTGCGCTGCGGCGCGGGGCAGCGAGCTCT

GCCAGACGGCGCTGAGCCTGCACGGCCGCTT

CCGGCTGCTGGGCAACCCGCGCCGCAACGAC

CTCTCGCTGCGCGTCGAGCGCCTCGCCCTGG

CTGACGACCGCCGCTACTTCTGCCGCGTCGA

GTTCGCCGGCGACGTCCATGACCGCTACGAG

AGCCGCCACGGCGTCCGGCTGCACGTGACAG

CCGCGCCGCGGATCGTCAACATCTCGGTGCT

GCCCAGTCCGGCTCACGCCTTCCGCGCGCTC

TGCACTGCCGAAGGGGAGCCGCCGCCCGCCC

TCGCCTGGTCCGGCCCGGCCCTGGGCAACAG

CTTGGCAGCCGTGCGGAGCCCGCGTGAGGGT

CACGGCCACCTAGTGACCGCCGAACTGCCCG

CACTGACCCATGACGGCCGCTACACGTGTAC

GGCCGCCAACAGCCTGGGCCGCTCCGAGGCC

AGCGTCTACCTGTTCCGCTTCCATGGCGCCA

GCGGGGCCTCGACGGTCGCCCTCCTGCTCGG

CGCTCTCGGCTTCAAGGCGCTGCTGCTGCTC

GGGGTCCTGGCCGCCCGCGCTGCCCGCCGCC

GCCCAGAGCATCTGGACACCCCGGACACCCC

ACCACGGTCCCAGGCCCAGGAGTCCAATTAT

GAAAATTTGAGCCAGATGAACCCCCGGAGCC

CACCAGCCACCATGTGCTCACCGTGA

SEQ ID NO: 43

QSSVTVQEGMCVHVRCSFSYPVDSQTDSDPV

HGYWFRAGNDISWKAPVATNNPAWAVQEE

TRDRFHLLGDPQTKNCTLSIRDARMSDAGRY

F

SEQ ID NO: 44

LTMQSSVTVQEGLCVHVPCSFSYPSHGWIYP

GPVVHGYWFREGANTDQDAPVATNNPARAVW

EETRDRFHLLGDPHTKNCTLSIRDARRSDAG

RYFFRMEKGSIKWNYKHHRLSVNVT

SEQ ID NO: 45

CAGACCAGCAAGCTGCTGACCATGCAGAGCA

GCGTGACCGTGCAGGAGGGCCTGTGCGTGCA

TGTGCCCTGCAGCTTCAGCTACCCCAGCCAC

GGCTGGATCTACCCCGGTCCCGTAGTGCACG

GCTACTGGTTCAGGGAGGGCGCCAACACCGA

CCAGGACGCTCCCGTGGCAACCAACAACCCC

GCCAGGGCCGTGTGGGAGGAGACCAGGGACA

GGTTCCACCTGCTGGGCGACCCCCACACCAA

GAACTGCACCCTGAGCATCAGGGACGCCAGG

AGGAGCGACGCCGGCAGGTACTTCTTCAGGA

TGGAGAAGGGGTCTATCAAGTGGAACTACAA

GCACCACCGGCTGAGCGTGAATGTGACCGCC

CTGACCCACCGGCCCAATATCCTCATCCCCG

GCACCCTGGAGAGCGGCTGCCCCCAGAATCT

TACCTGCAGCGTACCCTGGGCCTGCGAGCAG

GGCACCCCTCCAATGATCAGCTGGATCGGCA

CCAGCGTGAGCCCCCTGGACCCTAGTACCAC

CAGGAGCAGCGTGCTGACCCTGATCCCCCAG

CCCCAGGACCACGGAACCAGCCTGACCTGCC

AGGTGACCTTCCCCGGAGCCAGCGTAACCAC

CAACAAGACCGTGCACCTGAACGTGAGCTAC

CCACCCCAAAACCTGACCATGACCGTGTTCC

AGGGCGACGGCACGGTGAGCACCGTACTGGG

CAACGGCAGCTCTCTGAGCCTGCCCGAGGGC

CAGAGCTTGCGGCTGGTCTGCGCCGTGGATG

CTGTGGACAGCAACCCTCCCGCCAGGCTGAG

CCTGAGCTGGAGGGGCCTGACCCTGTGCCCC

AGCCAGCCCAGCAATCCCGGCGTGCTGGAGC

TGCCCTGGGTTCACCTGAGGGACGCTGCCGA

GTTCACATGTAGGGCCCAGAACCCCCTGGGC

TCTCAGCAGGTGTACCTGAACGTGTCTCTTC

AGAGTAAGGCCACCAGCGGCGTGACCCAAGG

AGGCTATATCCCCGAGGCTCCTAGAGATGGC

CAGGCCTATGTTCGGAAGGATGGCGAATGGG

TGCTGCTGAGCACCTTCCTTGAACCTCGAGG

GCCTACCATCAAGCCCTGTCCTCCATGCAAG

TGCCCCGCTCCTAATCTGCTCGGAGGCCCCA

GCGTGTTCATCTTCCCACCTAAGATCAAGGA

CGTGCTGATGATCTCTCTGAGCCCCATCGTG

ACCTGCGTGGTGGTGGATGTGTCCGAGGACG

ATCCCGATGTGCAGATCAGTTGGTTCGTGAA

CAACGTGGAAGTGCACACAGCCCAGACACAG

ACCCACAGAGAGGACTACAACAGCACCCTGA

GAGTGGTGTCTGCCCTGCCTATCCAGCACCA

GGATTGGATGAGCGGCAAAGAATTCAAGTGC

-continued

AAAGTGAACAACAAGGACCTGCCTGCTCCTA
TCGAGCGGACCATCTCTAAGCCTAAGGGCTC
TGTTAGAGCCCCTCAGGTGTACGTGCTGCCT
CCTCCAGAGGAAGAGATGACCAAGAAACAAG
TGACCCTGACCTGCATGGTCACCGACTTCAT
GCCCGAGGACATCTACGTGGAATGGACCAAC
AACGGCAAGACCGAGCTGAACTACAAGAACA
CCGAGCCTGTGCTGGACAGCGACGGCAGCTA
CTTCATGTACTCCAAGCTGCGCGTGGAAAAG
AAGAACTGGGTCGAGCGGAACAGCTACAGCT
GCTCTGTGGTGCACGAGGGCCTGCACAATCA
CCACACCACCAAGAGCTTCAGCCGTACGCCT
GGAAAG

SEQ ID NO: 46

CAGAAGTCCAACAGAAAGGACTACAGCCTGA
CCATGCAGAGCAGCGTGACAGTGCAAGAGGG
GATGTGCGTCCACGTCCGGTGCAGCTTTAGC
TACCCTGTGGACAGCCAGACCGACAGCGATC
CTGTGCACGGCTACTGGTTCAGAGCCGGCAA
CGACATCTCTTGGAAAGCCCCAGTGGCCACC
AACAATCCTGCCTGGGCTGTGCAAGAAGAGA
CACGGGACAGATTCCATCTGCTGGGCGACCC
TCAGACCAAGAACTGCACACTGAGCATCCGG
GACGCCAGAATGTCTGACGCCGGCAGATACT
TCTTCCGGATGGAAAAGGGCAACATCAAGTG
GAACTATAAGTACGACCAGCTGAGCGTGAAC
GTGACAGCCCTGACACACAGACCCAACATTC
TGATCCCCGGCACACTGGAAAGCGGCTGCTT
CCAGAATCTGACCTGCTCTGTGCCTTGGGCC
TGCGAGCAGGGAACACCTCCTATGATCAGCT
GGATGGGAACCAGCGTGTCCCCTCTGCACCC
TAGCACCACAAGATCCAGCGTGCTGACACTG
ATCCCTCAGCCTCAGCACCACGGCACAAGCC
TGACCTGTCAAGTTACACTTCCTGGCGCTGG
CGTGACCACCAACAGAACAATCCAGCTCAAC
GTGTCCTATCCTCCTCAGAACCTGACCGTGA
CCGTGTTCCAAGGCGAGGGCACAGCTTCTAC
AGCCCTGGGCAATAGCAGCAGCCTGTCTGTG
CTGGAAGGCCAGTCTCTGAGACTCGTGTGCG
CCGTGGATAGCAACCCTCCTGCTAGACTGAG
CTGGACTTGGCGGAGCCTGACACTGTACCCT

-continued

AGCCAGCCTAGCAATCCCCTGGTGCTGGAAC
TGCAAGTGCACCTGGGAGATGAGGGCGAGTT
CACCTGTAGAGCCCAGAATAGCCTGGGCAGC
CAGCACGTGTCCCTGAACCTGTCTCTGCAGC
AAGAGTACACCGGCAAGATGAGGCCTGTGTC
TGGCGTTCTGCTGGGAGCCGTGGGAGGCTAT
ATCCCCGAGGCTCCTAGAGATGGCCAGGCCT
ATGTTCGGAAGGATGGCGAATGGGTGCTGCT
GAGCACCTTCCTTGAACCTCGAGGGCCTACC
ATCAAGCCCTGTCCTCCATGCAAGTGCCCCG
CTCCTAATCTGCTCGGAGGCCCCAGCGTGTT
CATCTTCCCACCTAAGATCAAGGACGTGCTG
ATGATCTCTCTGAGCCCCATCGTGACCTGCG
TGGTGGTGGATGTGTCCGAGGACGATCCCGA
TGTGCAGATCAGTTGGTTCGTGAACAACGTG
GAAGTGCACACAGCCCAGACACAGACCCACA
GAGAGGACTACAACAGCACCCTGAGAGTGGT
GTCTGCCCTGCCTATCCAGCACCAGGATTGG
ATGAGCGGCAAAGAATTCAAGTGCAAAGTGA
ACAACAAGGACCTGCCTGCTCCTATCGAGCG
GACCATCTCTAAGCCTAAGGGCTCTGTTAGA
GCCCCTCAGGTGTACGTGCTGCCTCCTCCAG
AGGAAGAGATGACCAAGAAACAAGTGACCCT
GACCTGCATGGTCACCGACTTCATGCCCGAG
GACATCTACGTGGAATGGACCAACAACGGCA
AGACCGAGCTGAACTACAAGAACACCGAGCC
TGTGCTGGACAGCGACGGCAGCTACTTCATG
TACTCCAAGCTGCGCGTGGAAAAGAAGAACT
GGGTCGAGCGGAACAGCTACAGCTGCTCTGT
GGTGCACGAGGGCCTGCACAATCACCACACC
ACCAAGAGCTTCAGCCGTACGCCTGGAAAG

SEQ ID NO: 47

CAGAAGTCCAACAGAAAGGACTACAGCCTGA
CCATGCAGAGCAGCGTGACAGTGCAAGAGGG
GATGTGCGTCCACGTCCGGTGCAGCTTTAGC
TACCCTGTGGACAGCCAGACCGACAGCGATC
CTGTGCACGGCTACTGGTTCAGAGCCGGCAA
CGACATCTCTTGGAAAGCCCCAGTGGCCACC
AACAATCCTGCCTGGGCTGTGCAAGAAGAGA
CACGGGACAGATTCCATCTGCTGGGCGACCC
TCAGACCAAGAACTGCACACTGAGCATCCGG

-continued

GACGCCAGAATGTCTGACGCCGGCAGATACT
TCTTCCGGATGGAAAAGGGCAACATCAAGTG
GAACTATAAGTACGACCAGCTGAGCGTGAAC
GTGACAGCCCTGACACACAGACCCAACATTC
TGATCCCCGGCACACTGGAAAGCGGCTGCTT
CCAGAATCTGACCTGCTCTGTGCCTTGGGCC
TGCGAGCAGGGAACACCTCCTATGATCAGCT
GGATGGGAACCAGCGTGTCCCCTCTGCACCC
TAGCACCACAAGATCCAGCGTGCTGACACTG
ATCCCTCAGCCTCAGCACCACGGCACAAGCC
TGACCTGTCAAGTTACACTTCCTGGCGCTGG
CGTGACCACCAACAGAACAATCCAGCTCAAC
GTGTCCTATCCTGGTGGCGGAGGATCTGGCG
GAGGTGGAAGCGGCGGAGGCGGATCTCAGAA
GTCCAACAGAAAGGACTACAGCCTGACCATG
CAGAGCAGCGTGACAGTGCAAGAGGGGATGT
GCGTCCACGTCCGGTGCAGCTTTAGCTACCC
TGTGGACAGCCAGACCGACAGCGATCCTGTG
CACGGCTACTGGTTCAGAGCCGGCAACGACA
TCTCTTGGAAAGCCCCAGTGGCCACCAACAA
TCCTGCCTGGGCTGTGCAAGAAGAGACACGG
GACAGATTCCATCTGCTGGGCGACCCTCAGA
CCAAGAACTGCACACTGAGCATCCGGGACGC
CAGAATGTCTGACGCCGGCAGATACTTCTTC
CGGATGGAAAAGGGCAACATCAAGTGGAACT
ATAAGTACGACCAGCTGAGCGTGAACGTGAC
AGCCCTGACACACAGACCCAACATTCTGATC
CCCGGCACACTGGAAAGCGGCTGCTTCCAGA
ATCTGACCTGCTCTGTGCCTTGGGCCTGCGA
GCAGGGAACACCTCCTATGATCAGCTGGATG
GGAACCAGCGTGTCCCCTCTGCACCCTAGCA
CCACAAGATCCAGCGTGCTGACACTGATCCC
TCAGCCTCAGCACCACGGCACAAGCCTGACC
TGTCAAGTTACACTTCCTGGCGCTGGCGTGA
CCACCAACAGAACAATCCAGCTCAACGTGTC
CTATCCTGAACCTCGAGGGCCTACCATCAAG
CCCTGTCCTCCATGCAAGTGCCCCGCTCCTA
ATCTGCTCGGAGGCCCCAGCGTGTTCATCTT
CCCACCTAAGATCAAGGACGTGCTGATGATC
TCTCTGAGCCCCATCGTGACCTGCGTGGTGG

-continued

TGGATGTGTCCGAGGACGATCCCGATGTGCA
GATCAGTTGGTTCGTGAACAACGTGGAAGTG
CACACAGCCCAGACACAGACCCACAGAGAGG
ACTACAACAGCACCCTGAGAGTGGTGTCTGC
CCTGCCTATCCAGCACCAGGATTGGATGAGC
GGCAAAGAATTCAAGTGCAAAGTGAACAACA
AGGACCTGCCTGCTCCTATCGAGCGGACCAT
CTCTAAGCCTAAGGGCTCTGTTAGAGCCCCT
CAGGTGTACGTGCTGCCTCCTCCAGAGGAAG
AGATGACCAAGAAACAAGTGACCCTGACCTG
CATGGTCACCGACTTCATGCCCGAGGACATC
TACGTGGAATGGACCAACAACGGCAAGACCG
AGCTGAACTACAAGAACACCGAGCCTGTGCT
GGACAGCGACGGCAGCTACTTCATGTACTCC
AAGCTGCGCGTGGAAAAGAAGAACTGGGTCG
AGCGGAACAGCTACAGCTGCTCTGTGGTGCA
CGAGGGCCTGCACAATCACCACACCACCAAG
AGCTTCAGCCGTACGCCTGGAAAG

SEQ ID NO: 48

CAGAAGTCCAACAGAAAGGACTACAGCCTGA
CCATGCAGAGCAGCGTGACAGTGCAAGAGGG
GATGTGCGTCCACGTCCGGTGCAGCTTTAGC
TACCCTGTGGACAGCCAGACCGACAGCGATC
CTGTGCACGGCTACTGGTTCAGAGCCGGCAA
CGACATCTCTTGGAAAGCCCCAGTGGCCACC
AACAATCCTGCCTGGGCTGTGCAAGAAGAGA
CACGGGACAGATTCCATCTGCTGGGCGACCC
TCAGACCAAGAACTGCACACTGAGCATCCGG
GACGCCAGAATGTCTGACGCCGGCAGATACT
TCTTCCGGATGGAAAAGGGCAACATCAAGTG
GAACTATAAGTACGACCAGCTGAGCGTGAAC
GTGACAGCCCTGACACACAGACCCAACATTC
TGATCCCCGGCACACTGGAAAGCGGCTGCTT
CCAGAATCTGACCTGCTCTGTGCCTTGGGCC
TGCGAGCAGGGAACACCTCCTATGATCAGCT
GGATGGGAACCAGCGTGTCCCCTCTGCACCC
TAGCACCACAAGATCCAGCGTGCTGACACTG
ATCCCTCAGCCTCAGCACCACGGCACAAGCC
TGACCTGTCAAGTTACACTTCCTGGCGCTGG
CGTGACCACCAACAGAACAATCCAGCTCAAC
GTGTCCTATCCTCCTCAGAACCTGACCGTGA

-continued

CCGTGTTCCAAGGCGAGGGCACAGCTTCTAC
AGCCCTGGGCAATAGCAGCAGCCTGTCTGTG
CTGGAAGGCCAGTCTCTGAGACTCGTGTGCG
CCGTGGATAGCAACCCTCCTGCTAGACTGAG
CTGGACTTGGCGGAGCCTGACACTGTACCCT
AGCCAGCCTAGCAATCCCCTGGTGCTGGAAC
TGCAAGTGCACCTGGGAGATGAGGGCGAGTT
CACCTGTAGAGCCCAGAATAGCCTGGGCAGC
CAGCACGTGTCCCTGAACCTGTCTCTGCAGC
AAGAGTACACCGGCAAGATGAGGCCTGTGTC
TGGCGTTCTGCTGGGAGCCGTGGGAGAACCT
CGAGGGCCTACCATCAAGCCCTGTCCTCCAT
GCAAGTGCCCCGCTCCTAATCTGCTCGGAGG
CCCCAGCGTGTTCATCTTCCCACCTAAGATC
AAGGACGTGCTGATGATCTCTCTGAGCCCCA
TCGTGACCTGCGTGGTGGTGGATGTGTCCGA
GGACGATCCCGATGTGCAGATCAGTTGGTTC
GTGAACAACGTGGAAGTGCACACAGCCCAGA
CACAGACCCACAGAGAGGACTACAACAGCAC
CCTGAGAGTGGTGTCTGCCCTGCCTATCCAG
CACCAGGATTGGATGAGCGGCAAAGAATTCA
AGTGCAAAGTGAACAACAAGGACCTGCCTGC
TCCTATCGAGCGGACCATCTCTAAGCCTAAG
GGCTCTGTTAGAGCCCCTCAGGTGTACGTGC
TGCCTCCTCCAGAGGAAGAGATGACCAAGAA
ACAAGTGACCCTGACCTGCATGGTCACCGAC
TTCATGCCCGAGGACATCTACGTGGAATGGA
CCAACAACGGCAAGACCGAGCTGAACTACAA
GAACACCGAGCCTGTGCTGGACAGCGACGGC
AGCTACTTCATGTACTCCAAGCTGCGCGTGG
AAAAGAAGAACTGGGTCGAGCGGAACAGCTA
CAGCTGCTCTGTGGTGCACGAGGGCCTGCAC
AATCACCACACCACCAAGAGCTTCAGCCGTA
CGCCTGGAAAGGGTGGCGGAGGATCTGGCGG
AGGTGGAAGCGGCGGAGGCGGATCTCAGAAG
TCCAACAGAAAGGACTACAGCCTGACCATGC
AGAGCAGCGTGACAGTGCAAGAGGGGATGTG
CGTCCACGTCCGGTGCAGCTTTAGCTACCCT
GTGGACAGCCAGACCGACAGCGATCCTGTGC
ACGGCTACTGGTTCAGAGCCGGCAACGACAT
CTCTTGGAAAGCCCCAGTGGCCACCAACAAT

-continued

CCTGCCTGGGCTGTGCAAGAAGAGACACGGG
ACAGATTCCATCTGCTGGGCGACCCTCAGAC
CAAGAACTGCACACTGAGCATCCGGGACGCC
AGAATGTCTGACGCCGGCAGATACTTCTTCC
GGATGGAAAAGGGCAACATCAAGTGGAACTA
TAAGTACGACCAGCTGAGCGTGAACGTGACA
GCCCTGACACACAGACCCAACATTCTGATCC
CCGGCACACTGGAAAGCGGCTGCTTCCAGAA
TCTGACCTGCTCTGTGCCTTGGGCCTGCGAG
CAGGGAACACCTCCTATGATCAGCTGGATGG
GAACCAGCGTGTCCCCTCTGCACCCTAGCAC
CACAAGATCCAGCGTGCTGACACTGATCCCT
CAGCCTCAGCACCACGGCACAAGCCTGACCT
GTCAAGTTACACTTCCTGGCGCTGGCGTGAC
CACCAACAGAACAATCCAGCTCAACGTGTCC
TATCCTCCTCAGAACCTGACCGTGACCGTGT
TCCAAGGCGAGGGCACAGCTTCTACAGCCCT
GGGCAATAGCAGCAGCCTGTCTGTGCTGGAA
GGCCAGTCTCTGAGACTCGTGTGCGCCGTGG
ATAGCAACCCTCCTGCTAGACTGAGCTGGAC
TTGGCGGAGCCTGACACTGTACCCTAGCCAG
CCTAGCAATCCCCTGGTGCTGGAACTGCAAG
TGCACCTGGGAGATGAGGGCGAGTTCACCTG
TAGAGCCCAGAATAGCCTGGGCAGCCAGCAC
GTGTCCCTGAACCTGTCTCTGCAGCAAGAGT
ACACCGGCAAGATGAGGCCTGTGTCTGGCGT
TCTGCTGGGAGCCGTGGGA

SEQ ID NO: 49

QKSNRKDYSLTMQSSVTVQEGMCVHVRCSFS
YPVDSQTDSDPVHGYWFRAGNDISWKAPVAT
NNPAWAVQEETRDRFHLLGDPQTKNCTLSIR
DARMSDAGRYFFRMEKGNIKWNYKYDQLSVN
VTALTHRPNILIPGTLESGCFQNLTCSVPWA
CEQGTPPMISWMGTSVSPLHPSTTRSSVLTL
IPQPQHHGTSLTCQVTLPGAGVTTNRTIQLN
VSYPPQNLTVTVFQGEGTASTALGNSSSLSV
LEGQSLRLVCAVDSNPPARLSWTWRSLTLYP
SQPSNPLVLELQVHLGDEGEFTCRAQNSLGS
QHVSLNLSLQQEYTGKMRPVSGVLLGAVGEP
RGPTIKPCPPCKCPAPNLLGGPSVFIFPPKI
KDVLMISLSPIVTCVVVDVSEDDPDVQISWF

VNNVEVHTAQTQTHREDYNSTLRVVSALPIQ

HQDWMSGKEFKCKVNNKDLPAPIERTISKPK

GSVRAPQVYVLPPPEEEMTKKQVTLTCMVTD

FMPEDIYVEWTNNGKTELNYKNTEPVLDSDG

SYFMYSKLRVEKKNWVERNSYSCSVVHEGLH

NHHTTKSFSRTPGK

SEQ ID NO: 50

CAGAAGTCCAACAGAAAGGACTACAGCCTGA

CCATGCAGAGCAGCGTGACAGTGCAAGAGGG

GATGTGCGTCCACGTCCGGTGCAGCTTTAGC

TACCCTGTGGACAGCCAGACCGACAGCGATC

CTGTGCACGGCTACTGGTTCAGAGCCGGCAA

CGACATCTCTTGGAAAGCCCCAGTGGCCACC

AACAATCCTGCCTGGGCTGTGCAAGAAGAGA

CACGGGACAGATTCCATCTGCTGGGCGACCC

TCAGACCAAGAACTGCACACTGAGCATCCGG

GACGCCAGAATGTCTGACGCCGGCAGATACT

TCTTCCGGATGGAAAAGGGCAACATCAAGTG

GAACTATAAGTACGACCAGCTGAGCGTGAAC

GTGACAGCCCTGACACACAGACCCAACATTC

TGATCCCCGGCACACTGGAAAGCGGCTGCTT

CCAGAATCTGACCTGCTCTGTGCCTTGGGCC

TGCGAGCAGGGAACACCTCCTATGATCAGCT

GGATGGGAACCAGCGTGTCCCCTCTGCACCC

TAGCACCACAAGATCCAGCGTGCTGACACTG

ATCCCTCAGCCTCAGCACCACGGCACAAGCC

TGACCTGTCAAGTTACACTTCCTGGCGCTGG

CGTGACCACCAACAGAACAATCCAGCTCAAC

GTGTCCTATCCTCCTCAGAACCTGACCGTGA

CCGTGTTCCAAGGCGAGGGCACAGCTTCTAC

AGCCCTGGGCAATAGCAGCAGCCTGTCTGTG

CTGGAAGGCCAGTCTCTGAGACTCGTGTGCG

CCGTGGATAGCAACCCTCCTGCTAGACTGAG

CTGGACTTGGCGGAGCCTGACACTGTACCCT

AGCCAGCCTAGCAATCCCCTGGTGCTGGAAC

TGCAAGTGCACCTGGGAGATGAGGGCGAGTT

CACCTGTAGAGCCCAGAATAGCCTGGGCAGC

CAGCACGTGTCCCTGAACCTGTCTCTGCAGC

AAGAGTACACCGGCAAGATGAGGCCTGTGTC

TGGCGTTCTGCTGGGAGCCGTGGGAGAACCT

CGAGGGCCTACCATCAAGCCCTGTCCTCCAT

GCAAGTGCCCCGCTCCTAATCTGCTCGGAGG

CCCCAGCGTGTTCATCTTCCCACCTAAGATC

AAGGACGTGCTGATGATCTCTCTGAGCCCCA

TCGTGACCTGCGTGGTGGTGGATGTGTCCGA

GGACGATCCCGATGTGCAGATCAGTTGGTTC

GTGAACAACGTGGAAGTGCACACAGCCCAGA

CACAGACCCACAGAGAGGACTACAACAGCAC

CCTGAGAGTGGTGTCTGCCCTGCCTATCCAG

CACCAGGATTGGATGAGCGGCAAAGAATTCA

AGTGCAAAGTGAACAACAAGGACCTGCCTGC

TCCTATCGAGCGGACCATCTCTAAGCCTAAG

GGCTCTGTTAGAGCCCCTCAGGTGTACGTGC

TGCCTCCTCCAGAGGAAGAGATGACCAAGAA

ACAAGTGACCCTGACCTGCATGGTCACCGAC

TTCATGCCCGAGGACATCTACGTGGAATGGA

CCAACAACGGCAAGACCGAGCTGAACTACAA

GAACACCGAGCCTGTGCTGGACAGCGACGGC

AGCTACTTCATGTACTCCAAGCTGCGCGTGG

AAAAGAAGAACTGGGTCGAGCGGAACAGCTA

CAGCTGCTCTGTGGTGCACGAGGGCCTGCAC

AATCACCACACCACCAAGAGCTTCAGCCGTA

CGCCTGGAAAG

SEQ ID NO: 51

LQVQESVTVQEGLCVLVPCTFFHPIPYYDKN

SPVHGYWFREGAIISRDSPVATNKLDQEVQE

ETQGRFRLLGDPSRNNCSLSIVDARRRDNGS

YFFRMERGSTKYSYKSPQLSVHVT

SEQ ID NO: 52

LQVQESVTVQEGLCVLVPCTFFHPIPYYDKN

SPVHGYWFREGAIISRDSPVATNKLDQEVQE

ETQGRFRLLGDPSRNNCSLSIVDARRRDNGS

YFFRMERGSTKYSYKSPQLSVHVTDLTHRPK

ILIPGTLEPGHSKNLTCSVSWACEQGTPPIF

SWLSAAPTSLGPRTTHSSVLIITPRPQDHGT

NLTCQVKFAGAGVTTERTI

SEQ ID NO: 53

MGWSCIILFLVATATGVHSDPNFWLQVQESV

TVQEGLCVLVPCTFFHPIPYYDKNSPVHGYW

FREGAIISRDSPVATNKLDQEVQEETQGRFR

LLGDPSRNNCSLSIVDARRRDNGSYFFRMER

GSTKYSYKSPQLSVHVTDLTHRPKILIPGTL

EPGHSKNLTCSVSWACEQGTPPIFSWLSAAP

-continued

TSLGPRTTHSSVLIITPRPQDHGTNLTCQVK
FAGAGVTTERTIQLNVTYVPQNPTTGIFPGD
GSGKQETRAGVVHGYIPEAPRDGQAYVRKDG
EWVLLSTFLEPRGPTIKPCPPCKCPAPNLLG
GPSVFIFPPKIKDVLMISLSPIVTCVVVDVS
EDDPDVQISWFVNNVEVHTAQTQTHREDYNS
TLRVVSALPIQHQDWMSGKEFKCKVNNKDLP
APIERTISKPKGSVRAPQVYVLPPPEEEMTK
KQVTLTCMVTDFMPEDIYVEWTNNGKTELNY
KNTEPVLDSDGSYFMYSKLRVEKKNWVERNS
YSCSVVHEGLHNHHTTKSFSRTPGK

SEQ ID NO: 54

ATGGGCTGGTCCTGCATCATCCTGTTTCTGG
TGGCCACAGCCACAGGCGTGCACAGCGATCC
CAATTTCTGGCTGCAAGTGCAAGAGTCCGTG
ACCGTGCAAGAGGGCCTGTGTGTGCTGGTGC
CCTGCACCTTCTTTCACCCCATTCCTTACTA
CGACAAGAACAGCCCTGTGCACGGCTACTGG
TTTAGAGAGGGCGCCATCATCAGCAGAGATA
GCCCTGTGGCCACCAACAAGCTGGACCAAGA
GGTGCAAGAAGAGACACAGGGCAGATTCAGA
CTGCTGGGCGACCCCAGCAGAAACAACTGCA
GCCTGTCTATCGTGGACGCCAGGCGGAGAGA
CAACGGCAGCTACTTCTTCCGGATGGAACGG
GGCAGCACCAAGTACAGCTACAAGAGCCCTC
AGCTGTCCGTGCACGTGACCGACCTGACACA
CAGACCCAAGATTCTGATCCCCGGCACACTG
GAACCTGGCCACAGCAAGAATCTGACCTGCT
CCGTGTCCTGGGCCTGCGAACAGGGAACCCC
TCCTATCTTTAGCTGGCTGAGCGCCGCTCCT
ACATCTCTGGGCCCTAGAACAACACACAGCA
GCGTGCTGATCATCACCCCTAGACCTCAGGA
CCACGGCACCAACCTGACCTGCCAAGTGAAA
TTTGCTGGCGCTGGCGTGACCACCGAGAGAA
CCATCCAGCTGAACGTGACCTACGTGCCACA
GAACCCTACCACCGGCATCTTTCCAGGCGAC
GGCTCTGGCAAGCAAGAAACAAGAGCTGGCG
TGGTGCACGGCTATATCCCCGAGGCTCCTAG
AGATGGCCAGGCCTATGTTCGGAAGGATGGC
GAATGGGTGCTGCTGAGCACCTTCCTTGAAC

-continued

CTCGAGGGCCTACCATCAAGCCCTGTCCTCC
ATGCAAGTGCCCCGCTCCTAATCTGCTCGGA
GGCCCCAGCGTGTTCATCTTCCCACCTAAGA
TCAAGGACGTGCTGATGATCTCTCTGAGCCC
CATCGTGACCTGCGTGGTGGTGGATGTGTCC
GAGGACGATCCCGATGTGCAGATCAGTTGGT
TCGTGAACAACGTGGAAGTGCACACAGCCCA
GACACAGACCCACAGAGAGGACTACAACAGC
ACCCTGAGAGTGGTGTCTGCCCTGCCTATCC
AGCACCAGGATTGGATGAGCGGCAAAGAATT
CAAGTGCAAAGTGAACAACAAGGACCTGCCT
GCTCCTATCGAGCGGACCATCTCTAAGCCTA
AGGGCTCTGTTAGAGCCCCTCAGGTGTACGT
GCTGCCTCCTCCAGAGGAAGAGATGACCAAG
AAACAAGTGACCCTGACCTGCATGGTCACCG
ACTTCATGCCCGAGGACATCTACGTGGAATG
GACCAACAACGGCAAGACCGAGCTGAACTAC
AAGAACACCGAGCCTGTGCTGGACAGCGACG
GCAGCTACTTCATGTACTCCAAGCTGCGCGT
GGAAAAGAAGAACTGGGTCGAGCGGAACAGC
TACAGCTGCTCTGTGGTGCACGAGGGCCTGC
ACAATCACCACACCACCAAGAGCTTCAGCCG
TACGCCTGGAAAGTA

SEQ ID NO: 55

MGWSCIILFLVATATGVHSDPNFWLQVQESV
TVQEGLCVLVPCTFFHPIPYYDKNSPVHGYW
FREGAIISRDSPVATNKLDQEVQEETQGRFR
LLGDPSRNNCSLSIVDARRRDNGSYFFRMER
GSTKYSYKSPQLSVHVTDLTHRPKILIPGTL
EPGHSKNLTCSVSWACEQGTPPIFSWLSAAP
TSLGPRTTHSSVLIITPRPQDHGTNLTCQVK
FAGAGVTTERTIQLNVTYVPQNPTTGIFPGD
GSGKQETRAGVVHGGGGSGGGGSGYIPEAPR
DGQAYVRKDGEWVLLSTFLEPRGPTIKPCPP
CKCPAPNLLGGPSVFIFPPKIKDVLMISLSP
IVTCVVVDVSEDDPDVQISWFVNNVEVHTAQ
TQTHREDYNSTLRVVSALPIQHQDWMSGKEF
KCKVNNKDLPAPIERTISKPKGSVRAPQVYV
LPPPEEEMTKKQVTLTCMVTDFMPEDIYVEW
TNNGKTELNYKNTEPVLDSDGSYFMYSKLRV

-continued

EKKNWVERNSYSCSVVHEGLHNHHTTKSFSR
TPGK

SEQ ID NO: 56

ATGGGCTGGTCCTGCATCATCCTGTTTCTGG
TGGCCACAGCCACAGGCGTGCACAGCGATCC
CAATTTCTGGCTGCAAGTGCAAGAGTCCGTG
ACCGTGCAAGAGGGCCTGTGTGTGCTGGTGC
CCTGCACCTTCTTTCACCCCATTCCTTACTA
CGACAAGAACAGCCCTGTGCACGGCTACTGG
TTTAGAGAGGGCGCCATCATCAGCAGAGATA
GCCCTGTGGCCACCAACAAGCTGGACCAAGA
GGTGCAAGAAGAGACACAGGGCAGATTCAGA
CTGCTGGGCGACCCCAGCAGAAACAACTGCA
GCCTGTCTATCGTGGACGCCAGGCGGAGAGA
CAACGGCAGCTACTTCTTCCGGATGGAACGG
GGCAGCACCAAGTACAGCTACAAGAGCCCTC
AGCTGTCCGTGCACGTGACCGACCTGACACA
CAGACCCAAGATTCTGATCCCCGGCACACTG
GAACCTGGCCACAGCAAGAATCTGACCTGCT
CCGTGTCCTGGGCCTGCGAACAGGGAACCCC
TCCTATCTTTAGCTGGCTGAGCGCCGCTCCT
ACATCTCTGGGCCCTAGAACAACACACAGCA
GCGTGCTGATCATCACCCCTAGACCTCAGGA
CCACGGCACCAACCTGACCTGCCAAGTGAAA
TTTGCTGGCGCTGGCGTGACCACCGAGAGAA
CCATCCAGCTGAACGTGACCTACGTGCCACA
GAACCCTACCACCGGCATCTTTCCAGGCGAC
GGCTCTGGCAAGCAAGAAACAAGAGCTGGCG
TGGTGCACGGAGGCGGAGGATCTGGCGGAGG
TGGAAGTGGCTATATCCCCGAGGCTCCTAGA
GATGGCCAGGCCTATGTTCGGAAGGATGGCG
AATGGGTGCTGCTGAGCACCTTCCTTGAACC
TCGAGGGCCTACCATCAAGCCCTGTCCTCCA
TGCAAGTGCCCCGCTCCTAATCTGCTCGGAG
GCCCCAGCGTGTTCATCTTCCCACCTAAGAT
CAAGGACGTGCTGATGATCTCTCTGAGCCCC
ATCGTGACCTGCGTGGTGGTGGATGTGTCCG
AGGACGATCCCGATGTGCAGATCAGTTGGTT
CGTGAACAACGTGGAAGTGCACACAGCCCAG
ACACAGACCCACAGAGAGGACTACAACAGCA

-continued

CCCTGAGAGTGGTGTCTGCCCTGCCTATCCA
GCACCAGGATTGGATGAGCGGCAAAGAATTC
AAGTGCAAAGTGAACAACAAGGACCTGCCTG
CTCCTATCGAGCGGACCATCTCTAAGCCTAA
GGGCTCTGTTAGAGCCCCTCAGGTGTACGTG
CTGCCTCCTCCAGAGGAAGAGATGACCAAGA
AACAAGTGACCCTGACCTGCATGGTCACCGA
CTTCATGCCCGAGGACATCTACGTGGAATGG
ACCAACAACGGCAAGACCGAGCTGAACTACA
AGAACACCGAGCCTGTGCTGGACAGCGACGG
CAGCTACTTCATGTACTCCAAGCTGCGCGTG
GAAAAGAAGAACTGGGTCGAGCGGAACAGCT
ACAGCTGCTCTGTGGTGCACGAGGGCCTGCA
CAATCACCACACCACCAAGAGCTTCAGCCGT
ACGCCTGGAAAGTAG

SEQ ID NO: 57

MGWSCIILFLVATATGVHSDPNFWLQVQESV
TVQEGLCVLVPCTFFHPIPYYDKNSPVHGYW
FREGAIISRDSPVATNKLDQEVQEETQGRFR
LLGDPSRNNCSLSIVDARRRDNGSYFFRMER
GSTKYSYKSPQLSVHVTDLTHRPKILIPGTL
EPGHSKNLTCSVSWACEQGTPPIFSWLSAAP
TSLGPRTTHSSVLIITPRPQDHGTNLTCQVK
FAGAGVTTERTIQLNVTYVPQNPTTGIFPGD
GSGKQETRAGVVHEPRGPTIKPCPPCKCPAP
NLLGGPSVFIFPPKIKDVLMISLSPIVTCVV
VDVSEDDPDVQISWFVNNVEVHTAQTQTHRE
DYNSTLRVVSALPIQHQDWMSGKEFKCKVNN
KDLPAPIERTISKPKGSVRAPQVYVLPPPEE
EMTKKQVTLTCMVTDFMPEDIYVEWTNNGKT
ELNYKNTEPVLDSDGSYFMYSKLRVEKKNWV
ERNSYSCSVVHEGLHNHHTTKSFSRTPGKGG
GGSGGGGSGYIPEAPRDGQAYVRKDGEWVLL
STFL

SEQ ID NO: 58

ATGGGCTGGTCCTGCATCATCCTGTTTCTGG
TGGCCACAGCCACAGGCGTGCACAGCGATCC
CAATTTCTGGCTGCAACTGCAAGAGTCCGTG
ACCGTGCAAGAGGGCCTGTGTGTGCTGGTGC
CCTGCACCTTCTTTCACCCCATTCCTTACTA
CGACAAGAACAGCCCTGTGCACGGCTACTGG
TTTAGAGAGGGCGCCATCATCAGCAGAGATA

-continued

GCCCTGTGGCCACCAACAAGCTGGACCAAGA

GGTGCAAGAAGAGACACAGGGCAGATTCAGA

CTGCTGGGCGACCCCAGCAGAAACAACTGCA

GCCTGTCTATCGTGGACGCCAGGCGGAGAGA

CAACGGCAGCTACTTCTTCCGGATGGAACGG

GGCAGCACCAAGTACAGCTACAAGAGCCCTC

AGCTGTCCGTGCACGTGACCGACCTGACACA

CAGACCCAAGATTCTGATCCCCGGCACACTG

GAACCTGGCCACAGCAAGAATCTGACCTGCT

CCGTGTCCTGGGCCTGCGAACAGGGAACCCC

TCCTATCTTTAGCTGGCTGAGCGCCGCTCCT

ACATCTCTGGGCCCTAGAACAACACACAGCA

GCGTGCTGATCATCACCCCTAGACCTCAGGA

CCACGGCACCAACCTGACCTGCCAAGTGAAA

TTTGCTGGCGCTGGCGTGACCACCGAGAGAA

CCATCCAGCTGAACGTGACCTACGTGCCACA

GAACCCTACCACCGGCATCTTTCCAGGCGAC

GGCTCTGGCAAGCAAGAAACAAGAGCTGGCG

TGGTGCACGAACCTCGAGGGCCTACCATCAA

GCCCTGTCCTCCATGCAAGTGCCCCGCTCCT

AATCTGCTCGGAGGCCCCAGCGTGTTCATCT

TCCCACCTAAGATCAAGGACGTGCTGATGAT

CTCTCTGAGCCCCATCGTGACCTGCGTGGTG

GTGGATGTGTCCGAGGACGATCCCGATGTGC

AGATCAGTTGGTTCGTGAACAACGTGGAAGT

GCACACAGCCCAGACACAGACCCACAGAGAG

GACTACAACAGCACCCTGAGAGTGGTGTCTG

CCCTGCCTATCCAGCACCAGGATTGGATGAG

CGGCAAAGAATTCAAGTGCAAAGTGAACAAC

AAGGACCTGCCTGCTCCTATCGAGCGGACCA

TCTCTAAGCCTAAGGGCTCTGTTAGAGCCCC

TCAGGTGTACGTGCTGCCTCCTCCAGAGGAA

GAGATGACCAAGAAACAAGTGACCCTGACCT

GCATGGTCACCGACTTCATGCCCGAGGACAT

CTACGTGGAATGGACCAACAACGGCAAGACC

GAGCTGAACTACAAGAACACCGAGCCTGTGC

TGGACAGCGACGGCAGCTACTTCATGTACTC

CAAGCTGCGCGTGGAAAAGAAGAACTGGGTC

GAGCGGAACAGCTACAGCTGCTCTGTGGTCC

ACGAGGGCCTGCACAATCACCACACCACCAA

-continued

GAGCTTCAGCCGTACGCCTGGAAAGGGAGGC

GCAGGATCTGGCGGAGCTGGAAGTGGCTATA

TCCCCGAGGCTCCTAGAGATGGCCAGGCCTA

TGTTCGGAAGGATGGCGAATGGGTGCTGCTG

AGCACCTTCCTTTAG

SEQ ID NO: 59

MGWSCIILFLVATATGVHSDPNFWLQVQESV

TVQEGLCVLVPCTFFHPIPYYDKNSPVHGYW

FREGAIISRDSPVATNKLDQEVQEETQGRFR

LLGDPSRNNCSLSIVDARRRDNGSYFFRMER

GSTKYSYKSPQLSVHVTDLTHRPKILIPGTL

EPCHSKNLTCSVSWACEQGTPPIFSWLSAAP

TSLGPRTTHSSVLIITPRPQDHGTNLTCQVK

FAGAGVTTERTIQLNVTYVPQNPTTGIFPGD

GSCKQETRAGVVHGGGGSGGGGSGGGGSDPN

FWLQVQESVTVQEGLCVLVPCTFFHPIPYYD

KNSPVHGYWFREGAIISRDSPVATNKLDQEV

QEETQGRFRLLGDPSRNNCSLSIVDARRRDN

GSYFFRMERGSTKYSYKSPQLSVHVTDLTHR

PKILIPGTLEPGHSKNLTCSVSWACEQGTPP

IFSWLSAAPTSLGPRTTHSSVLIITPRPQDH

GTNLTCQVKFAGAGVTTERTIQLNVTYVPQN

PTTGIFPGDGSGKQETRAGVVHEPRGPTIKP

CPPCKCPAPNLLGGPSVFIFPPKIKDVLMIS

LSPIVTCVVVDVSEDDPDVQISWFVNNVEVH

TAQTQTHREDYNSTLRVVSALPIQHQDWMSG

KEFKCKVNNKDLPAPIERTISKPKGSVRAPQ

VYVLPPPEEEMTKKQVTLTCMVTDFMPEDIY

VEWTNNGKTELNYKNTEPVLDSDGSYFMYSK

LRVEKKNWVERNSYSCSVVHEGLHNHHTTKS

FSRTPGK

SEQ ID NO: 60

MGWSCIILFLVATATGVHSDPNFWLQVQESV

TVQEGLCVLVPCTFFHPIPYYDKNSPVHGYW

FREGAIISRDSPVATNKLDQEVQEETQGRFR

LLGDPSRNNCSLSIVDARRRDNGSYFFRMER

GSTKYSYKSPQLSVHVTDLTHRPKILIPGTL

EPGHSKNLTCSVSWACEQGTPPIFSWLSAAP

TSLGPRTTHSSVLIITPRPQDHGTNLTCQVK

FAGAGVTTERTIQLNVTYVPQNPTTGIFPGD

GSGKQETRAGVVHEPRGPTIKPCPPCKCPAP

NLLGGPSVFIFPPKIKDVLMISLSPIVTCVV

-continued

VDVSEDDPDVQISWFVNNVEVHTAQTQTHRE

DYNSTLRVVSALPIQHQDWMSGKEFKCKVNN

KDLPAPIERTISKPKGSVRAPQVYVLPPPEE

EMTKKQVTLTCMVTDFMPEDIYVEWTNNGKT

ELNYKNTEPVLDSDGSYFMYSKLRVEKKNWV

ERNSYSCSVVHEGLHNHHTTKSFSRTPGKGG

GGSGGGGSGGGGSDPNFWLQVQESVTVQEGL

CVLVPCTFFHPIPYYDKNSPVHGYWFREGAI

ISRDSPVATNKLDQEVQEETQGRFRLLGDPS

RNNCSLSIVDARRRDNGSYFFRMERGSTKYS

YKSPQLSVHVTDLTHRPKILIPGTLEPGHSK

NLTCSVSWACEQGTPPIFSWLSAAPTSLGPR

TTHSSVLIITPRPQDHGTNLTCQVKFAGAGV

TTERTIQLNVTYVPQNPTTGIFPGDGSGKQE

TRAGVVH

SEQ ID NO: 61

MGWSCIILFLVATATGVHSQKSNRKDYSLTM

QSSVTVQEGMCVHVRCSFSYPVDSQTDSDPV

HGYWFRAGNDISWKAPVATNNPAWAVQEETR

DRFHLLGDPQTKNCTLSIRDARMSDAGRYFF

RMEKGNIKWNYKYDQLSVNVTALTHRPNILI

PGTLESGCFQNLTCSVPWACEQGTPPMISWM

GTSVSPLHPSTTRSSVLTLIPQPQHHGTSLT

CQVTLPGAGVTTNRTIQLNVSYPPQNLTVTV

FQGEGTASTALGNSSSLSVLEGQSLRLVCAV

DSNPPARLSWTWRSLTLYPSQPSNPLVLELQ

VHLGDEGEFTCRAQNSLGSQHVSLNLSLQQE

YTGKMRPVSGVLLGAVGGGGGSGGGGSGYIP

EAPRDGQAYVRKDGEWVLLSTFLEPRGPTIK

PCPPCKCPAPNLLGGPSVFIFPPKIKDVLMI

SLSPIVTCVVVDVSEDDPDVQISWFVNNVEV

HTAQTQTHREDYNSTLRVVSALPIQHQDWMS

GKEFKCKVNNKDLPAPIERTISKPKGSVRAP

QVYVLPPPEEEMTKKQVTLTCMVTDFMPEDI

YVEWTNNGKTELNYKNTEPVLDSDGSYFMYS

KLRVEKKNWVERNSYSCSVVHEGLHNHHTTK

SFSRTPGK

SEQ ID NO: 62

MGWSCIILFLVATATGVHSQKSNRKDYSLTM

QSSVTVQEGMCVHVRCSFSYPVDSQTDSDPV

HGYWFRAGNDISWKAPVATNNPAWAVQEETR

-continued

DRFHLLGDPQTKNCTLSIRDARMSDAGRYFF

RMEKGNIKWNYKYDQLSVNVTALTHRPNILI

PGTLESGCFQNLTCSVPWACEQGTPPMISWM

GTSVSPLHPSTTRSSVLTLIPQPQHHGTSLT

CQVTLPGAGVTTNRTIQLNVSYPPQNLTVTV

FQGEGTASTALGNSSSLSVLEGQSLRLVCAV

DSNPPARLSWTWRSLTLYPSQPSNPLVLELQ

VHLGDEGEFTCRAQNSLGSQHVSLNLSLQQE

YTGKMRPVSGVLLGAVGEPRGPTIKPCPPCK

CPAPNLLGGPSVFIFPPKIKDVLMISLSPIV

TCVVVDVSEDDPDVQISWFVNNVEVHTAQTQ

THREDYNSTLRVVSALPIQHQDWMSGKEFKC

KVNNKDLPAPIERTISKPKGSVRAPQVYVLP

PPEEEMTKKQVTLTCMVTDFMPEDIYVEWTN

NGKTELNYKNTEPVLDSDGSYFMYSKLRVEK

KNWVERNSYSCSVVHEGLHNHHTTKSFSRTP

GKGGGGSGGGGSGYIPEAPRDGQAYVRKDGE

WVLLSTFL

SEQ ID NO: 63

MGWSCIILFLVATATGVHSQTSKLLTMQSSV

TVQEGLCVHVPCSFSYPSHGWIYPGPVVHGY

WFREGANTDQDAPVATNNPARAVWEETRDRF

HLLGDPHTKNCTLSIRDARRSDAGRYFFRME

KGSIKWNYKHHRLSVNVTALTHRPNILIPGT

LESGCPQNLTCSVPWACEQGTPPMISWIGTS

VSPLDPSTTRSSVLTLIPQPQDHGTSLTCQV

TFPGASVTTNKTVHLNVSYPPQNLTMTVFQG

DGTVSTVLGNGSSLSLPEGQSLRLVCAVDAV

DSNPPARLSLSWRGLTLCPSQPSNPGVLELP

WVHLRDAAEFTCRAQNPLGSQQVYLNVSLQS

KATSGVTQGGGGGSGGGGSGYIPEAPRDGQA

YVRKDGEWVLLSTFLEPRGPTIKPCPPCKCP

APNLLGGPSVFIFPPKIKDVLMISLSPIVTC

VVVDVSEDDPDVQISWFVNNVEVHTAQTQTH

REDYNSTLRVVSALPIQHQDWMSGKEFKCKV

NNKDLPAPIERTISKPKGSVRAPQVYVLPPP

EEEMTKKQVTLTCMVTDFMPEDIYVEWTNNG

KTELNYKNTEPVLDSDGSYFMYSKLRVEKKN

WVERNSYSCSVVHEGLHNHHTTKSFSRTPGK

SEQ ID NO: 64

MGWSCIILFLVATATGVHSQTSKLLTMQSSV

TVQEGLCVHVPCSFSYPSHGWIYPGPVVHGY

-continued

WFREGANTDQDAPVATNNPARAVWEETRDRF
HLLGDPHTKNCTLSIRDARRSDAGRYFFRME
KGSIKWNYKHHRLSVNVTALTHRPNILIPGT
LESGCPQNLTCSVPWACEQGTPPMISWIGTS
VSPLDPSTTRSSVLTLIPQPQDHGTSLTCQV
TFPGASVTTNKTVHLNVSYPPQNLTMTVFQG
DGTVSTVLGNGSSLSLPEGQSLRLVCAVDAV
DSNPPARLSLSWRGLTLCPSQPSNPGVLELP
WVHLRDAAEFTCRAQNPLGSQQVYLNVSLQS
KATSGVTQGEPRGPTIKPCPPCKCPAPNLLG
GPSVFIFPPKIKDVLMISLSPIVTCVVVDVS
EDDPDVQISWFVNNVEVHTAQTQTHREDYNS
TLRVVSALPIQHQDWMSGKEFKCKVNNKDLP
APIERTISKPKGSVRAPQVYVLPPPEEEMTK
KQVTLTCMVTDFMPEDIYVEWTNNGKTELNY
KNTEPVLDSDGSYFMYSKLRVEKKNWVERNS
YSCSVVHEGLHNHHTTKSFSRTPGKGGGGSG
GGGSGYIPEAPRDGQAYVRKDGEWVLLSTFL

SEQ ID NO: 65

QTSKLLTMQSSVTVQEGLCVHVPCSFSYPSH
GWIYPGPVVHGYWFREGANTDQDAPVATNNP
ARAVWEETRDRFHLLGDPHTKNCTLSIRDAR
RSDAGRYFFRMEKGSIKWNYKHHRLSVNVTA
LTHRPNILIPGTLESGCPQNLTCSVPWACEQ
GTPPMISWIGTSVSPLDPSTTRSSVLTLIPQ
PQDHGTSLTCQVTFPGASVTTNKTVH

SEQ ID NO: 66

QTSKLLTMQSSVTVQEGLCVHVPCSFSYPSH
GWIYPGPVVHGYWFREGANTDQDAPVATNNP
ARAVWEETRDRFHLLGDPHTKNCTLSIRDAR
RSDAGRYFFRMEKGSIKWNYKHHRLSVNVTA
LTHRPNILIPGTLESGCPQNLTCSVPWACEQ
GTPPMISWIGTSVSPLDPSTTRSSVLTLIPQ
PQDHGTSLTCQVTFPGASVTTNKTVHLNVSY
PPQNLTMTVFQGDGTVSTVLGNGSSLSLPEG
QSLRLVCAVDAVDSNPPARLSLSWRGLTLCP
SQPSNPGVLELPWVHLRDAAEFTCRAQNPLG
SQQVYLNVSLQSKATSGVTQG

SEQ ID NO: 67

MGWSCIILFLVATATGVHSQTSKLLTMQSSV
TVQEGLCVHVPCSFSYPSHGWIYPGPVVHGY
WFREGANTDQDAPVATNNPARAVWEETRDRF

-continued

HLLGDPHTKNCTLSIRDARRSDAGRYFFRME
KGSIKWNYKHHRLSVNVTALTHRPNILIPGT
LESGSPQNLTCSVPWACEQGTPPMISWIGTS
VSPLDPSTTRSSVLTLIPQPQDHGTSLTCQV
TFPGASVTTNKTVHLNVSYPPQNLTMTVFQG
DGTVSTVLGNGSSLSLPEGQSLRLVCAVDAV
DSNPPARLSLSWRGLTLYPSQPSNPGVLELP
WVHLRDAAEFTCRAQNPLGSQQVYLNVSLQS
KATSGVTQGGYIPEAPRDGQAYVRKDGEWVL
LSTFLEPRGPTIKPCPPCKCPAPNLLGGPSV
FIFPPKIKDVLMISLSPIVTCVVVDVSEDDP
DVQISWFVNNVEVHTAQTQTHREDYNSTLRV
VSALPIQHQDWMSGKEFKCKVNNKDLPAPIE
RTISKPKGSVRAPQVYVLPPPEEEMTKKQVT
LTCMVTDFMPEDIYVEWTNNGKTELNYKNTE
PVLDSDGSYFMYSKLRVEKKNWVERNSYSCS
VVHEGLHNHHTTKSFSRTPGK

SEQ ID NO: 68 atgggatggagctgtatcatcctcttcttgg
tagcaacagctacaggtgtacactcccagac
cagcaagctgctgaccatgcagagcagcgtg
accgtgcaggagggcctgtgcgtgcatgtgc
cctgcagcttcagctaccccagccacggctg
gatctaccccggtcccgtagtgcacggctac
tggttcagggagggcgccaacaccgaccagg
acgctcccgtggcaaccaacaaccccgccag
ggccgtgtgggaggagaccagggacaggttc
cacctgctgggcgacccccacaccaagaact
gcaccctgagcatcagggacgccaggaggag
cgacgccggcaggtacttcttcaggatggag
aaggggtctatcaagtggaactacaagcacc
accggctgagcgtgaatgtgaccgccctgac
ccaccggcccaatatcctcatccccggcacc
ctggagagcggcagcccccagaatcttacct
gcagcgtaccctgggcctgcgagcagggcac
ccctccaatgatcagctggatcggcaccagc
gtgagcccccctggaccctagtaccaccagga
gcagcgtgctgaccctgatcccccagcccca
ggaccacggaaccagcctgacctgccaggtg
accttccccggagccagcgtaaccaccaaca
agaccgtgcacctgaacgtgagctacccacc -continued ccaaaacctgaccatgaccgtgttccagggc
gacggcacggtgagcaccgtactgggcaacg
gcagctctctgagcctgcccgagggccagag
cttgcggctggtctgcgccgtggatgctgtg
gacagcaaccctcccgccaggctgagcctga
gctggaggggcctgaccctgtaccccagcca
gcccagcaatcccggcgtgctggagctgccc
tgggttcacctgagggacgctgccgagttca
catgtagggcccagaaccccctgggctctca
gcaggtgtacctgaacgtgtctcttcagagt
aaggccaccagcggcgtgacccaaggaggct
atatccccgaggctcctagagatggccaggc
ctatgttcggaaggatggcgaatgggtgctg
ctgagcaccttccttgaacctcgagggccta
ccatcaagccctgtcctccatgcaagtgccc
cgctcctaatctgctcggaggccccagcgtg
ttcatcttcccacctaagatcaaggacgtgc
tgatgatctctctgagccccatcgtgacctg
cgtggtggtggatgtgtccgaggacgatccc
gatgtgcagatcagttggttcgtgaacaacg
tggaagtgcacacagcccagacacagaccca -continued cagagaggactacaacagcaccctgagagtg
gtgtctgccctgcctatccagcaccaggatt
ggatgagcggcaaagaattcaagtgcaaagt
gaacaacaaggacctgcctgctcctatcgag
cggaccatctctaagcctaagggctctgtta
gagcccctcaggtgtacgtgctgcctcctcc
agaggaagagatgaccaagaaacaagtgacc
ctgacctgcatggtcaccgacttcatgcccg
aggacatctacgtggaatggaccaacaacgg
caagaccgagctgaactacaagaacaccgag
cctgtgctggacagcgacggcagctacttca
tgtactccaagctgcgcgtggaaaagaagaa
ctgggtcgagcggaacagctacagctgctct
gtggtgcacgagggcctgcacaatcaccaca
ccaccaagagcttcagccgtacgcctggaaa
gtag

SEQ ID NO: 69

GGGGSGGGGS

SEQ ID NO: 70

GGP

SEQ ID NO: 71

GGGGS

SEQ ID NO: 72

GGGGS

What is claimed is:

1. An isolated polypeptide comprising:

a) a lectin domain comprising a Sialic acid-binding immunoglobulin-type lectin (Siglec) sialic acid binding V-set immunoglobulin-like domain of Siglec-7 or Siglec-9, or a variant thereof;

b) a trimerization domain; and c) a dimerization domain, wherein the lectin domain, the trimerization domain, and the dimerization domain are covalently linked together in an N- to C-terminal orientation; and wherein the polypeptide comprises SEQ ID NO: 7, SEQ ID NO: 8, or amino acids 20-610 of SEQ ID NO: 67.

2. A multimeric protein comprising a homo-hexameric protein complex formed by the polypeptides of claim 1.

3. The multimeric protein of claim 2, wherein, in the homo-hexameric protein complex:

a) the first, second and third polypeptides are trimerized at their respective trimerization domains;

b) the fourth, fifth, and sixth polypeptides are trimerized at their respective trimerization domains;

c) the first and second polypeptides are dimerized at their respective dimerization domains;

d) the third and fourth polypeptides are dimerized at their respective dimerization domains; and e) the fifth and sixth polypeptides are dimerized at their respective dimerization domains.

4. A pharmaceutical composition comprising the multimeric protein of claim 2.

* * * * *